US012805905B2

(12) United States Patent
Richter et al.

(10) Patent No.: US 12,805,905 B2
(45) Date of Patent: Nov. 24, 2026

(54) MULTI-SHIELD SPINAL ACCESS SYSTEM

(71) Applicant: Medos International Sàrl, Le Locle (CH)

(72) Inventors: Jörn Richter, Kandern (DE); Christopher L. Ramsay, West Wareham, MA (US); Paul Maguire, Hope Valley, RI (US); John C. Voellmicke, Franklin, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 18/987,841

(22) Filed: Dec. 19, 2024

(65) Prior Publication Data

US 2025/0195105 A1 Jun. 19, 2025

Related U.S. Application Data

(63) Continuation of application No. 18/091,255, filed on Dec. 29, 2022, now Pat. No. 12,193,704, which is a (Continued)

(51) Int. Cl.

*A61B 17/34* (2006.01)
*A61B 1/00* (2006.01)

(Continued)

(52) U.S. Cl.

CPC ...... *A61B 17/3421* (2013.01); *A61B 1/00045* (2013.01); *A61B 1/00089* (2013.01);

(Continued)

(58) Field of Classification Search

CPC .......... A61B 5/6877; A61B 2017/0256; A61B 2017/0262

See application file for complete search history.

(56) References Cited

U.S. PATENT DOCUMENTS 4,132,227 A 1/1979 Ibe
4,318,401 A 3/1982 Zimmerman (Continued)

FOREIGN PATENT DOCUMENTS

CN 2659368 Y 12/2004
CN 1735380 A 2/2006

(Continued)

OTHER PUBLICATIONS

Australian Examination Report for Application No. 2018225113, issued Jul. 15, 2022 (4 pages).

(Continued)

*Primary Examiner* — Matthew J Lawson

(74) *Attorney, Agent, or Firm* — Barnes & Thornburg LLP

(57) ABSTRACT

An access device for accessing an intervertebral disc having an outer shield comprising an access shield with a larger diameter (~16-30 mm) that reaches from the skin down to the facet line, with an inner shield having a second smaller diameter (~5-12 mm) extending past the access shield and reaches down to the disc level. This combines the benefits of the direct visual microsurgical/mini open approaches and the percutaneous, "ultra-MIS" techniques.

20 Claims, 92 Drawing Sheets

Related U.S. Application Data continuation of application No. 16/352,654, filed on Mar. 13, 2019, now Pat. No. 11,559,328, which is a continuation-in-part of application No. 15/697,494, filed on Sep. 7, 2017, now Pat. No. 11,000,312, which is a continuation-in-part of application No. 15/437,792, filed on Feb. 21, 2017, now Pat. No. 10,874,425, which is a continuation-in-part of application No. 15/254,877, filed on Sep. 1, 2016, now Pat. No. 10,987,129.

(60) Provisional application No. 62/214,297, filed on Sep. 4, 2015.

(51) Int. Cl.

| | |
|---|---|
| ***A61B 1/012*** | (2006.01) |
| ***A61B 1/018*** | (2006.01) |
| ***A61B 1/05*** | (2006.01) |
| ***A61B 1/055*** | (2006.01) |
| ***A61B 1/07*** | (2006.01) |
| ***A61B 1/12*** | (2006.01) |
| ***A61B 1/233*** | (2006.01) |
| ***A61B 1/267*** | (2006.01) |
| ***A61B 1/313*** | (2006.01) |
| ***A61B 1/317*** | (2006.01) |
| ***A61B 1/32*** | (2006.01) |
| ***A61B 5/00*** | (2006.01) |
| ***A61B 5/06*** | (2006.01) |
| ***A61B 5/24*** | (2021.01) |
| ***A61B 17/00*** | (2006.01) |
| ***A61B 17/02*** | (2006.01) |
| ***A61B 17/32*** | (2006.01) |
| ***A61B 17/60*** | (2006.01) |
| ***A61B 17/70*** | (2006.01) |
| ***A61B 18/18*** | (2006.01) |
| ***A61B 34/20*** | (2016.01) |
| ***A61B 90/00*** | (2016.01) |
| ***A61B 90/50*** | (2016.01) |
| ***A61B 90/57*** | (2016.01) |
| ***A61F 2/44*** | (2006.01) |
| ***A61F 2/46*** | (2006.01) |
| ***A61M 29/00*** | (2006.01) |
| *A61B 17/16* | (2006.01) |
| *A61B 17/17* | (2006.01) |
| *A61B 17/56* | (2006.01) |
| *A61B 18/00* | (2006.01) |
| *A61B 34/00* | (2016.01) |
| *A61B 34/30* | (2016.01) |
| *A61B 90/30* | (2016.01) |

(52) U.S. Cl.

CPC ...... *A61B 1/00091* (2013.01); *A61B 1/00094* (2013.01); *A61B 1/00096* (2013.01); *A61B 1/00103* (2013.01); *A61B 1/00128* (2013.01); *A61B 1/00133* (2013.01); *A61B 1/00135* (2013.01); *A61B 1/00154* (2013.01); *A61B 1/012* (2013.01); *A61B 1/018* (2013.01); *A61B 1/05* (2013.01); *A61B 1/051* (2013.01); *A61B 1/055* (2013.01); *A61B 1/07* (2013.01); *A61B 1/126* (2013.01); *A61B 1/233* (2013.01); *A61B 1/2676* (2013.01); *A61B 1/3132* (2013.01); *A61B 1/3135* (2013.01); *A61B 1/317* (2013.01); *A61B 1/32* (2013.01); *A61B 5/068* (2013.01); *A61B 5/24* (2021.01); *A61B 5/4041* (2013.01); *A61B 5/407* (2013.01); *A61B 17/00234* (2013.01); *A61B 17/0218* (2013.01); *A61B 17/025* (2013.01); *A61B 17/0293* (2013.01); *A61B 17/320068* (2013.01); *A61B 17/3423* (2013.01); *A61B 17/3462* (2013.01); *A61B 17/60* (2013.01); *A61B 17/7032* (2013.01); *A61B 17/7074* (2013.01); *A61B 17/708* (2013.01); *A61B 18/1815* (2013.01); *A61B 34/20* (2016.02); *A61B 90/03* (2016.02); *A61B 90/361* (2016.02); *A61B 90/50* (2016.02); *A61B 90/57* (2016.02); *A61F 2/4455* (2013.01); *A61F 2/4611* (2013.01); *A61M 29/00* (2013.01); *A61B 1/00149* (2013.01); *A61B 2017/00022* (2013.01); *A61B 2017/00053* (2013.01); *A61B 2017/00261* (2013.01); *A61B 2017/00296* (2013.01); *A61B 2017/00314* (2013.01); *A61B 2017/0034* (2013.01); *A61B 2017/00345* (2013.01); *A61B 2017/00407* (2013.01); *A61B 2017/00477* (2013.01); *A61B 2017/00557* (2013.01); *A61B 2017/00738* (2013.01); *A61B 2017/00831* (2013.01); *A61B 2017/00858* (2013.01); *A61B 2017/00871* (2013.01); *A61B 2017/00946* (2013.01); *A61B 2017/00991* (2013.01); *A61B 17/0206* (2013.01); *A61B 2017/0256* (2013.01); *A61B 2017/0262* (2013.01); *A61B 17/1637* (2013.01); *A61B 17/1671* (2013.01); *A61B 17/1703* (2013.01); *A61B 17/1757* (2013.01); *A61B 2017/320075* (2017.08); *A61B 17/3403* (2013.01); *A61B 17/3439* (2013.01); *A61B 2017/3443* (2013.01); *A61B 2017/3445* (2013.01); *A61B 2017/3447* (2013.01); *A61B 2017/345* (2013.01); *A61B 2017/3454* (2013.01); *A61B 2017/347* (2013.01); *A61B 2017/3484* (2013.01); *A61B 2017/564* (2013.01); *A61B 17/70* (2013.01); *A61B 17/7083* (2013.01); *A61B 2018/00339* (2013.01); *A61B 2018/00565* (2013.01); *A61B 2018/00577* (2013.01); *A61B 2018/00601* (2013.01); *A61B 2018/00839* (2013.01); *A61B 2018/1861* (2013.01); *A61B 2018/1869* (2013.01); *A61B 2034/2055* (2016.02); *A61B 34/30* (2016.02); *A61B 34/70* (2016.02); *A61B 2090/034* (2016.02); *A61B 2090/036* (2016.02); *A61B 2090/08021* (2016.02); *A61B 90/30* (2016.02); *A61B 2090/306* (2016.02); *A61B 2090/371* (2016.02); *A61B 2090/3916* (2016.02); *A61B 2090/3937* (2016.02); *A61B 2090/3979* (2016.02); *A61B 2090/3983* (2016.02); *A61B 2218/002* (2013.01); *A61B 2218/007* (2013.01); *A61F 2002/4635* (2013.01)

(56) References Cited

U.S. PATENT DOCUMENTS

| | | | |
|---|---|---|---|
| 4,573,448 | A | 3/1986 | Kambin |
| 4,646,738 | A | 3/1987 | Trott |
| 4,678,459 | A | 7/1987 | Onik et al. |
| 4,807,593 | A | 2/1989 | Ito |
| 4,863,430 | A | 9/1989 | Klyce et al. |
| 4,874,375 | A | 10/1989 | Ellison |
| 4,888,146 | A | 12/1989 | Dandeneau |
| 5,080,662 | A | 1/1992 | Paul |
| 5,195,541 | A | 3/1993 | Obenchain |
| 5,207,213 | A | 5/1993 | Auhll et al. |
| 5,285,795 | A | 2/1994 | Ryan et al. |
| 5,395,317 | A | 3/1995 | Kambin |
| 5,439,464 | A | 8/1995 | Shapiro |

(56) References Cited

U.S. PATENT DOCUMENTS

| | | | |
|---|---|---|---|
| 5,529,580 | A | 6/1996 | Kusunoki et al. |
| 5,540,706 | A | 7/1996 | Aust et al. |
| 5,569,290 | A | 10/1996 | McAfee |
| 5,591,187 | A | 1/1997 | Dekel |
| 5,601,569 | A | 2/1997 | Pisharodi |
| 5,615,690 | A | 4/1997 | Giurtino et al. |
| 5,618,293 | A | 4/1997 | Sample et al. |
| 5,662,300 | A | 9/1997 | Michelson |
| 5,688,222 | A | 11/1997 | Hluchy et al. |
| 5,697,888 | A | 12/1997 | Kobayashi et al. |
| 5,716,355 | A | 2/1998 | Jackson et al. |
| 5,730,754 | A | 3/1998 | Obenchain |
| 5,733,242 | A | 3/1998 | Rayburn et al. |
| 5,735,792 | A | 4/1998 | Vanden Hoek et al. |
| 5,749,602 | A | 5/1998 | Delaney et al. |
| 5,792,044 | A | 8/1998 | Foley et al. |
| 5,820,623 | A | 10/1998 | Ng |
| 5,885,300 | A | 3/1999 | Tokuhashi et al. |
| 5,894,369 | A | 4/1999 | Akiba et al. |
| 5,899,425 | A | 5/1999 | Corey, Jr. et al. |
| 5,928,137 | A | 7/1999 | Green |
| 5,954,635 | A | 9/1999 | Foley et al. |
| 5,976,075 | A | 11/1999 | Beane et al. |
| 5,989,183 | A | 11/1999 | Reisdorf et al. |
| 6,017,333 | A | 1/2000 | Bailey |
| 6,033,105 | A | 3/2000 | Barker et al. |
| 6,053,907 | A | 4/2000 | Zirps |
| 6,063,021 | A | 5/2000 | Hossain et al. |
| 6,110,182 | A | 8/2000 | Mowlai-Ashtiani |
| 6,126,592 | A | 10/2000 | Proch et al. |
| 6,139,563 | A | 10/2000 | Cosgrove, III et al. |
| 6,200,322 | B1 | 3/2001 | Branch et al. |
| 6,217,509 | B1 | 4/2001 | Foley et al. |
| 6,234,961 | B1 | 5/2001 | Gray |
| 6,283,966 | B1 | 9/2001 | Houfburg |
| 6,286,179 | B1 | 9/2001 | Byrne |
| 6,296,644 | B1 | 10/2001 | Saurat et al. |
| 6,322,498 | B1 | 11/2001 | Gravenstein et al. |
| 6,354,992 | B1 | 3/2002 | Kato |
| 6,357,710 | B1 | 3/2002 | Fielden et al. |
| 6,371,968 | B1 | 4/2002 | Kogasaka et al. |
| 6,383,191 | B1 | 5/2002 | Zdeblick et al. |
| 6,432,109 | B1 | 8/2002 | Letendart et al. |
| 6,447,446 | B1 | 9/2002 | Smith et al. |
| 6,468,289 | B1 | 10/2002 | Bonutti |
| 6,520,495 | B1 | 2/2003 | La Mendola |
| 6,558,407 | B1 | 5/2003 | Ivanko et al. |
| 6,575,899 | B1 | 6/2003 | Foley et al. |
| 6,579,281 | B2 | 6/2003 | Palmer et al. |
| 6,596,008 | B1 | 7/2003 | Kambin |
| 6,626,830 | B1 | 9/2003 | Califiore et al. |
| 6,648,915 | B2 | 11/2003 | Sazy |
| 6,663,563 | B1 | 12/2003 | Sharratt |
| 6,676,597 | B2 | 1/2004 | Guenst et al. |
| 6,679,833 | B2 | 1/2004 | Smith et al. |
| 6,685,724 | B1 | 2/2004 | Haluck |
| 6,688,564 | B2 | 2/2004 | Salvermoser et al. |
| 6,758,809 | B2 | 7/2004 | Briscoe et al. |
| 6,808,505 | B2 | 10/2004 | Kadan |
| 6,887,198 | B2 | 5/2005 | Phillips et al. |
| 6,983,930 | B1 | 1/2006 | La Mendola et al. |
| 7,001,342 | B2 | 2/2006 | Faciszewski |
| 7,087,058 | B2 | 8/2006 | Cragg |
| 7,104,986 | B2 | 9/2006 | Hovda et al. |
| 7,137,949 | B2 | 11/2006 | Scirica et al. |
| 7,179,261 | B2 | 2/2007 | Sicvol et al. |
| 7,182,731 | B2 | 2/2007 | Nguyen et al. |
| 7,226,413 | B2 | 6/2007 | McKinley |
| 7,341,556 | B2 | 3/2008 | Shalman |
| 7,434,325 | B2 | 10/2008 | Foley et al. |
| 7,491,168 | B2 | 2/2009 | Raymond et al. |
| 7,591,790 | B2 | 9/2009 | Pflueger |
| 7,594,888 | B2 | 9/2009 | Raymond et al. |
| 7,618,431 | B2 | 11/2009 | Roehm, III et al. |
| 7,636,596 | B2 | 12/2009 | Solar |
| 7,637,905 | B2 | 12/2009 | Saadat et al. |
| 7,641,659 | B2 | 1/2010 | Emstad et al. |
| 7,715,925 | B2 | 5/2010 | Hafer et al. |
| 7,766,313 | B2 | 8/2010 | Panosian |
| 7,771,384 | B2 | 8/2010 | Ravo |
| 7,794,456 | B2 | 9/2010 | Sharps et al. |
| 7,794,469 | B2 | 9/2010 | Kao et al. |
| 7,811,303 | B2 | 10/2010 | Fallin et al. |
| 7,931,579 | B2 | 4/2011 | Bertolero et al. |
| 7,946,981 | B1 | 5/2011 | Cubb |
| 7,951,141 | B2 | 5/2011 | Sharps et al. |
| 7,959,564 | B2 | 6/2011 | Ritland |
| 7,988,623 | B2 | 8/2011 | Pagliuca et al. |
| 8,007,492 | B2 | 8/2011 | DiPoto et al. |
| 8,038,606 | B2 | 10/2011 | Otawara |
| 8,043,381 | B2 | 10/2011 | Hestad et al. |
| 8,062,218 | B2 | 11/2011 | Sebastian et al. |
| 8,079,952 | B2 | 12/2011 | Fujimoto |
| 8,092,464 | B2 | 1/2012 | McKay |
| 8,096,944 | B2 | 1/2012 | Harrel |
| 8,202,216 | B2 | 6/2012 | Melkent et al. |
| 8,206,357 | B2 | 6/2012 | Bettuchi |
| 8,230,863 | B2 | 7/2012 | Ravikumar et al. |
| 8,236,006 | B2 | 8/2012 | Hamada |
| 8,267,896 | B2 | 9/2012 | Hartoumbekis et al. |
| 8,303,492 | B2 | 11/2012 | Ito |
| 8,333,690 | B2 | 12/2012 | Ikeda |
| 8,337,532 | B1 | 12/2012 | McLean et al. |
| 8,360,970 | B2 | 1/2013 | Mangiardi |
| 8,372,131 | B2 | 2/2013 | Hestad et al. |
| 8,382,048 | B2 | 2/2013 | Nesper et al. |
| 8,397,335 | B2 | 3/2013 | Gordin et al. |
| 8,419,625 | B2 | 4/2013 | Ito |
| 8,435,174 | B2 | 5/2013 | Cropper et al. |
| 8,460,180 | B1 | 6/2013 | Zarate et al. |
| 8,460,186 | B2 | 6/2013 | Ortiz et al. |
| 8,460,310 | B2 | 6/2013 | Stern |
| 8,518,087 | B2 | 8/2013 | Lopez et al. |
| 8,535,220 | B2 | 9/2013 | Mondschein |
| 8,556,809 | B2 | 10/2013 | Vijayanagar |
| 8,585,726 | B2 | 11/2013 | Yoon et al. |
| 8,602,979 | B2 | 12/2013 | Kitano |
| 8,622,894 | B2 | 1/2014 | Banik et al. |
| 8,636,655 | B1 | 1/2014 | Childs |
| 8,648,932 | B2 | 2/2014 | Talbert et al. |
| 8,688,186 | B1 | 4/2014 | Mao et al. |
| 8,690,764 | B2 | 4/2014 | Clark et al. |
| 8,721,536 | B2 | 5/2014 | Marino et al. |
| 8,727,975 | B1 | 5/2014 | Pfabe et al. |
| 8,740,779 | B2 | 6/2014 | Yoshida |
| 8,784,421 | B2 | 7/2014 | Carrison et al. |
| 8,821,378 | B2 | 9/2014 | Morgenstern Lopez et al. |
| 8,834,507 | B2 | 9/2014 | Mire et al. |
| 8,845,734 | B2 | 9/2014 | Weiman |
| 8,852,242 | B2 | 10/2014 | Morgenstern Lopez et al. |
| 8,870,753 | B2 | 10/2014 | Boulais et al. |
| 8,870,756 | B2 | 10/2014 | Maurice |
| 8,876,712 | B2 | 11/2014 | Yee et al. |
| 8,888,689 | B2 | 11/2014 | Poll et al. |
| 8,888,813 | B2 | 11/2014 | To |
| 8,894,573 | B2 | 11/2014 | Loftus et al. |
| 8,894,653 | B2 | 11/2014 | Solsberg et al. |
| 8,926,502 | B2 | 1/2015 | Levy et al. |
| 8,932,207 | B2 | 1/2015 | Greenburg et al. |
| 8,932,360 | B2 | 1/2015 | Womble et al. |
| 8,936,545 | B2 | 1/2015 | To |
| 8,936,605 | B2 | 1/2015 | Greenberg |
| 8,952,312 | B2 | 2/2015 | Blanquart et al. |
| 8,961,404 | B2 | 2/2015 | Ito |
| 8,972,714 | B2 | 3/2015 | Talbert et al. |
| 8,974,381 | B1 | 3/2015 | Lovell et al. |
| 8,986,199 | B2 | 3/2015 | Weisenburgh, II et al. |
| 8,992,580 | B2 | 3/2015 | Bar et al. |
| 9,028,522 | B1 | 5/2015 | Prado |
| 9,050,036 | B2 | 6/2015 | Poll et al. |
| 9,050,037 | B2 | 6/2015 | Poll et al. |
| 9,050,146 | B2 | 6/2015 | Woolley et al. |
| 9,055,936 | B2 | 6/2015 | Mire et al. |
| 9,072,431 | B2 | 7/2015 | Adams et al. |

(56) References Cited

U.S. PATENT DOCUMENTS

| | | | |
|---|---|---|---|
| 9,078,562 | B2 | 7/2015 | Poll et al. |
| 9,123,602 | B2 | 9/2015 | Blanquart |
| 9,131,948 | B2 | 9/2015 | Fang et al. |
| 9,144,374 | B2 | 9/2015 | Maurice, Jr. |
| 9,153,609 | B2 | 10/2015 | Blanquart |
| 9,179,947 | B2 | 11/2015 | Bass |
| 9,198,674 | B2 | 12/2015 | Benson et al. |
| 9,211,059 | B2 | 12/2015 | Drach et al. |
| 9,216,016 | B2 | 12/2015 | Fiechter et al. |
| 9,216,125 | B2 | 12/2015 | Sklar |
| 9,226,647 | B2 | 1/2016 | Sugawara |
| 9,232,935 | B2 | 1/2016 | Brand et al. |
| 9,247,997 | B2 | 2/2016 | Stefanchik et al. |
| 9,265,491 | B2 | 2/2016 | Lins et al. |
| 9,277,928 | B2 | 3/2016 | Morgenstern Lopez |
| 9,289,249 | B2 * | 3/2016 | Ramsay ............. A61B 17/7076 |
| 9,307,972 | B2 | 4/2016 | Lovell et al. |
| 9,320,419 | B2 | 4/2016 | Kirma et al. |
| RE46,007 | E | 5/2016 | Banik |
| RE46,062 | E | 7/2016 | James |
| 9,386,971 | B1 | 7/2016 | Casey et al. |
| 9,387,313 | B2 | 7/2016 | Culbert et al. |
| 9,414,828 | B2 | 8/2016 | Abidin et al. |
| 9,462,234 | B2 | 10/2016 | Blanquart et al. |
| 9,486,296 | B2 | 11/2016 | Mire et al. |
| 9,492,194 | B2 | 11/2016 | Morgenstern Lopez et al. |
| 9,509,917 | B2 | 11/2016 | Blanquart et al. |
| 9,510,853 | B2 | 12/2016 | Aljuri et al. |
| 9,516,239 | B2 | 12/2016 | Blanquart et al. |
| 9,522,017 | B2 | 12/2016 | Poll et al. |
| 9,526,401 | B2 | 12/2016 | Saadat et al. |
| 9,579,012 | B2 | 2/2017 | Vazales et al. |
| 9,603,510 | B2 | 3/2017 | Ammirati |
| 9,603,610 | B2 | 3/2017 | Richter et al. |
| 9,610,007 | B2 | 4/2017 | Kienzle et al. |
| 9,610,095 | B2 | 4/2017 | To |
| 9,622,650 | B2 | 4/2017 | Blanquart |
| 9,629,521 | B2 | 4/2017 | Ratnakar |
| 9,641,815 | B2 | 5/2017 | Richardson et al. |
| 9,655,605 | B2 | 5/2017 | Serowski et al. |
| 9,655,639 | B2 | 5/2017 | Mark |
| 9,668,643 | B2 | 6/2017 | Kennedy, II et al. |
| 9,675,235 | B2 | 6/2017 | Lieponis |
| 9,700,378 | B2 | 7/2017 | Mowlai-Ashtiani |
| 9,706,905 | B2 | 7/2017 | Levy |
| 10,111,712 | B2 | 10/2018 | Chegini et al. |
| 10,500,699 | B2 | 12/2019 | Chang |
| 10,561,427 | B2 | 2/2020 | Weitzman et al. |
| 10,576,231 | B2 | 3/2020 | Gunday et al. |
| 10,682,130 | B2 | 6/2020 | White et al. |
| 10,758,220 | B2 | 9/2020 | White et al. |
| 10,869,659 | B2 | 12/2020 | Thommen et al. |
| 10,874,425 | B2 | 12/2020 | Thommen et al. |
| 10,987,129 | B2 | 4/2021 | Thommen et al. |
| 11,000,312 | B2 | 5/2021 | Thommen et al. |
| 11,331,090 | B2 | 5/2022 | Thommen et al. |
| 11,344,190 | B2 | 5/2022 | Thommen et al. |
| 11,439,380 | B2 | 9/2022 | Thommen et al. |
| 11,559,328 | B2 | 1/2023 | Richter et al. |
| 11,672,562 | B2 | 6/2023 | Thommen et al. |
| 11,712,264 | B2 | 8/2023 | Thommen et al. |
| 11,744,447 | B2 | 9/2023 | Thommen et al. |
| 11,793,546 | B2 | 10/2023 | Thommen et al. |
| 11,801,070 | B2 | 10/2023 | White et al. |
| 11,806,043 | B2 | 11/2023 | White et al. |
| 11,883,064 | B2 | 1/2024 | Thommen et al. |
| 11,950,766 | B2 | 4/2024 | Thommen et al. |
| 12,150,636 | B2 | 11/2024 | Thommen et al. |
| 12,193,704 | B2 | 1/2025 | Richter et al. |
| 12,383,302 | B2 | 8/2025 | Thommen et al. |
| 12,402,909 | B2 | 9/2025 | Thommen et al. |
| 12,496,093 | B2 | 12/2025 | Thommen et al. |
| 12,507,880 | B2 | 12/2025 | White et al. |
| 2002/0022762 | A1 | 2/2002 | Beane et al. |
| 2002/0035313 | A1 | 3/2002 | Scirica et al. |
| 2002/0091390 | A1 | 7/2002 | Michelson |
| 2002/0138020 | A1 | 9/2002 | Pflueger |
| 2002/0165560 | A1 | 11/2002 | Danitz et al. |
| 2003/0083555 | A1 | 5/2003 | Hunt et al. |
| 2003/0083688 | A1 | 5/2003 | Simonson |
| 2003/0171744 | A1 | 9/2003 | Leung et al. |
| 2003/0191474 | A1 | 10/2003 | Cragg et al. |
| 2004/0092940 | A1 | 5/2004 | Zwirnmann |
| 2004/0122446 | A1 | 6/2004 | Solar |
| 2004/0127992 | A1 | 7/2004 | Serhan et al. |
| 2004/0143165 | A1 | 7/2004 | Alleyne |
| 2004/0158260 | A1 | 8/2004 | Blau et al. |
| 2004/0158286 | A1 | 8/2004 | Roux et al. |
| 2004/0176763 | A1 | 9/2004 | Foley et al. |
| 2004/0249246 | A1 | 12/2004 | Campos |
| 2005/0021040 | A1 | 1/2005 | Bertagnoli |
| 2005/0075540 | A1 | 4/2005 | Shluzas et al. |
| 2005/0075644 | A1 | 4/2005 | DiPoto et al. |
| 2005/0080435 | A1 | 4/2005 | Smith et al. |
| 2005/0085692 | A1 | 4/2005 | Kiehn et al. |
| 2005/0090848 | A1 | 4/2005 | Adams |
| 2005/0107671 | A1 | 5/2005 | McKinley |
| 2005/0137461 | A1 | 6/2005 | Marchek et al. |
| 2005/0165420 | A1 | 7/2005 | Cha |
| 2005/0187570 | A1 | 8/2005 | Nguyen et al. |
| 2005/0192589 | A1 | 9/2005 | Raymond et al. |
| 2005/0256525 | A1 | 11/2005 | Culbert et al. |
| 2006/0020165 | A1 | 1/2006 | Adams |
| 2006/0041270 | A1 | 2/2006 | Lenker et al. |
| 2006/0052671 | A1 | 3/2006 | McCarthy |
| 2006/0074445 | A1 | 4/2006 | Gerber et al. |
| 2006/0142643 | A1 | 6/2006 | Parker |
| 2006/0161189 | A1 | 7/2006 | Harp |
| 2006/0173521 | A1 * | 8/2006 | Pond .................. A61B 17/7092 607/116 |
| 2006/0200186 | A1 | 9/2006 | Marchek et al. |
| 2006/0206118 | A1 | 9/2006 | Kim et al. |
| 2006/0241350 | A1 | 10/2006 | Nowitzke et al. |
| 2006/0264895 | A1 | 11/2006 | Flanders |
| 2007/0016223 | A1 | 1/2007 | Pagliuca et al. |
| 2007/0049794 | A1 | 3/2007 | Glassenberg et al. |
| 2007/0055259 | A1 | 3/2007 | Norton et al. |
| 2007/0129634 | A1 | 6/2007 | Hickey et al. |
| 2007/0149975 | A1 | 6/2007 | Oliver et al. |
| 2007/0162223 | A1 | 7/2007 | Clark |
| 2007/0173879 | A1 | 7/2007 | Pandey |
| 2007/0203396 | A1 | 8/2007 | McCutcheon et al. |
| 2007/0213716 | A1 | 9/2007 | Lenke et al. |
| 2007/0225556 | A1 | 9/2007 | Ortiz et al. |
| 2007/0249899 | A1 | 10/2007 | Seifert |
| 2007/0255100 | A1 | 11/2007 | Barlow et al. |
| 2007/0260113 | A1 | 11/2007 | Otawara |
| 2007/0260120 | A1 | 11/2007 | Otawara |
| 2007/0260184 | A1 | 11/2007 | Justis et al. |
| 2007/0270866 | A1 | 11/2007 | von Jako |
| 2008/0015621 | A1 | 1/2008 | Emanuel |
| 2008/0033251 | A1 | 2/2008 | Araghi |
| 2008/0064921 | A1 | 3/2008 | Larkin et al. |
| 2008/0064928 | A1 | 3/2008 | Otawara |
| 2008/0081951 | A1 | 4/2008 | Frasier et al. |
| 2008/0139879 | A1 | 6/2008 | Olson et al. |
| 2008/0147109 | A1 | 6/2008 | Kambin et al. |
| 2008/0183189 | A1 | 7/2008 | Teichman et al. |
| 2008/0188714 | A1 | 8/2008 | McCaffrey |
| 2008/0242930 | A1 | 10/2008 | Hanypsiak et al. |
| 2008/0260342 | A1 | 10/2008 | Kuroiwa |
| 2009/0012578 | A1 | 1/2009 | Carrez et al. |
| 2009/0018566 | A1 | 1/2009 | Escudero et al. |
| 2009/0024158 | A1 | 1/2009 | Viker |
| 2009/0062604 | A1 | 3/2009 | Minosawa et al. |
| 2009/0062871 | A1 | 3/2009 | Chin et al. |
| 2009/0076549 | A1 | 3/2009 | Lim et al. |
| 2009/0105543 | A1 | 4/2009 | Miller et al. |
| 2009/0125032 | A1 | 5/2009 | Gutierrez et al. |
| 2009/0149857 | A1 | 6/2009 | Culbert et al. |
| 2009/0156898 | A1 | 6/2009 | Ichimura |
| 2009/0187080 | A1 | 7/2009 | Seex |
| 2009/0240111 | A1 | 9/2009 | Kessler et al. |
| 2009/0247831 | A1 | 10/2009 | Miyamoto et al. |

(56) References Cited

U.S. PATENT DOCUMENTS

| | | | | |
|---|---|---|---|---|
| 2009/0253964 | A1 | 10/2009 | Miyamoto | |
| 2009/0253965 | A1 | 10/2009 | Miyamoto | |
| 2009/0259184 | A1 | 10/2009 | Okoniewski | |
| 2009/0264895 | A1 | 10/2009 | Gasperut et al. | |
| 2009/0287061 | A1 | 11/2009 | Feigenbaum et al. | |
| 2009/0318765 | A1 | 12/2009 | Torii | |
| 2010/0004651 | A1 | 1/2010 | Biyani | |
| 2010/0022841 | A1 | 1/2010 | Takahashi et al. | |
| 2010/0036384 | A1* | 2/2010 | Gorek | A61B 17/7091 606/104 |
| 2010/0076476 | A1 | 3/2010 | To et al. | |
| 2010/0081875 | A1 | 4/2010 | Fowler et al. | |
| 2010/0114147 | A1 | 5/2010 | Biyani | |
| 2010/0151161 | A1 | 6/2010 | Da Rolo | |
| 2010/0161060 | A1 | 6/2010 | Schaller et al. | |
| 2010/0204703 | A1* | 8/2010 | Gao | B25B 23/1427 606/104 |
| 2010/0240961 | A1 | 9/2010 | Aferzon | |
| 2010/0256446 | A1 | 10/2010 | Raju | |
| 2010/0268241 | A1 | 10/2010 | Flom et al. | |
| 2010/0280325 | A1 | 11/2010 | Ibrahim et al. | |
| 2010/0284580 | A1 | 11/2010 | OuYang et al. | |
| 2010/0286477 | A1 | 11/2010 | OuYang et al. | |
| 2010/0312053 | A1 | 12/2010 | Larsen | |
| 2010/0312103 | A1* | 12/2010 | Gorek | A61B 17/1703 600/425 |
| 2010/0317928 | A1 | 12/2010 | Subramaniam | |
| 2010/0324506 | A1 | 12/2010 | Pellegrino et al. | |
| 2011/0009905 | A1 | 1/2011 | Shluzas | |
| 2011/0028791 | A1 | 2/2011 | Marino et al. | |
| 2011/0040333 | A1 | 2/2011 | Simonson et al. | |
| 2011/0054507 | A1 | 3/2011 | Batten et al. | |
| 2011/0056500 | A1 | 3/2011 | Shin et al. | |
| 2011/0073594 | A1 | 3/2011 | Bonn | |
| 2011/0098628 | A1 | 4/2011 | Yeung et al. | |
| 2011/0106261 | A1 | 5/2011 | Chin et al. | |
| 2011/0112588 | A1 | 5/2011 | Linderman et al. | |
| 2011/0125158 | A1 | 5/2011 | Diwan et al. | |
| 2011/0130634 | A1 | 6/2011 | Solitario, Jr. et al. | |
| 2011/0201888 | A1 | 8/2011 | Verner | |
| 2011/0230965 | A1 | 9/2011 | Schell et al. | |
| 2011/0251597 | A1 | 10/2011 | Bharadwaj et al. | |
| 2011/0257478 | A1 | 10/2011 | Kleiner et al. | |
| 2011/0295070 | A1 | 12/2011 | Yasunaga | |
| 2011/0319941 | A1 | 12/2011 | Bar et al. | |
| 2012/0016192 | A1 | 1/2012 | Jansen et al. | |
| 2012/0029412 | A1 | 2/2012 | Yeung et al. | |
| 2012/0095296 | A1 | 4/2012 | Trieu et al. | |
| 2012/0101338 | A1 | 4/2012 | Cormac | |
| 2012/0111682 | A1 | 5/2012 | Andre | |
| 2012/0116170 | A1 | 5/2012 | Vayser et al. | |
| 2012/0157788 | A1 | 6/2012 | Serowski et al. | |
| 2012/0172664 | A1 | 7/2012 | Hayman et al. | |
| 2012/0197320 | A1 | 8/2012 | Bereczki | |
| 2012/0209273 | A1 | 8/2012 | Zaretzka et al. | |
| 2012/0221007 | A1 | 8/2012 | Batten et al. | |
| 2012/0232350 | A1 | 9/2012 | Seex | |
| 2012/0232552 | A1 | 9/2012 | Morgenstern Lopez et al. | |
| 2012/0259173 | A1 | 10/2012 | Waldron et al. | |
| 2012/0265022 | A1 | 10/2012 | Menn | |
| 2012/0296171 | A1 | 11/2012 | Lovell et al. | |
| 2012/0298820 | A1 | 11/2012 | Manolidis | |
| 2012/0303039 | A1* | 11/2012 | Chin | A61B 17/0206 606/191 |
| 2012/0316400 | A1 | 12/2012 | Vijayanagar | |
| 2012/0323080 | A1 | 12/2012 | DeRidder et al. | |
| 2013/0030535 | A1 | 1/2013 | Foley et al. | |
| 2013/0103067 | A1 | 4/2013 | Fabro et al. | |
| 2013/0103103 | A1 | 4/2013 | Mire et al. | |
| 2013/0150670 | A1 | 6/2013 | Cormac | |
| 2013/0150674 | A1 | 6/2013 | Haig et al. | |
| 2013/0172674 | A1 | 7/2013 | Kennedy, II et al. | |
| 2013/0172676 | A1 | 7/2013 | Levy et al. | |
| 2013/0211202 | A1 | 8/2013 | Perez-Cruet et al. | |
| 2013/0282022 | A1 | 10/2013 | Yousef | |
| 2013/0289354 | A1 | 10/2013 | Ainsworth et al. | |
| 2013/0289399 | A1 | 10/2013 | Choi et al. | |
| 2013/0303846 | A1 | 11/2013 | Cybulski et al. | |
| 2013/0304106 | A1 | 11/2013 | Breznock | |
| 2013/0331730 | A1 | 12/2013 | Fenech et al. | |
| 2014/0025121 | A1 | 1/2014 | Foley et al. | |
| 2014/0066940 | A1 | 3/2014 | Fang et al. | |
| 2014/0074170 | A1 | 3/2014 | Mertens et al. | |
| 2014/0088367 | A1 | 3/2014 | DiMauro et al. | |
| 2014/0128979 | A1 | 5/2014 | Womble et al. | |
| 2014/0142584 | A1 | 5/2014 | Sweeney | |
| 2014/0148647 | A1 | 5/2014 | Okazaki | |
| 2014/0163319 | A1 | 6/2014 | Blanquart et al. | |
| 2014/0165796 | A1* | 6/2014 | Gauthier | B25G 1/005 81/479 |
| 2014/0180321 | A1 | 6/2014 | Dias et al. | |
| 2014/0194697 | A1 | 7/2014 | Seex | |
| 2014/0215736 | A1 | 8/2014 | Gomez et al. | |
| 2014/0221749 | A1 | 8/2014 | Grant et al. | |
| 2014/0222092 | A1 | 8/2014 | Anderson et al. | |
| 2014/0243604 | A1 | 8/2014 | Vennard et al. | |
| 2014/0257296 | A1 | 9/2014 | Morgenstern Lopez | |
| 2014/0257332 | A1* | 9/2014 | Zastrozna | A61B 34/30 606/130 |
| 2014/0257489 | A1 | 9/2014 | Warren et al. | |
| 2014/0261545 | A1 | 9/2014 | Jenkins et al. | |
| 2014/0275793 | A1 | 9/2014 | Song | |
| 2014/0275799 | A1 | 9/2014 | Schuele | |
| 2014/0276840 | A1 | 9/2014 | Richter et al. | |
| 2014/0276916 | A1 | 9/2014 | Ahluwalia et al. | |
| 2014/0277204 | A1 | 9/2014 | Sandhu | |
| 2014/0285644 | A1 | 9/2014 | Richardson et al. | |
| 2014/0318582 | A1 | 10/2014 | Mowlai-Ashtiani | |
| 2014/0336764 | A1 | 11/2014 | Masson et al. | |
| 2014/0357945 | A1 | 12/2014 | Duckworth | |
| 2014/0371763 | A1 | 12/2014 | Poll et al. | |
| 2014/0378985 | A1 | 12/2014 | Mafi | |
| 2015/0018623 | A1 | 1/2015 | Friedrich et al. | |
| 2015/0065795 | A1 | 3/2015 | Titus | |
| 2015/0073218 | A1 | 3/2015 | Ito | |
| 2015/0087913 | A1 | 3/2015 | Dang et al. | |
| 2015/0094610 | A1 | 4/2015 | Morgenstern Lopez et al. | |
| 2015/0112398 | A1 | 4/2015 | Morgenstern Lopez et al. | |
| 2015/0133727 | A1 | 5/2015 | Bacich et al. | |
| 2015/0164496 | A1 | 6/2015 | Karpowicz et al. | |
| 2015/0216593 | A1 | 8/2015 | Biyani | |
| 2015/0223671 | A1 | 8/2015 | Sung et al. | |
| 2015/0223676 | A1 | 8/2015 | Bayer et al. | |
| 2015/0230697 | A1 | 8/2015 | Phee et al. | |
| 2015/0238073 | A1 | 8/2015 | Charles et al. | |
| 2015/0250377 | A1 | 9/2015 | Iizuka | |
| 2015/0257746 | A1 | 9/2015 | Seifert | |
| 2015/0272694 | A1 | 10/2015 | Charles | |
| 2015/0313585 | A1 | 11/2015 | Abidin et al. | |
| 2015/0313633 | A1 | 11/2015 | Gross et al. | |
| 2015/0327757 | A1 | 11/2015 | Rozenfeld et al. | |
| 2015/0335389 | A1 | 11/2015 | Greenberg | |
| 2015/0342619 | A1 | 12/2015 | Weitzman | |
| 2015/0342621 | A1 | 12/2015 | Jackson, III | |
| 2015/0366552 | A1 | 12/2015 | Sasaki et al. | |
| 2015/0374213 | A1 | 12/2015 | Maurice, Jr. | |
| 2015/0374354 | A1 | 12/2015 | Boyd et al. | |
| 2016/0007982 | A1 | 1/2016 | Liu et al. | |
| 2016/0015467 | A1 | 1/2016 | Vayser et al. | |
| 2016/0030061 | A1 | 2/2016 | Thommen et al. | |
| 2016/0066965 | A1 | 3/2016 | Chegini et al. | |
| 2016/0067003 | A1 | 3/2016 | Chegini et al. | |
| 2016/0074029 | A1 | 3/2016 | O'Connell et al. | |
| 2016/0095505 | A1 | 4/2016 | Johnson et al. | |
| 2016/0106408 | A1 | 4/2016 | Ponmudi et al. | |
| 2016/0143682 | A1* | 5/2016 | Overes | A61B 17/8875 606/104 |
| 2016/0166135 | A1 | 6/2016 | Fiset | |
| 2016/0174814 | A1 | 6/2016 | Igov | |
| 2016/0175004 | A1 | 6/2016 | Dejima | |
| 2016/0192921 | A1 | 7/2016 | Pimenta et al. | |
| 2016/0213500 | A1 | 7/2016 | Beger et al. | |
| 2016/0228280 | A1 | 8/2016 | Schuele et al. | |
| 2016/0235284 | A1 | 8/2016 | Yoshida et al. | |

(56) References Cited

U.S. PATENT DOCUMENTS

| | | | | |
|---|---|---|---|---|
| 2016/0235427 | A1* | 8/2016 | Rudser | A61B 17/8875 |
| 2016/0256036 | A1 | 9/2016 | Gomez et al. | |
| 2016/0287264 | A1 | 10/2016 | Chegini et al. | |
| 2016/0296220 | A1 | 10/2016 | Mast et al. | |
| 2016/0324541 | A1 | 11/2016 | Pellegrino et al. | |
| 2016/0345952 | A1 | 12/2016 | Kucharzyk et al. | |
| 2016/0353978 | A1 | 12/2016 | Miller et al. | |
| 2016/0367294 | A1 | 12/2016 | Boyd et al. | |
| 2017/0003493 | A1 | 1/2017 | Zhao | |
| 2017/0007226 | A1 | 1/2017 | Fehling | |
| 2017/0007294 | A1 | 1/2017 | Iwasaka et al. | |
| 2017/0020627 | A1 | 1/2017 | Tesar et al. | |
| 2017/0027606 | A1 | 2/2017 | Cappelleri et al. | |
| 2017/0042408 | A1 | 2/2017 | Washburn et al. | |
| 2017/0042411 | A1 | 2/2017 | Kang et al. | |
| 2017/0065269 | A1 | 3/2017 | Thommen et al. | |
| 2017/0065287 | A1 | 3/2017 | Silva et al. | |
| 2017/0086878 | A1* | 3/2017 | Geist | A61M 29/00 |
| 2017/0086939 | A1 | 3/2017 | Vayser et al. | |
| 2017/0105770 | A1 | 4/2017 | Woolley et al. | |
| 2017/0135699 | A1 | 5/2017 | Wolf | |
| 2017/0156755 | A1 | 6/2017 | Poll et al. | |
| 2017/0156814 | A1 | 6/2017 | Thommen et al. | |
| 2017/0196549 | A1 | 7/2017 | Piskun et al. | |
| 2017/0224391 | A1 | 8/2017 | Biester et al. | |
| 2017/0245930 | A1 | 8/2017 | Brannan et al. | |
| 2017/0280969 | A1 | 10/2017 | Levy et al. | |
| 2017/0296038 | A1 | 10/2017 | Gordon et al. | |
| 2017/0311789 | A1 | 11/2017 | Mulcahey et al. | |
| 2018/0008138 | A1 | 1/2018 | Thommen et al. | |
| 2018/0008253 | A1 | 1/2018 | Thommen et al. | |
| 2018/0014858 | A1 | 1/2018 | Biester et al. | |
| 2018/0014890 | A1 | 1/2018 | Stanton et al. | |
| 2018/0098788 | A1 | 4/2018 | White et al. | |
| 2018/0098789 | A1 | 4/2018 | White et al. | |
| 2018/0110503 | A1 | 4/2018 | Flock et al. | |
| 2018/0110506 | A1 | 4/2018 | Thommen et al. | |
| 2018/0153592 | A1 | 6/2018 | Larson | |
| 2018/0214016 | A1 | 8/2018 | Thommen et al. | |
| 2018/0249992 | A1* | 9/2018 | Truckey | A61B 17/025 |
| 2018/0311051 | A1 | 11/2018 | Donaldson et al. | |
| 2018/0333061 | A1 | 11/2018 | Pracyk et al. | |
| 2019/0105459 | A1* | 4/2019 | Lajarín Barquero | A61M 19/00 |
| 2019/0209154 | A1 | 7/2019 | Richter et al. | |
| 2019/0216454 | A1 | 7/2019 | Thommen et al. | |
| 2019/0216486 | A1 | 7/2019 | Weitzman | |
| 2019/0374236 | A1 | 12/2019 | Weitzman et al. | |
| 2020/0268368 | A1 | 8/2020 | White et al. | |
| 2020/0360048 | A1 | 11/2020 | White et al. | |
| 2020/0367737 | A1 | 11/2020 | Matsumoto et al. | |
| 2021/0052298 | A1 | 2/2021 | Thommen et al. | |
| 2021/0186316 | A1 | 6/2021 | Thommen et al. | |
| 2021/0204973 | A1 | 7/2021 | Thommen et al. | |
| 2021/0282806 | A1 | 9/2021 | Thommen et al. | |
| 2022/0192700 | A1 | 6/2022 | Thommen et al. | |
| 2022/0249125 | A1 | 8/2022 | Thommen et al. | |
| 2022/0265134 | A1 | 8/2022 | Thommen et al. | |
| 2022/0378408 | A1 | 12/2022 | Thommen et al. | |
| 2023/0135764 | A1 | 5/2023 | Richter et al. | |
| 2024/0023987 | A1 | 1/2024 | Thommen et al. | |
| 2024/0023989 | A1 | 1/2024 | White et al. | |
| 2024/0206909 | A1 | 6/2024 | Thommen et al. | |
| 2025/0152158 | A1 | 5/2025 | Thommen et al. | |

FOREIGN PATENT DOCUMENTS

| | | | |
|---|---|---|---|
| CN | 1742685 | A | 3/2006 |
| CN | 101141928 | A | 3/2008 |
| CN | 101426437 | A | 5/2009 |
| CN | 201290744 | Y | 8/2009 |
| CN | 101594830 | A | 12/2009 |
| CN | 101815476 | A | 8/2010 |
| CN | 102448380 | A | 5/2012 |
| CN | 202211669 | U | 5/2012 |
| CN | 102843984 | A | 12/2012 |
| CN | 202740102 | U | 2/2013 |
| CN | 102727309 | B | 11/2014 |
| CN | 102497828 | B | 9/2015 |
| CN | 102821673 | B | 6/2016 |
| CN | 103976779 | B | 9/2016 |
| CN | 106659375 | A | 5/2017 |
| CN | 106794032 | A | 5/2017 |
| CN | 103533904 | B | 6/2017 |
| CN | 105286776 | B | 11/2017 |
| CN | 107126254 | B | 1/2020 |
| CN | 111278365 | A | 6/2020 |
| DE | 9415039 | U1 | 11/1994 |
| DE | 29916026 | U1 | 11/1999 |
| DE | 20309079 | U1 | 8/2003 |
| EP | 0537116 | A1 | 4/1993 |
| EP | 0890341 | A1 | 1/1999 |
| EP | 0807415 | B1 | 12/2003 |
| EP | 0891156 | B1 | 7/2004 |
| EP | 2491848 | B1 | 1/2014 |
| GB | 2481727 | B | 5/2012 |
| JP | H05207962 | A | 8/1993 |
| JP | H0681501 | A | 3/1994 |
| JP | H08126605 | A | 5/1996 |
| JP | H08278456 | A | 10/1996 |
| JP | H11313795 | A | 11/1999 |
| JP | 2000126190 | A | 5/2000 |
| JP | 2000511788 | A | 9/2000 |
| JP | 2001520906 | A | 11/2001 |
| JP | 2002519094 | A | 7/2002 |
| JP | 2002541901 | A | 12/2002 |
| JP | 2007007438 | A | 1/2007 |
| JP | 2007508050 | A | 4/2007 |
| JP | 2008508943 | A | 3/2008 |
| JP | 2009543612 | A | 12/2009 |
| JP | 2011512943 | A | 4/2011 |
| JP | 2012045325 | A | 3/2012 |
| JP | 2012527327 | A | 11/2012 |
| JP | 2012527930 | A | 11/2012 |
| JP | 2013059688 | A | 4/2013 |
| JP | 2013538624 | A | 10/2013 |
| JP | 2014054561 | A | 3/2014 |
| JP | 2014517710 | A | 7/2014 |
| JP | 2015500680 | A | 1/2015 |
| JP | 2015521913 | A | 8/2015 |
| JP | 2019505312 | A | 2/2019 |
| JP | 2022079758 | A | 5/2022 |
| WO | 1996029014 | A1 | 9/1996 |
| WO | 1997034536 | A2 | 9/1997 |
| WO | 2001056490 | A1 | 8/2001 |
| WO | 2001089371 | A1 | 11/2001 |
| WO | 2002002016 | A1 | 1/2002 |
| WO | 2004039235 | A2 | 5/2004 |
| WO | 2004103430 | A2 | 12/2004 |
| WO | 2006017507 | A2 | 2/2006 |
| WO | 2006096517 | A2 | 9/2006 |
| WO | 2007059068 | A1 | 5/2007 |
| WO | 2008121162 | A1 | 10/2008 |
| WO | 2009033207 | A1 | 3/2009 |
| WO | 2009108318 | A2 | 9/2009 |
| WO | 2010111629 | A2 | 9/2010 |
| WO | 2010135537 | A2 | 11/2010 |
| WO | 2010138083 | A1 | 12/2010 |
| WO | 2012004766 | A2 | 1/2012 |
| WO | 2012040239 | A1 | 3/2012 |
| WO | 2012122294 | A1 | 9/2012 |
| WO | 2013033426 | A2 | 3/2013 |
| WO | 2013059640 | A1 | 4/2013 |
| WO | 2013074396 | A1 | 5/2013 |
| WO | 2014041540 | A1 | 3/2014 |
| WO | 2014050236 | A1 | 4/2014 |
| WO | 2014100761 | A2 | 6/2014 |
| WO | 2014185334 | A1 | 11/2014 |
| WO | 2014188796 | A1 | 11/2014 |
| WO | 2015026793 | A1 | 2/2015 |
| WO | 2015033907 | A1 | 3/2015 |
| WO | 2015175635 | A1 | 11/2015 |
| WO | 2016111373 | A1 | 7/2016 |
| WO | 2016131077 | A1 | 8/2016 |
| WO | 2016168673 | A1 | 10/2016 |

(56) References Cited

FOREIGN PATENT DOCUMENTS

| | | | |
|---|---|---|---|
| WO | 2016201292 | A1 | 12/2016 |
| WO | 2017006684 | A1 | 1/2017 |
| WO | 2017015480 | A1 | 1/2017 |
| WO | 2017040873 | A1 | 3/2017 |
| WO | 2017083648 | A1 | 5/2017 |
| WO | 2017162895 | A1 | 9/2017 |
| WO | 2018131039 | A1 | 7/2018 |
| WO | 2018147225 | A1 | 8/2018 |
| WO | 2018165365 | A2 | 9/2018 |
| WO | 2019026206 | A1 | 2/2019 |
| WO | 2019050666 | A1 | 3/2019 |
| WO | 2021209987 | A1 | 10/2021 |

OTHER PUBLICATIONS

Chinese Office Action for Application No. 201880013056.7, dated Mar. 25, 2021 (15 pages).
Chinese Office Action for Application No. 201880013056.7, dated Oct. 26, 2021 (6 Pages).
Chinese Office Action for Application No. 201880016688.9, dated Mar. 8, 2022, with Translation (21 pages).
Chinese Decision of Reexamination issued for 201680051245.4, dated Aug. 23, 2022, (23 pages).
Chinese Office Action and Search Report issued for Application No. 201880058099, dated Nov. 2, 2022 (14 pages).
Chinese First Search and Written Opinion for Application No. CN201980027429.0 dated Jan. 2, 2024 (10 pages).
Chinese First Search and Written Opinion for Application No. CN202080035605 dated Jan. 8, 2024 (10 pages).
Chinese Office Action issued for Application No. 202110037202.3 dated Nov. 24, 2023 (14 pages).
Chinese Second Office Action for Application No. CN 202080035605.8 dated May 23, 2024 (9 pages).
Clinical Workbook of Neurosurgery in Xijing [M], edited by Fei Zhou, Xi'an: Fourth Military Medical University Press, Aug. 2012, pp. 431-432: an endoscope with a diameter of 3.7 mm is used for intramedullary examination).
Extended European Search Report for Application No. 16843037.9; issued Mar. 14, 2019 (8 pages).
Extended European Search Report for Application No. 18758290.3, issued Nov. 27, 2020 (7 pages).
Extended European Search Report for Application No. 20212396.4, issued Sep. 23, 2021 (9 pages).
Extended European Search Report for Application No. 18854503.2, issued Apr. 15, 2021 (10 pages).
Extended European Search Report for Application No. 19758283.6, issued Sep. 28, 2021 (8 pages).
Extended European Search Report for Application No. 18764249.1, issued Mar. 11, 2022 (8 pages).
Extended European Search Report for Application No. 18764504.9, issued Mar. 18, 2022 (7 pages).
Extended European Search Report for Application No. 18764370.5, issued Mar. 25, 2022 (8 pages).
European Search Report for Application No. 24156567, issued Jun. 6, 2024 (8 pages).
European Search Report for Application No. 24190167.7 sued Oct. 7, 2024 (11 pages).
Hott, J. S., et al., "A new table-fixed retractor for anterior odontoid screw fixation: technical note," J Neurosurg (Spine 3), 2003, v. 98, pp. 118-120.
International Search Report and Written Opinion for Application No. PCT/US2015/043554, mailed Nov. 19, 2015 (8 pages).
International Search Report and Written Opinion for Application No. PCT/US2015/048485, mailed Feb. 9, 2016. (16 pages).
International Search Report and Written Opinion for Application No. PCT/US2015/060978, mailed Feb. 15, 2016 (8 pages).
Invitation to Pay Additional Fees for Application No. PCT/US2016/050022, mailed Nov. 3, 2016 (2 pages).
International Search Report and Written Opinion for Application No. PCT/US2016/050022, issued Feb. 1, 2017 (19 pages).
International Preliminary Report on Patentability issued for Application No. PCT/US2016/050022, mailed Mar. 15, 2018.
International Search Report and Written Opinion for Application No. PCT/US2018/018905, mailed May 7, 2018 (10 pages).
International Search Report for Application No. PCT/IB2018/057367, mailed Jan. 29, 2019, (4 pages).
International Search Report and Written Opinion for Application No. PCT/US2018/021449, mailed Aug. 27, 2018 (13 pages).
International Search Report and Written Opinion for Application No. PCT/US2018/021454, mailed Jul. 3, 2018 (16 pages).
International Search Report and Written Opinion for Application No. PCT/US2018/021466 mailed Jul. 3, 2018 (8 pages).
International Search Report and Written Opinion for Application No. PCT/US2018/047136, mailed Jan. 23, 2019 (9 pages).
International Search Report and Written Opinion for Application No. PCT/EP2020/056706, mailed Jun. 9, 2020 (17 pages).
International Search Report and Written Opinion issued for Application No. PCT/US2018/021472, issued Jul. 19, 2018.
International Search Report and Written Opinion for Application No. PCT/US19/18700, mailed May 3, 2019 (7 Pages).
Iprenburg, M, "Percutaneous Transforaminal Endoscopic Discectomy: The Thessys Method," in Lewandrowski, K., et al., Minimally Invasive Spinal Fusion Techniques, Summit Communications, 2008 pp. 65-81.
Japanese Office Action issued in Appln. No. JP 2018-511695, mailed May 26, 2020 (21 pages).
Japanese Office Action for Application No. JP 2019-548591, issued Oct. 5, 2021, (14 pages).
Japanese Office Action for Application No. JP 2019-545263, issued Jan. 4, 2022 (11 pages).
Japanese Office Action for Application No. JP 2019-545263, issued Aug. 9, 2022 (8 pages).
Japanese Office Action for Application No. JP 2020-513791, issued May 17, 2022 (8 pages).
Japanese Office Action for Application No.JP 2020-177880, issued May 31, 2022 (3 pages).
Japanese Decision to Grant a Patent for Application No. JP 2020-177880, issued Dec. 6, 2022 (2 pages).
Japanese Decision to Grant Patent for Application No. JP 2020-544278, issued Mar. 14, 2023.
Japanese Notice of Reasons for Refusal for Application No. JP 2021-554717, dated Nov. 9, 2023 (4 pages).
Jung, K., et al., "A hands-free region-of-interest selection interface for solo surgery with a wide-angle endoscope: preclinical proof of concept," Surg Endosc, 2017, v. 31, pp. 974-980.
Regan, J. M. et al., "Burr Hole Washout versus Craniotomy for Chronic Subdural Hematoma: Patient Outcome and Cost Analysis," Plos One, Jan. 22, 2015, DOI:10.1371/journal.pone.0115085.
Shalayev, S. G. et al, "Retrospective analysis and modifications of retractor systems for anterior odontoid screw fixation," Neurosurg Focus 16 (1):Article 14, 2004, pp. 1-4.
Japanese Notice of Reasons for Refusal for Application No. JP 2024-001761 dated Feb. 10, 2025 (8 pages).
U.S. Appl. No. 15/254,877, filed Sep. 1, 2016, Multi-Shield Spinal Access System, Medos International Sàrl.
U.S. Appl. No. 15/437,792, filed Feb. 21, 2017, Multi-Shield Spinal Access System, Medos International Sàrl.
U.S. Appl. No. 15/692,845, filed Aug. 31, 2017, Surgical Visualization Systems and Methods, Medos International Sàrl.
U.S. Appl. No. 15/697,494, filed Sep. 7, 2017, Multi-Shield Spinal Access System, Medos International Sàrl.
U.S. Appl. No. 15/786,846, filed Oct. 18, 2017, Devices and Methods for Surgical Retraction, Medos International Sàrl.
U.S. Appl. No. 15/786,858, filed Oct. 18, 2017, Devices and Methods for Providing Access, Medos International Sàrl.
U.S. Appl. No. 15/786,891, filed Oct. 18, 2017, Surgical Access Port Stabilization, Medos International Sàrl.
U.S. Appl. No. 15/786,923, filed Oct. 18, 2017, Surgical Instrument Connector and Related Methods, Medos International Sàrl.
U.S. Appl. No. 15/901,435, filed Oct. 18, 2017, Surgical Instrument Connectors and Related Methods, Medos International Sàrl.

(56) References Cited

OTHER PUBLICATIONS

U.S. Appl. No. 15/931,839, filed May 14, 2020, Surgical Access Port Stablization, Medos International Sàrl.
U.S. Appl. No. 15/966,293, filed Apr. 30, 2018, Neural Monitoring Devices and Methods, DePuy Synthes Products, Inc.
U.S. Appl. No. 16/352,654, filed Mar. 31, 2019, Multi-Shield Spinal Access System, Medos International Sàrl.
U.S. Appl. No. 16/362,497, filed Mar. 22, 2019, Surgical Instrument Connectors and Related Methods, Medos International Sàrl.
U.S. Appl. No. 16/985,200, filed Aug. 4, 2020, Devices and Methods for Providing Surgical Access, Medos International Sàrl.
U.S. Appl. No. 17/089,695, filed Nov. 4, 2020, Multi-Shield Spinal Access System, Medos International Sàrl.
U.S. Appl. No. 17/159,129, filed Jan. 26, 2021, Multi-Shield Spinal Access System, Medos International Sàrl.
U.S. Appl. No. 17/192,889, filed Mar. 5, 2021, Surgical Visualization Systems and Related Methods, Medos International Sàrl.
U.S. Appl. No. 17/214,759, filed Mar. 26, 2021, Multi-Shield Spinal Access System, Medos International Sàrl.
U.S. Appl. No. 17/692,942, filed Mar. 11, 2022, Multi-Shield Spinal Access System, Medos International Sàrl.
U.S. Appl. No. 17/728,967, filed Apr. 25, 2022, Surgical Visualization Systems and Related Methods, Medos International Sàrl.
U.S. Appl. No. 17/740,305, filed May 9, 2022, Surgical Visualization Systems and Related Methods, Medos International Sàrl.
U.S. Appl. No. 17/884,523, filed Aug. 8, 2022, Surgical Instrument Connectors and Related Methods, Medos International Sàrl.
U.S. Appl. No. 18/091,255, filed Dec. 29, 2022, Multi-Shield Spinal Access System, Medos International Sàrl.
U.S. Appl. No. 18/479,058, filed Sep. 30, 2023, Surgical Access Port Stabilization, Medos International Sàrl.
U.S. Appl. No. 18/479,048, filed Sep. 30, 2023, Surgical Visualization Systems and Related Methods, Medos International Sàrl.
U.S. Appl. No. 18/479,059, filed Sep. 30, 2023, Devices and Methods for Providing Surgical Access, Medos International Sàrl.
U.S. Appl. No. 18/401,037, filed Dec. 29, 2023, Multi-Shield Spinal Access Sytem, Medos International Sàrl.
U.S. Appl. No. 18/951,589, filed Nov. 18, 2024, Surgical Instrument Connector and Related Methods, Medos International Sàrl.
European Search Report for Application No. 24190243.6 issued Mar. 12, 2025 (8 pages).

* cited by examiner

MULTI-SHIELD SPINAL ACCESS SYSTEM

CROSS-REFERENCE TO RELATED APPLICATIONS

This application is a continuation U.S. application Ser. No. 18/091,255, filed Dec. 29, 2022. U.S. application Ser. No. 18/091,255 is a continuation of U.S. application Ser. No. 16/352,654, filed on Mar. 13, 2019, and now issued as U.S. Pat. No. 11,559,328. U.S. application Ser. No. 16/352,654 is a continuation-in-part of U.S. application Ser. No. 15/697,494, filed on Sep. 7, 2017, and now issued as U.S. Pat. No. 11,000,312. U.S. application Ser. No. 15/697,494 is a continuation-in-part of U.S. application Ser. No. 15/437,792, filed on Feb. 21, 2017, and now issued as U.S. Pat. No. 10,874,425. U.S. application Ser. No. 15/437,792 is a continuation-in-part of U.S. application Ser. No. 15/254,877, filed on Sep. 1, 2016, and now issued as U.S. Pat. No. 10,987,129. U.S. application Ser. No. 15/254,877 claims priority to U.S. Provisional Application No. 62/214,297, filed on Sep. 4, 2015. Each of these applications is hereby incorporated by reference in its entirety.

BACKGROUND OF THE INVENTION

Today, microsurgical spinal bone resections and spinal decompressions which are performed under microscopic view through mini-open tubes and retractors are becoming the standard of spinal surgical care. These access tools normally have inner diameters between about 16 mm and 30 mm. Where, as here, the approach and decompression technique are familiar to spinal surgeons, and where standard equipment and instruments can be used, these known technologies should be considered as a base from which further innovation can be made.

However, the anatomic window of Kambin's triangle, through which safe disc access is possible, has very limited dimensions. This access window can be enlarged by resecting at least a part of the superior articular process. But either way, the length of a working shield needed to safely introduce the implant to the intervertebral space via this approach must be in the region of about 8-12 mm in diameter, reaching from the facet joint line to the disc entry point.

SUMMARY OF THE INVENTION

The present inventors envision introducing a second, inner shield through the above-mentioned first, outer shield. The second inner shield extends past the first outer shield to arrive next to nervous tissue, thereby shielding the nerves from instruments or devices passing through to the disc space. During this step, the outer shield allows the visual, safe placement of the inner shield.

In one embodiment, there is provided an outer shield (which can be, for example, a tube or a blade) comprising an access shield with a larger diameter (~12-30 mm) that reaches from the skin down to the bone line, with an inner shield having a second smaller diameter (~5-12 mm) extending past the access shield and reaches down to the disc level. This combines the benefits of the direct visual from microsurgical/mini open approaches and percutaneous techniques (FIGS. 1*a*-1*b* and 2).

The outer shield has a number of features and advantages. First, it enables separation and protection of surrounding of soft tissue and visualization during a standard microsurgical decompression/bone resection work under microscopic view-based on a standard procedure that a surgeon who is familiar with MIS techniques is able to perform. Second, it enables separation and protection of surrounding of soft tissue and visualization during detection and removal of the facet joint, or parts of the facet joint-based on a standard procedure that a surgeon who is familiar with MIS technique is able to perform. Third, it enables identification, preparation and protection of sensitive (e.g., neural) tissue (exiting nerve root, traversing nerve root, dura) under direct visual control underneath the border between retraction-sensitive and non-retraction sensitive tissues (e.g., the facet line) based on a standard procedure that a surgeon who is familiar with MIS technique is able to perform. Fourth, it enables insertion of the inner shield and potential docking of the inner shield in the disc space or at the vertebrae under direct visual control.

Likewise, the inner shield has a number of features and advantages. First, it enables protection of nervous tissue (exiting nerve root, transverse nerve root, dura) against instruments that are introduced into the intervertebral disc. Second, it enables guidance of intradiscal instrumentation (discectomy instruments, visualization instruments, discectomy verification instruments, implant insertion instruments, bone graft filling instruments). Third, because of its small size, the shield can be inserted with minimal damage or trauma to bone and soft tissue in the area of the posterior column of the spine, comparable to percutaneous access instruments Therefore, in accordance with the present invention, there is provided a method of accessing an intervertebral disc in a patient, comprising the steps of:

a) making an incision in a skin of the patient,
b) percutaneously inserting through the incision an outer shield having a substantially tubular shape (such as a tube or a multi-slotted retractor), the outer shield having a length adapted to extend from the incision to a border between sensitive and insensitive tissue (e.g., a superior articular process (SAP), or a lamina), in the spine of the patient,
c) stabilization of this outer shield to a pedicle anchor,
d) insertion of an outer shield integrated optical visualization instrument,
e) resecting a portion of the superior articular process, and/or performing a microsurgical decompression procedure,
f) inserting or deploying an inner shield through or from the outer shield so that a distal end portion of the inner shield extends to the disc, the inner shield having an outer surface,
g) contacting the outer surface of the shield to a nerve root to shield the nerve root,
h) microsurgical decompression of any tissue deemed to be causing nerve impingement,
i) extraction of the intervertebral disc material including the removal of the cartilaginous material from the vertebral endplates,
j) insertion of the interbody device, and
k) deployment of a mechanism of stabilization to stabilize the intervertebral segment.

Also in accordance with the present invention, there is provided a method of accessing an intervertebral disc in a patient, comprising the steps of:

a) making an incision in a skin of the patient,
b) percutaneously inserting through the incision an outer shield having a substantially tubular shape,
c) stabilization of this outer shield to a pedicle anchor, d) inserting an inner shield through the outer shield so that a distal end portion of the inner shield extends to the disc, the inner shield having an outer surface, e) contacting the outer surface of the shield to a nerve root to shield the nerve root, f) microsurgical decompression of any tissue deemed to be causing nerve impingement, g) extraction of the intervertebral disc material including the removal of the cartilaginous material from the vertebral endplates, h) insertion of the interbody device, and i) deployment of a mechanism of stabilization to stabilize the intervertebral segment.

Also in accordance with the present invention, there is provided an access device for accessing an intervertebral disc, comprising:

a) an outer shield having a substantially tubular portion, a length adapted to extend from an incision to a border between sensitive and insensitive tissue (e.g., an articular process or a lamina), a proximal end portion, a distal end portion, an outer surface, and a longitudinal throughbore defining an inner surface, b) an inner shield having i) a first substantially tubular portion having a proximal end portion, a distal end portion, a longitudinal through-bore defining an inner surface, and an outer surface defining a diameter, and ii) a longitudinal flange extending distally from the distal end portion of the substantially tubular portion, wherein the outer surface of the inner shield substantially nests within the inner surface of the outer shield so that the flange extends distally past the distal end portion of the outer shield.

In one aspect, a multi-tool is provided that includes a shaft component having an elongate body that defines a central longitudinal axis extending from a proximal handle to a distal tip. The multi-tool can further include a body having an opening for receiving the shaft component therethrough and one or more coupling features configured to receive one or more surgical devices therein such that the surgical devices interface with the shaft component while disposed within the body. There can also be an actuation feature formed on the body that is configured to engage the shaft component to toggle the shaft component between an unlocked configuration and a locked configuration relative to the body.

The multi-tool described above can have a variety of modifications and/or additional features that are within the scope of the present disclosure. For example, in some embodiments, the surgical devices of the multi-tool can be any of a nerve-mapping tool and a navigation array. In some embodiments, the shaft component can form an electrical connection at the interface with the surgical devices. This electrical connection can be formed by a bias element disposed between the shaft component and the surgical devices. In some embodiments, the shaft component can include a proximal handle having a conductor thereon for forming the electrical connection.

In some embodiments, the body can be configured to removably detach from any of the shaft component and the surgical devices. For example, the actuation feature can further include a button that is configured to be depressed by a user to detach the body from the shaft component. The body can include a slider that slides in a proximal-distal direction relative to the body to lock an axial position of the shaft component to the body. A longitudinal position of the shaft component can be stationary in the locked configuration. In some embodiments, one or more of the coupling features can include a modular attachment arm for coupling the surgical devices thereto. The modular attachment arm can include a pin received through the axis thereof, the one or more devices being configured to receive the pin therein for snapping the modular attachment arm to the modular attachment arm. The modular attachment arm, in some embodiments, can be keyed such that the surgical devices are prevented from coupling to the modular attachment arm in all but one orientation.

In another aspect, a surgical device is provided that includes a shaft component configured to be inserted into a target site within a patient, the shaft component having an elongate body that defines a central longitudinal axis extending from a proximal handle to a distal tip. The surgical device can further include a locking handle configured to engage the shaft component with the locking handle including a base clamp having an opening for receiving the proximal handle of the shaft component therethrough and one or more ports configured to receive one or more surgical devices therein; and a top clamp extending proximally from the base clamp. The base clamp and the top clamp of the surgical device can also be configured to rotate relative to one another to move the multi-tool between an open position in which the shaft component can translate or rotate relative to the locking handle and a closed position in which the shaft component is prevented from translating or rotating relative to the locking handle.

The surgical device described above can have a variety of modifications and/or additional features that are within the scope of the present disclosure. For example, in some embodiments, the locking handle can include a core therein for coupling to the shaft component and the one or more surgical devices. Further, in some embodiments, the shaft component can interface with the surgical devices disposed through the core to establish an electrical connection therebetween. Still further, in some embodiments, the core can be made of an overmolded material.

In some embodiments, the shaft component can include a locking groove configured to receive a retention feature of the locking handle therein for securing the shaft component to the locking handle. Further, in some embodiments, the shaft component can include a stopper configured to abut any of the top clamp and the base clamp to prevent proximal advancement of the shaft component relative to the locking handle.

In certain embodiments, the top clamp is disposed substantially perpendicular to the base clamp in the open position and the top clamp is aligned with the base clamp in the closed position. The top clamp can include an opening configured to receive the shaft component therethrough. Further, in some embodiments, the top clamp can be received in an indentation formed in the base clamp. Still further, in some embodiments the top clamp can further include a mating tab configured to engage abutment surfaces on the base clamp to couple the top clamp to the base clamp.

In another aspect, a surgical method is provided that includes making an incision in a target site of a patient. The method can include inserting a shaft component into the target site to dock the shaft component therein, the shaft component being coupled to a body with an opening for receiving the shaft component therethrough and one or more coupling features configured to receive one or more surgical devices therein such that the surgical devices are configured to interface with the shaft component while disposed within the body, wherein the surgical devices guide the shaft component into the target site; and advancing an access port over the shaft component into the target location.

In some embodiments, the method includes surgical devices that are any of a nerve-mapping tool and a navigation array. Further, the navigation array can be calibrated prior to inserting the shaft component into the target site. Still further, in some embodiments the method includes inserting a screw into the target location under guidance of the navigation array.

In some embodiments, the shaft component can be inserted under finger pressure. In other embodiments, the shaft component can be inserted under manual force. In some embodiments, the method includes sweeping the distal tip of the shaft component across the target site to dock the shaft component within the target site.

In certain embodiments, the method can further include removing the body from the shaft component. The method can further include depressing a button formed on the body to release the shaft component from the body. In some embodiments, the method can include advancing one or more dilators over the shaft component into the target site to increase a size of the target site. Further, the method can include removing one or more dilators from the target site.

In certain embodiments, the method can include advancing one or more tools through the access port into the target site. The one or more tools can include a plug that is received in the access port to extend proximally from the access port. Still further, in some embodiments, the method can include adjusting an orientation of the plug in multiple directions of freedom to manipulate a position of the access port within the target site. In other embodiments, the method can include inserting a second shaft component through the plug to adjust the orientation of the plug.

In certain embodiments, the method can include visualizing the trajectory of the shaft component within the target site. Visualizing the trajectory can further include advancing a camera through one or more channels of the access port into the target site. The method further include the camera and the shaft component being advanced through separate channels in the access port.

DETAILED DESCRIPTION OF THE INVENTION

Figure 1A:
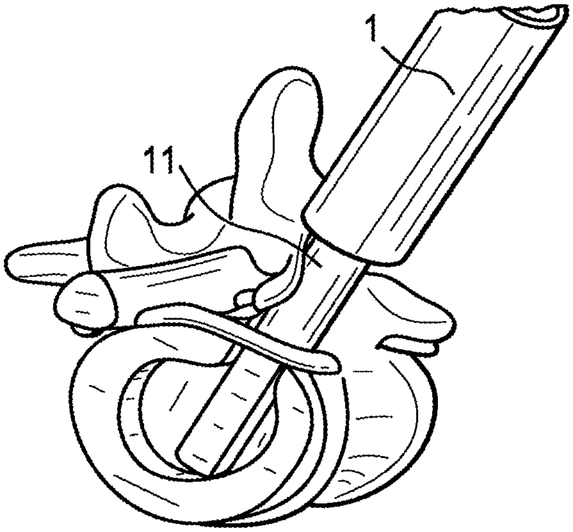
FIG. 1*a* shows an interbody device delivered through the access device.
Figure 1B:
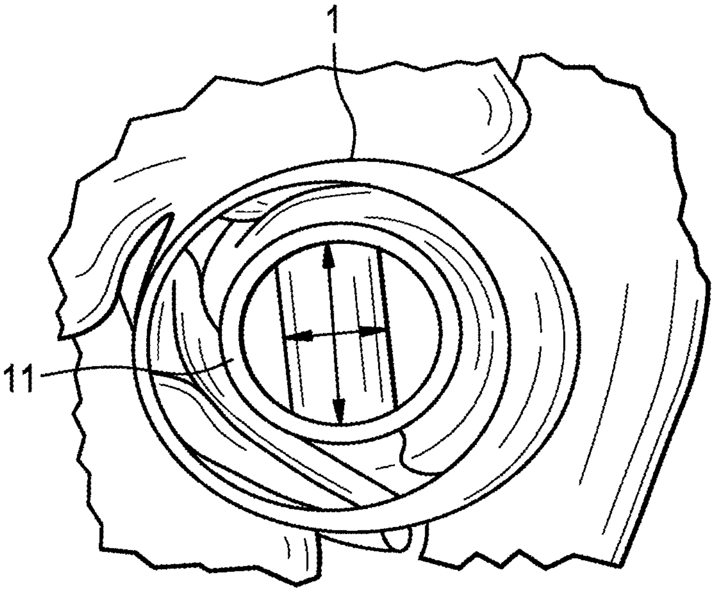
FIG. 1*b* shows an end view of the access device.
Figure 2A:
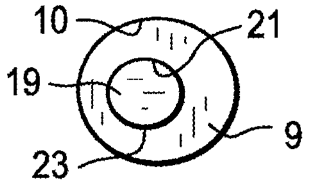
FIGS. 2*a* and 2*b* are different views of a tube-in-tube embodiment of the access device.
Figure 2B:
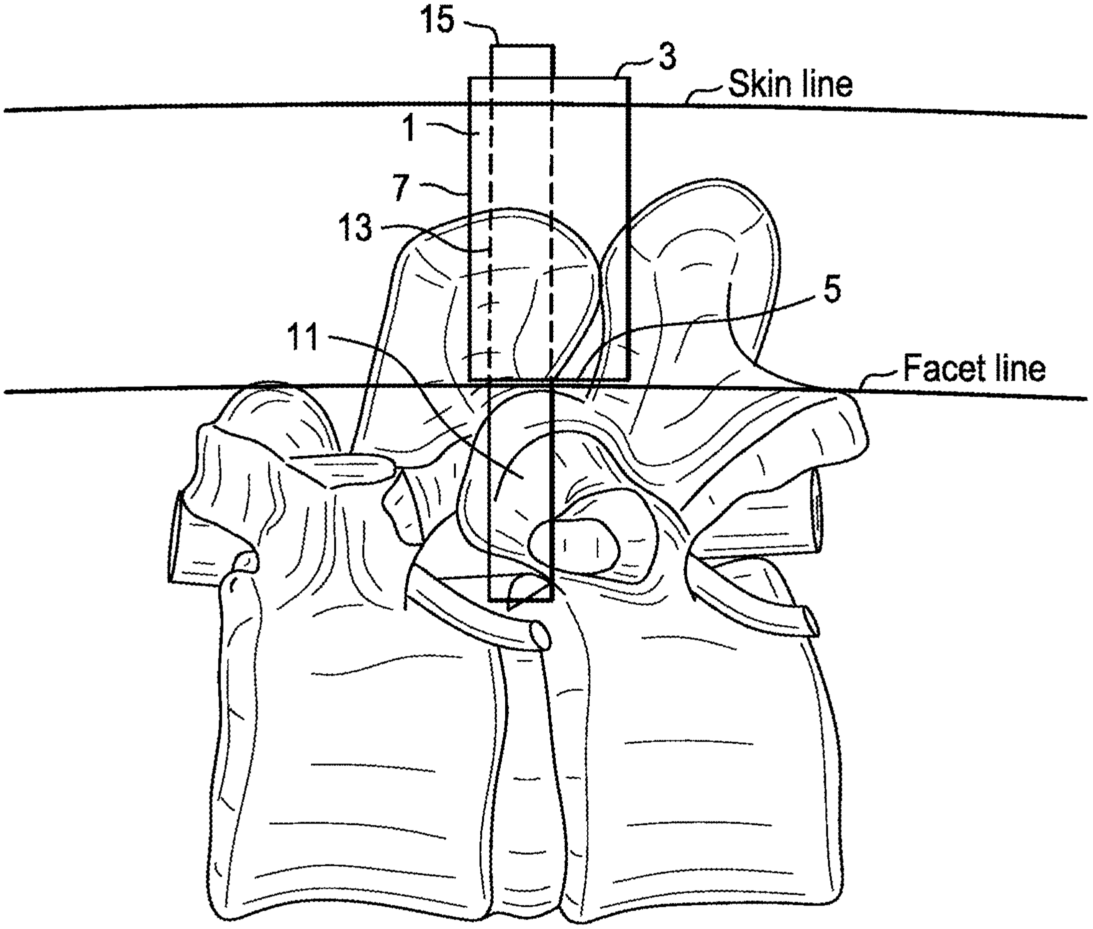

Fluoroscopic visualization is performed to define the incision site of the initial reference array placement, as well as the incision for access to the intervertebral disc.

Generally, the shields of the present invention can be applied to any of the conventional approaches commonly used in spine surgery. However, given the clinical benefit of the access device and its underlying rationale, it is preferably suitable to use these shields in either interlaminar, extraforaminal or transforaminal approaches to the intervertebral disc.

Now referring to FIGS. 1-7, there is provided an access device for accessing an intervertebral disc, comprising:

a) an outer shield 1 having a substantially tubular portion, a length adapted to extend from an incision to a border between sensitive and insensitive tissue (e.g., an articular process), a proximal end portion 3, a distal end portion 5, an outer surface 7, and a longitudinal through-bore 9 defining an inner surface 10, b) an inner shield 11 having i) a first substantially tubular portion 13 having a proximal end portion 15, a distal end portion 17, a longitudinal through-bore 19 defining an inner surface 21, and an outer surface 23 defining a diameter, and ii) a longitudinal flange 25 extending distally from the distal end portion of the substantially tubular portion, wherein the outer surface of the inner shield substantially nests within the inner surface of the outer shield so that the flange extends distally past the distal end portion of the outer shield, and the distal end portion of the substantially tubular portion of the inner shield extends distally past the distal end of the outer shield.

Outer Shield Embodiments

Figure 3A:
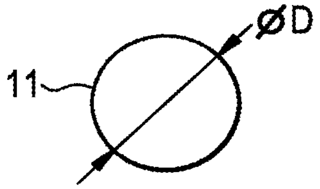
FIGS. 3*a*-3*d* show different axial cross section of the inner shield.
Figure 3B:
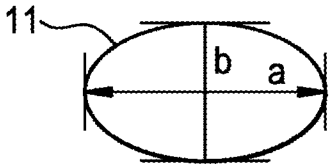
Figure 3C:
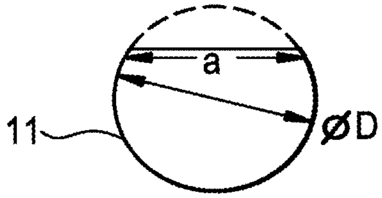
Figure 3D:
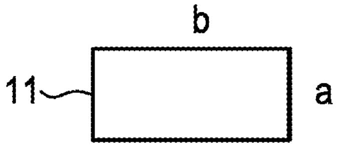

In the design of the outer shield, traditional tube or split tube/retractor concepts can be used. Newer concepts such as a "flexible tube" could also be adopted. The outer shield can be a simple cylindrical tube. It may also be a split tube, in the manner that conventional retractors are considered to be split tubes. It can be a flexible tube. It can be a tube with a slot running from the proximal end to the distal end. Various shape embodiments could be:

a) a cylindrical tube with an inner diameter D (FIG. 3*a*);

b) an oval tube with a height a different than a length b (FIG. 3*b*);

c) a "half moon" tube having a substantially circular or oval cross section of diameter D, with a section cut (or chord) "a" (FIG. 3*c*); and d) a rectangular tube with height a and width b (FIG. 3*d*).

In some embodiments, the shape of the distal end portion 5 includes an unsymmetrical shape for better tissue retraction lateral to the SAP.

The outer shield can be preferably used with a variety of access window sizes (i.e., widths) ranging from 6 mm to 25 mm and lengths ranging from 40 mm to 200 mm. Typically, the outer shield comprises a feature that allows for the attachment of a stabilization mechanism that allows for appropriate flexibility in attachment (e.g. a ball joint). In one embodiment, the outer shield has a customized feature adapted for the introduction of an endoscope or camera that allows the endoscope to be introduced to a predetermined depth where the working window at the distal portion of the outer shield can be visualized.

Inner Shield Embodiments

Now referring to FIGS. 3*a*-3*d*, the inner shield 11 may encompass various designs as well.

In a first embodiment, the inner shield is a fully surrounding (i.e., extending for 360 degrees) stiff tube. It may possess various cross-sections, such as:

e) a cylindrical tube with an inner diameter D (FIG. 3*a*);

f) an oval tube with a height a different than a length b (FIG. 3*b*);

g) a "half moon" tube having a circular cross section of diameter D, with a section cut (or chord) "a" (FIG. 3*c*); and h) a rectangular tube with height a and width b (FIG. 3*d*).

The inner shield may possess different longitudinal shapes. For example, in a second embodiment, and now referring to FIGS. 4-7, the inner shield 11 is a funnel-shaped (e.g. necked) tube (as in FIG. 4). In this embodiment, it changes its cross sectional shape/area along the shield, with a bigger diameter/working zone at the proximal portion, and the length of this zone with a bigger diameter is adjusted to be the part of the inner shield that will be nested within the outer shield, and a smaller diameter/working zone where the inner shield is extending the outer shield.

This design increases the range of motion of intradiscal tools and enables better visualization.

Figure 4:
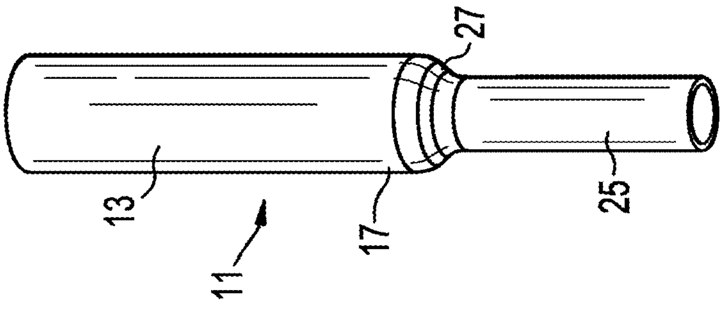
FIG. 4 shows a necked, funnel-shaped embodiment of the inner shield.

In FIG. 4, the flange is a second substantially tubular portion 25 having a diameter less than the diameter of the first substantially tubular portion 13 of the inner shield. A necked region 27 is disposed between the first and second substantially tubular portions.

In some embodiments, the inner shield may be in the form of one of a plurality of retractor blades.

Figure 6:
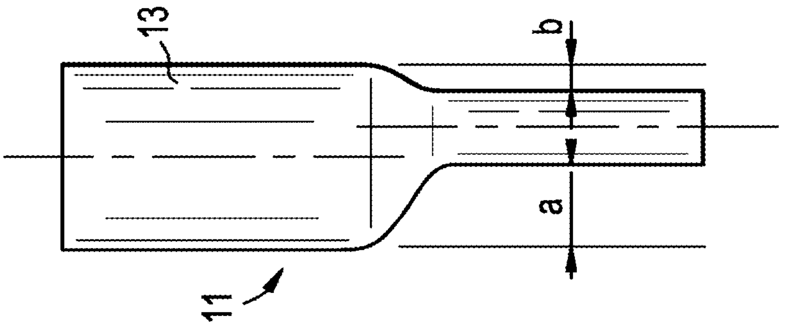
FIGS. 5-6 show different longitudinal cross sections of concentric and nonconcentric inner shields.
Figure 5:
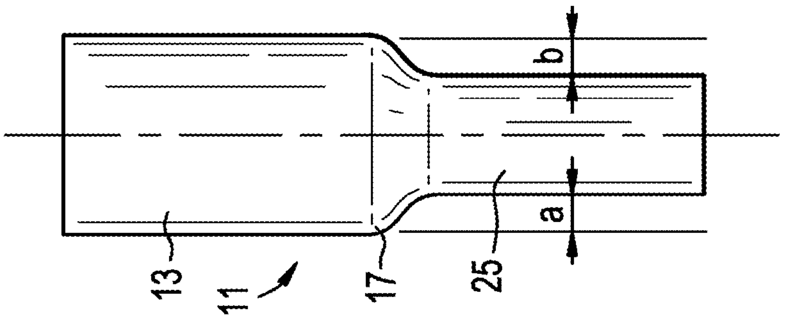

In tubular embodiments, the smaller tube can be a concentric with the larger tube, or not concentric therewith. In FIG. 5, the first and second substantially tubular portions of the inner shield are concentric (a=b). In FIG. 6, the first and second substantially tubular portions of the inner shield are not concentric (a>b).

Figure 7:
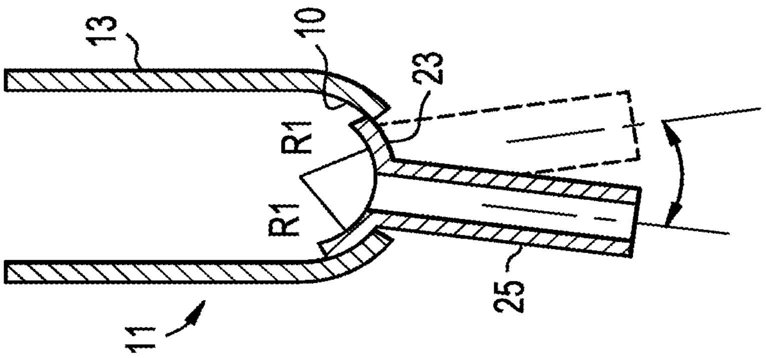
FIG. 7 shows a jointed access device.

In some embodiments, there is provided a spherical joint between the larger and the smaller tubes, allowing the angle to change between the two tubes (FIG. 7). In FIG. 7, the outer surface 23 of the inner shield substantially nests within the inner surface 10 of the outer shield so that the proximal end of the substantially tubular portion of the inner shield terminates within the outer shield. Also, the distal end portion of the inner shield narrows distally to define a first radius R1, and the proximal end portion of the inner shield narrows distally to define a second radius, and the proximal end portion of the inner shield nests within the distal end portion of the outer shield to allow polyaxial pivoting of the inner shield.

In some embodiments, the inner shield is a partially surrounding tube/shield, or "flange," designed only to protect the nerves. For some applications, the only purpose of the inner tube might be to shield/protect the exiting nerve root. In this case, the inner shield might be simplified to a cylinder with a flange 25 extending distally therefrom, so that the flange is only a shield of about a quarter of a full circle. See FIG. 8*a*, or FIG. 9 if mounted on the outer shield.

Depth Adjustment of Nerve Protector

The aforementioned outer shield can be positioned and fixed in its depth through a mechanism which relies on interference between the outer shield and the inner shield at any location along either the outer shield or inner shield.

Figure 8B:
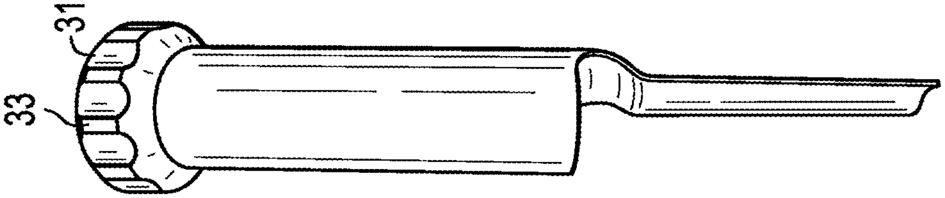
FIG. 8*b* shows an inner shield with a proximal stop.
Figure 8A:
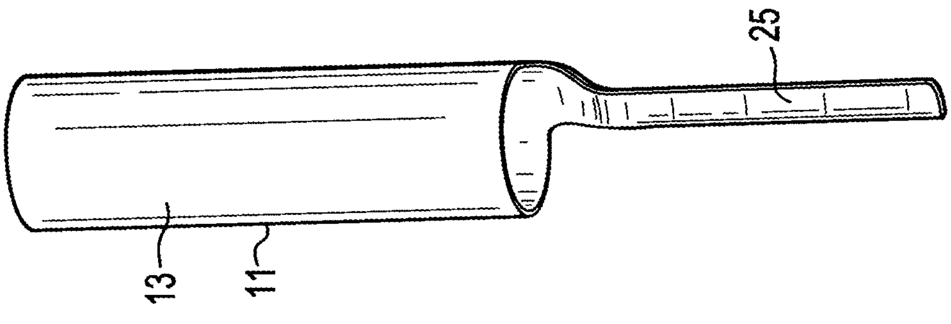
FIG. 8*a* shows a flanged embodiment of the inner shield.

In FIG. 8*b*, the proximal end portion of the first substantially tubular portion 13 of the inner shield comprises a stop 31 adapted to abut the proximal end portion of the outer shield, the stop being adapted to prevent excessive distal movement of the inner shield. Preferably, the stop extends substantially radially about the proximal end portion of the substantially tubular portion of the inner shield. The stop may also further comprise a textured radial surface 33 adapted for gripping. It acts as both a stop and as a handle to twist the shield.

Figure 9:
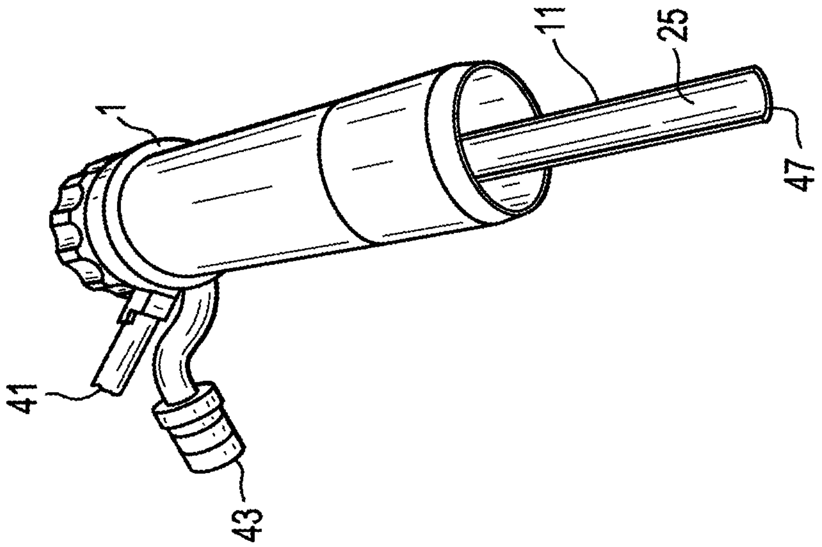
FIG. 9 shows an access device with two ports attached to the outer shield; one port is a connector to hold the outer tube, while the other is an interface for a light source.

In FIG. 9, the outer surface of the inner shield substantially nests within the inner surface of the outer shield so that the proximal end portion of the substantially tubular portion of the inner shield extends proximally past the proximal end of the outer shield. Also in FIG. 9, the outer surface of the outer shield further comprises a first port 41 adapted for connecting to a navigation instrument or a stabilization point, and a second port 43 adapted for connecting to a camera/light system.

Navigation of Outer Shield

The first port allows the outer shield to be navigated to determine its position (depth and orientation) in relation to the treatment site. In one embodiment, the outer surface of the outer shield has a feature that allows for the direct or indirect attachment of a navigation instrument. In another embodiment, the inner surface of the outer shield has a feature that allows for the direct or indirect attachment of a navigation instrument.

Endoscope in the Outer Shield

In some embodiments, the outer shield has an integrated endoscope that can be set in a fixed or variable (angle or circumferential) position relative to the anatomy. This endoscopic visualization can be utilized in subsequent surgical steps, including bone removal, inner shield deployment, discectomy and implant insertion. Preferably, the endoscope has an integrated lens cleaning mechanism for automated lens cleaning in situ.

Figure 10:
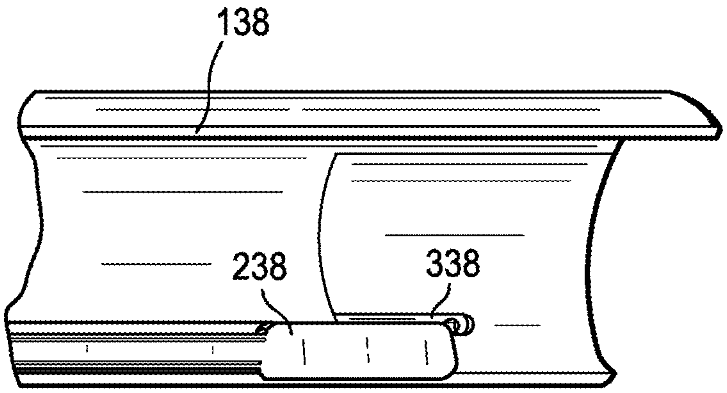
FIG. 10 discloses a cross-section of an outer tube wherein the outer tube wall has a first channel adapted for containing a visualization unit (such as a camera) and a second channel adapted for containing a cleaning system (such as a lens cleaning device)

FIG. 10 discloses a cross-section of an outer tube wherein the outer tube wall 138 has a first channel 238 adapted for containing a camera and a second channel 338 adapted for containing a lens cleaning device.

Figure 11:
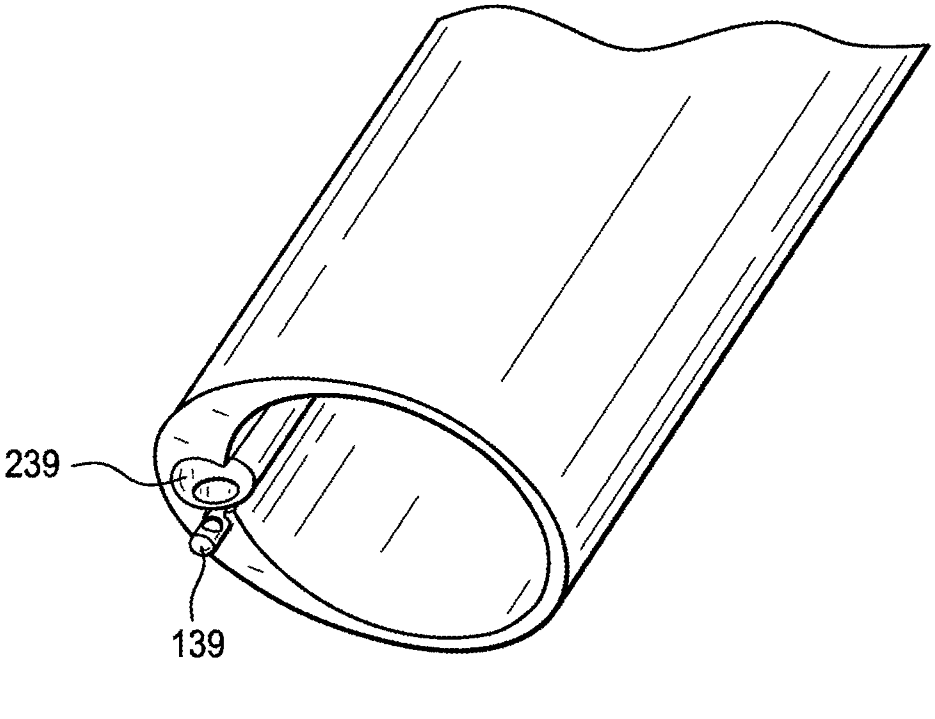
FIG. 11 discloses a cross-section of an outer tube wherein the outer tube wall contains a lens cleaning device and a camera.

FIG. 11 discloses a cross-section of an outer tube wherein the outer tube wall contains a lens cleaning device 139 and a camera 239.

Figure 12:
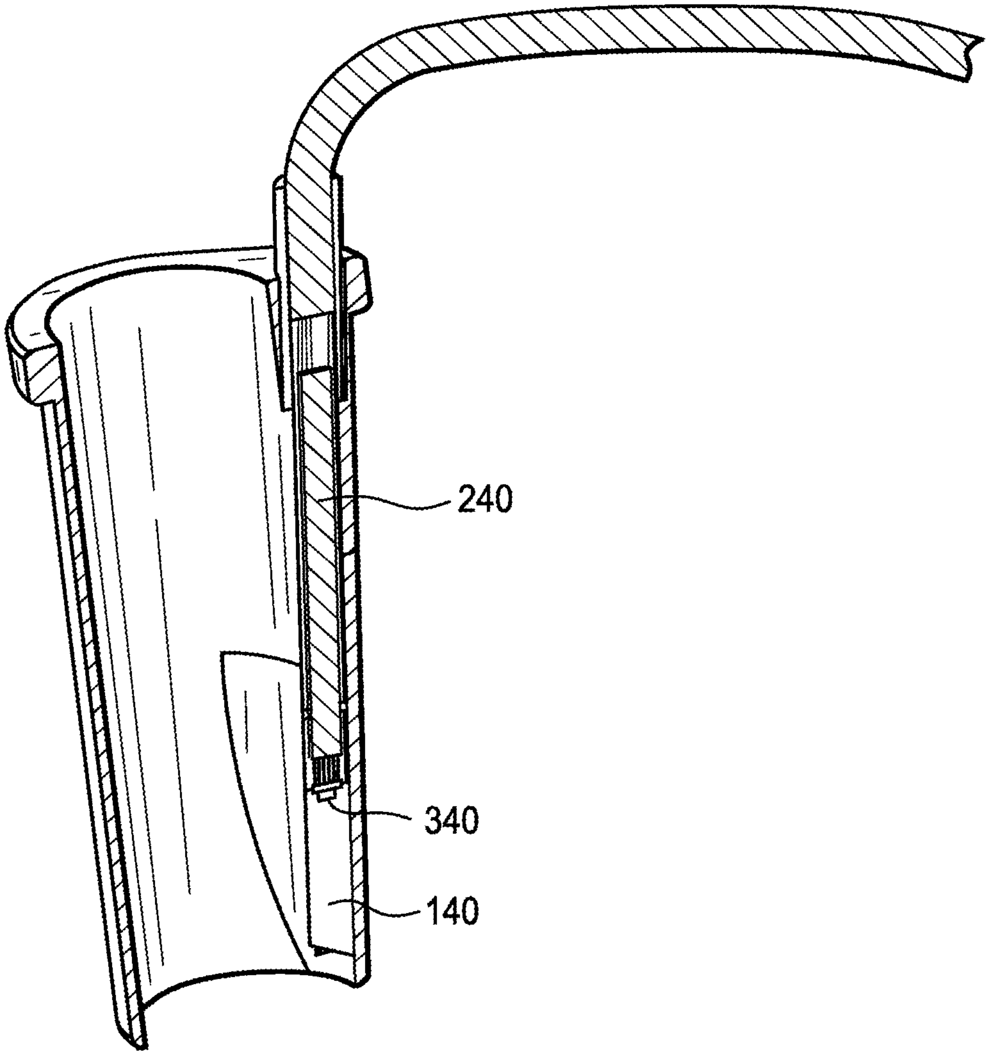
FIG. 12 discloses a chip-on-tip embodiment including a cross-section of an outer tube wherein the outer tube wall has a channel containing an endoscope having a video chip near its distal end.

FIG. 12 discloses a chip-on-tip embodiment including a cross-section of an outer tube wherein the outer tube wall has a channel 140 containing an endoscope 240 having a video chip 340 near its distal end.

Figure 13:
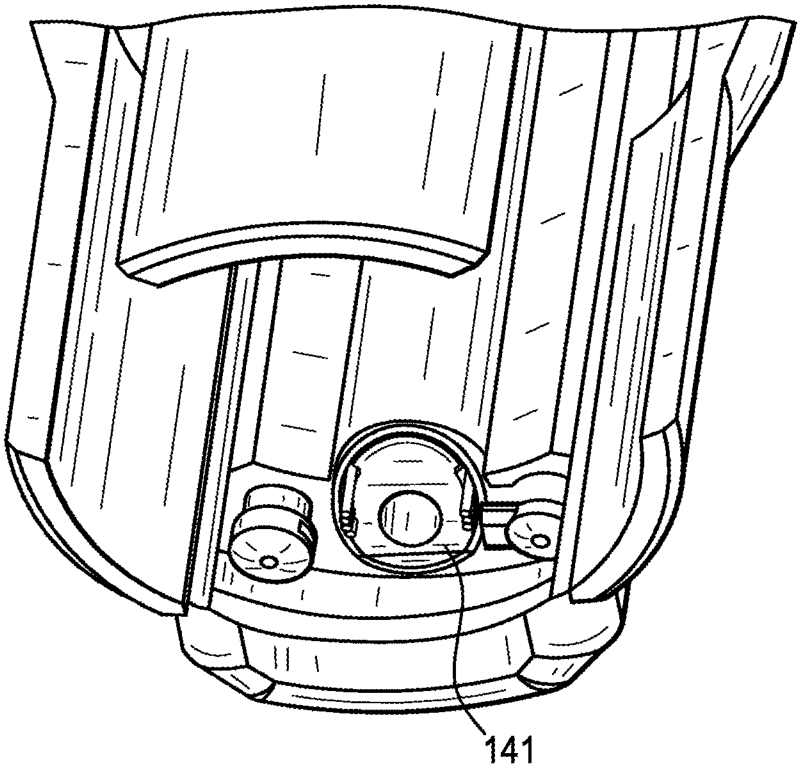
FIG. 13 discloses a distal end of an outer tube featuring a video chip near its distal end.

FIG. 13 discloses a distal end of an outer tube featuring a video chip 141 near its distal end.

Fixed Endoscope

The endoscope can be a chip-on-tip type of endoscope having an outer diameter less than 5 mm and having an incremental length substantially matching the length of the outer shield. The benefits of an integrated chip-on-tip endoscope/outer shield embodiment include the relatively free space within the bore of the outer shield, thereby enhancing visualization.

Preferably, the endoscope is angled within the port or has a built-in lens angle such that, at final positioning within the port, the circumference of the distal portion of the outer shield is visible and the area within the circumference is visible as well.

In some embodiments, the endoscope can be removed from the wall of the outer shield and inserted independently into the outer shield bore to inspect the treatment site (e.g. into the disc space for confirmation of adequate discectomy).

Figure 14:
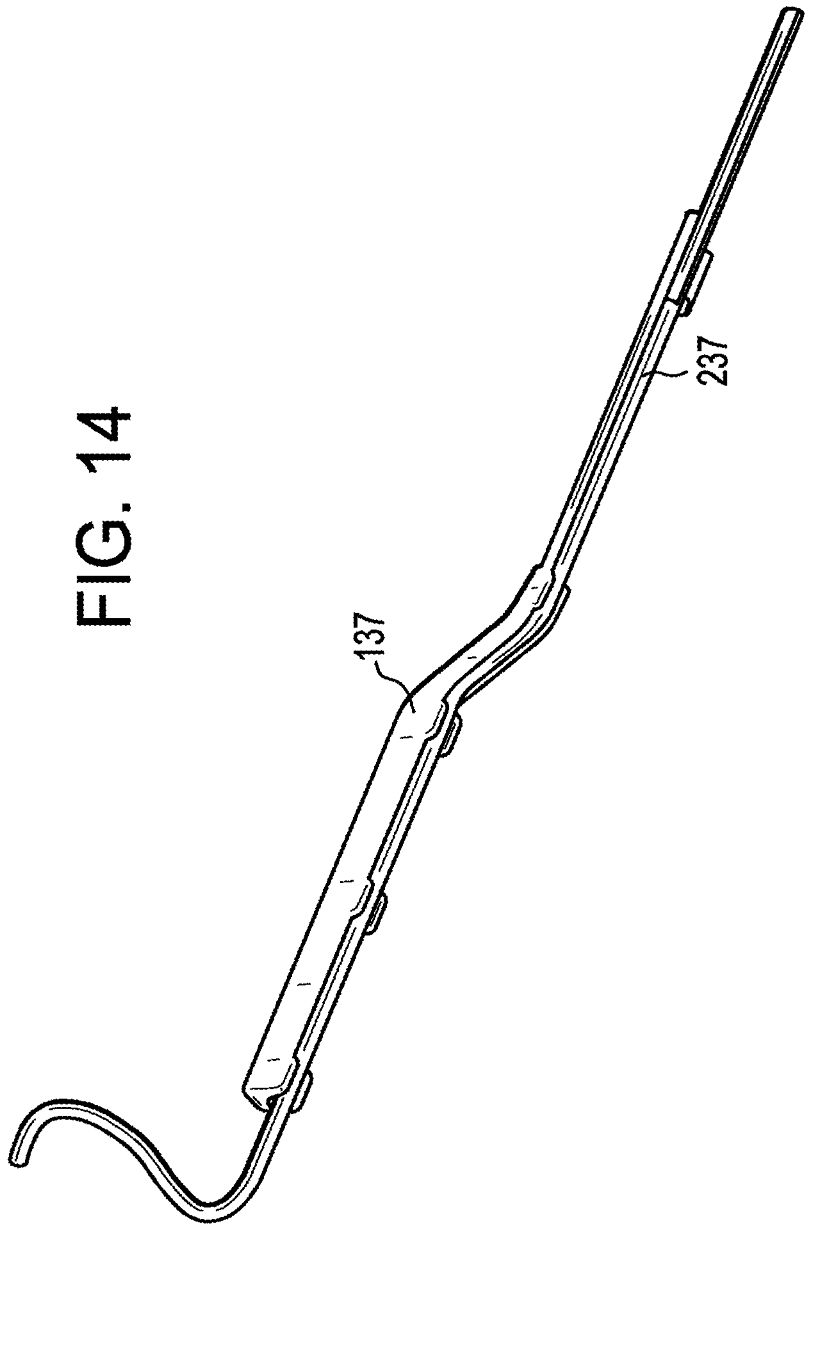
FIG. 14 discloses a scope holder for an endoscope.

FIG. 14 discloses a scope holder 137 for an endoscope 237.

Still referring to FIG. 9, in some embodiments, the flange 25 of the inner shield has an arcuate transverse cross-section. In some embodiments, the arcuate transverse cross-section of the flange defines an outer surface 47 of the flange having a curvature substantially similar to a curvature of the inner surface 10 of the outer shield. Preferably, the flange defines a second substantially tubular portion having a diameter less than or equal to the diameter of the first substantially tubular portion of the inner shield.

Figure 16:
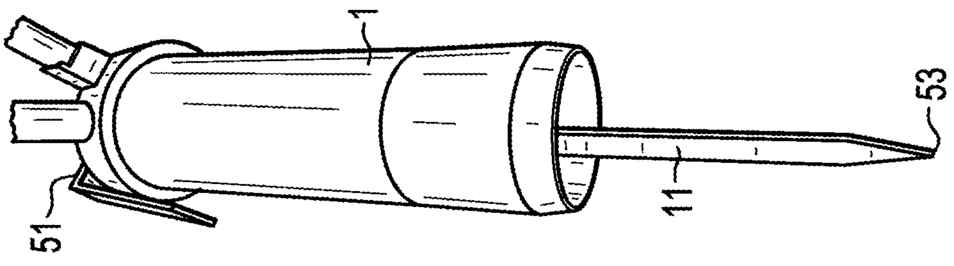
FIG. 16 shows an access device with a distal sharpened tip on the inner shield within an outer shield.
Figure 15B:
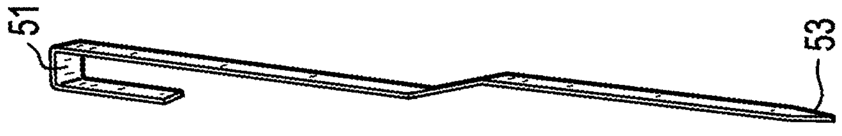
FIGS. 15*a*-15*b* show inner shield having proximal elbows.
Figure 15A:
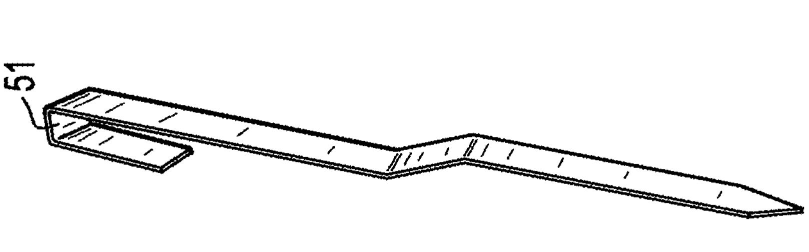

Now referring to FIGS. 15*a*-15*b* and 16, the inner shield can be a single blade that can be mounted/hooked to the outer tube. In this case, elbow 51 functions as a stop and also as a connector to the outer tube. Also, the proximal end of the inner shield may form an anchoring spike 53.

There are a number of ways to fix or locate the inner shield onto the disc and/or onto the outer shield. In one embodiment, which provides safety of the inner shield against slippage/dislocation, involves mounting it distally (onto or within the vertebral endplates or disc annulus) and/or proximally (onto the outer shield).

Distal fixation of the inner shield with the anatomy may include: a) fixation within disc annulus, b) fixation against vertebrae; c) fixation against other structures; d) K-Wires that are distally extending through the walls of the inner shield and anchored to the anatomy; and e) spikes extending the distal part (FIG. 15) to be anchored to the anatomy.

Figure 17:
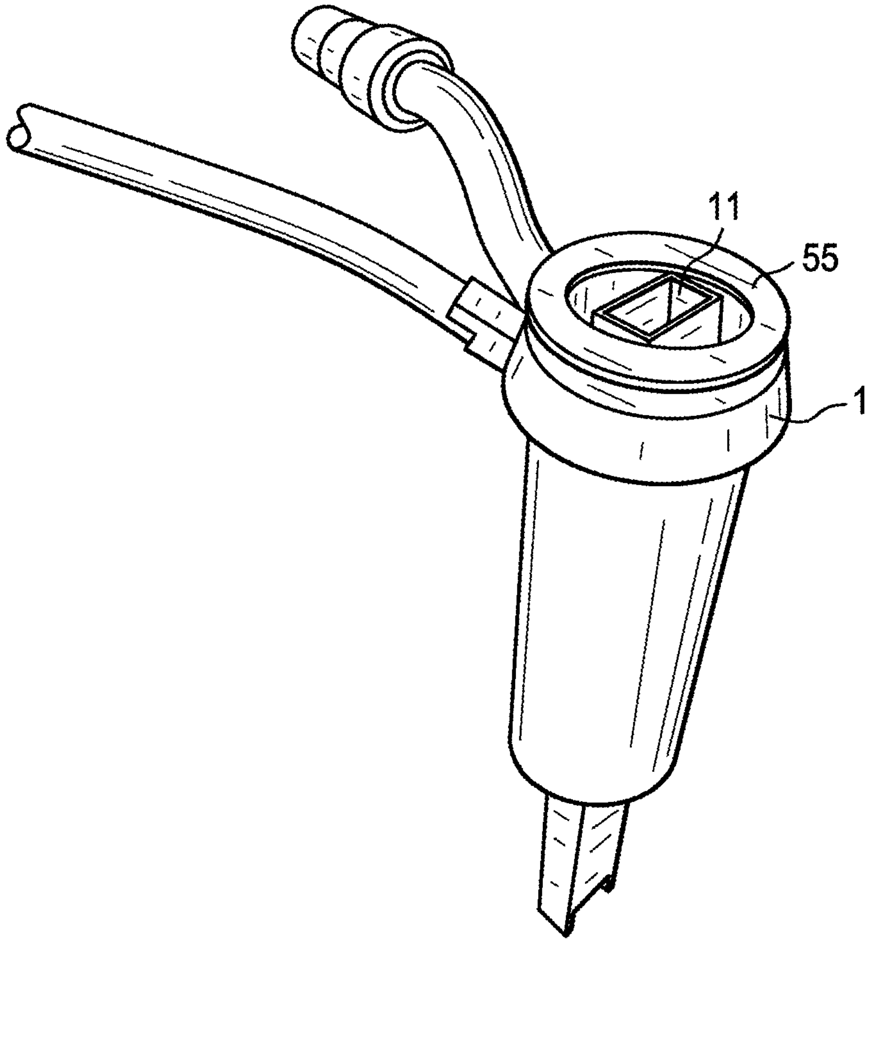
FIG. 17 shows an access device with a positioning ring between the inner and outer shields.

Proximal fixation of inner shield upon the outer shield may involve a positioning ring or a depth adjustment. Now referring to FIG. 17, proximal fixation of inner shield upon the outer shield may involve a positioning ring 55. Assuming the outer shield would be fixed relative to the anatomy, there would be the option of having positioning rings having the shape of the outer tube at the outside, and of the inner tube on the inside. When placed over the inner shield and into the outer shield, such a ring would stabilize the location or at least the orientation of the proximal inner shield against the outer shield, and—by considering the assumption above—also against the anatomy.

Figure 18:
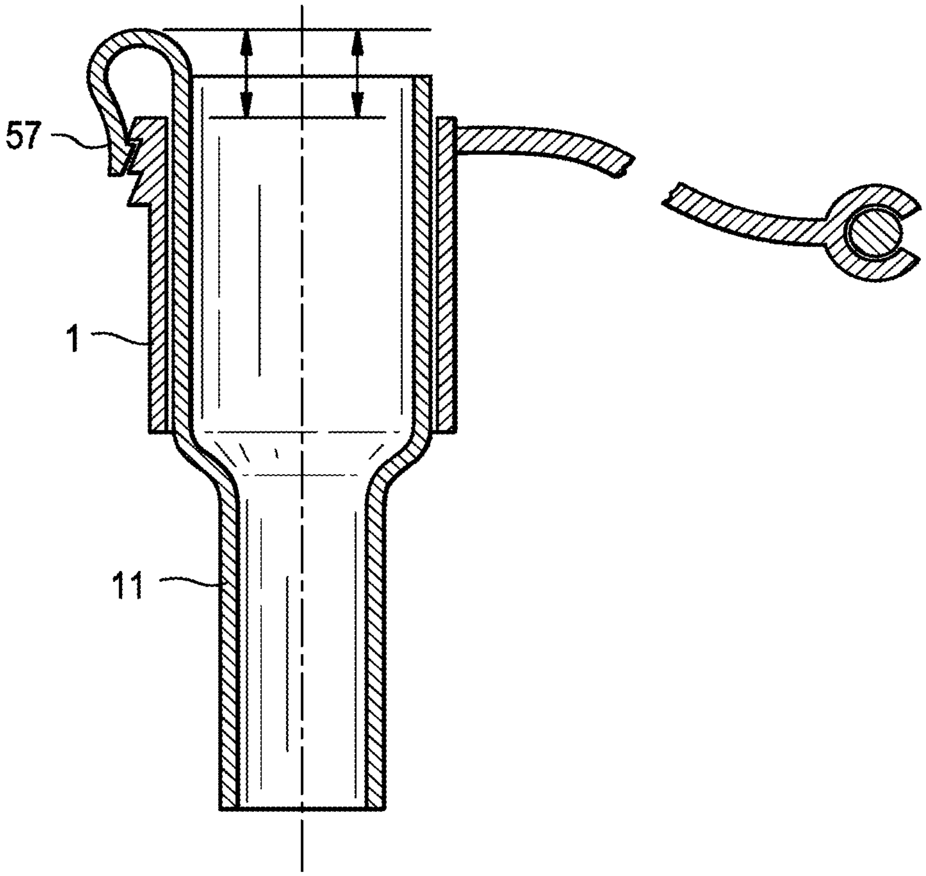
FIG. 18 shows an access device with a depth adjustment means formed by the inner and outer shields.

Now referring to FIG. 18, proximal fixation of inner shield upon the outer shield may involve a depth adjustment means 57. This would additionally stabilize or anchor the tip location of inner shield against the anatomy—via anchoring or hooking the inner shield into the outer shield via ratchet system. The ratchet system can also be located between the inner surface of the outer shield, and the outer surface of the inner shield or within the wall of the outer shield. It may further include a spring system to increase friction between the inner and outer shields.

Inner Shield Deployment (Circumferential)

Embodiments having separate outer and inner shields allow for the independent positioning of the inner shield relative to the outer shield. Also, the use of a smaller inner shield (relative to the outer shield) allows for maximum visualization at the entrance where no retraction-sensitive tissues reside. This maximum visualization allows for accurate placement of the inner shield. Where retraction-sensitive tissues reside distal the outer shield, a relatively smaller inner shield allows for minimum retraction while providing an access through or past these tissues. Preferably, the inner diameter of the inner shield is no more than 40%-100% of the inner diameter of the outer shield.

In some embodiments, the inner shield-outer shield configuration is replaced by a) a primary shield having a substantially tubular shape having a cutout, and b) a secondary shield having a shape that is substantially insertable into the cutout. Preferably, the primary shield has a substantially annular shape and the secondary shield has an arcuate cross-section that substantially matches the annular shape of the primary shield. This embodiment allows the secondary shield to be tilted with respect to the primary shield.

Inner Shield Deployment (Radial)

In another nerve protection embodiment, the motion of retraction of the shields is radial rather than rotational. In these embodiments, a straight or bayonetted inner shield may be used. The inner shield may be positioned over the area in which the protected tissue is to be located. The flange shield can then be angled into the center of the access window at the distal end of the outer shield e.g. towards the caudal pedicle. It can then be subsequently advanced longitudinally onto the medial side of the nerve root, into the "safe zone" as described by Kambin. It is subsequently angled such that the distal tip of the inner shield is angled laterally, wherein its outer distal surface gently pushes the existing nerve root away and/or shields it against the tools that are further introduced medially to the shield for intradiscal work. This embodiment may be constructed such that the inner shield substantially nests either a) within the wall of the outer shield (FIG. 19), b) inside the inner surface of the outer shield (FIG. 21), or c) outside the outer surface of the outer shield. In some embodiments, the inner shield is built into the wall of the outer shield or even outside the outer shield.

Figure 19:
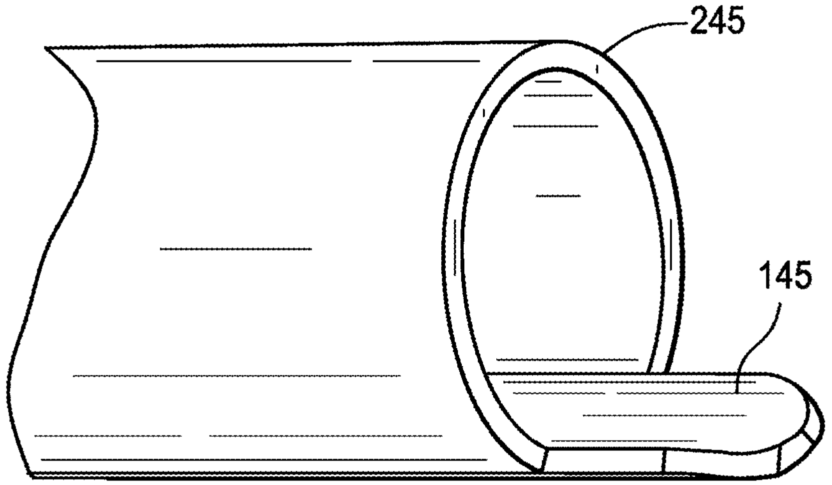
FIG. 19 discloses an integrated retractor having a flat inner face housed within a cutout of an outer tube 245.
Figure 20:
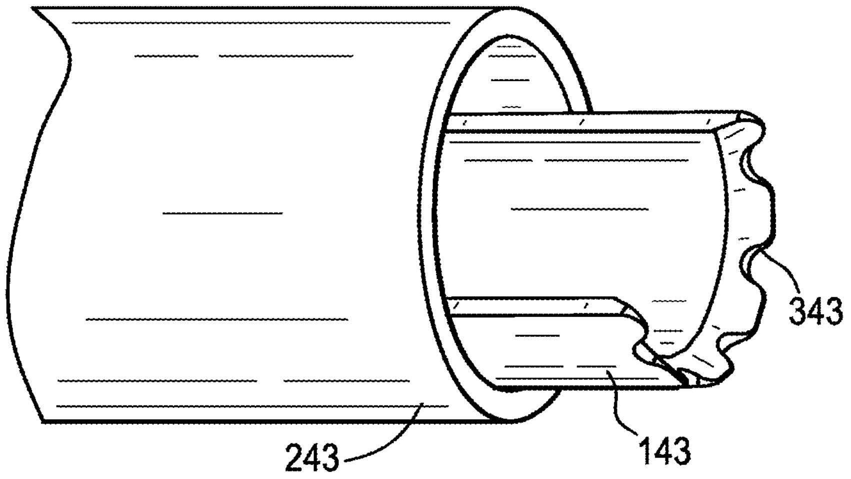
FIG. 20 shows the embodiment of FIG. 48.

FIG. 19 discloses an integrated retractor having a flat inner face 145 housed within a cutout of an outer tube 245.

Figure 21:
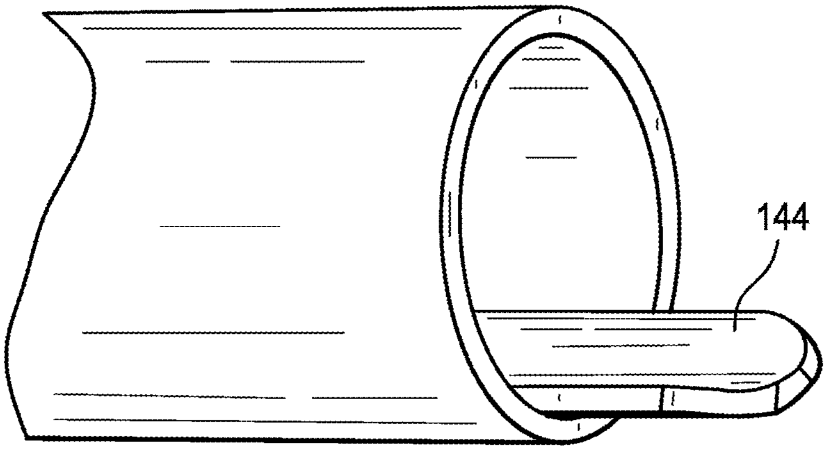
FIG. 21 discloses a retractor having a flat inner face housed within an outer tube.

FIG. 21 discloses a retractor having a flat inner face 144 housed within an outer tube.

In other embodiments, an outer tube can have a retractor nesting with the outer face of the outer tube.

Depth Control of Nerve Protector

The aforementioned outer shield can be controlled in its depth through a mechanism that relies on interference between the outer shield and the inner shield at any location along either the outer shield or inner shield.

There are a number of avenues by which the present device can be used to distract the disc space and/or provide nerve protection upon mounting.

In one distraction embodiment, a revolution spreader is used. This is a conventional concept involves an ovoid or rectangular cross-sectional shaped rod that is inserted into the disc with its smaller dimension directed towards the vertebral endplates. After turning the spreader by 90° under force, the larger dimension is directed towards the vertebral endplates, which distracts the disc by the difference of the two cross sectional dimensions.

In a second distraction embodiment, as now referring to FIGS. 22-24*b*, the inner shield may comprise a spreader, which includes a frame 60, a cranial blade 61, and a caudal blade 63.

Figure 22:
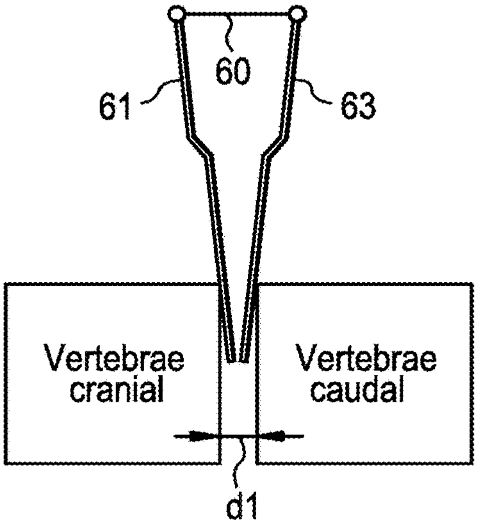
FIGS. 22-24*b* show a distraction embodiment.
Figure 23:
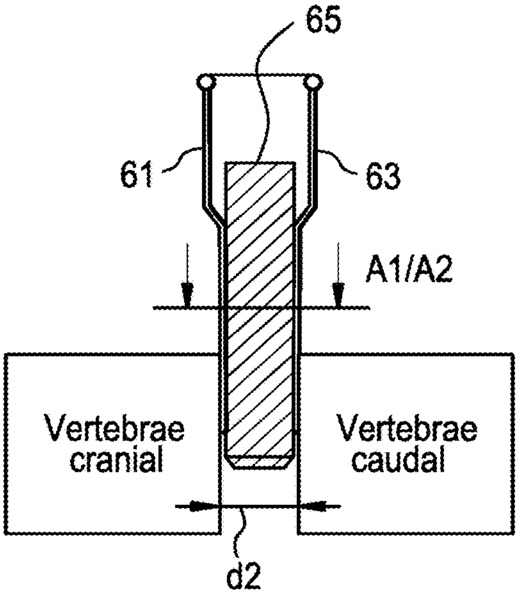
Figure 24A:
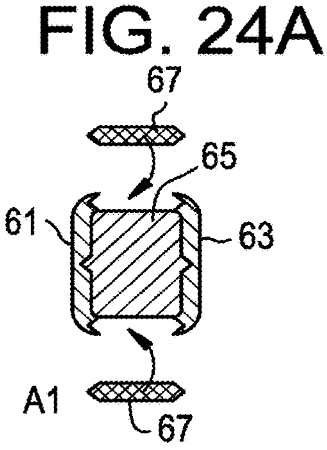
Figure 24B:
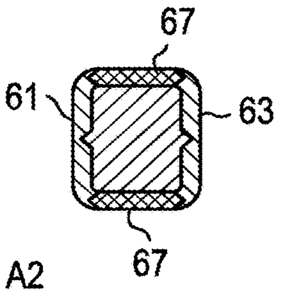

The spreader with respective cranial 61 and caudal 63 distraction blades in cranial and caudal locations is introduced into the disc in a collapsed/tapered configuration (FIG. 22). The spreader blades are then distracted with an inner core 65 (the core matching a counter geometry on the blade to not slip away sideways), elevating the intervertebral height from d1 to d2 (FIGS. 22-23). The side walls 67 matching to the inner core height are then introduced medially/laterally (FIG. 24*a*), to circumferentially close the four-wall shield. Once the inner core is removed, the stacked shield keeps the vertebral bodies separated in distracted condition (FIG. 24*b*).

Figure 26:
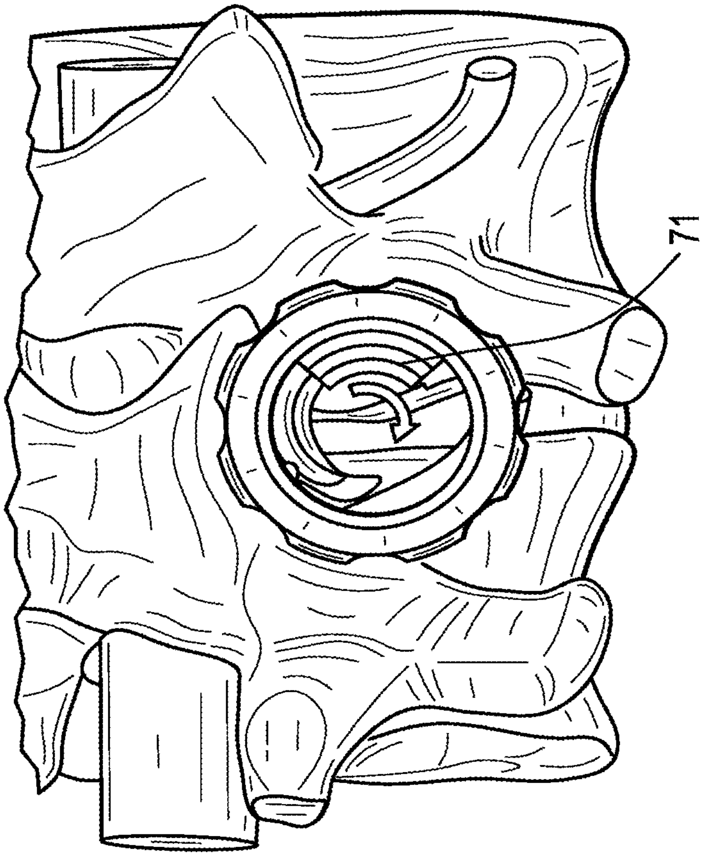
FIGS. 25-30 show an access device with an extending shield.
Figure 25:
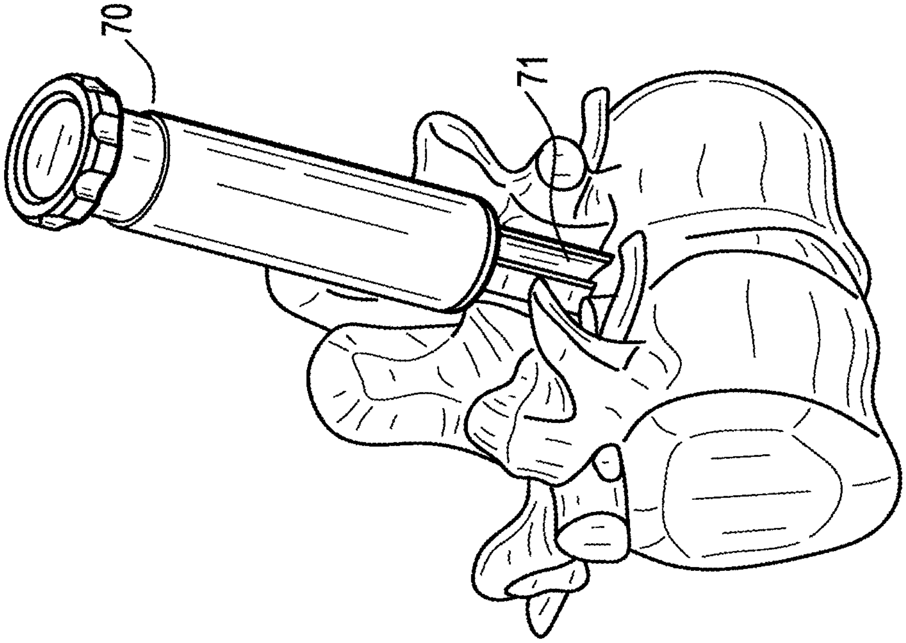
Figure 27:
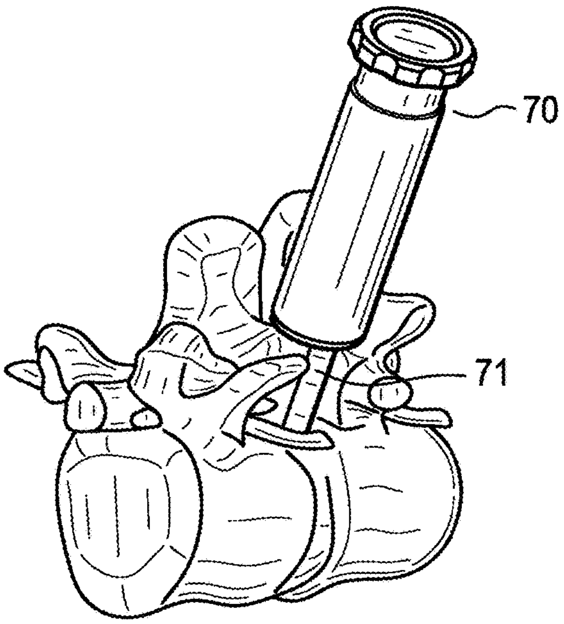
Figure 29:
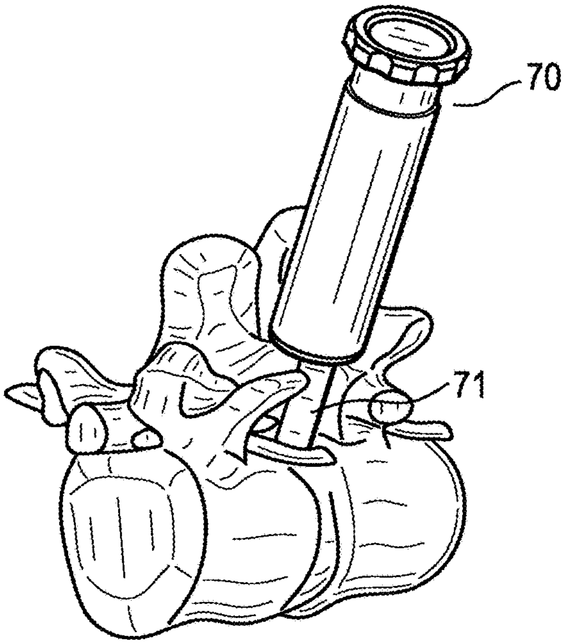
Figure 28:
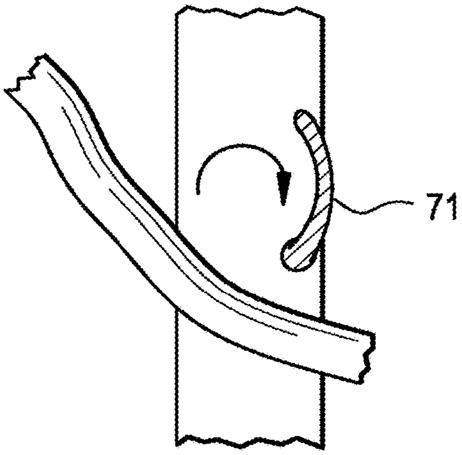
Figure 30:
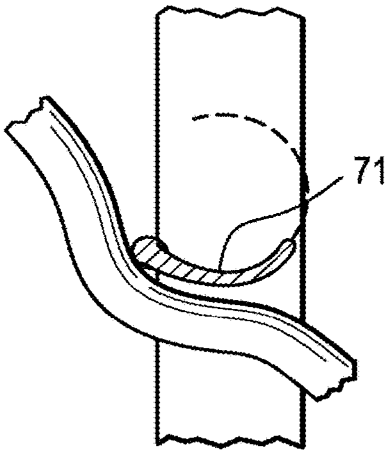
Figure 31:
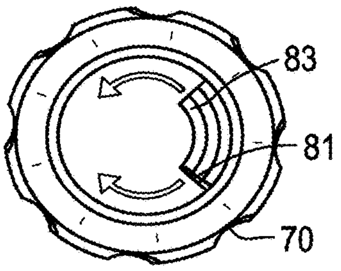
FIG. 31 shows an access device with an inner and outer shield.
Figure 33:
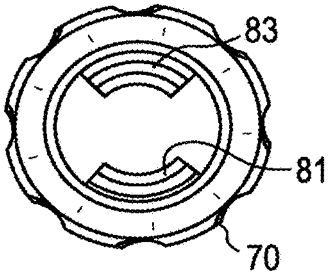
FIGS. 32-34 show in inner shield.
Figure 32:
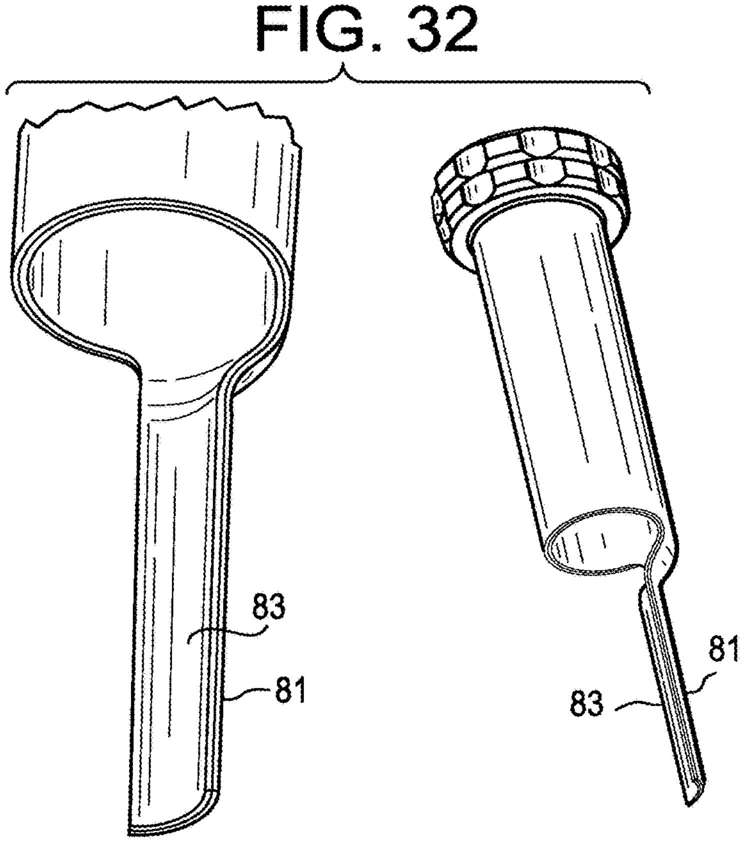
Figure 34:
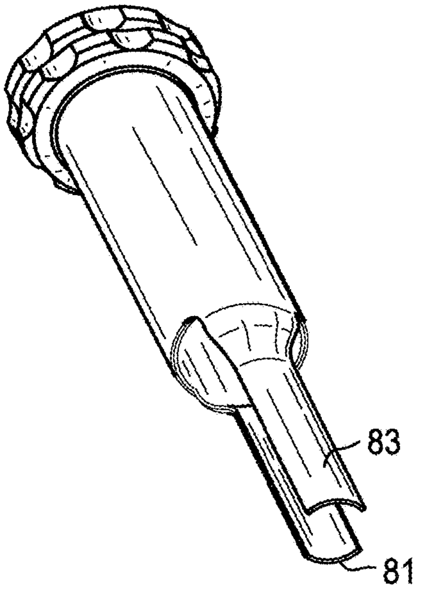

Now referring to FIGS. 25-26, the inner shield may further comprise a rotating flange 71 that moves laterally/medially upon rotation to shield the nerve root.

In a nerve protection embodiment, and now referring to FIGS. 27-30, a rotation funnel 70 is used. Preferably, the flange shield 71 can be smartly introduced to protect the exiting nerve root while being inserted. This shield can be directed towards the caudal pedicle if introduced through the outer shield. This location is a "safe zone." Once the distal tip reaches the disc level, the inner shield can be turned clockwise by about 90° (i.e., rotated), so that the flange gently pushes the exiting nerve root away, and/or shields it against the tools that are further introduced medially to the shield, for intradiscal work.

In a second nerve protection embodiment, and now referring to FIGS. 31-34, a concentrically-arrayed multi-shield is used to gently move and/or shield nerves. The rotation funnel principle can also be applied for more than one rotating shield. A single shield may be suitable if the protection only has to be provided against a structure that lies on one single side. In other situations, however, the shield entry towards the disc would be bounded both medially and laterally by the traversing and the exiting nerves, so the inner shield needs to shield against two opposing structures. In this case, the two concentrically-arranged outer 81 and inner 83 rotating flanges are turned by 90° in respective clockwise and counterclockwise directions to reach an end configuration wherein the opposed shields protect the nerves from the tools that are further introduced for intradiscal work.

In another nerve protection embodiment, a radially-retracting multi-shield is used to gently move and/or shield nerves. The radially-retracting principle can also be applied to more than one radially retracting shield.

Figure 35:
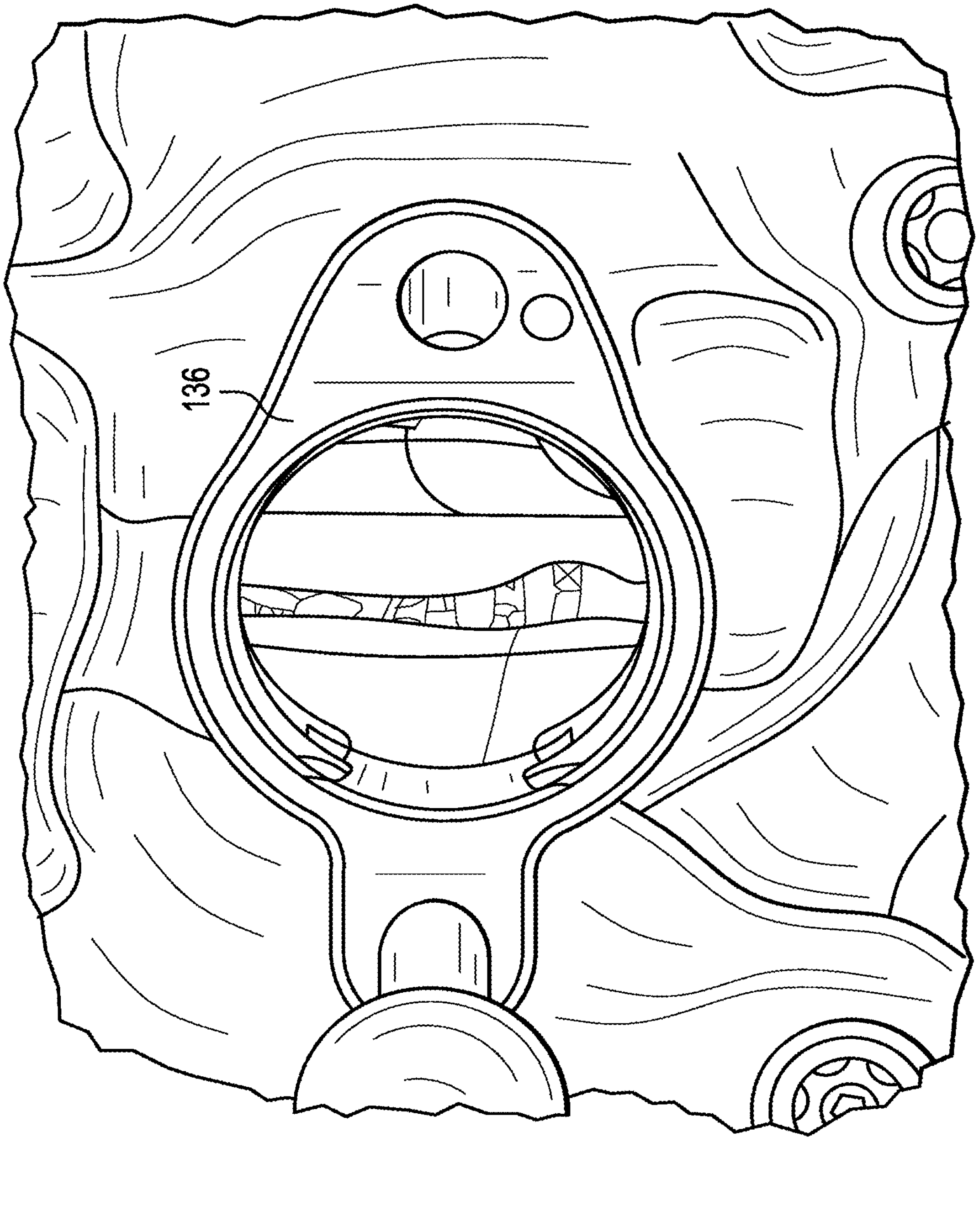
FIG. 35 discloses a radial soft tissue retractor.

FIG. 35 discloses a radial soft tissue retractor 136.

Figure 36:
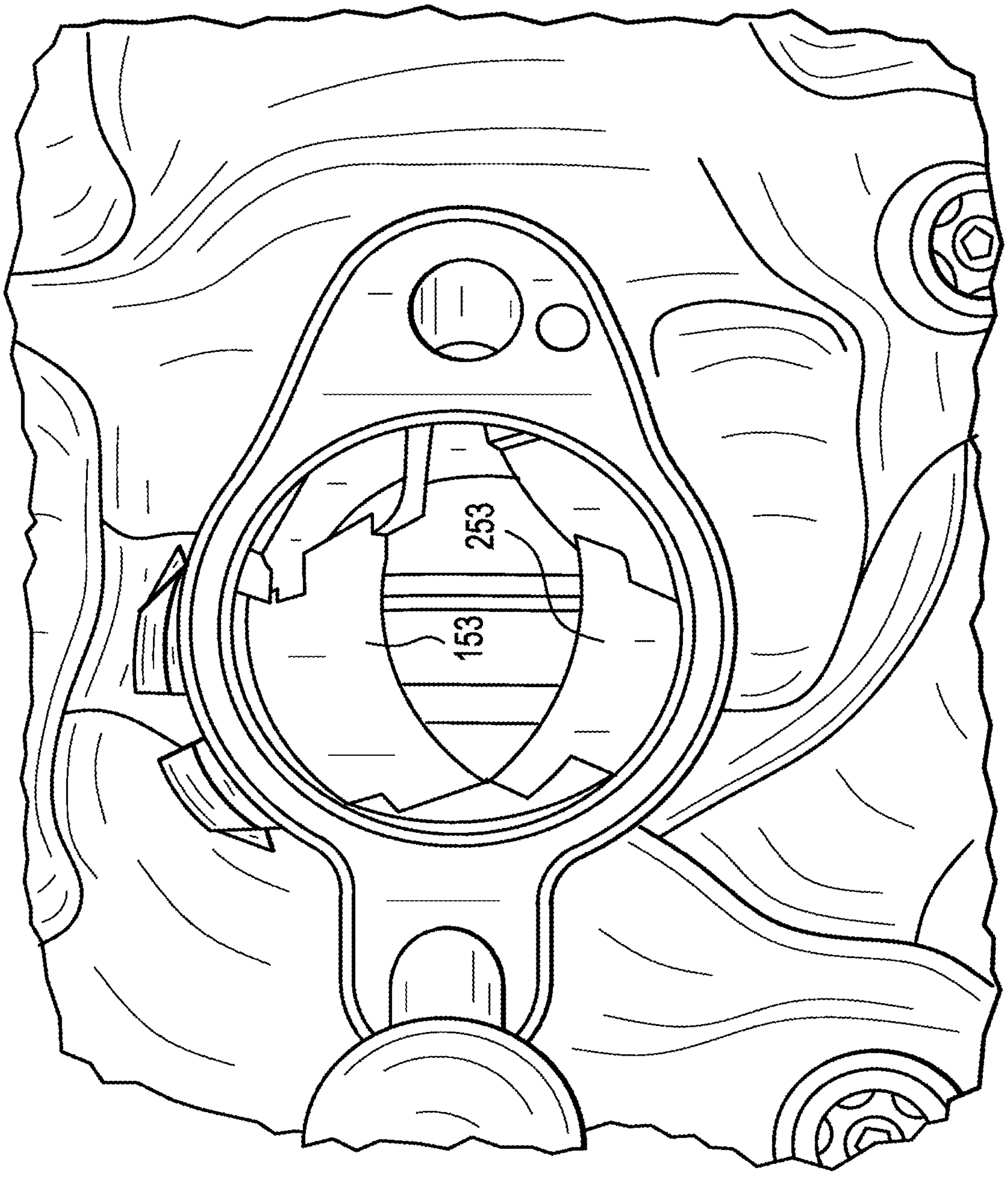
FIG. 36 discloses an outer tube/inner retractor assembly wherein the first inner retractor and second inner retractor both tilt inwards to retract soft tissue.

FIG. 36 discloses an outer tube/inner retractor assembly wherein the first inner retractor 153 and second inner retractor 253 both tilt inwards to retract soft tissue.

A single shield may be suitable if the protection only has to be provided against a structure that lies on one single side. In other situations, however, the shield entry into the disc would be bounded both medially and laterally by the traversing and the exiting nerves, so that the inner shield needs to shield against two opposing structures. In this case, the two opposing inner flanges are initially positioned towards the center of the outer tube access window and subsequently retracted outwards to shield the opposing nerves from the tools that are further introduced for intradiscal work.

FIGS. 37-46 disclose a preferred method of surgery involving the tube-in-tube access device.

Figure 37:
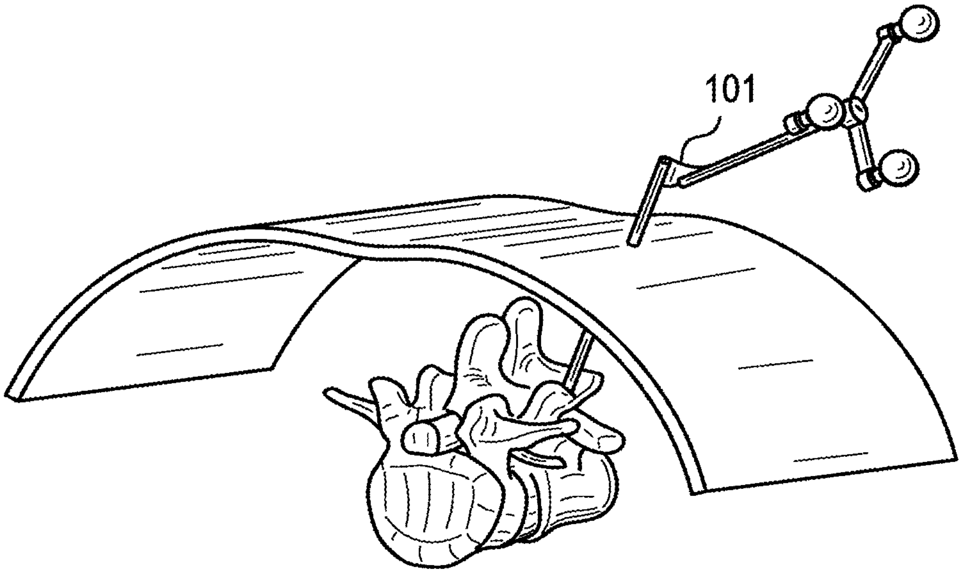
FIGS. 37-46 disclose a preferred method of surgery involving the access device.

In one embodiment, and now referring to FIG. 37, the surgeon places a pedicle screw-based anchor, adds a navigation reference frame 101 to the anchor, and uses a commercial navigation system for navigation. In some embodiments, a navigation array is placed onto the anatomy with reference to an anatomical feature that is symmetrically substantially adjacent the treatment site (e.g. contralateral cranial or caudal pedicle).

In some embodiments, there is navigation of the probe to a facet capsule or disc space through Kambin's triangle. Preferably, subsequent to fascia and muscle dissection, a probe enabled with navigation visualization is introduced to achieve an initial anchoring point. In one embodiment, the probe is inserted into the disc space by being indexed off the lateral border of the superior articulating process and may be optionally enabled with/supported by a nerve detection and/or visualization function. In another embodiment, the probe is introduced into the facet capsule.

In some embodiments, there is dilation over a navigated probe. Subsequent to the initial anchoring point, dilation is performed to prepare the surgical site for the size of port required to perform the treatment. Sequential dilation up to the preferred size port window is then performed. The port is then introduced over the associated dilator. In one embodiment, the initial anchoring is in the disc space and concentric sequential dilation device(s) would be used in order to retract tissue concentrically around the initial anchoring point (exposing the lateral portion of the SAP on the lateral aspect and Kambin's triangle on the medial aspect). In another embodiment, the initial anchoring is in the facet capsule and eccentric sequential dilation device(s) could be used to focus tissue retraction laterally over the lateral portion of the SAP and Kambin's triangle.

In some embodiments, the outer shield is stabilized onto an anatomical reference. The outer sleeve has a substantially tubular portion having a point or feature designed for attachment to a stabilization mechanism, which in turn is fixed to an anatomical feature on the vertebral body either cranial or caudal to the treatment site.

Figure 38:
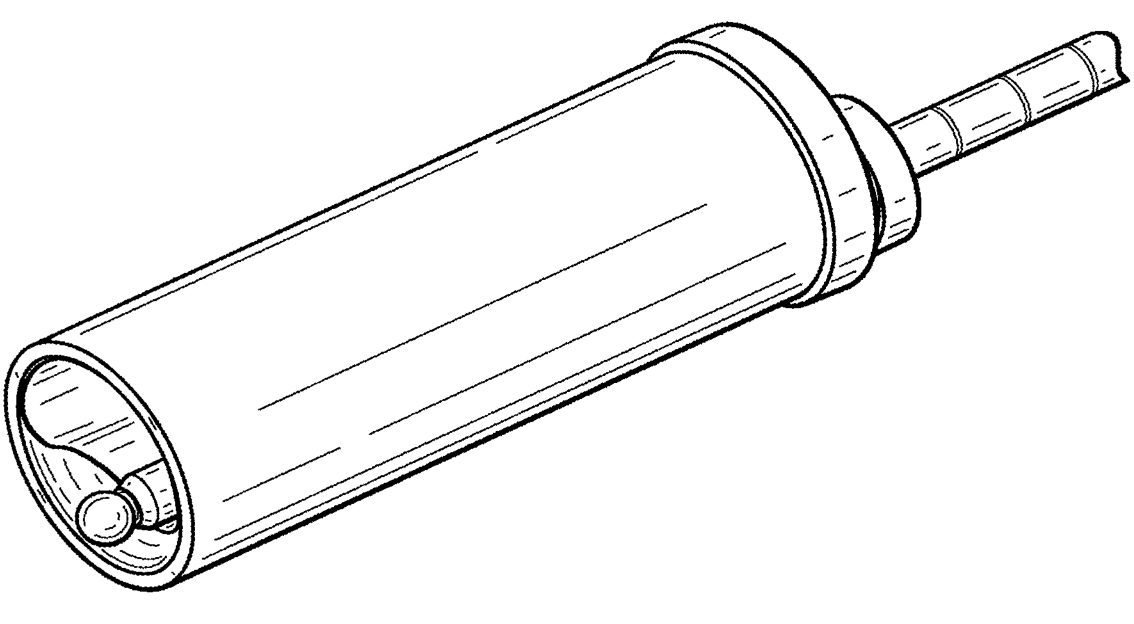

FIG. 38 discloses an outer tube into which a plug containing a template for guiding a bone cutting device.

In some embodiments, the outer sleeve is attached to a stabilization mechanism. In one embodiment, this stabilization device would be a device of sufficient length to reach an anatomical fixation point (e.g. pedicle screw) on the contralateral side of the treatment site. The mechanism (including its connection feature connecting to both the outer shield and the anatomical anchor) allows for sufficient flexibility of placement of the outer shield and sufficient stabilization to hold the outer shield in place until it is released by the user. The method of stabilization would be such that the user can dictate the degree of stiffness.

In another embodiment, this device has sufficient length to reach an anatomical fixation point (e.g. pedicle screw) on the ipsilateral side of the treatment site. Likewise, the mechanism (including its connection feature to both outer shield and anatomical anchor) would allow for sufficient flexibility of placement of the outer shield and sufficient stabilization to hold the outer shield in place until released by the user. The method of stabilization would be such that the user can dictate the degree of stiffness.

In another embodiment, this device would be a device of sufficient length to reach an anatomical fixation point (e.g. pedicle screw) on midline of the patient. Likewise, the mechanism (including its connection feature to both outer shield and anatomical anchor) would allow for sufficient flexibility of placement of the outer shield and sufficient stabilization to hold the outer shield in place unless released by the user. The method of stabilization would be such that the user can dictate the degree of stiffness.

Figure 39A:
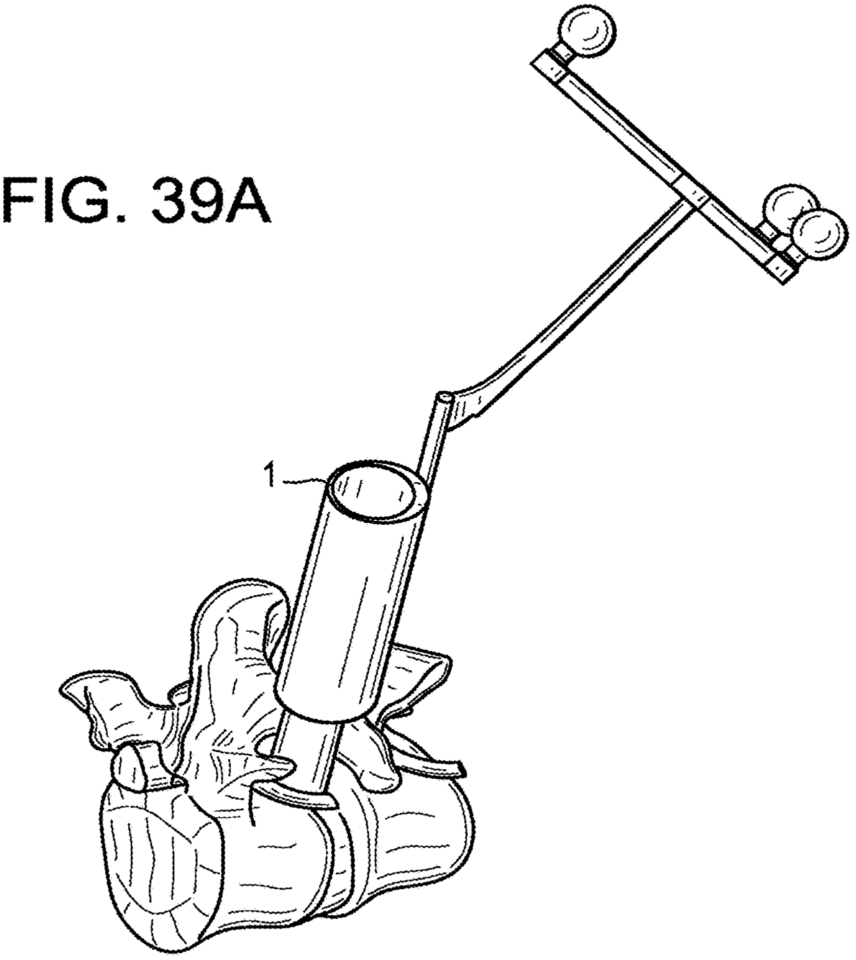
Figure 39B:
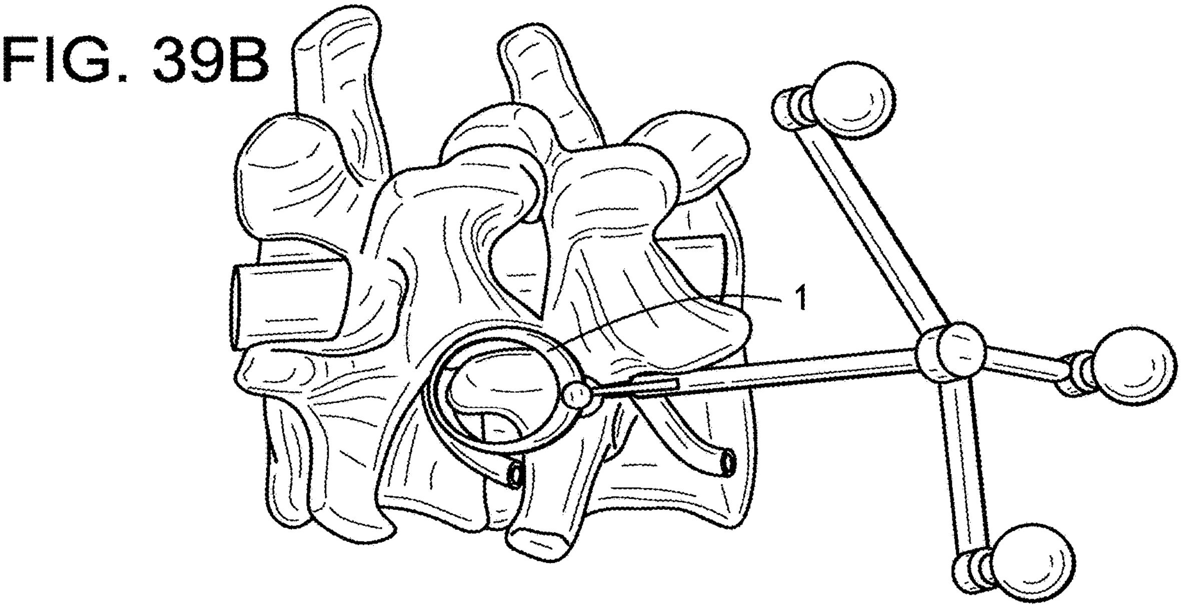

Now referring to FIGS. 39*a*-39*b*, the surgeon then dilates the tissue superior to the pedicle-based anchor, and inserts an outer shield 1, connected to the anchor, with its proximal end directed to the superior articular process. Blunt dissection up to the bone is carried out over the affected intervertebral disc, and muscle retraction over the affected intervertebral disc is then carried out. This retraction involves blunt dissection of the muscle and fascia to bone level under direct visualization.

Figure 40:
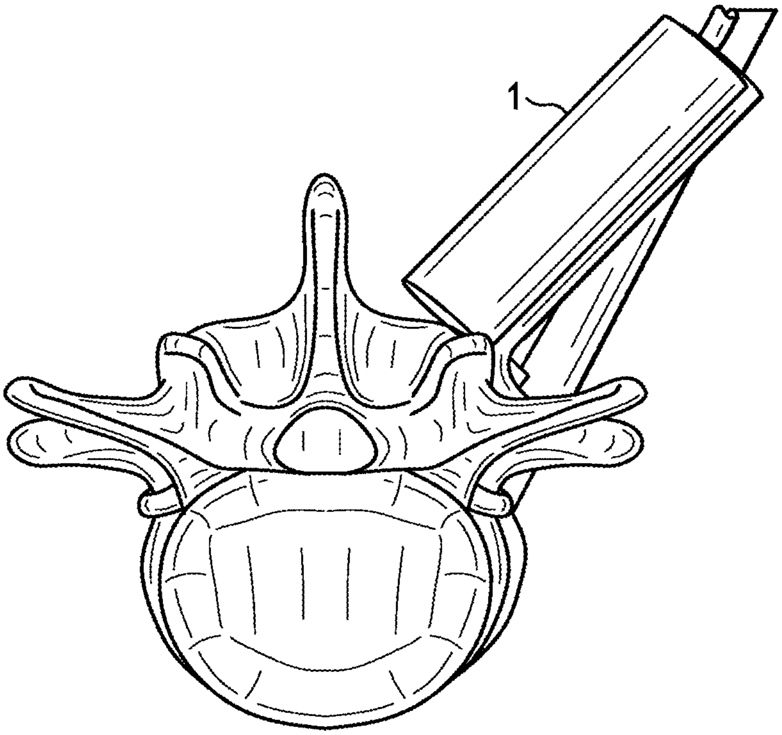

Now referring to FIG. 40, the surgeon then turns the outer shield 1 to the interlaminar space, preforms a central, bilateral decompression as required by the pathology, and then turns the shield back to its original position.

In some embodiments, an alternative to angling the access channel medially from the incision site could be the use of an alternative access site that would be more medial. In some embodiments, the initial anchoring point in the disc space will be medial to the inferior articulating process. For the embodiment having an initial anchoring point in the facet capsule, the dilation of the eccentric dilators will be medial from the capsule. Also, portions of the lamina and the inferior articulating process will be removed through the bone removal segment.

Figure 41:
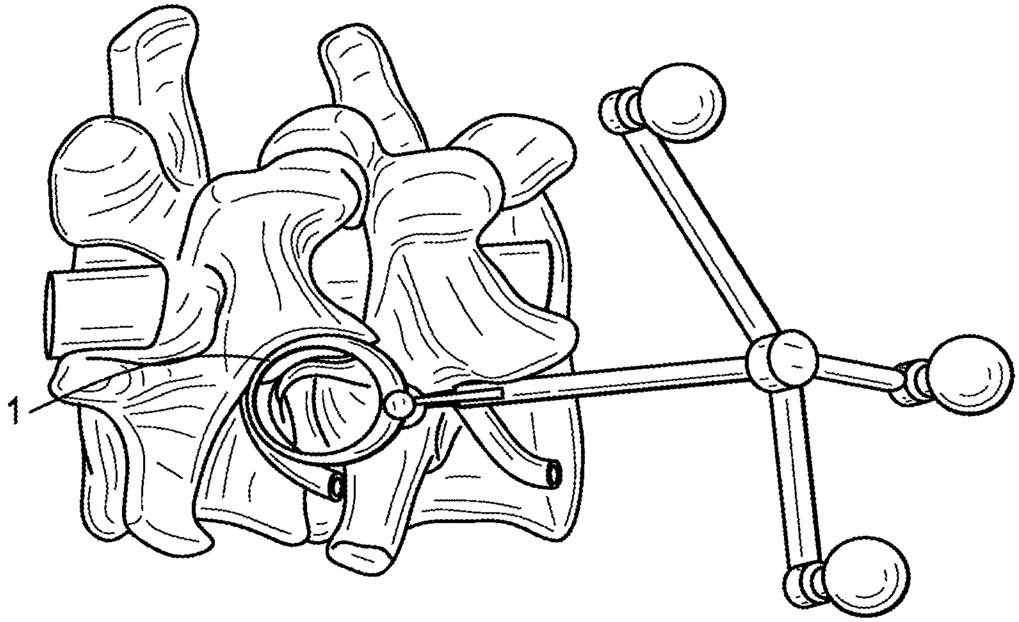

Now referring to FIG. 41, the surgeon then inserts a bone removal tool (not shown) into the outer shield tube and resects the lateral portion of the superior articular process to medially extend the traditional Kambin's triangle.

Under either direct or endoscopic visualization, a bone removal device is introduced to the outer shield and utilized to remove at least the lateral portion of the SAP. Such a device is available in lengths and sizes allowing for its safe introduction and use through an access window from 40 mm to 200 mm and a window size from 10 mm-25 mm.

In one embodiment, this bone removal device is an ultrasonic cutting device. In another embodiment, this bone removal device is a reciprocating cutting surface. In yet another embodiment, this bone removal device is a revolving cutting tool. In another embodiment, this bone removal device is a mechanical punch with a stroke length between 10 mm-30 mm. Removal of the bone can be performed in such a manner that sizes smaller than the access size will be excised and removed. The bone removal can be performed with the use of a template independently inserted into the outer shield and used to guide the direction of bone cutting and removal.

A Negative Template is a plug-like device that is inserted in the outer Access Tube. It contains a longitudinal cut-out in different shapes, depending on the cross-sectional shape of the tissue that needs to be removed respective of the cross-sectional shape of the tissue that needs to be covered and therefore protected from any surgical interactions. By inserting a cutting device like, e.g., a Milling Bit, into the longitudinal cut-out the surgeon is able to remove the tissue without the risk of endangering the covered tissue/structures. In combination with a proximal stop-system (on proximal end of outer Access Tube and/or shaft of milling system) the surgeon can remove the tissue layer by layer. The layer thickness and therefore the progression of the cutting procedure can be controlled via the stop system supported by a scale. This system allows the surgeon to perform safe tissue removal with a controlled serial work flow: check anatomical situation→adjust stop system to define cross-sectional thickness of tissue that needs to be removed→insert milling system until the stop system is engaged→mill/cut tissue (also blindly) in plane (2D)→remove milling system→check anatomical situation→adjust stop system.

A serial workflow can be considered to be safer than a parallel workflow, since the surgeon only needs to take care of one parameter at a time (here: planar position of milling bit followed by its depth followed by planar position of milling bit . . . ) whereas a parallel workflow requires the control of two or more parameters at a time (here: planar position of milling bit in parallel to its depth).

Navigation of SAP Removal can be carried out with the aforementioned bone removal device adapted to be navigated through its mechanical or visual connection with a navigation system.

Figure 42:
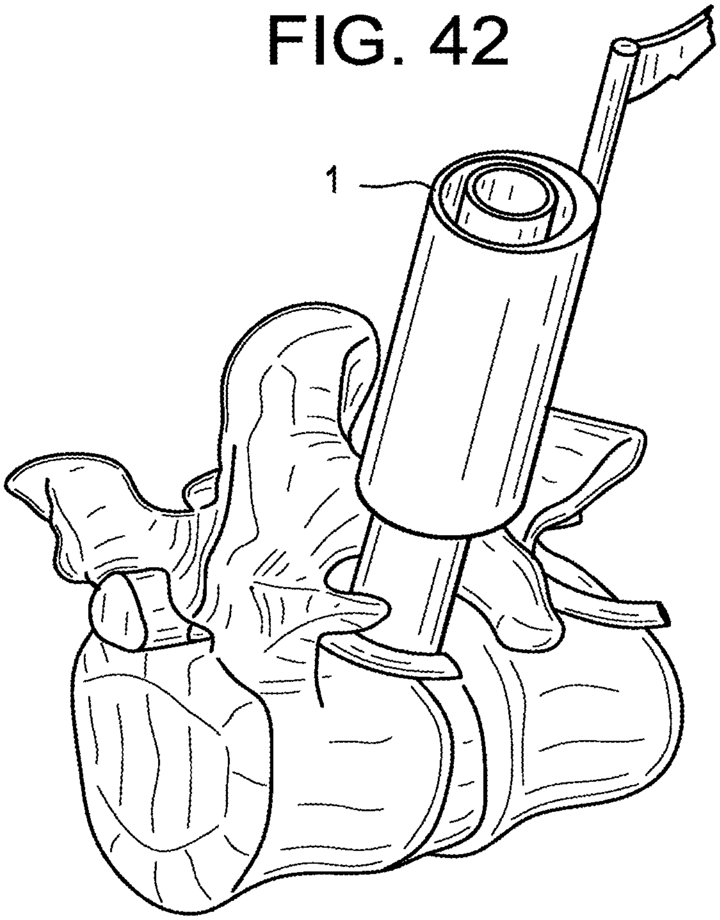
Figure 43:
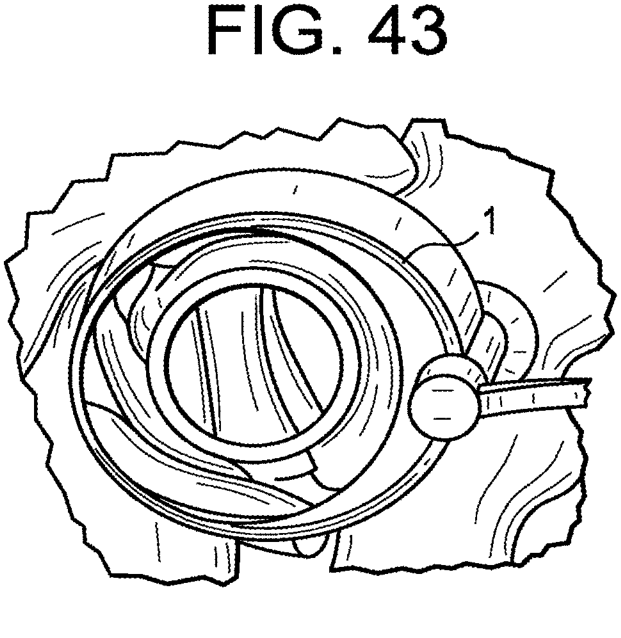

Now referring to FIGS. 42-43, the surgeon then inserts the inner shield tube into the outer shield tube, which acts to extend the outer tube anteriorly from the facet line until the tip of the inner shield reaches the level of the disc. The nerve root is protected by the inner shield.

Figure 44:
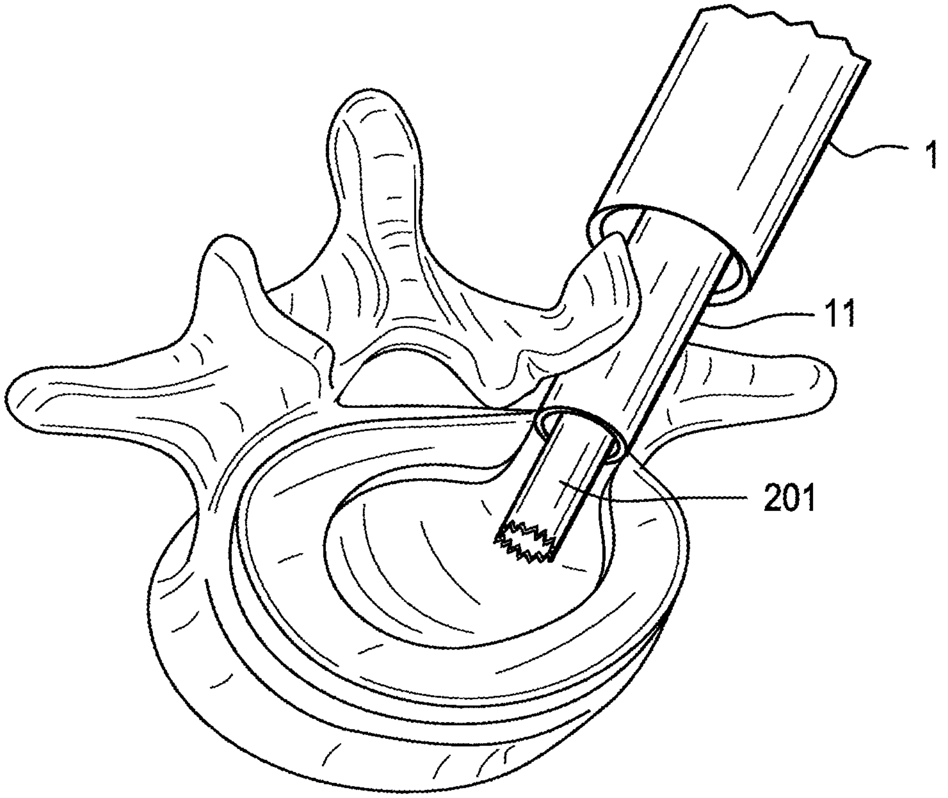

Now referring to FIG. 44, the surgeon then identifies the disc, spreads the disc with a wedged osteotome; checks the mobilization, and removes the posterior rim, osteophytes and annulus until a minimum annular window is opened. The surgeon then inserts a disc removal tool 201 into the access device, removes the disc and prepares the endplates.

An alternative embodiment to the prescribed disc clearing step in FIG. 44, would be to have the disc removal tool navigated through its mechanical or visual connection with a navigation system.

Figure 45:
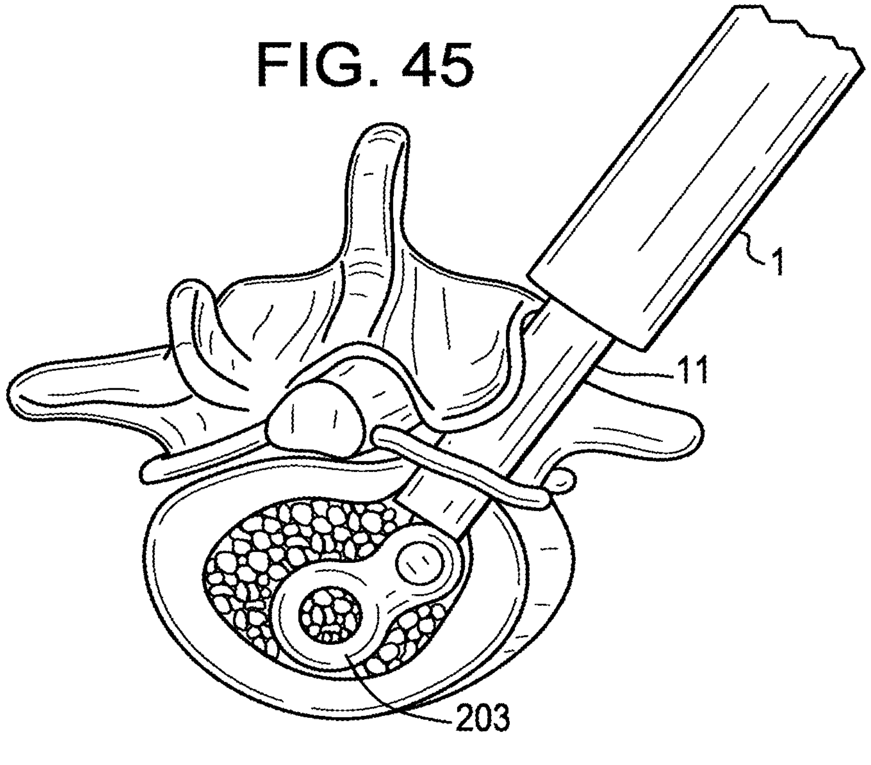

Now referring to FIG. 45, the surgeon then performs temporary disc space distraction, fills parts of the disc space with bone graft and inserts a fusion cage 203 into the remaining disc space.

Figure 46:
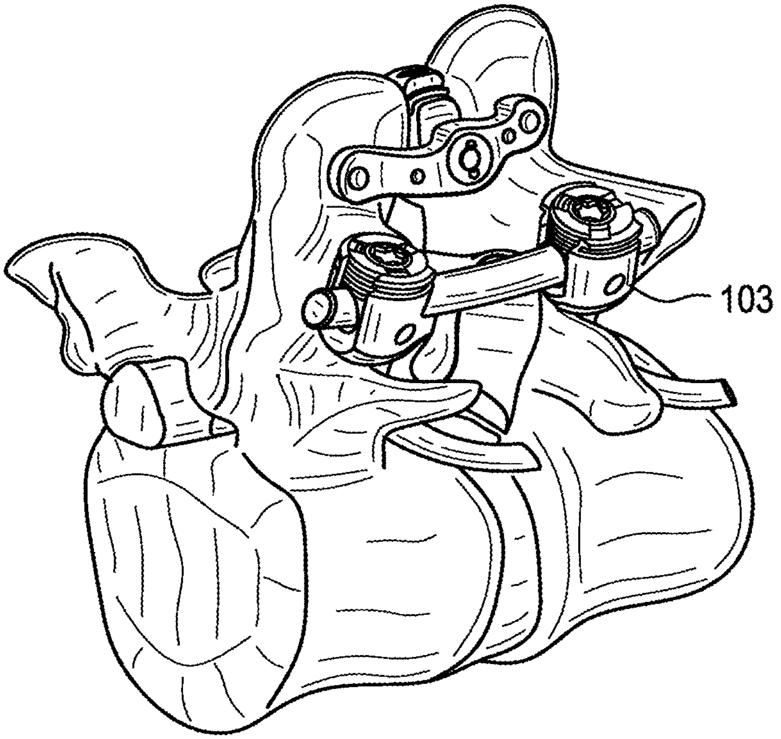

Now referring to FIG. 46, the surgeon then adds posterior fixation 103.

Viewing Element

In some embodiments, a visualization element based on the chip-on-tip technology and integrated into the wall of the port is used. This embodiment has a number of advantages over a standard rod-lens endoscope that is mounted at the tube wall:

Manufacturing costs. The chip-on-tip technology allows a very cost efficient manufacturing, therefore can be marketed as a 'single use' instrument.

Rigid portion only at distal tip. Whereas a standard rod-lens endoscope system has a stiff, cylindrical shape throughout the whole tube, the chip-on-top endoscope may have a non-cylindric configuration at the proximal outer tube end. Preferably, this shape is a flat cable shape. In some novel embodiments, in relation to a standard rod-lens-endoscope, the chip-on-tip endoscope has a relatively short "stiff" section (about 20 mm), where the proximal portion consists of a cable that can be flexible. In other embodiments, the stiff portion is shorter (producing a smaller chip-assembly) and actively articulating concepts are used to change the lens angle. Due to the cable's integration in the tube wall, the shape of the port window is maintained throughout the procedure. For example, a 5 mm chip on tip endoscope turns a 15 mm circular access window into a kidney shaped access window.

Size/weight of camera unit. A standard rod-lens endoscope has a standard eyepiece that is a universal interface with a certain size. The camera that is connected to such a system has to be built in a certain dimension to be compatible with the eyepiece. This requirement produces a relatively bulky camera attachment (approx. 3 cm-6 cm in diameter, approx. 5 cm-10 cm in length) having a number of drawbacks. First, this large camera construct can be a physical obstacle to work, especially if the trajectory of the working port changes or interferes with the camera. Secondly, the dimension and weight of this conventional construct becomes significant enough to produce certain undesirable forces upon the rod-lens-endoscope, especially in bending. Thirdly, the relatively fragile conventional rod-lens-endoscope has to be embedded in stabilizing structures such as metal tubes, thereby further reducing the active working window.

With the chip-on-tip embodiments disclosed herein having its chip cable embedded in the wall of the outer tube, the cable that exits at the proximal outer tube wall does not produce similar forces upon the working port. Also, respecting the attachment mechanisms that mount the chip-on-tip endoscope in the tube-wall, the lack of bending forces produced thereby raise the possibility of adopting relatively thin attachment options that mechanically do not need to be very stable.

Working Environment. Conventionally, a constant fluid environment (permanent flow of saline solution) is used in spine endoscopy applications. However, in a mini-open and microsurgical environment, the fluid environment is not helpful, as the anatomical conditions are very different. Accordingly, in the preferred novel procedures described herein, the chip-on-tip endoscope works in a dry, open air environment. However, the open, dry air environment in which the chip-on-tip endoscope is used may produce an undesired condensation effect upon the lens component of the endoscope. For example, a colder lens in a humid body temperature environment may fog up. Moreover, drill debris, burr debris or smoke from monopolar scalpels or hemostatic tools can likewise affect the lens of the endoscope so as to reduce visibility. Accordingly, it may be desirable to periodically clean the lens of the chip-on-tip endoscope.

Nerve Deflection (Tube in Tube)

In minimally invasive spine surgery conducted through portals, a set of dilators is often used to prepare the site for reception of the portal. One such technology is shown in US Patent Publication US 2012-0232552 (Morgenstern). In this conventional technology (which has eccentric dilators), the outer diameter of any one of the dilators is identical to the inner diameter of the next successive (outer) dilator. This identity of diameters is necessary for fluoroscopy assisted, percutaneous muscle dilation.

Since some embodiments of the present application describe a procedure between the level of the facet joint and the disc, the surgical site is dissected under direct visualization. Accordingly, the diameters of successive dilators used in these novel procedures do not have to match. Relaxation of the "exact diameter" requirement in these novel procedures allows the surgeon freedom in many tube design areas. For example, it allows the use of tubes that are tapered. It also allows the surgeon the freedom to use outer and inner ports that are not coaxial. It further allows the trajectories of the inner port relative to the outer port to vary in angulation within certain treatment steps. Lastly, it allows the trajectories of the inner port relative to the outer port to vary in distance within certain treatment steps.

Because fluoroscopy-assisted, percutaneous muscle dilation is carried out without direct visualization, it is a blind procedure whose use has limitations. These limitations include the inability to carry out surgical steps that require direct visualization out of safety considerations. One such treatment step requiring direct visualization is direct decompression of bony and ligamentous tissue that is directly adjacent to nerve structures.

Because some embodiments described herein allow for direct visualization of delicate anatomical structures, those embodiments further specifically allow direct decompression of bony and ligamentous tissue that is directly adjacent to nerve structures and more generally allow manipulation or removal of tissue adjacent the tubes through a very tissue-preserving "tube-in-tube" access port.

Morgenstern further describes a method in which a guide wire is directly introduced through the disc space to Kambin's triangle, under fluoroscopy guidance (i.e., no direct visualization). Morgenstern further describes the possibility of using electrically-based nerve monitoring probes. Moreover Morgenstern describes a method of enlarging the spinous process by subsequently rasping away bone from the SAP and the pedicle.

The novel procedures described herein only perform non-visualized procedures (e.g., dilation) in a safe zone above the facet line. In the anatomically more critical zone between the level of the facet joint and the disc, the novel procedures dissect the surgical site under direct visualization, thereby allowing the surgeon to spare as much of the bone as is possible and as is meaningful.

Navigation

Navigation enhances static x-ray, CT, or MRI data by intra-operatively showing in real-time where the instruments used actually are in relation to the anatomy of the patient. Therefore it increases the safety of those instruments by showing their shape, trajectory and positioning and even more importantly it supports the surgeon to keep instrument orientation during the performed manipulations.

Without wishing to be tied to a theory, it is believed that one reason why minimally invasive techniques are not often used is the significantly higher x-ray exposure needed to keep orientation in comparison to mini-open techniques, where the surgeon still has direct visualization and so can actually see the active site with a microscope or loupe. The x-ray exposure is an even greater for the surgeon who is exposed to the radiation on a frequent basis. This challenge is addressed by the implementation of navigation technology in the novel procedures described herein because they allow the reduction of x-ray exposure to an ideal minimal total of two x-rays for registration purposes. Once a single lateral shot and a single anterior-posterior shot have been registered, all used instruments (e.g., Jamshidi-Needle, Pointer, Dilators, Access Tube, Osteotome, Expandable Cage itself, Disc Removal Device . . . ) can be projected in these static fluoro-images in real time. Another positive effect is a significant savings of time. Having the navigation system in place also helps the surgeon to understand the orientation (trajectory and depth) of the endoscope and therefore to understand what he or she actually sees with the camera. This can either be achieved by navigating the camera directly or indirectly by setting the camera in a fixed position integrated into a navigated Access Tube.

The Jamshidi-Needle, Pointer, Dilators, and Access Tube Instruments can all be navigated with only one Instrument, the FOX-Navigation-Multi-Tool or "multi-tool." The multi-tool can include integrated or built-in neuromonitoring, e.g., for detecting the presence, proximity, health, or other attributes of nerve tissue. The multi-tool can include an electrode, transducer, or other energy delivery element for applying energy to tissue, e.g., to ablate or cauterize the tissue. The multi-tool can include an energy delivery element in the form of a microwave ablation element. The multi-tool can include an energy delivery element of the type used in the NEUWAVE system available from ETHICON, INC. of Cincinnati, Ohio. The energy delivery element can be built-into the multi-tool, or can be supported or guided to a target location using the multi-tool. The energy delivery element can be mounted on a shaft or needle coaxially received within or around another shaft component of the multi-tool. The multi-tool can be used to position the energy delivery element in proximity to a target location, such as an osseous bone tumor. Energy can be delivered from the energy delivery element to the tumor or other target location.

Figure 47A:
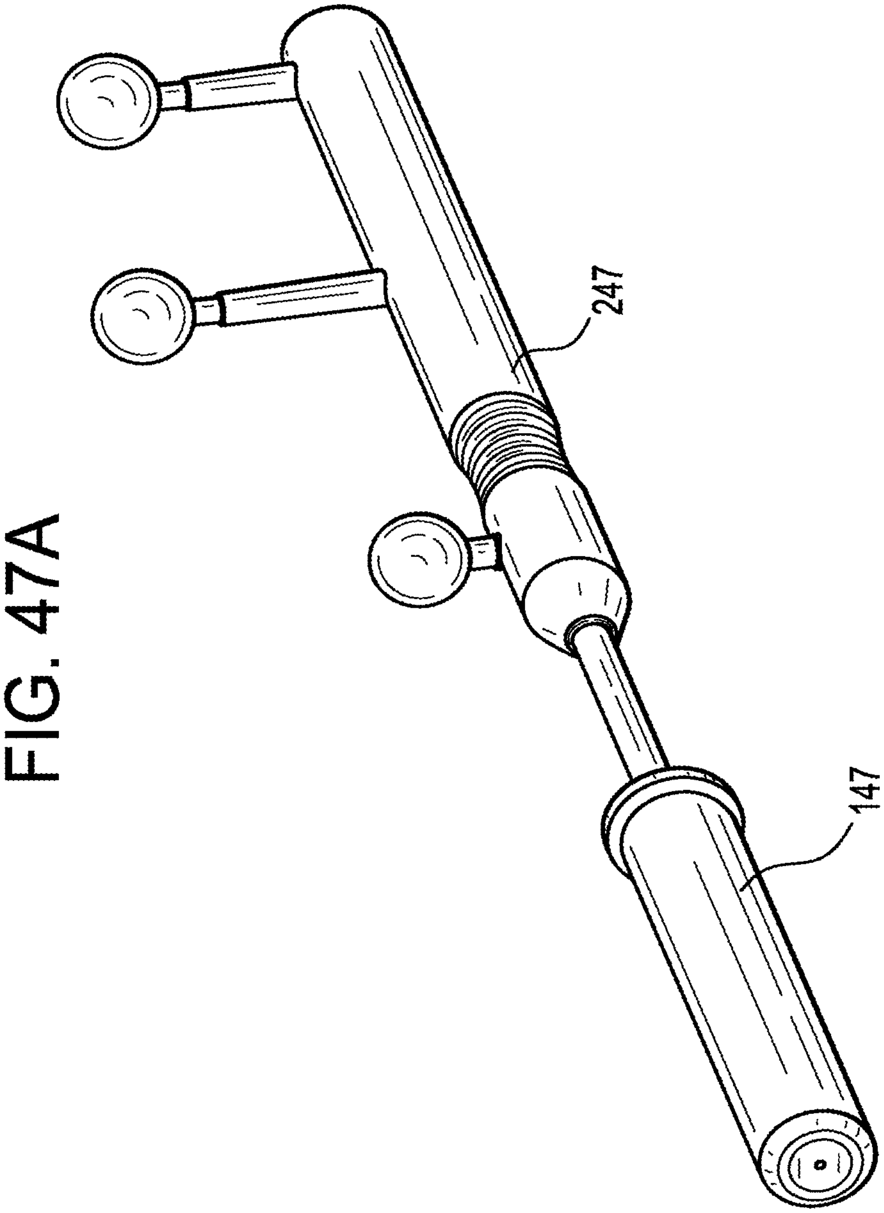
FIGS. 47*a*-47*c* disclose a Navigation plug comprising a base having an array attached thereto, wherein the plug is adapted to fit within an outer tube.
Figure 47B:
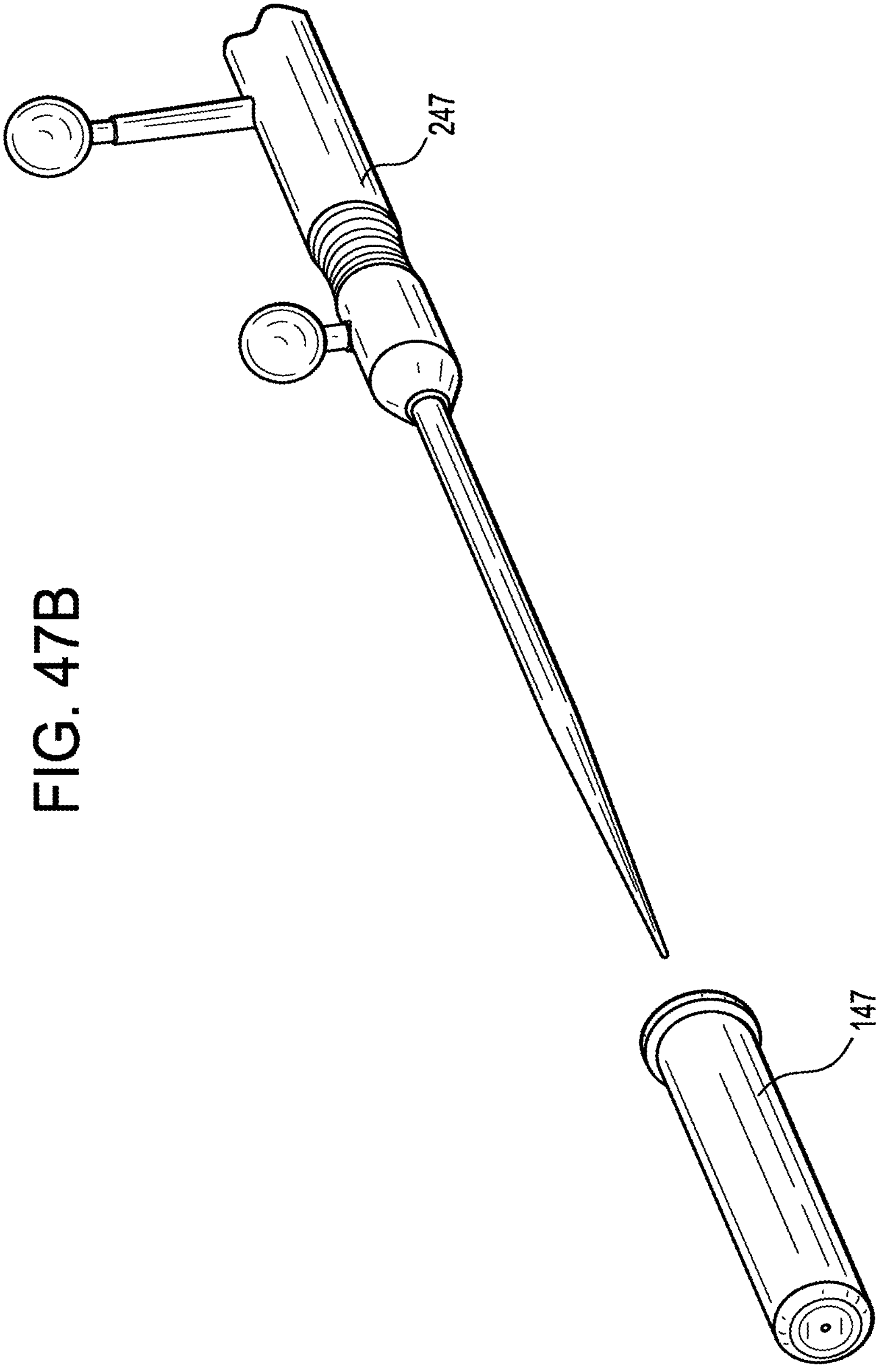
Figure 47C:
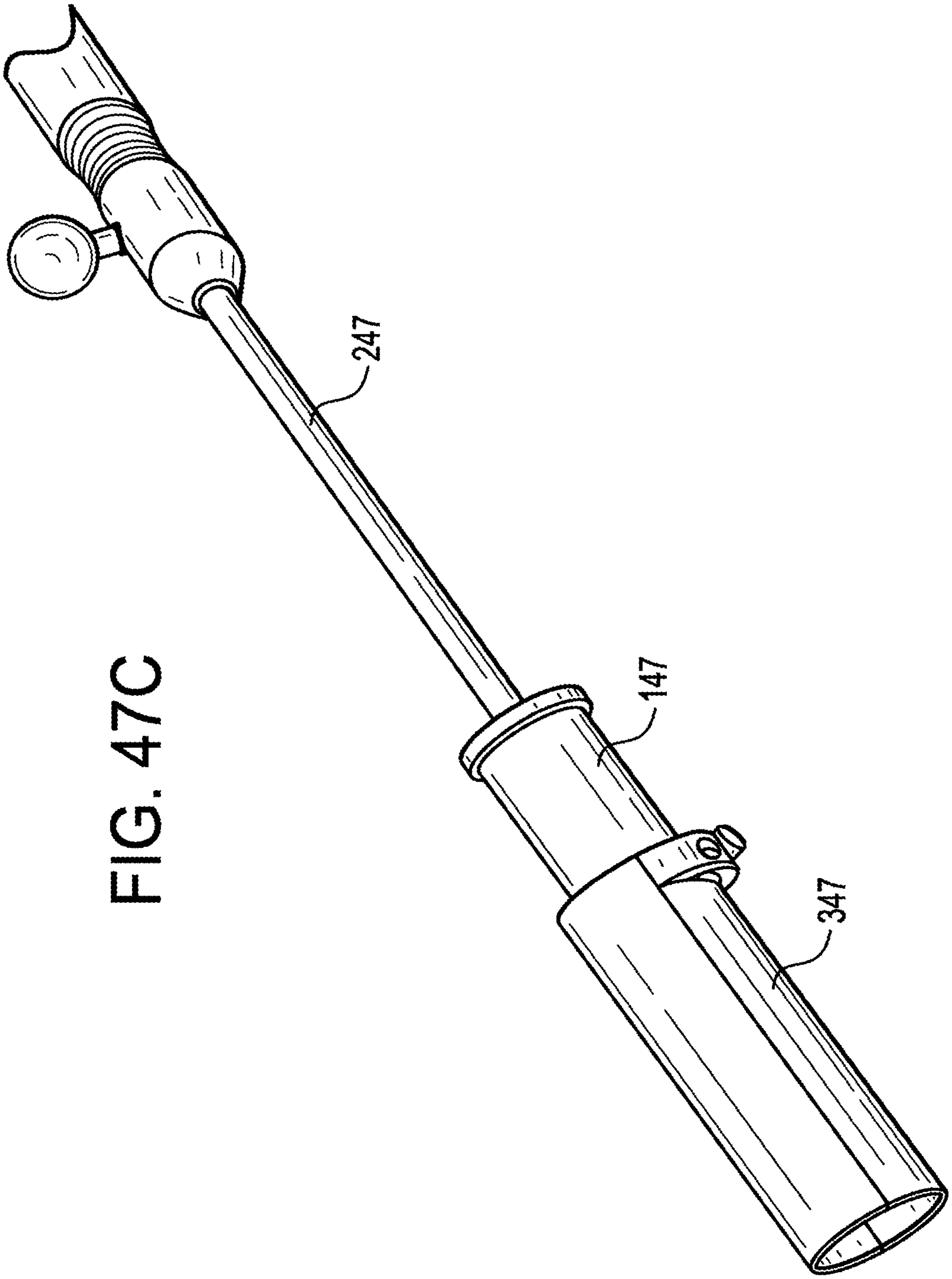

FIGS. 47*a*-47*c* disclose a Navigation plug comprising a base 147 having an array 247 attached thereto, wherein the plug is adapted to fit within an outer tube 347.

Bone Cutter

In some embodiments, the novel procedures use an Ultrasonic Bone Cutting device for SAP removal, which specifically cuts bone only and will not cut soft tissue. Embodiments based on a conventional Expandable Cage Device for interbody fusion may require an access window at least as large as 12 mm. Such a large window can only be achieved by (partly) removing the Superior Articulation Process (SAP) to extend the Kambin's Triangle. The Ultrasonic Bone Cutting Device adds significantly to the safety of this procedure since it does not cut nerves if accidently hit. If the cutting device blade is designed to be in the shape and diameter of the Inner Tube/Blade (i.e., a Cookie Cutter design) that approaches distally down to the level of the disc space, the SAP removal can be minimized (less trauma, less stress for patient, quicker recovery) and performed in a single step (faster than multiple step procedure).

Figure 48:
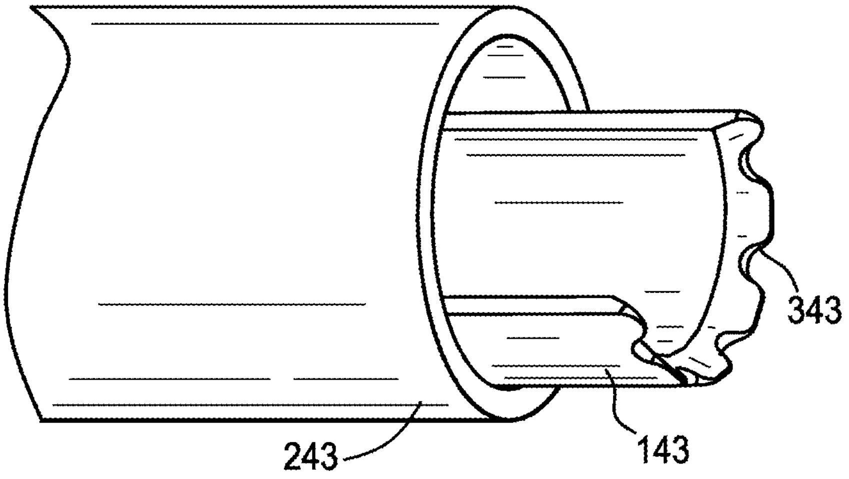
FIG. 48 discloses the cookie cutter-type distal end of an ultrasonic cutter extending from the end of an outer tube, wherein the distal end has a plurality of cutting teeth.

FIG. 48 discloses the cookie cutter-type distal end 143 of an ultrasonic cutter extending from the end of an outer tube 243, wherein the distal end 143 has a plurality of cutting teeth 343.

Another option to increase the safety of bone cutting is a depth-controlled manual milling of the bone with a negative guide. The negative guide covers those areas that will not be removed (negative template). The depth control allows the milling of the bone layer by level, under serial control of the surgeon. The reference for the depth control as well as the trajectory can be the outer Access Tube (also see paragraph navigation).

Figure 49A:
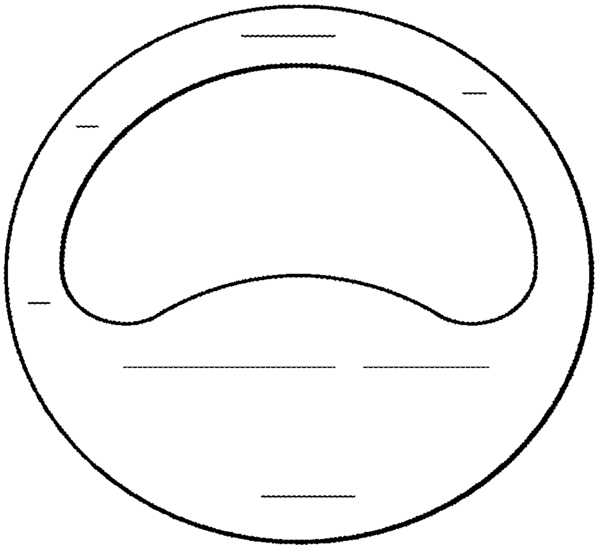
FIGS. 49*a*-49*b* disclose various cross-sections of the template for guiding a bone cutting device.
Figure 49B:
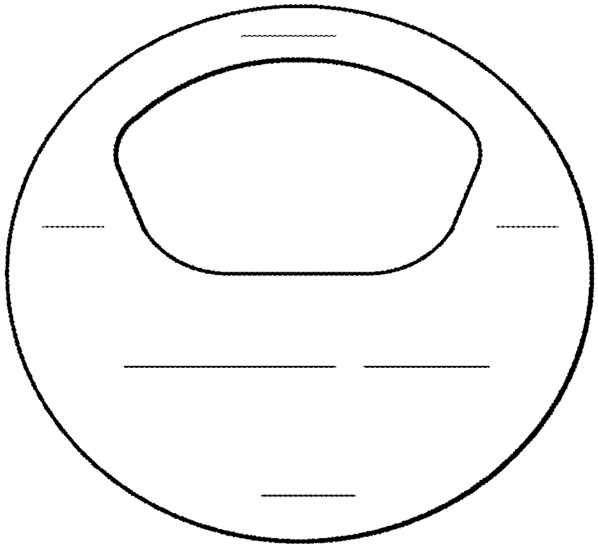

FIGS. 49*a*-49*b* disclose various cross-sections of the template for guiding a bone cutting device.

Bone Cutter

In some embodiments, the bone removal device is a harmonic scalpel having a cookie cutter design. The scalpel has a crescent-shaped cutting surface that interfaces with the outer tube. The scalpel is used as a single pass instrument, removing a predetermined amount of bone in a single pass. In some embodiments, the scalpel also has a tube that sprays water for irrigation, while the outer tube has a suction line for clearing the slurry of removed bone.

In some embodiments, the scalpel can be navigated and ride down a slot provided in the inside wall of the outer tube. The slot depth can be predetermined to provide depth-controlled milling, and to control where cutter goes. This is advantageous because it is believed that freehand cutting hits the nerves too easily. The shape and size of the cutting surface can define the specific area of bone to be removed. The specificity of cut is advantageous because it minimizes the amount of bone removal, which is beneficial in the highly enervated facet. Thus, a quicker procedure, less trauma (less pain), and more stable construct is realized.

Viewing Element (Olive)

In some embodiments, the chip viewing element can be angulated so it can see around a corner of the tube.

In a conventional endoscope, visualization is 2D (i.e., no depth perception), and so two nerves may look close together when they are actually 2 cm apart. Thus, in some embodiments, the endoscope is modified so that the chip acts like a range finder. In particular, the chip identifies and assesses a reference feature that is a known distance from chip, and then measures how far away a nerve is from chip (which is the tube end) based on that assessment.

Nerve Deflection (Tube in Tube)

In some embodiments, the outer shield has a pressure sensor thereon to measure the stress on the nerve. Using ultrasound techniques that can measure distance, the system can measure the elongation of nerve under retraction and define a maximum elongation limit (e.g., 20%), and then warn the surgeon if the elongation limit is exceeded. In some embodiments, the system integrates ultrasound into the port and thereby navigates the port.

In some embodiments, the surgeon navigates the camera. This allows the surgeon to understand orientation of the camera.

In some embodiments, visualization provides an axial view of the disc, so the surgeon can understand the location of the disc removal tool.

Neuromonitoring Analytics

Currently, neuromonitoring devices can be used to obtain an indication of potential nerve health or nerve damage, which may be induced in a surgical setting. This indication of nerve health is achieved by measuring electrical impulses between a nerve near a surgical site and a far end of the nerve. For example, impulses may be measured between a nerve root at the spine and some point found on the legs.

Nerve damage can be caused through direct manual contact with a nerve. Apart from gross damage such as severing or crushing the nerve, other lesser forces imparted on the nerve can also cause damage. For example, displacing the nerve, stretching it, or compressing it can cause significant damage. In some cases, extended application of such forces to the nerve can reduce blood flow through the nerve, again causing nerve damage. Often times, this exposure time is dependent on the amount of force applied. Accordingly, there appears to be no known steadfast rule as to how long the surgeon may be able to load a nerve.

Alternate forms of evaluating potential nerve damage besides neuromonitoring may bring new insights into nerve protection during a procedure. In this regard, nerve manipulation measurement could yield an indication of risk to the nerve. If a nerve is displaced for the procedure, it may be elongated or it may be displaced laterally. These alterations in the nerve's physical features could be measured and used to predict potential nerve damage. Accordingly, other potential features could be measured and used to predict potential nerve damage include arc length and the diameter of the nerve itself etc. These features may be measured in quantifiable terms via techniques such as ultrasound. The resulting measurements are and then analyzed (via software or manually) in terms of absolute value, percent change, or some other metric indicative of potential nerve risk/damage that can be obtained from a database or library. In some embodiments, these metrics can be used as predictors of the safe length of time that a nerve can have a given displacement or deformation without causing long term damage. Calculation or algorithms can also be used to determine a maximum safe deformation, or a maximum allowable time during which a nerve can have a given deformed feature.

This measurement could be obtained in many ways. It can be measured manually, optically or through some other form of imaging. This could occur in an open procedure, subcutaneously in an MIS or other type of procedure. Direct visualization could be completed with the use of a camera. Before and after images could be interpreted to calculate the amount of absolute deformation or percent change. The measurements can be obtained through modalities such as ultrasound, or other forms of imaging that can "see" soft tissue or identify nerve tissue relative to the surrounding tissue (X-ray, CAT/PET scan, MRI etc.).

Other measurement methods that can be used in accordance with this embodiment may include a) measurement of density change within the nerve due to loading, or b) change in blood flow. Such measurements can be obtained through radar, ultrasound, and other imaging methods.

In some neuromonitoring embodiments, it may be possible to measure impedance within the nerve or impulses, wherein this may be done locally relative to the specific deformation area of the nerve. In particular, in some embodiments discussed herein, the nerve shield could have a sensor on opposite edges of the shield that would contact the same nerve in two different nerve locations. These sensors would allow the surgeon to read electrical values such as impulses or resistance, before nerve distention and then measure it again as distention occurs or is achieved. The difference in these measured values could be an indicator as to the level of deformation. Any of the neuromonitoring features described above or elsewhere herein can be incorporated into or included in the multi-tool. For example, the above-described sensors can be mounted to a shaft component of the multi-tool, which can be used to position the sensors in proximity to nerve tissue.

Figure 50:
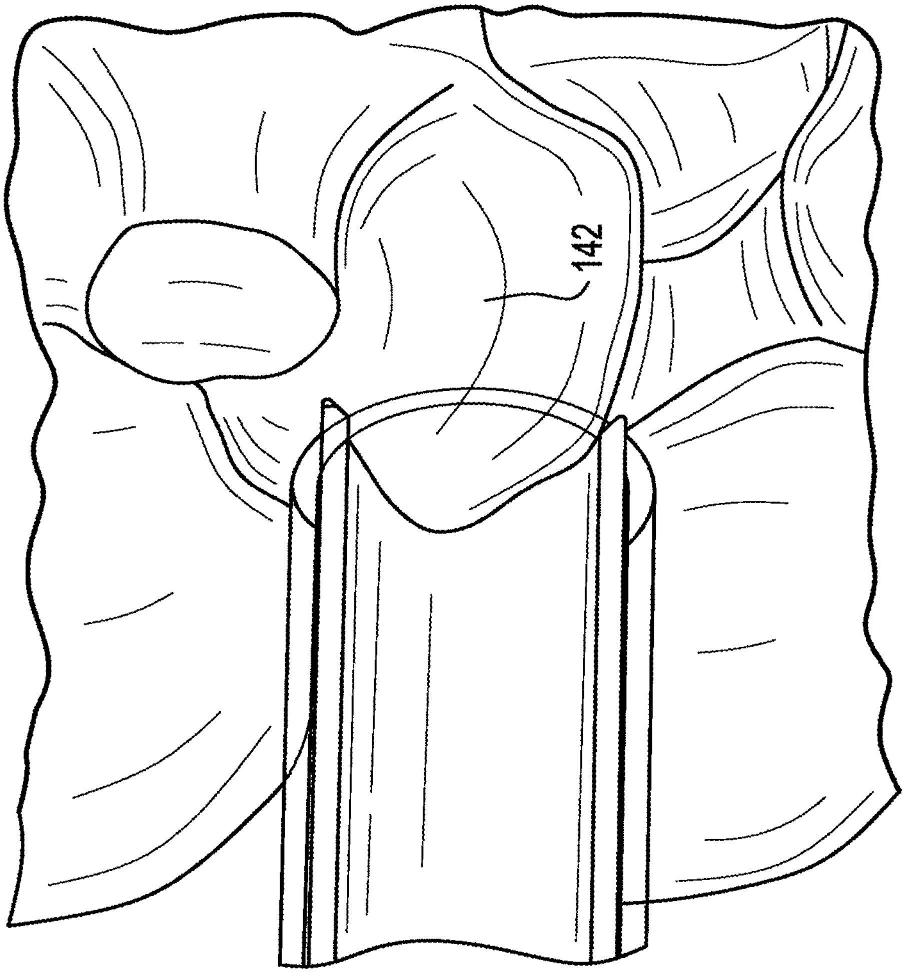
FIG. 50 discloses a cookie cutter-type distal end of an ultrasonic cutter having a semicircular cutting piece cutter bone.

FIG. 50 discloses a cookie cutter-type distal end 142 of an ultrasonic cutter having a semicircular cutting piece cutter bone.

Figure 51:
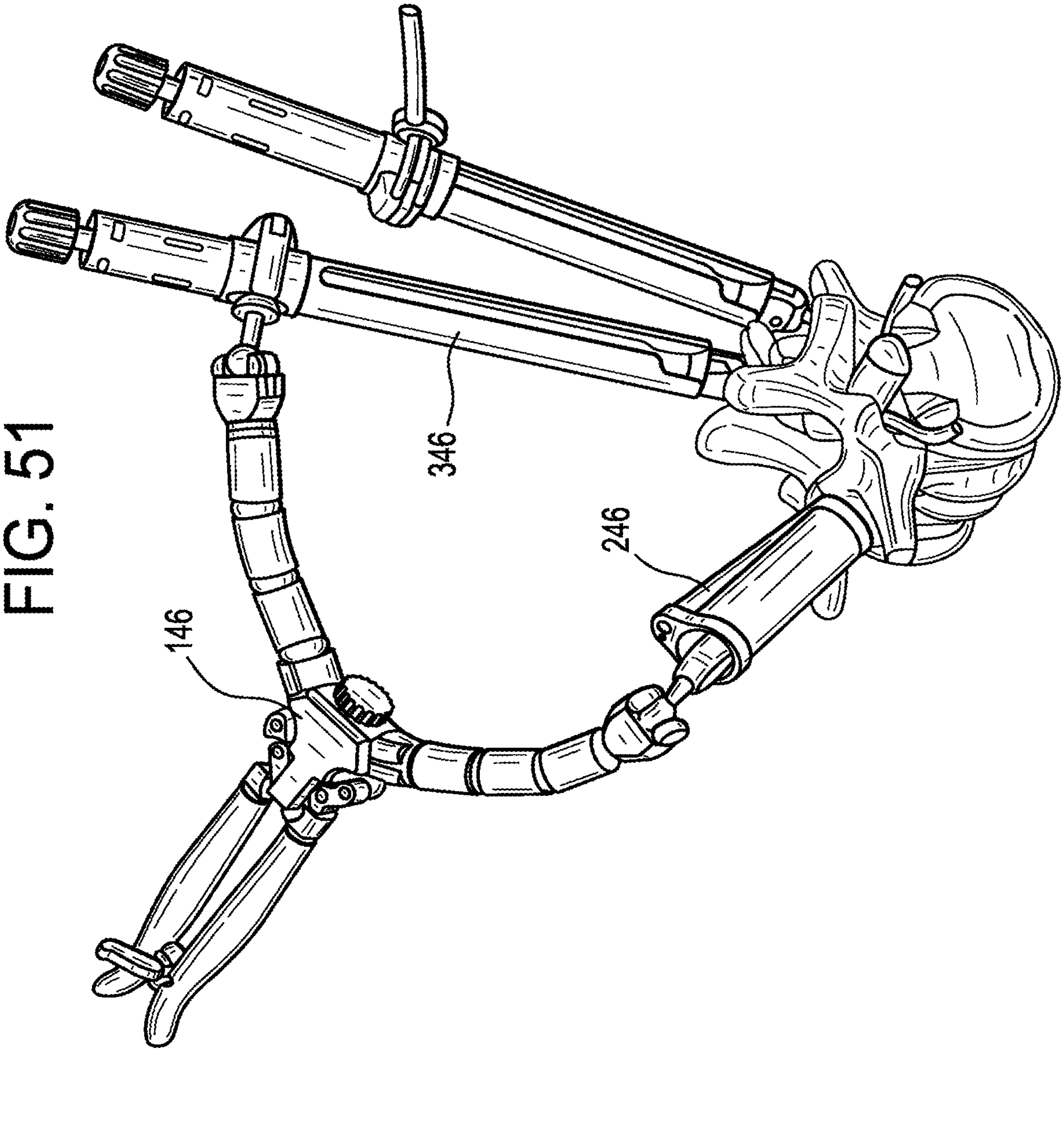
FIG. 51 discloses a mini flex arm connecting an outer tube and a screw extension.

FIG. 51 discloses a mini flex arm 146 connecting an outer tube 246 and a screw extension 346.

Figure 52:
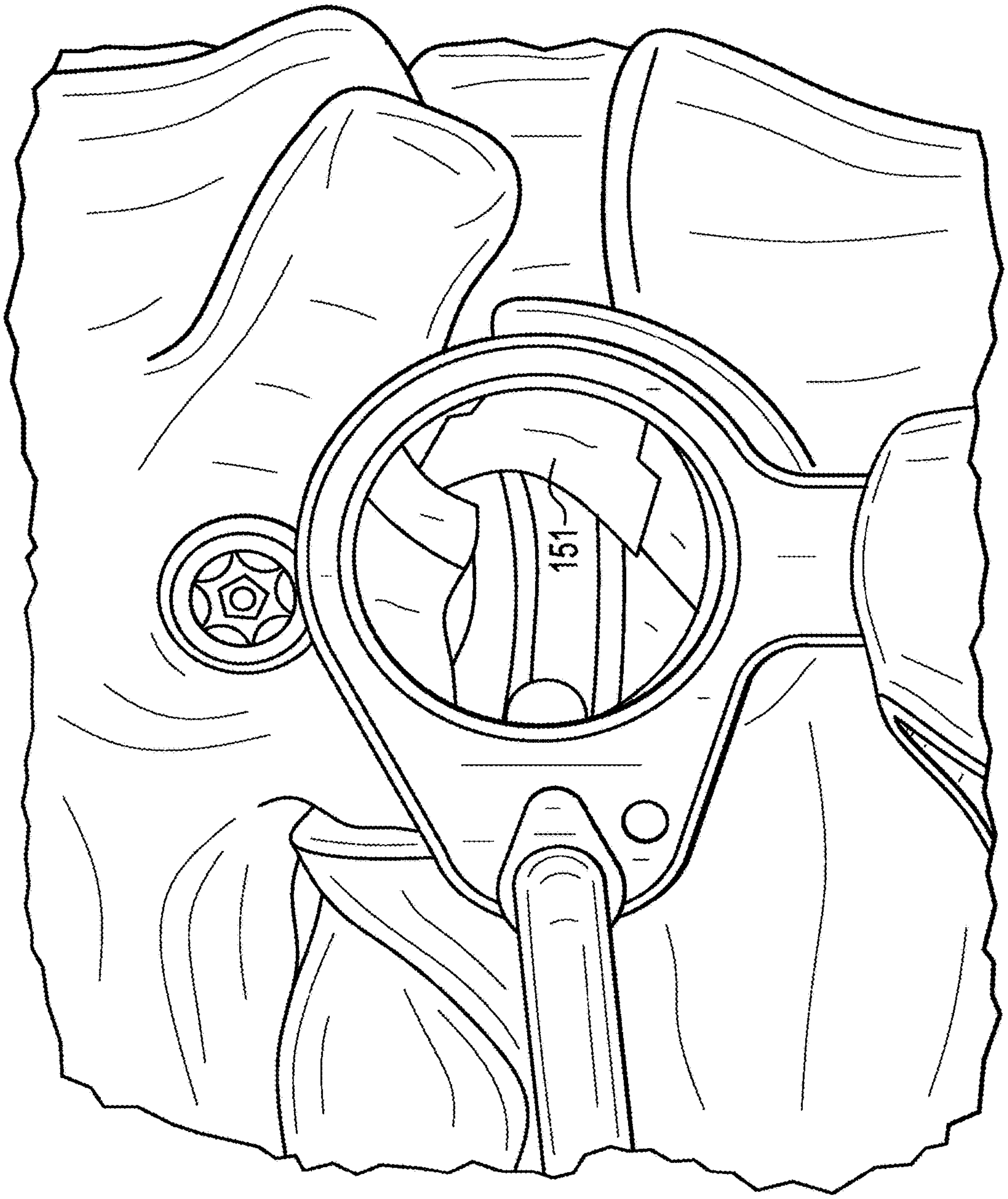
FIG. 52 discloses an outer tube/inner retractor assembly wherein the inner retractor is tilted inwards to retractor soft tissue.

FIG. 52 discloses an outer tube/inner retractor assembly wherein the inner retractor 151 is tilted inwards to retractor soft tissue.

Figure 53:
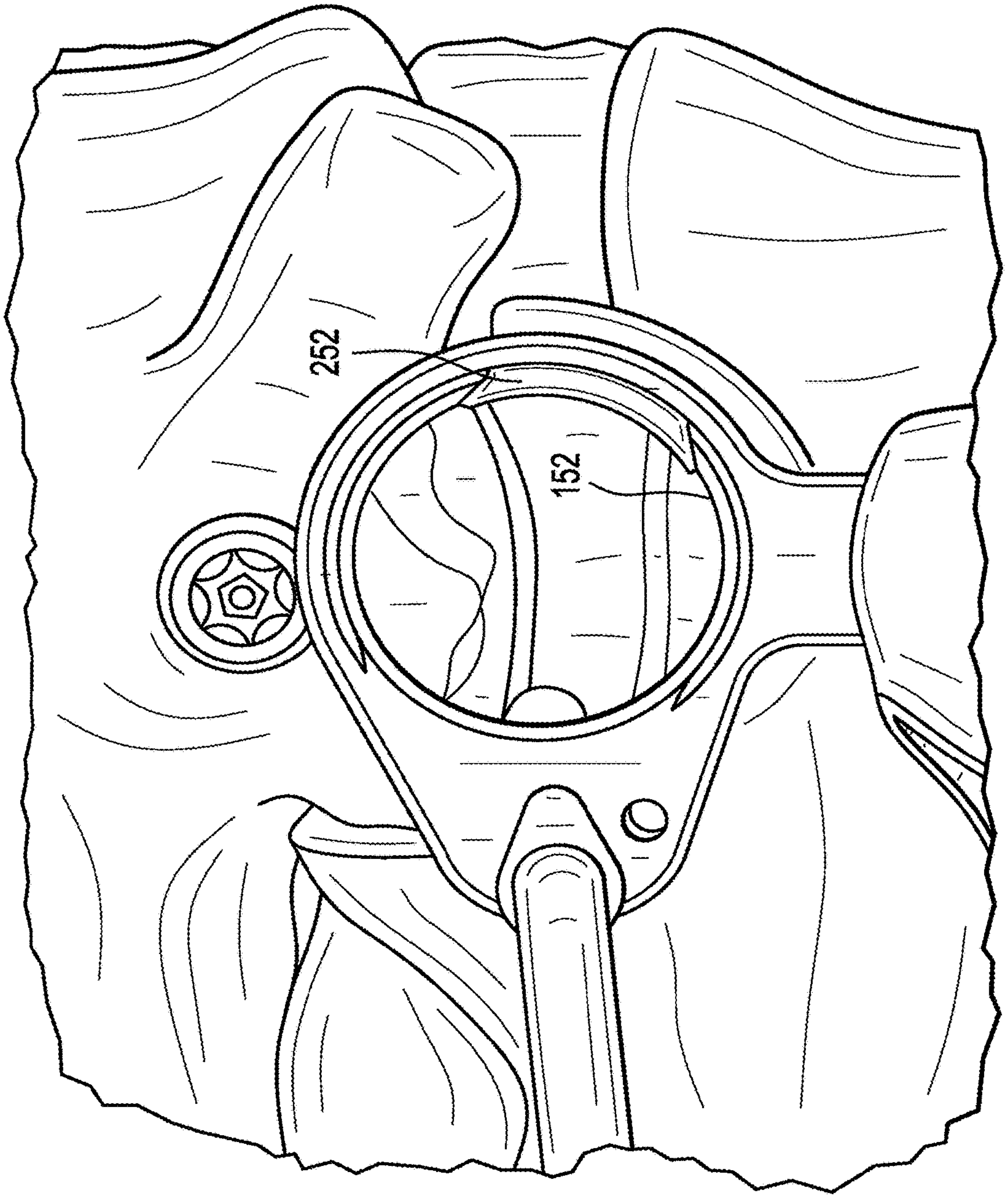
FIG. 53 discloses an outer tube/inner retractor assembly wherein the inner retractor runs parallel with the outer tube.

FIG. 53 discloses an outer tube/inner retractor assembly wherein the inner retractor 152 runs parallel with the outer tube 252.

Figure 54:
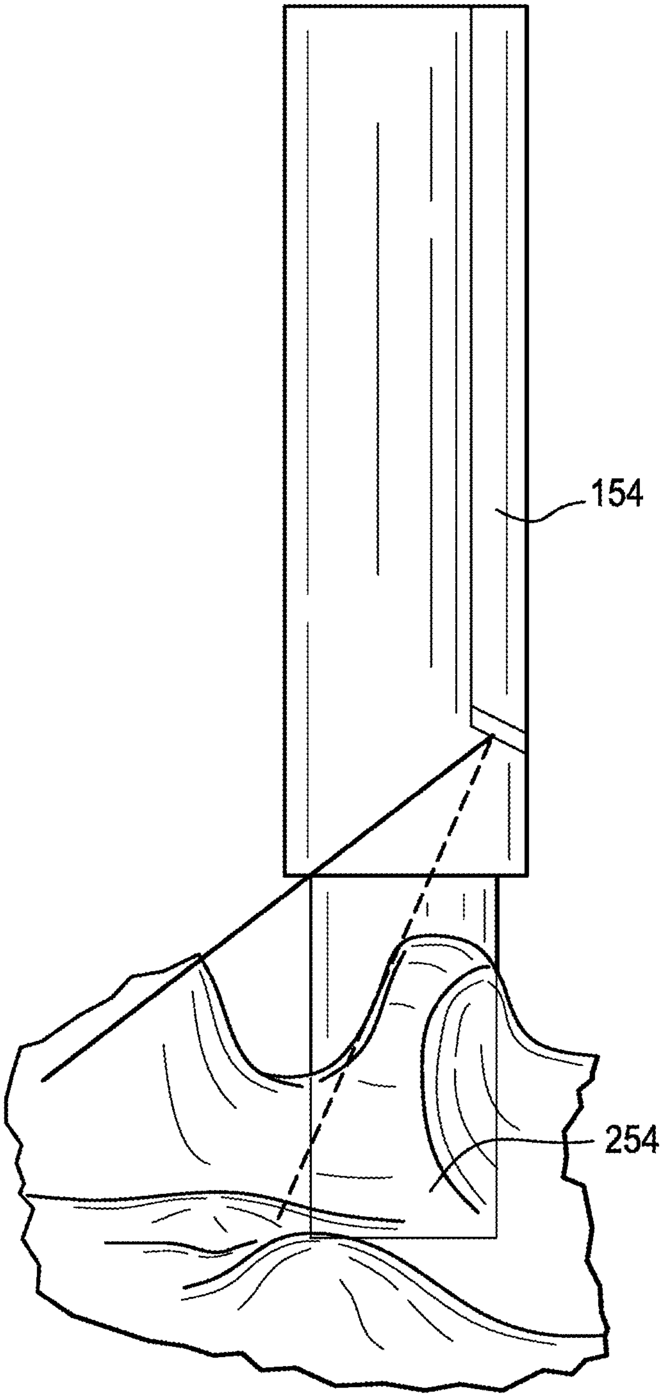
FIG. 54 discloses an endoscope housed within an outer tube, and an inner tube extending from the outer tube.

FIG. 54 discloses an endoscope 154 housed within an outer tube, and an inner tube 254 extending from the outer tube.

In many embodiments disclosed above, an inner shield nests within an outer shield. In an alternative embodiment to all such embodiments, however, the inner shield is replaced with a removable blade that is integrated into a cutout formed within the wall of the outer shield. In such cases, the outer surface of the inner shield substantially nests within the outer surface of the outer shield so that the flange extends distally past the distal end portion of the outer shield.

In many embodiments disclosed above, the proximal end portion of the substantially tubular portion of the inner shield comprises a stop adapted to abut the proximal end portion of the outer shield, the stop being adapted to prevent excessive distal movement of the inner shield. In other embodiments, the abutment occurs anywhere along the outer shield.

FIGS. 55-63 disclose some of the instruments used in preferred procedures disclosed herein.

Pedicle Post w/ Reference Array

Figure 55:
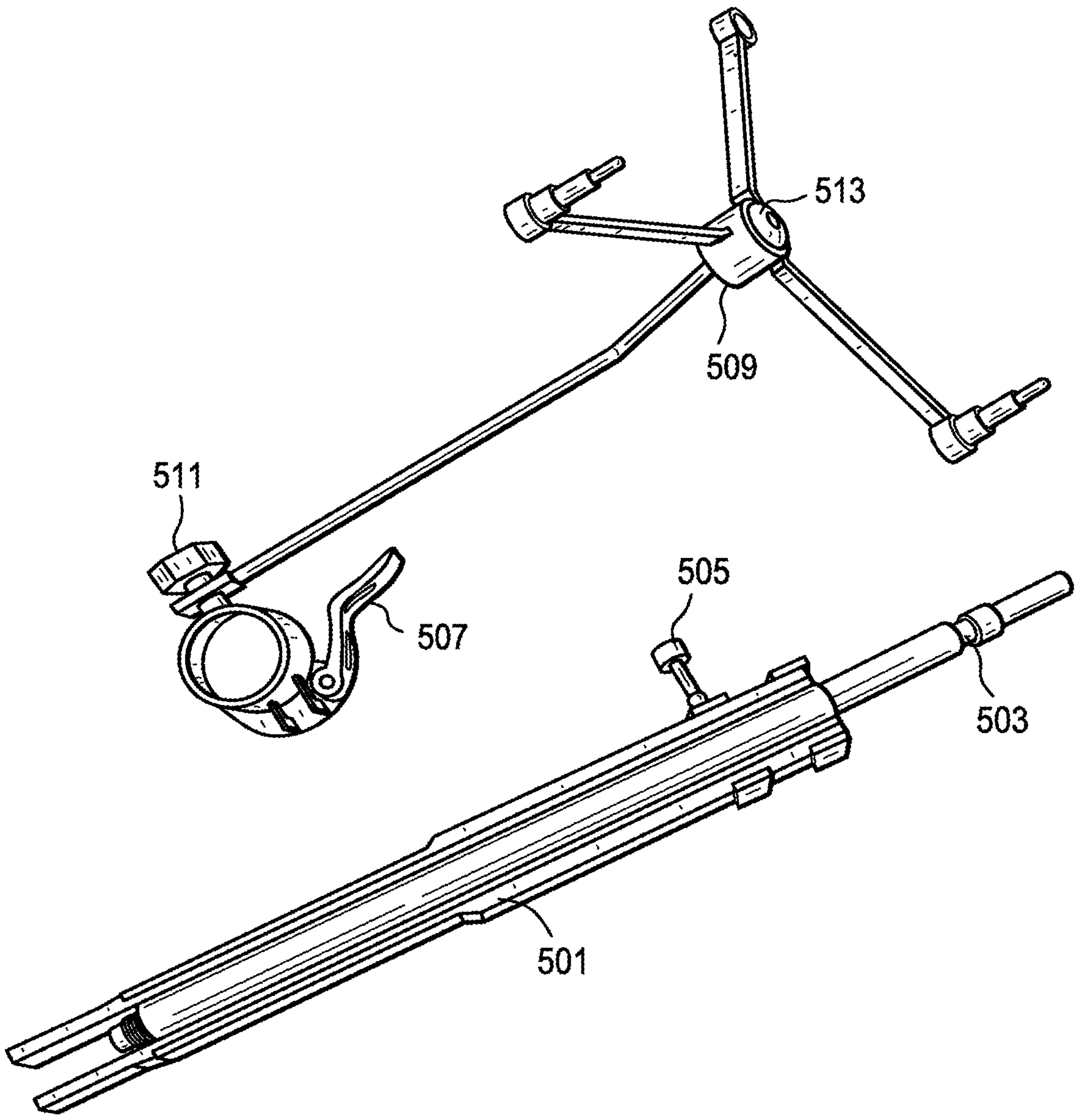
FIGS. 55-63 disclose some of the instruments used in preferred procedures disclosed herein.

Now referring to FIG. 55, a first step of a navigated procedure is the placement of a Pedicle Screw (such as Viper 2 or Viper Prime, available from DePuy Synthes Spine, Raynham, MA) in the contralateral caudal vertebral body followed by the insertion of a center core 501 including a polyaxial blocking post 503, which engages with the thread for a locking cap of the Pedicle Screw. When tightened, the polyaxiality of the screw is fully blocked. A screw 505 locks the Center Core with the Polyaxial Blocking Post. A clamp 507 with an eccentric lever securely connects the Reference Array 509 on the Pedicle Post. Two additional screw connections 511, 513 allow the surgeon to align the Reference Array set up with the cameras to the navigation system, which are most commonly places at the caudal side of the patient.

The Reference Array should directly be mounted on Blocking Core (see Pedicle Anchor). In some embodiments, there is an adjustable orientation of the array on the post. In some embodiments, care is taken to make sure that the distance between the handle and the top of the counter-torque insert is greater than the length of the screws. In some embodiments, the navigation array is strong enough to act as counter-torque for polyaxial blocking (which would be done before registration).

Multi-Tool

Figure 56:
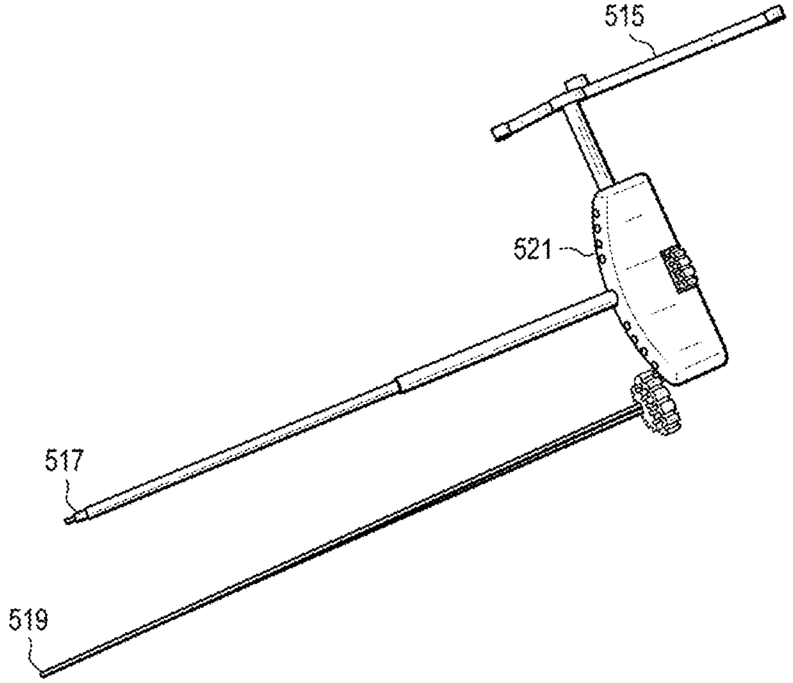

Now referring to FIG. 56, there is provided a Multi-Tool probe comprising a main body 515 including a Navigation Array (single piece), a Blunt Mandrin 517, a Sharp Mandrin 519, and a Detachable Handle 521. This set of features allows the surgeon to use the device as a Navigation Pointer (with Blunt Mandrin), a navigated Jamshidi-Needle (Sharp Tip), and a device to navigate the insertion of Dilation Tubes as well as the Access Tube (see below). This tool uses a single array and the resulting single registration procedure covers four functions. In some embodiments, the array is part of a detachable handle.

Figure 56A:
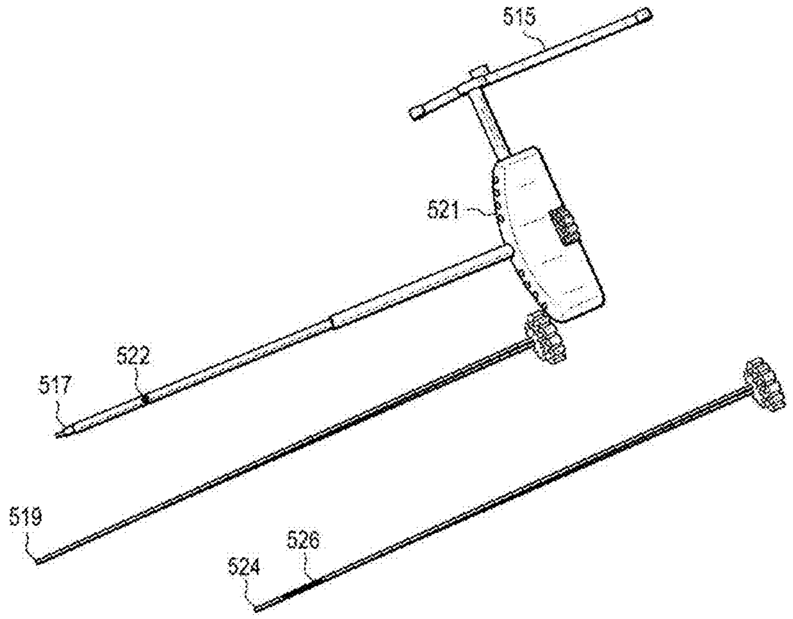

As noted above, the multi-tool can include integrated or built-in neuromonitoring, e.g., for detecting the presence, proximity, health, or other attributes of nerve tissue. For example, as shown in FIG. 56A, one or more shaft components of the multi-tool can include a neuromonitoring sensor 522. The sensor can include one or a plurality of sensors. The sensor can be configured to detect the presence, proximity, health, or other attributes of nerve tissue. For example, the sensor can be configured to assess nerve heath using functional near-infrared (fNIR) spectroscopy, e.g., as described in U.S. Application No. 62/507,930 filed on May 18, 2017, which is hereby incorporated herein by reference. As another example, the sensor can be configured to measure electrical nerve impulses, EEG, EMG, evoked potentials, or the like. Nerve assessment data can be communicated to the surgeon to inform subsequent surgical steps.

As also noted above, and as shown in FIG. 56A, the multi-tool can include an electrode, transducer, or other energy delivery element 526 for applying energy to tissue, e.g., to ablate or cauterize the tissue. The multi-tool can include an energy delivery element in the form of a microwave ablation element. The multi-tool can include an energy delivery element of the type used in the NEUWAVE system available from ETHICON, INC. of Cincinnati, Ohio. The energy delivery element can be built-into the multi-tool, or can be supported or guided to a target location using the multi-tool. The energy delivery element can be mounted on a shaft or needle 524. The needle can be coaxially received within or around another shaft component of the multi-tool. The multi-tool can be used to position the energy delivery element in proximity to a target location, such as an osseous bone tumor. Energy can be delivered from the energy delivery element to the tumor or other target location.

Pedicle Anchor

Figure 57:
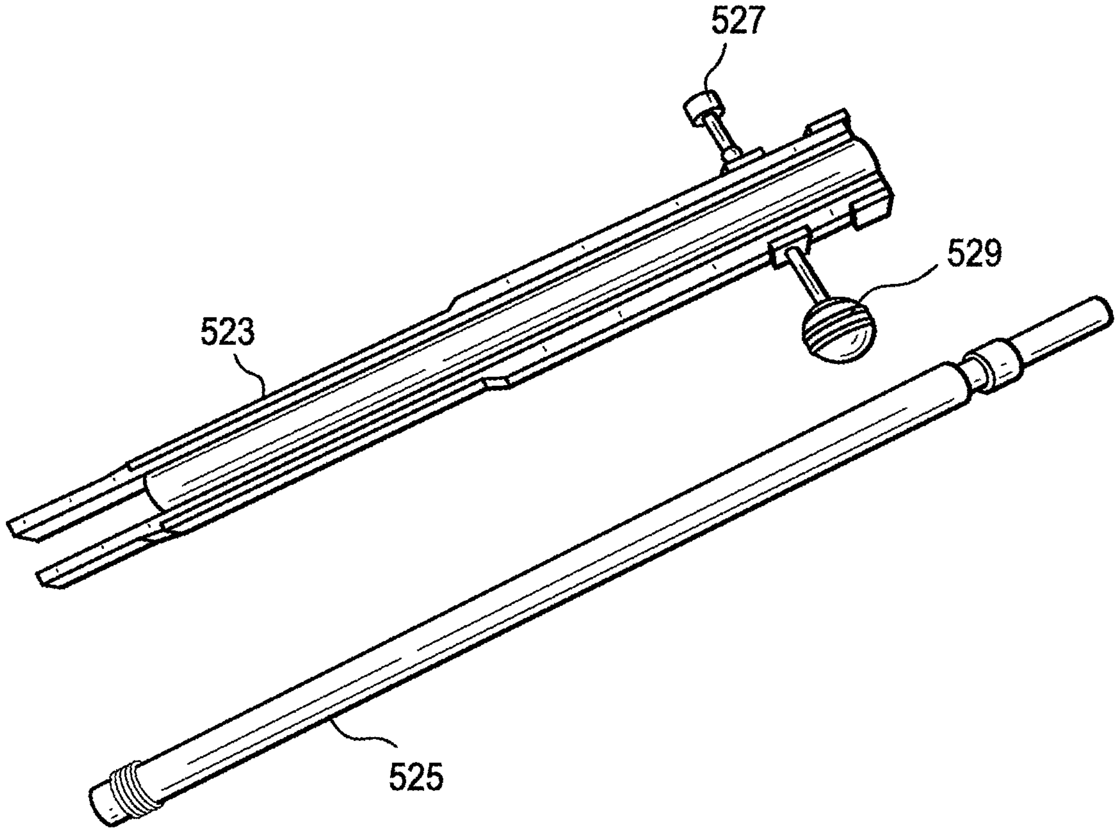

Now referring to FIG. 57, there is provided a Pedicle Anchor based on conventional screws that comprises a Center Core 523 including a Polyaxial Blocking Post 525, which engages with the thread for the Locking Cap of the Screw. When tightened, the polyaxiality of the screw is fully blocked. A screw 527 locks the Center Core with the Polyaxial Blocking Post. In other embodiments not including the above Pedicle Post with Reference Array, the interface to attached devices (Mini-Flex-Arm) is not realized by using a Clamp but by a non-detachable feature (sphere 529). This provides sufficient stability and is a simple add-on to existing screw systems.

Dilation Tubes

Figure 58:
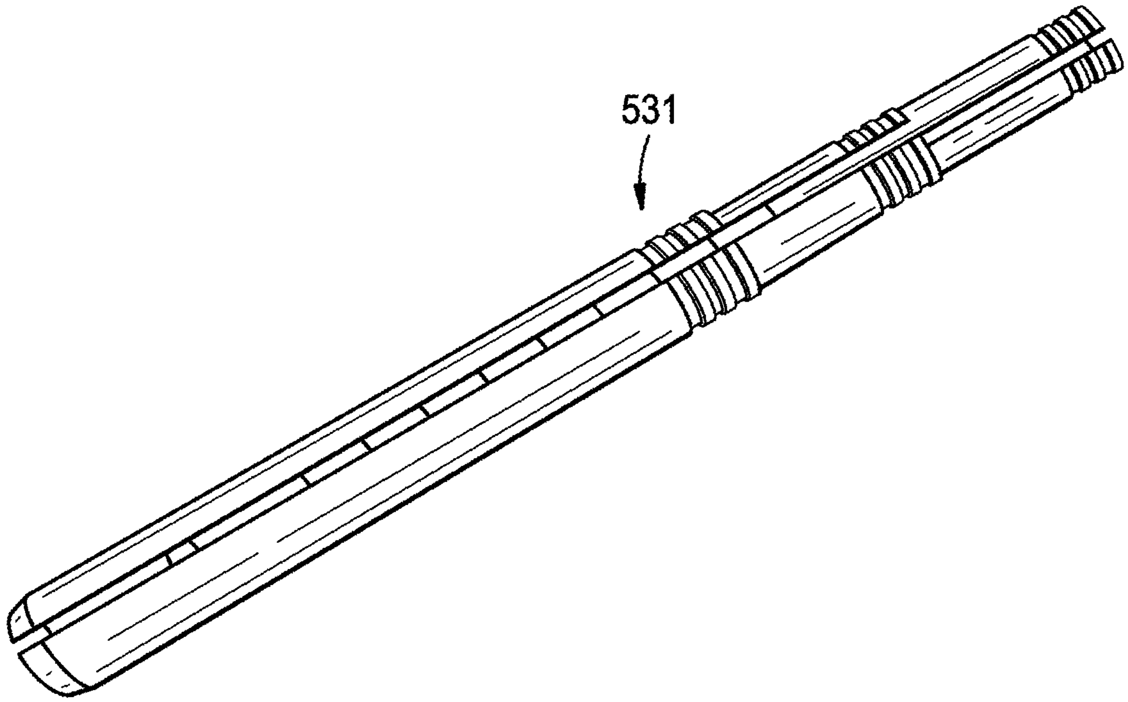

Now referring to FIG. 58, there is provided a dilation system comprising a set of Tubes 531 having outer diameters that match the current Access Tube (outer shield) inner diameters of 12 mm, 15 mm, and 18 mm. They are all circular shaped in the cross sectional plane and slotted in the longitudinal axis in order to be placed over the Multi-Tool probe (see above) and pass the connection of the Navigation Array with the cannulated cylindrical body of the Multi-Tool. In some embodiments, the set of Tubes have outer diameters (ODs) of OD1=12 mm, OD2=15 mm, and OD3=18 mm.

Mini-Flex Arm

Figure 59:
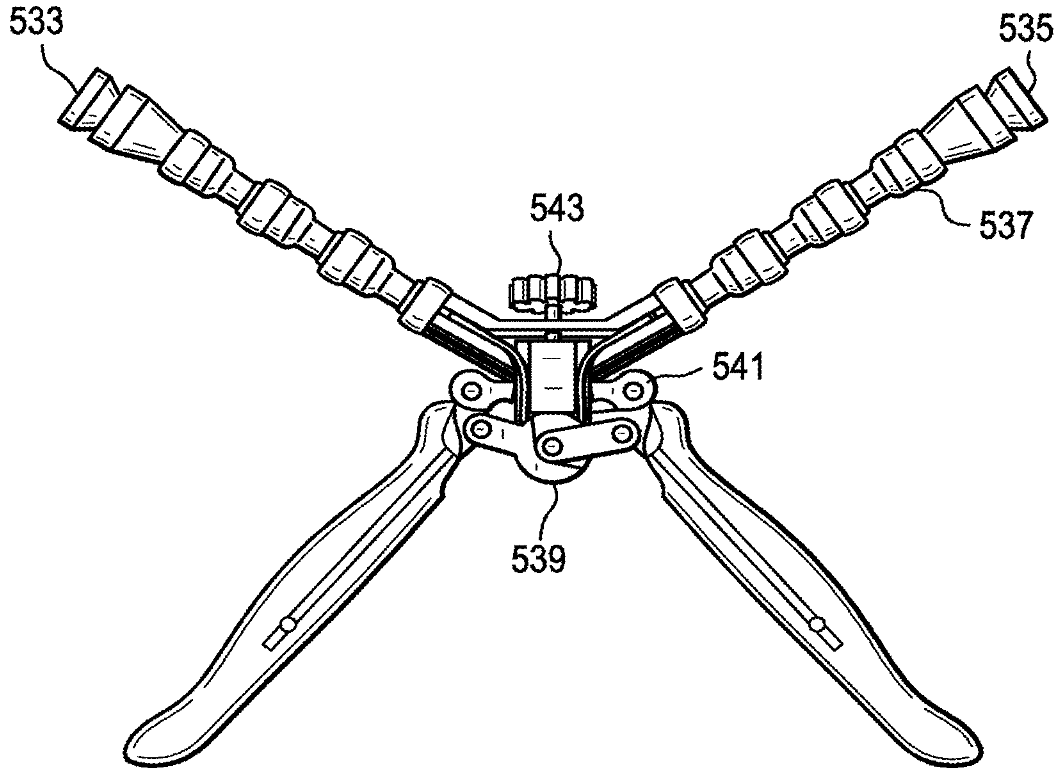

Now referring to FIG. 59, there is provided a Mini-Flex-Arm comprising of two clamps 533, 535 that are attached to spherical connectors on the Pedicle Anchor and Access Tube (outer shield) and therefore allows for a polyaxial adjustment to the attached devices. In an unlocked position, the segmented arms with ball and socket elements 537 in combination with the polyaxial clamps allow for a non-restricted 3-dimensional placement of the Access Tube (outer shield). The System can be locked with a single point handle 539 that tightens a multi-core wire 541. A potential elongation of the wire over time which would have a negative effect on the fixation properties of the device can be compensated on a screw 543 by adjusting the effective length of the wire.

Access Tube (Outer Shield) with Soft Tissue Retractor

Figure 60:
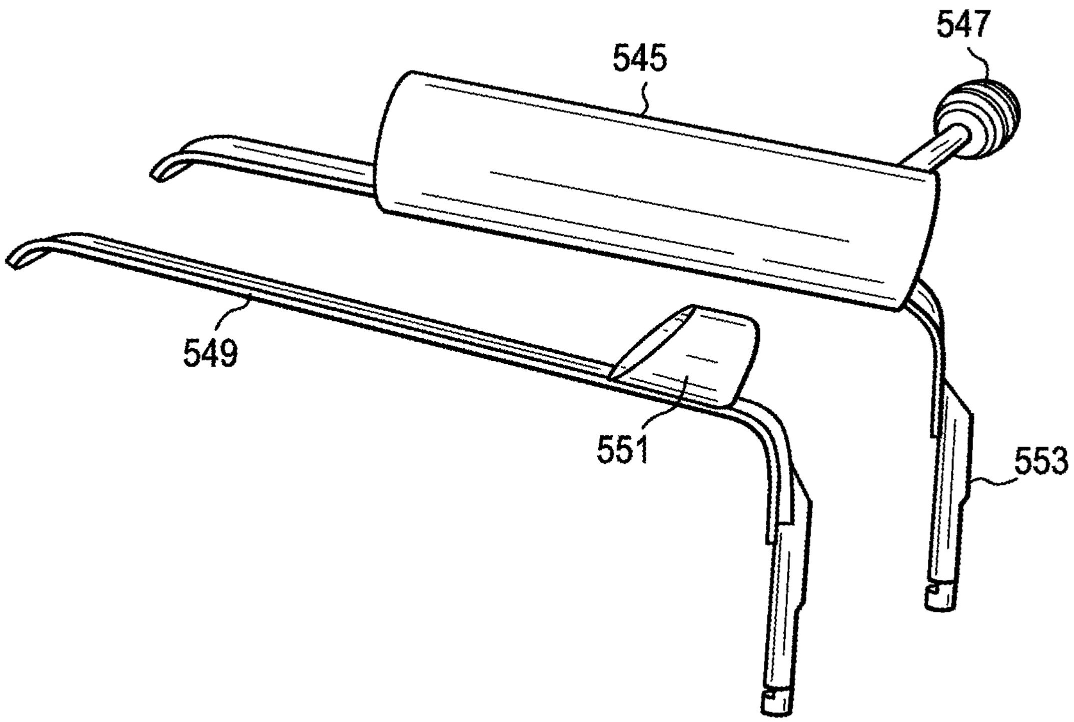

Now referring to FIG. 60, there is provided an Access Tube (outer shield) 545, which is a simple cylindrical tube with a distal flange, with a non-detachable feature (sphere 547) that connects it with the Mini-Flex-Arm. The Soft-Tissue-Retraction-Blade (inner shield) 549 is placed within the Access Tube. An attached spring 551 allows for a central insertion. As soon as the blades get released (handle, 553), the spring pushes the Blade (inner shield) against the inner wall of the Access Tube (outer shield) and therefore retracts the soft tissue on its distal end. The Blade (inner shield) remains free rotation and is held with the Access Tube (outer shield) by a pure fictional force. In some embodiments, there is the option to use two Soft-Tissue-Retraction Blades (inner shields) at the same time which would meet the requirements to use this embodiment for TLIF Procedures since it allows for the retraction of the transverse as well as the existing nerve. In some embodiments, the Detachable Handle is replaced by a simple permanent handle with a length of about 25 mm.

Access Tube (Outer Shield) with Integrated Endoscopy

Figure 61:
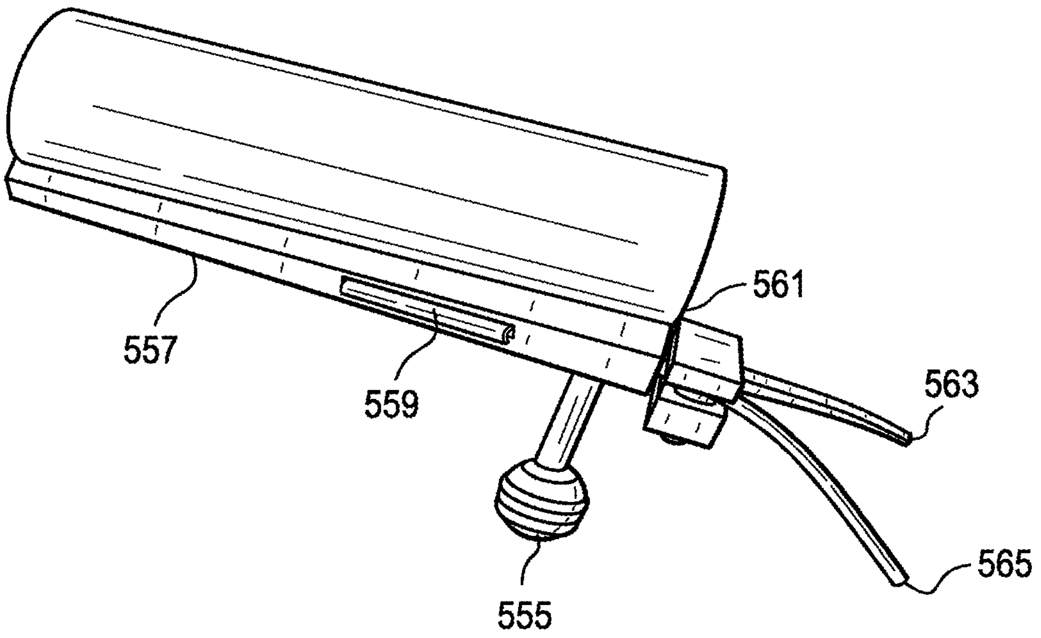

Now referring to FIG. 61, there is provided an Access Tube (outer shield) with an integrated endoscope and a non-detachable feature (sphere 555) that connects it with the Mini-Flex-Arm. The depth adjustable Endoscope System is held in a channel 557 that has a spring feature 559 to increase the friction and therefore hold the endoscope in place. The Endoscope system 561 consists of the endoscope itself (OD=4 mm) and 2 tubes, one for irrigation 563 and the other one for suction 565. In some embodiments, the Endoscope is depth adjustable. In some embodiments, the endoscope's channel will be parallel to the Access Tube (outer shield) Lumen.

Navigation Plug

Figure 62:
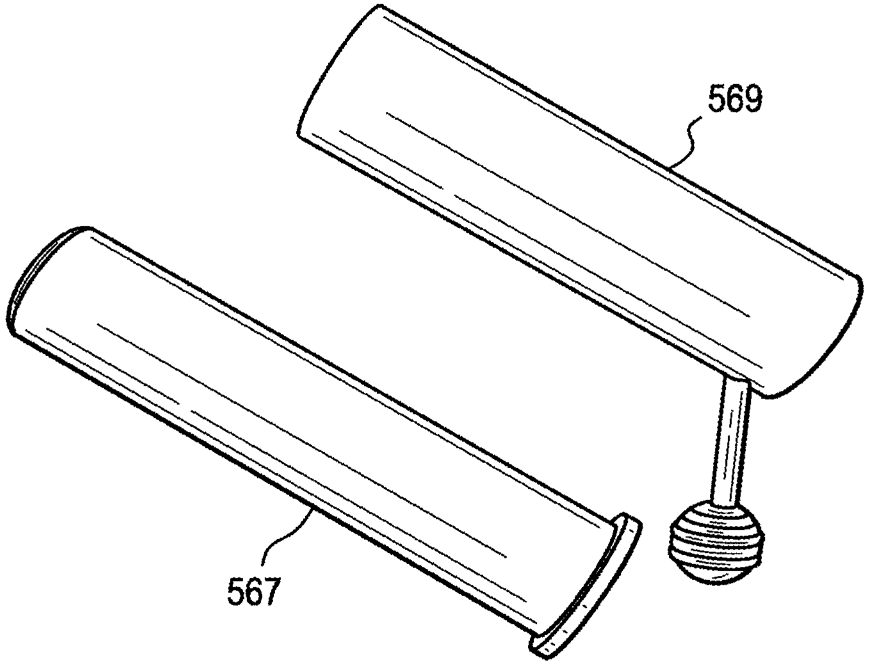

Now referring to FIG. 62, in some embodiments, there is a Navigation Plug 567 that is placed in the Access Tube (outer shield) 569 and allows the placement of the Multi-tool (see above) in the Center of the Access Tube (outer shield) flush with its distal end. This embodiment allows the visualization of the central longitudinal axis of the Access Tube (outer shield) as well as its distal end in the Navigation System. Because, in some embodiments, access trajectory is considered to be of higher importance than depth, the trajectory line could be graduated to offer information of depth in combination with known port length.

Discectomy Tool with Handle

Figure 63:
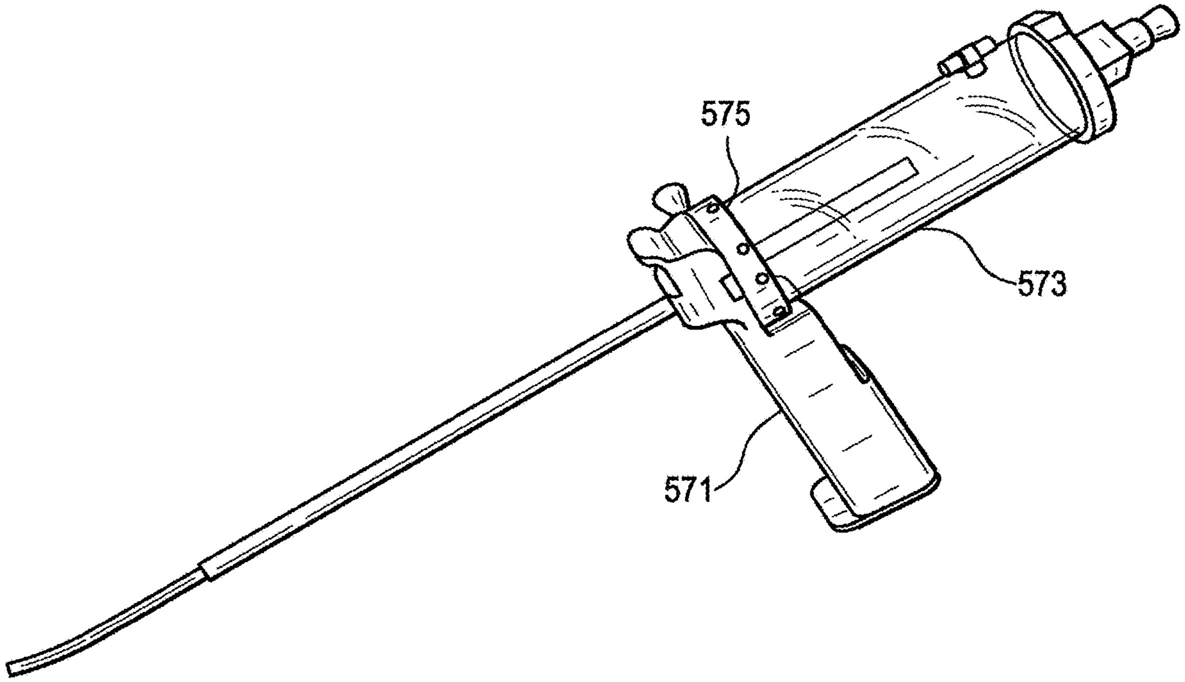

Now referring to FIG. 63, there is provided an attachable handle 571 directly attached to a standard suction-based discectomy tool 573 via an Adapter Plate 575 that clamps to the discectomy tool containment with 3 screws. In a first embodiment of this Adapter Plate, it only holds the attachable Handle, while in a second version it holds an additional Navigation Array. The Navigation Array is pre-calibrated: After letting the Navigation System know what specific discectomy tool is currently used, it shows the correct dimension and tip of the device in the pre-registered x-ray views in real time.

FIGS. 64-90 disclose some of the instruments in their contemplated in-spine use orientations in preferred procedures disclosed herein.

| | |
|---|---|
| Step 1 | Placement of Ref. Array |
| Step 2 | Placement of Pedicle Anchor |
| Step 3 | Placement of Access Tube |
| Step 4 | SAP removal |
| Step 5 | Soft Tissue Retraction |
| Step 6 | Disc Removal |
| Step 7 | Insertion of Expandable Cage and Bone Substitute |
| Step 8 | Posterior Stabilization |

Step 1 Placement of Reference Array

Figure 64:
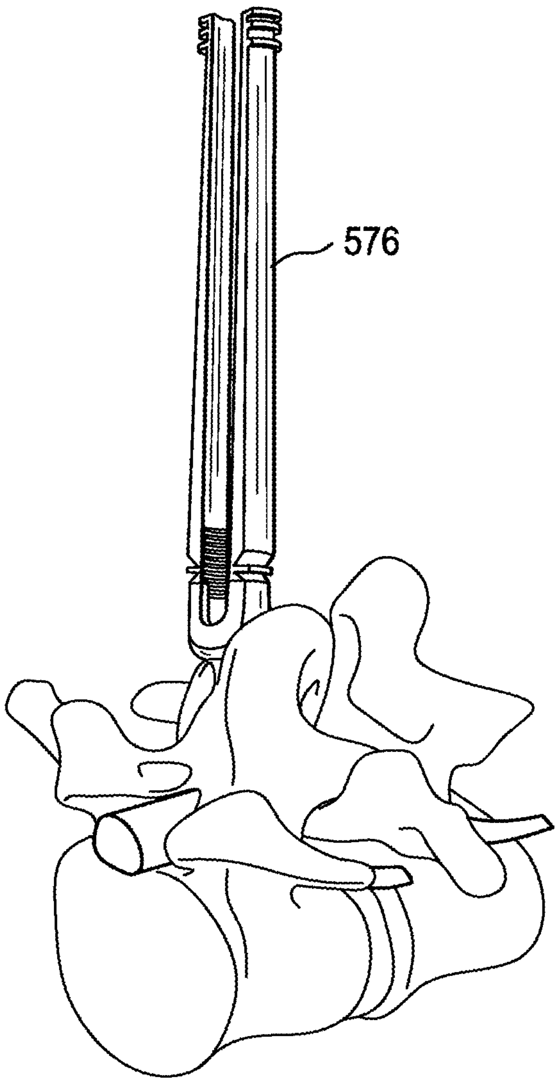
FIGS. 64-90 disclose some of the instruments in their contemplated in-spine use orientations in preferred procedures disclosed herein.
Figure 65:
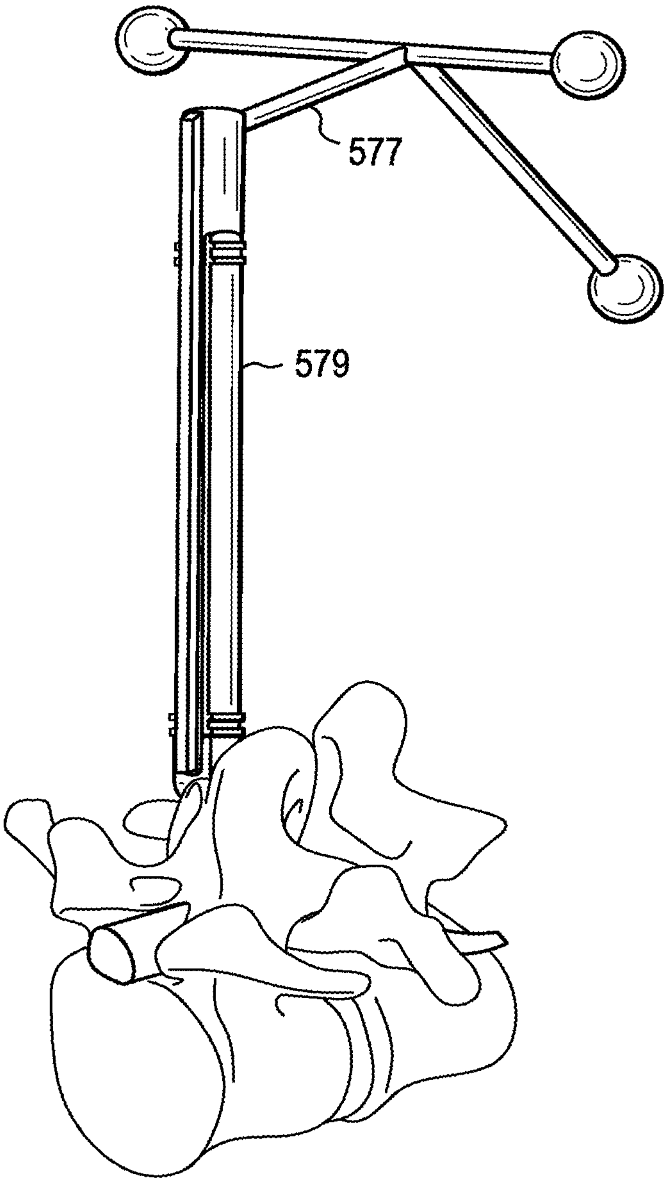

Now referring to FIGS. 64-65, in one embodiment, a polyaxial screw is inserted contra-laterally into the spine via post 576. A navigation reference array 577 is then fixed mounted on a Polyaxial Blocking Post 579, and engaged in the distal thread (not visible, inside screw/tab) for the Locking Cap of the Pedicle Screw.

Step 2 Placement of Pedicle Anchor

Figure 66:
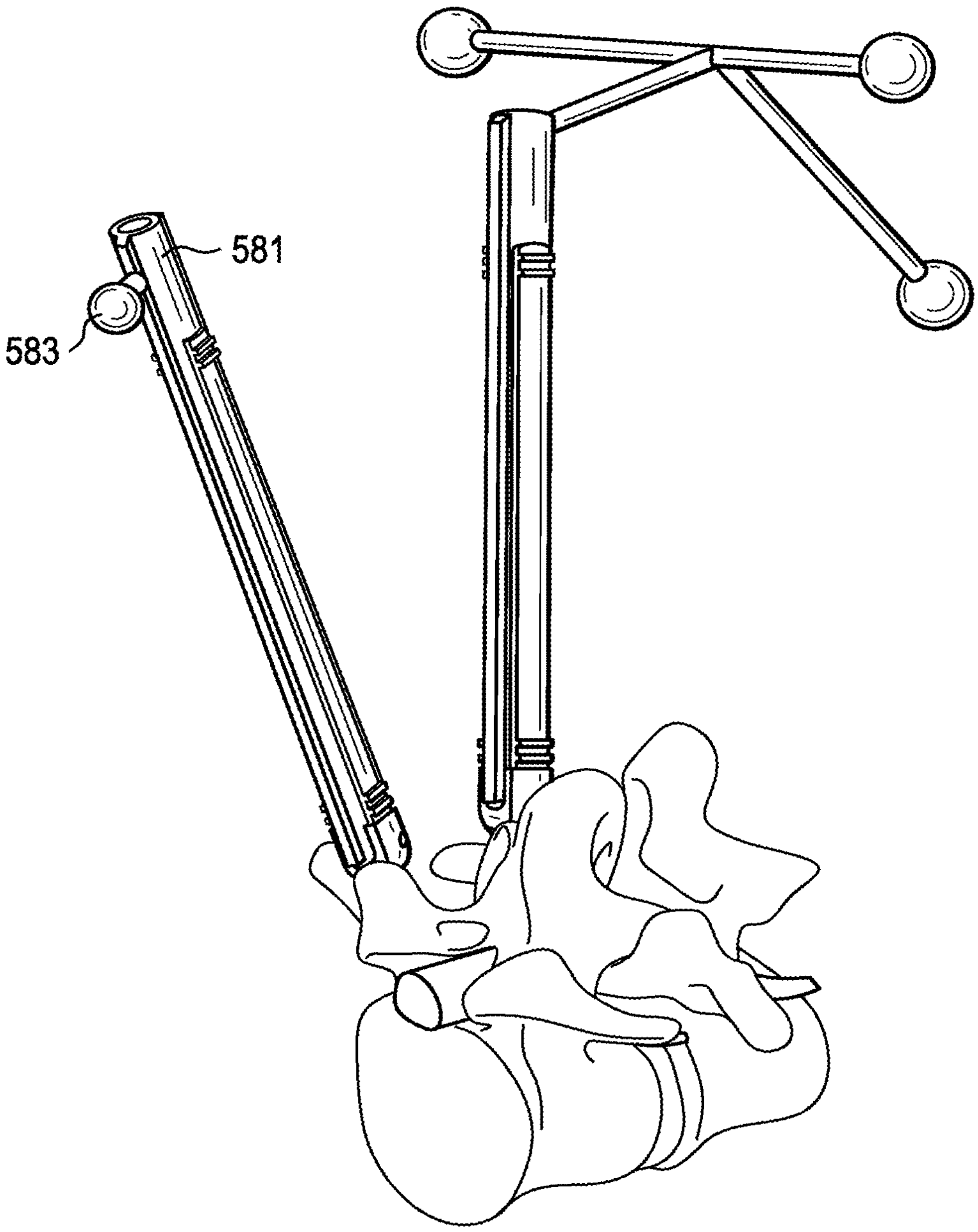

Now referring to FIG. 66, a pedicle Anchor 581 with Connector Interface 583 is placed on the contralateral side.

Figure 67:
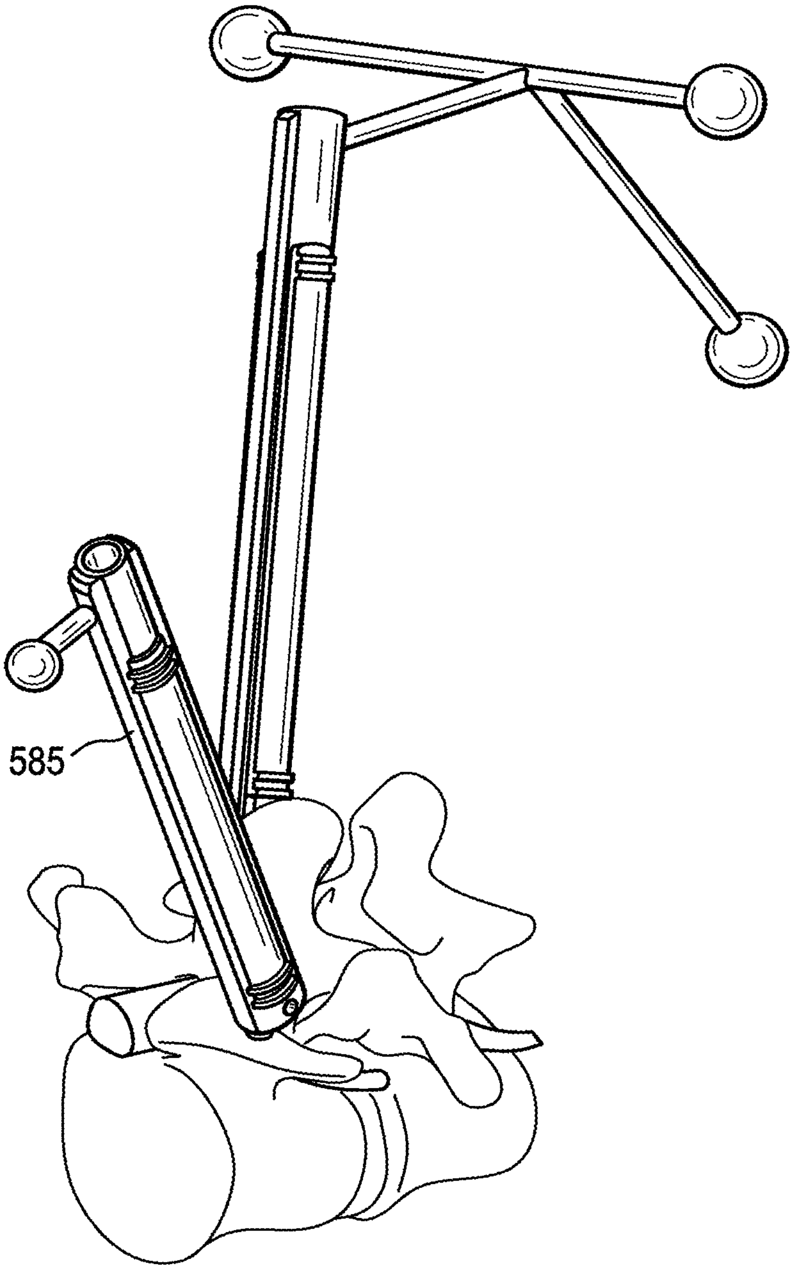

Now referring to FIG. 67, a pedicle anchor 585 is placed on the ipsilateral side.

Step 3 Placement of Access Tube

Figure 68:
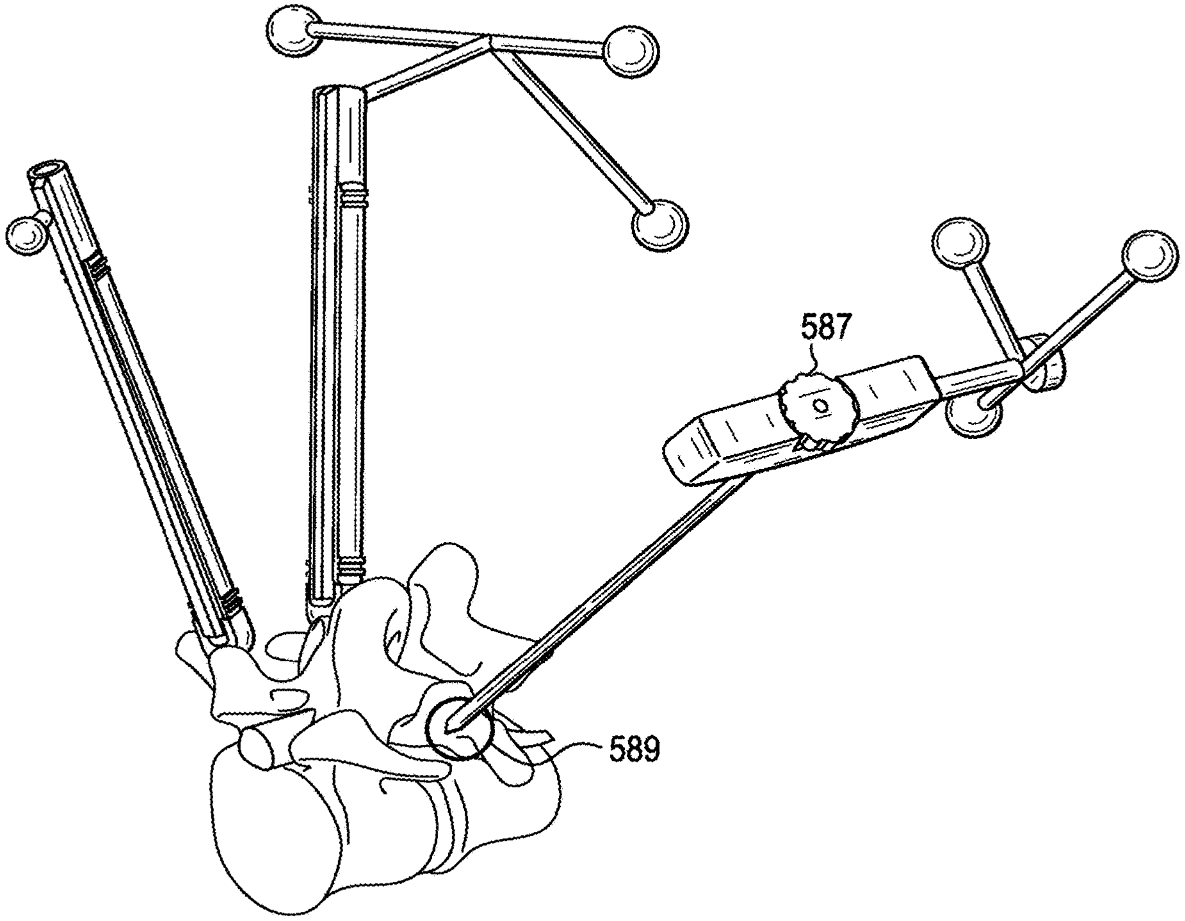

Now referring to FIG. 68, a Multitool 587 is inserted into the spine for determination of Target Area 589 and trajectory of Dilators/Access Tube. Neuromonitoring features of the multi-tool can be used during insertion or at any other desired time to avoid or navigate around nerve tissue, to safely retract nerve tissue, and/or to assess the health of nerve tissue. The multi-tool can integrate multiple components into a single navigated tool to reduce the number of instruments tracked separately during surgery, e.g., as part of a procedure to insert an access port into a patient during a surgical procedure. Additional embodiments of a multi-tool are described in connection with FIGS. 91-125 below.

Figure 69:
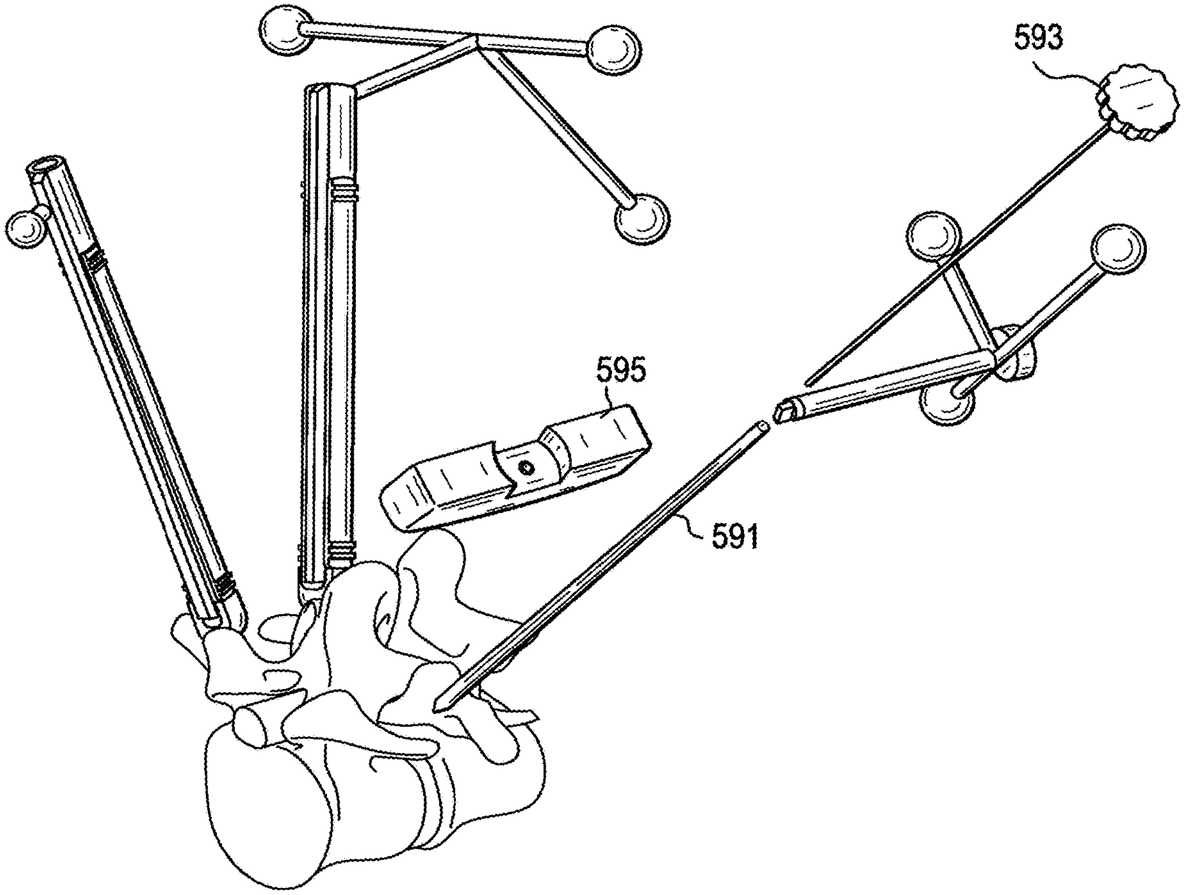

Now referring to FIG. 69, the K-Wire and Handle are removed from the multi-tool for next step. After placing the Multitool 591, the K-Wire 593 needs to be removed in order to allow the removal of the Handle 595.

Figure 70:
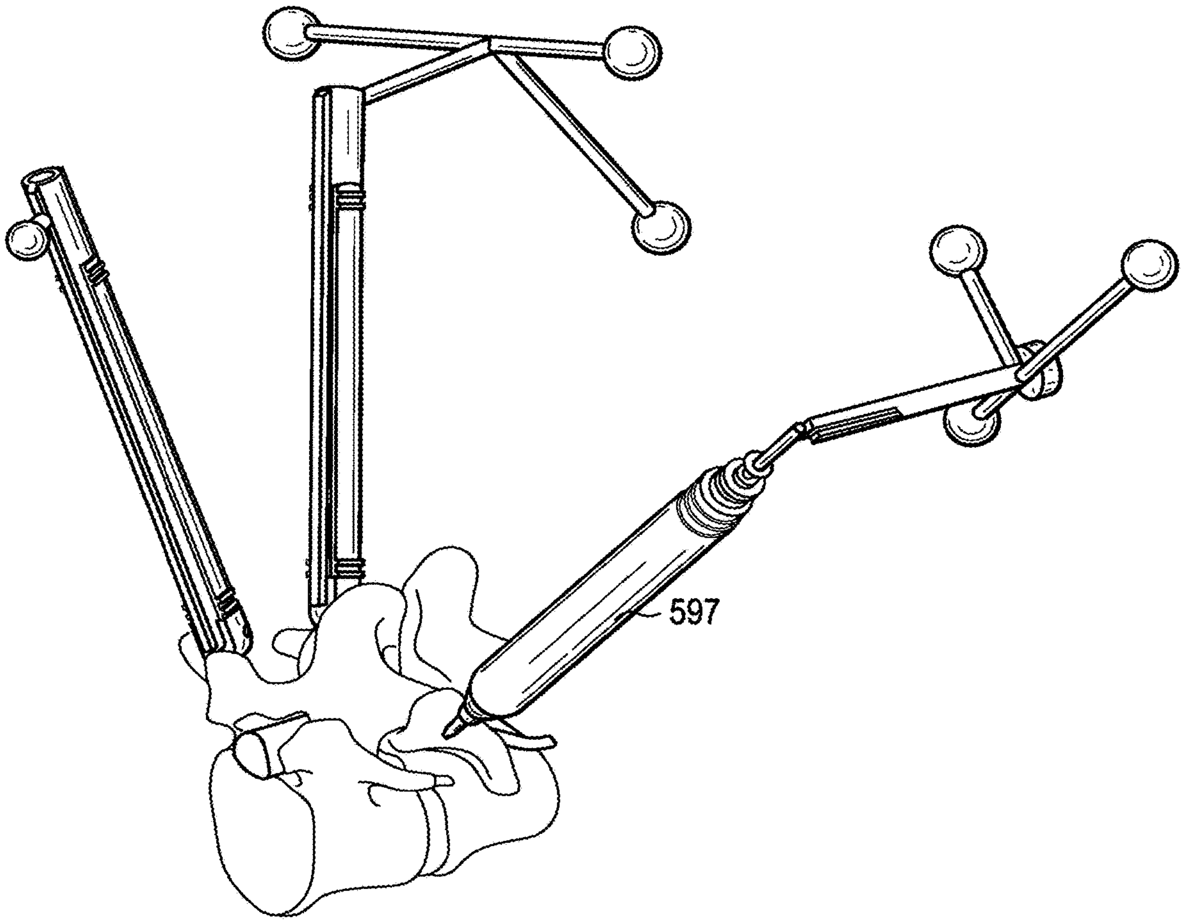

Now referring to FIG. 70, Multi-step dilation is carried out to prepare for Access Tube (outer shield) insertion. The removal of the handle (see previous step) allows the placement of the first, second and third dilators 597 to prepare for Access Tube insertion.

Figure 71:
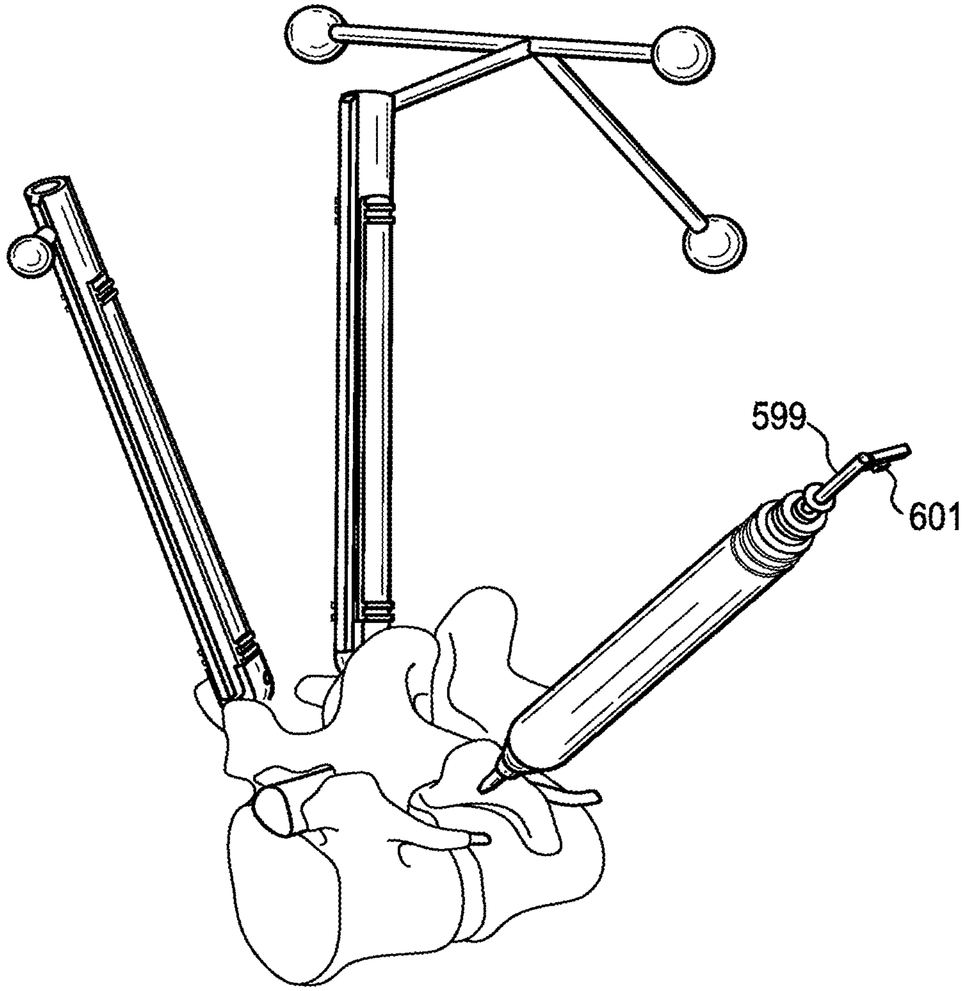

Now referring to FIG. 71, the navigation array is removed from the Multi-tool base. Since it is clinically important to keep the target point of the Access Tube (outer shield) positioning, the Access Port can be placed over the main Body 599 of the Multi-Tool by removing the Navigation Array, leaving behind the Navigation Array Interface 601, which allows a play free, load bearing and bi-unique fixation of the Reference Array.

Figure 72:
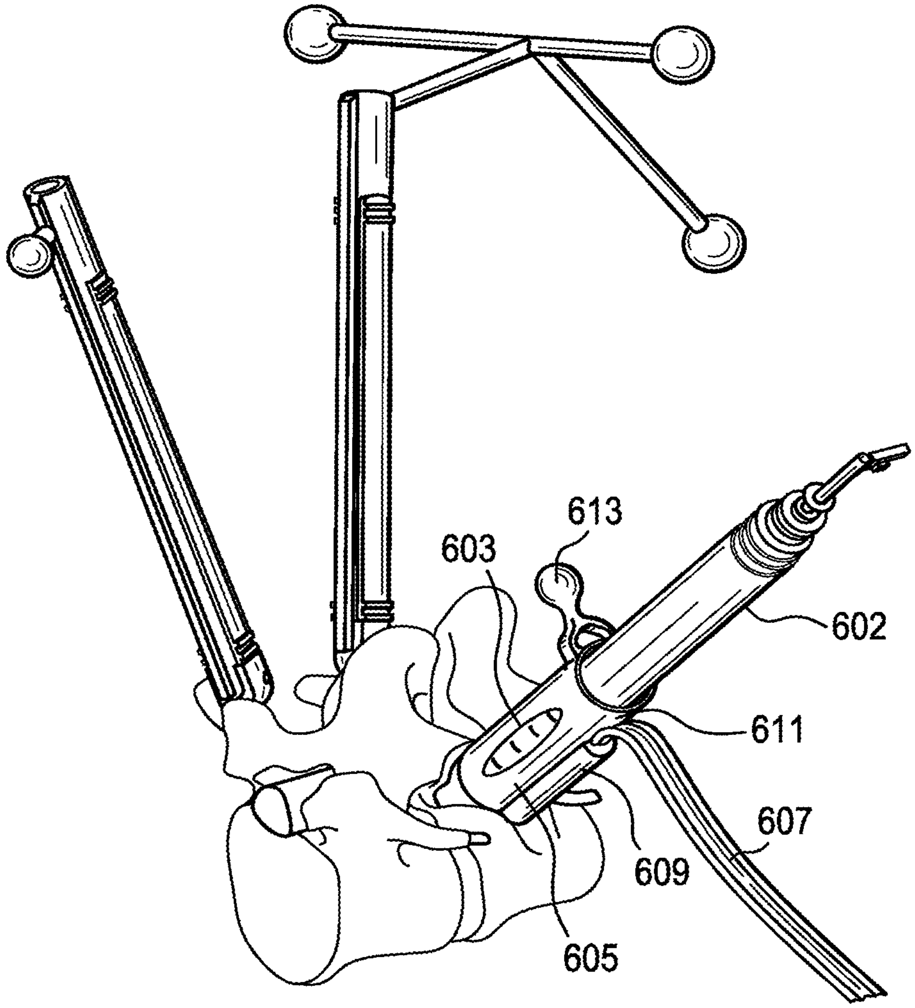

Now referring to FIG. 72, the Access Tube (outer shield) is inserted over the dilators 602 (wherein the viewing element Chip-on-tip scope is pre-mounted). The Access Tube (outer shield) is telescopic and can be adjusted in length, stabilized with a ratchet mechanism 603. It comprises a distal segment 605 that holds a depth adjustable Chip-on-Tip Camera 607 housed in a channel 609 which is integrated into the wall of the distal segment. A proximal portion of the access tube (outer shield) 611 slides over the distal segment and holds a connector interface 613.

Figure 73:
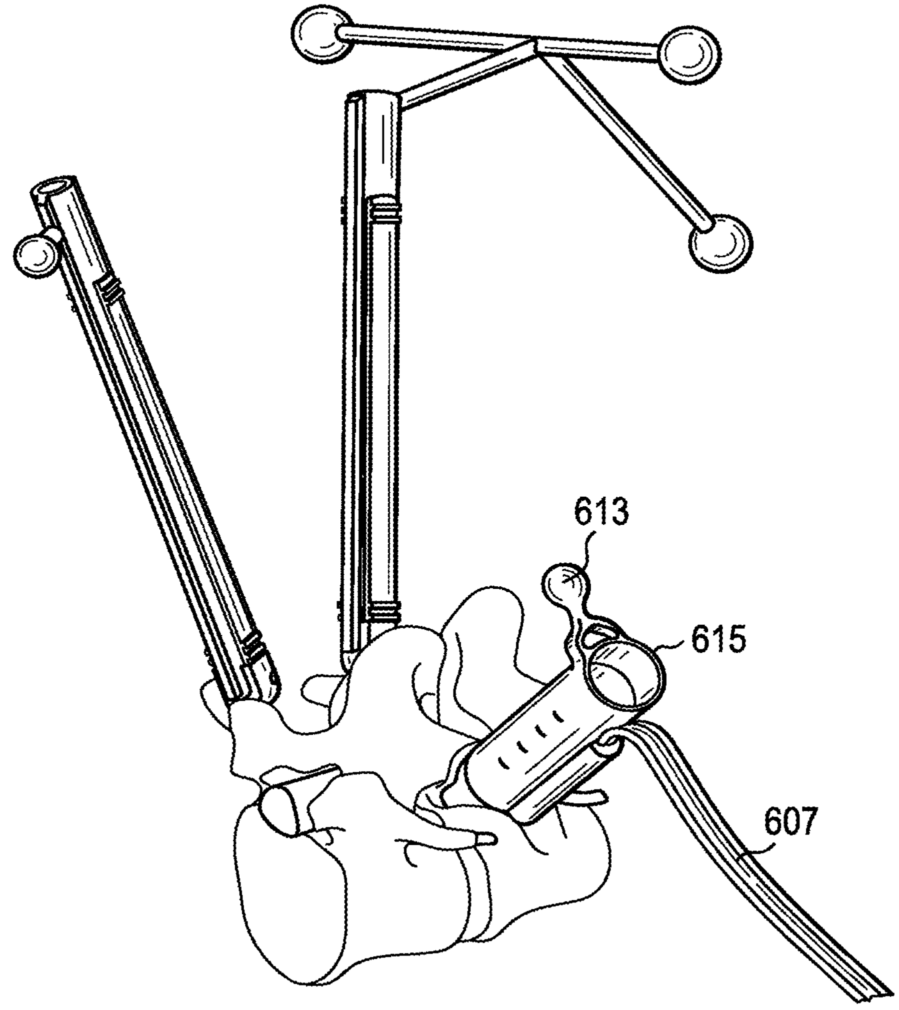

Now referring to FIG. 73, once the Dilators as well as the Body of the Multi-Tool have been removed, the Access Tube (outer shield) 615 offers free access to the SAP.

Figure 74:
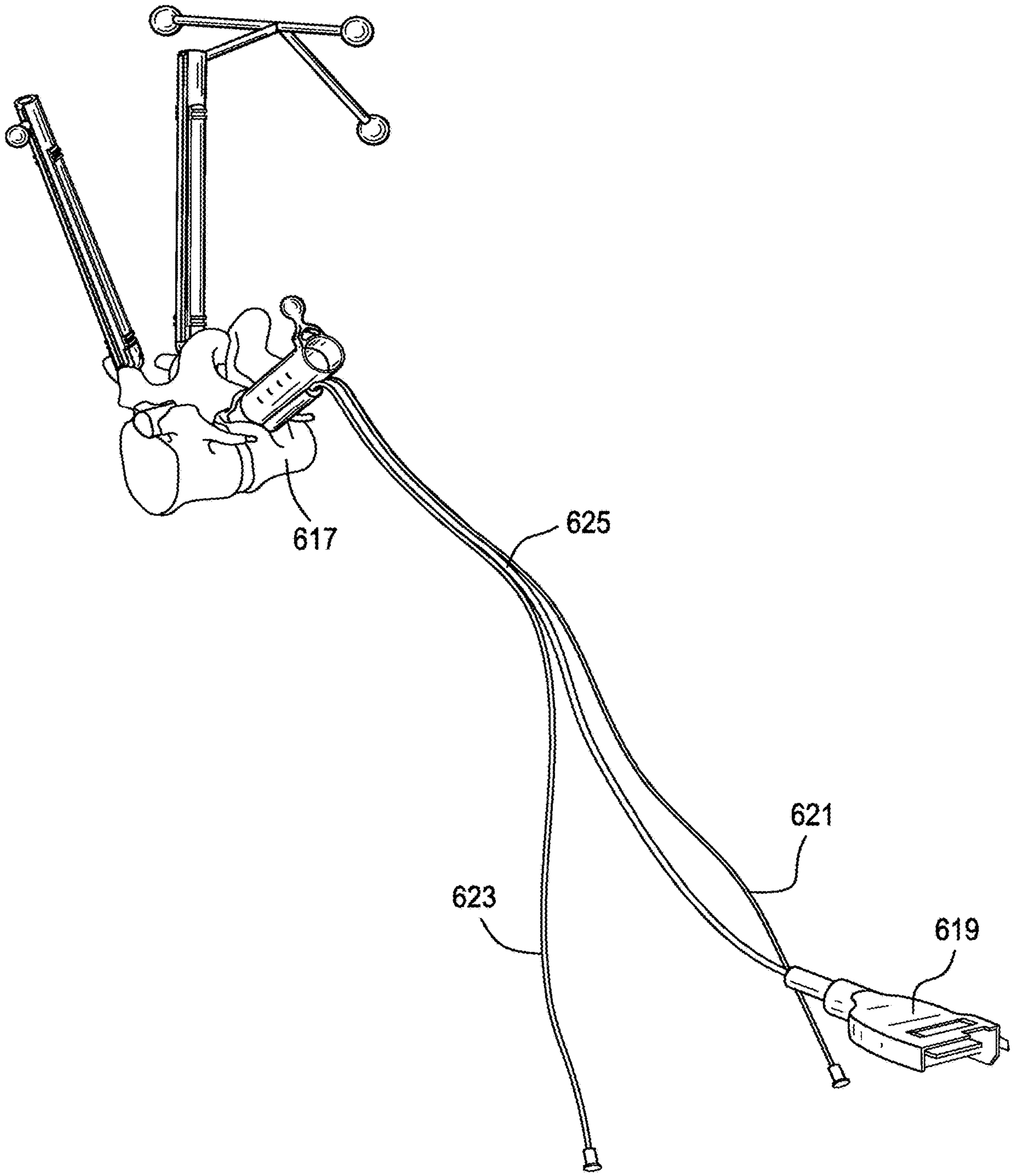

FIG. 74 discloses connectors to the Visualization Box and the Cleaning Box (water and suction). The Chip-on-Tip Camera comprises the actual Camera 617 disposed in the access tube (outer shield) and a main connector plug 619 that provides power supply, data cables and light to the Camera. There are also two tubes for irrigation and suction 621, 623 to provide a cleaning feature for the Camera Lens, which merge into a single cable 625 connected to the Camera and extending from the access tube (outer shield).

Figure 75:
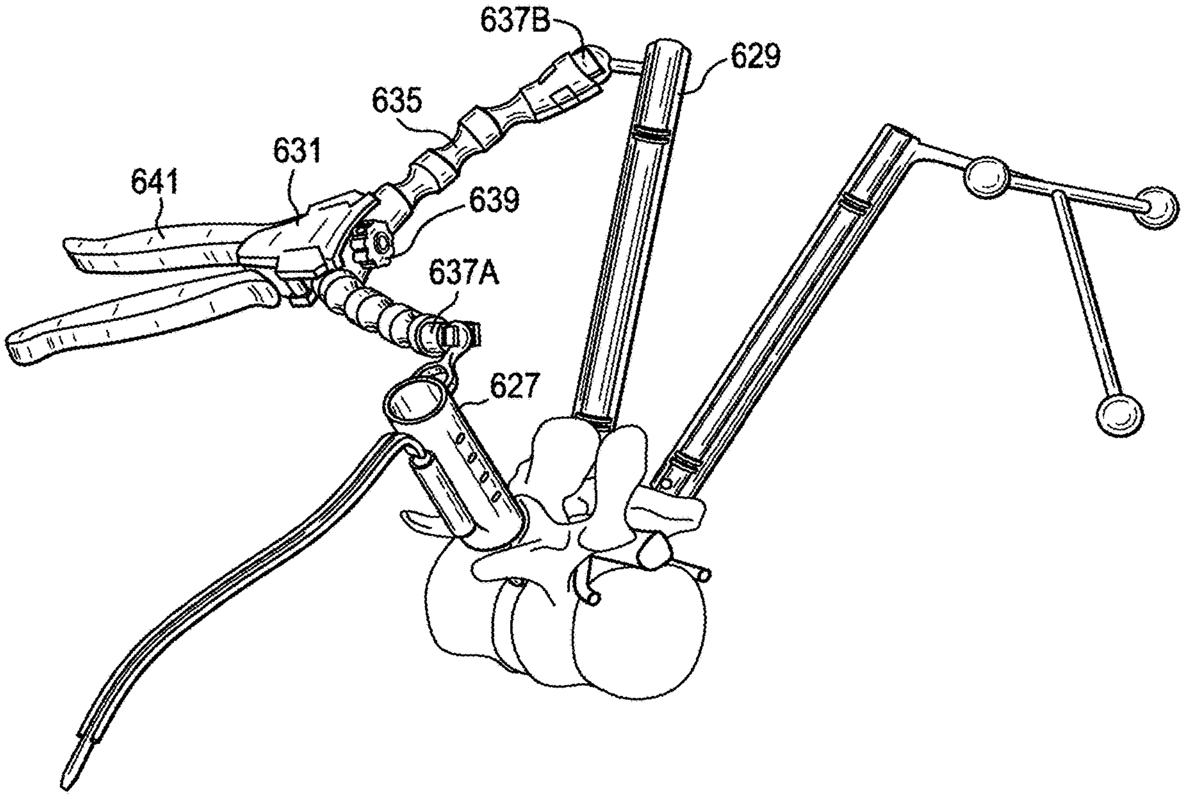

Now referring to FIG. 75, the Access Tube (outer shield) is fixed to the ipsilateral or contralateral pedicle anchor. The Access Tube 627 is rigidly attached to the contralateral 629 or ipsilateral (not shown) Pedicle Anchor via a Connector 631. This Connector allows the locking of the Access Tube in any 3D position. It comprises ball and socket segments 635, two Interface Clamps 637*a*, 637*b* and an inner wire (not visible) that is put under tension by an adjustable 639 single point fixation handle 641 and thereby blocks the single joints of the two Interface Clamps and segments by increasing their absolute friction. The single point fixation Connector is designed to minimize the accruing forces on the Access Tube, as well as the pedicle Anchor, during tightening of the construct. Another Connector Design (not shown) is reverse in function, in that it is permanently stable unless the inner wire is released via the single point fixation Handle.

Step 4 SAP Removal

Figure 76:
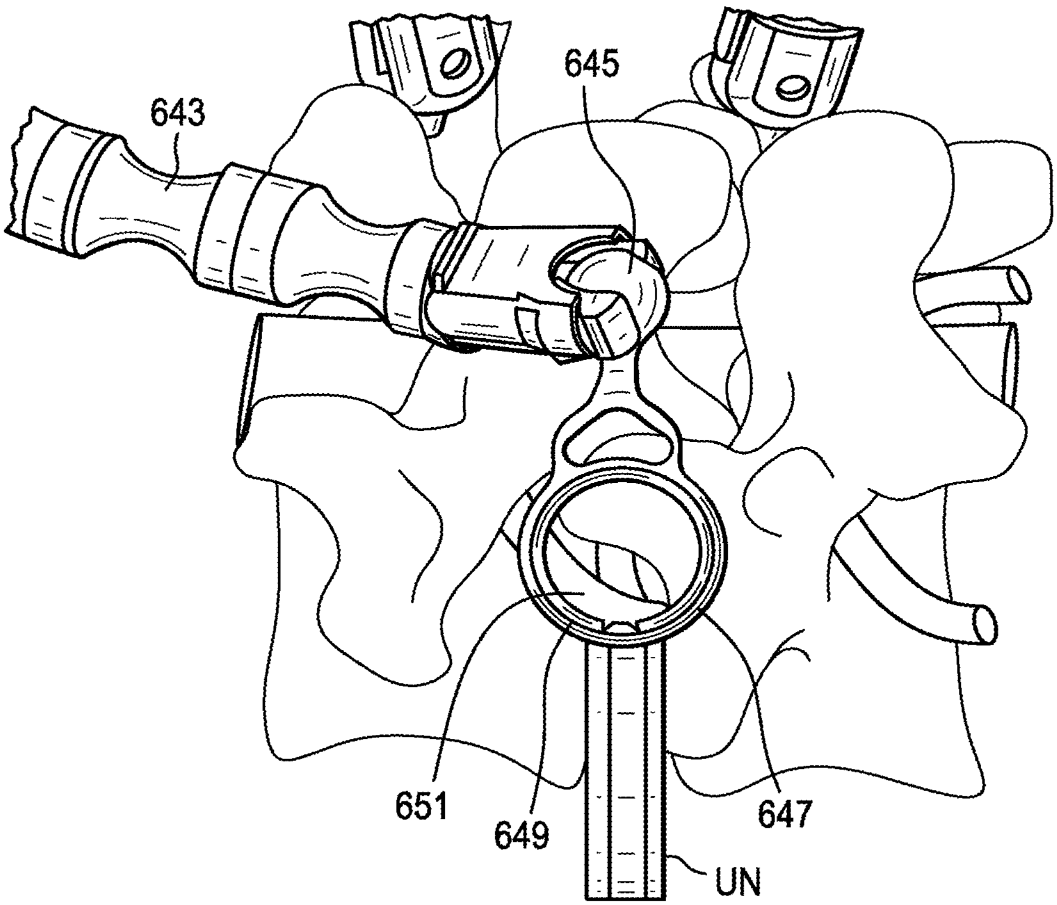

Now referring to FIG. 76, there is provided an axial view of the Access Tube, wherein the surgeon is ready to start cutting the SAP. Disclosed in the FIG. are Single segment 643 and Connector Interface 645 of the Mini-Flex arm, outer proximal portion 647 of a Telescopic Access Tube; Inner distal portion 649 of Telescopic Access Tube; Cable of integrated Chip-on-Tip Camera 651; and unretracted Nerve UN.

Figure 77:
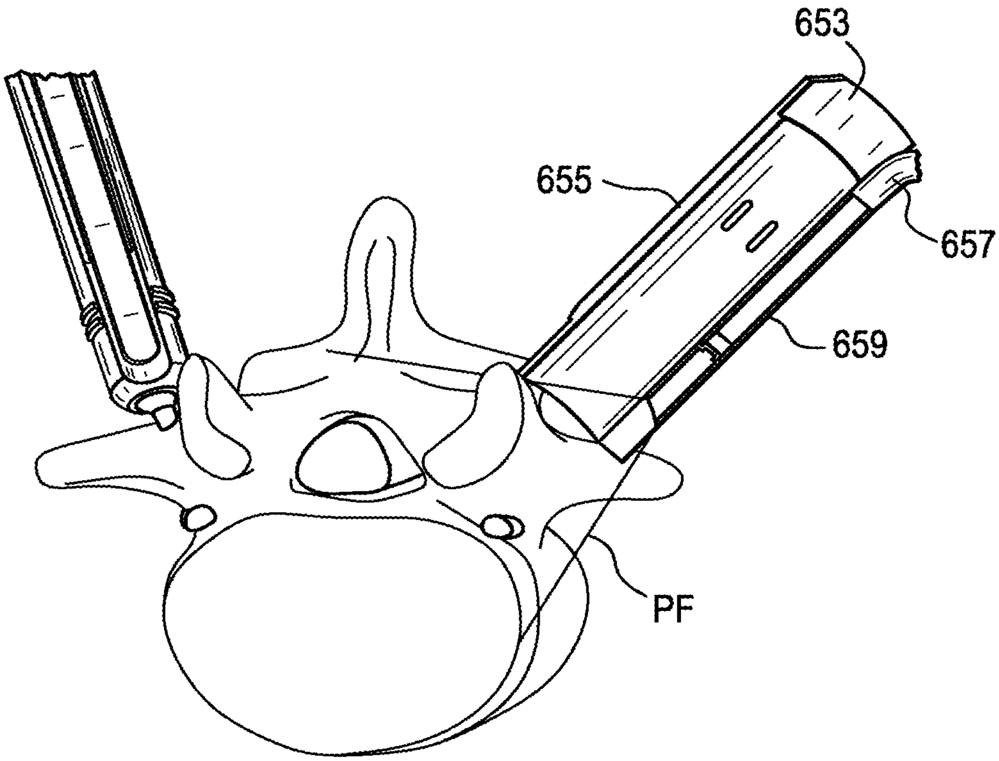

Now referring to FIG. 77, there is provided disposition of an Integrated Scope, which includes Outer proximal Tube 653 of Telescopic Access Tube; Inner distal Tube 655 of Telescopic Access Tube; Exiting Cable of integrated Chip-on-Tip Camera 657; Chip-on-Tip Camera in housing 659; and Projected field of view of Chip-on-Tip Camera PF.

Figure 78:
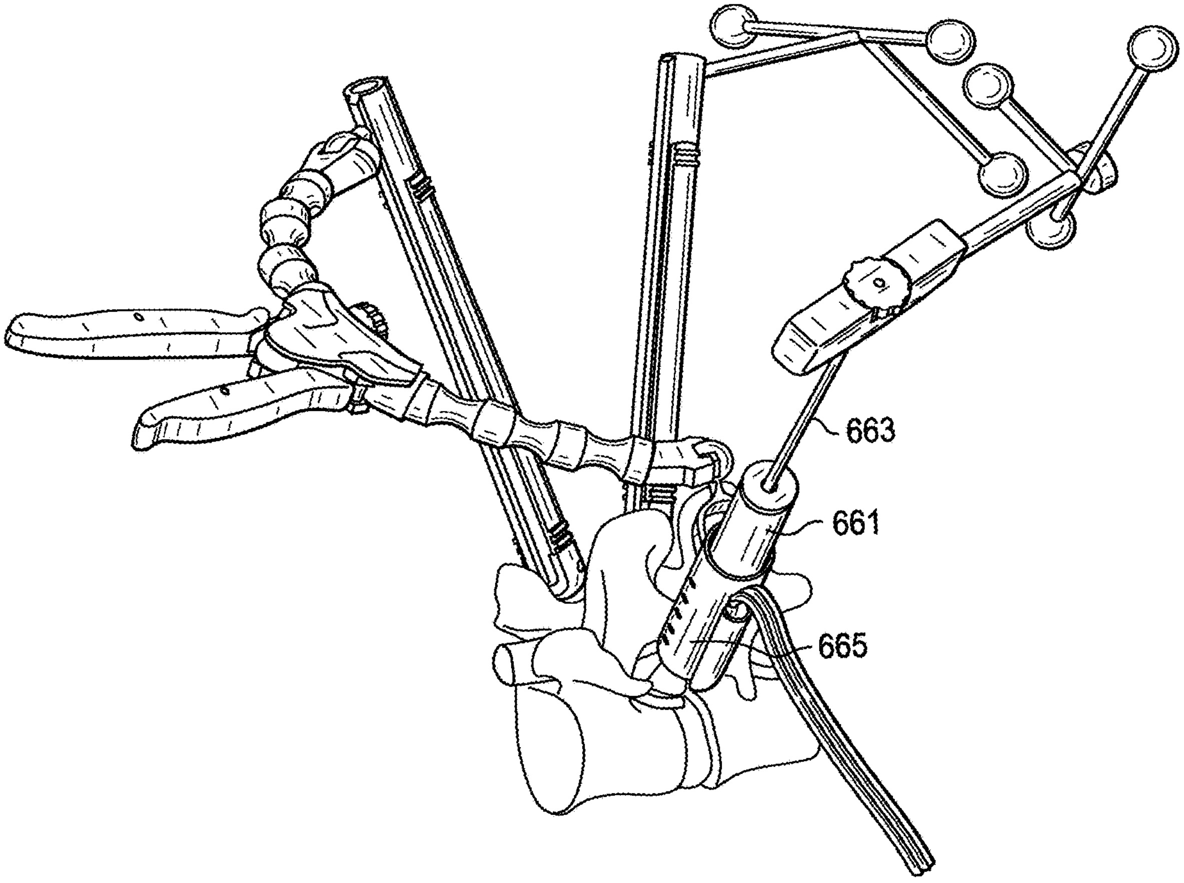

Now referring to FIG. 78, in some embodiments, there is optional Navigation of the Access Tube through use of the Multi-Tool with a Navigation Plug. In conjunction with a Navigation Plug 661, the Multi Tool 663 can also be used to visualize the trajectory as well as the distal end of the Access Tube 665 using navigation. The Navigation Plug sits on the proximal rim of the inner distal tube of the telescopic Access Tube, which leads to an accurate visualization of the depth perception independently from the position of the outer proximal tube and therefore total length of the Access Tube.

Figure 79:
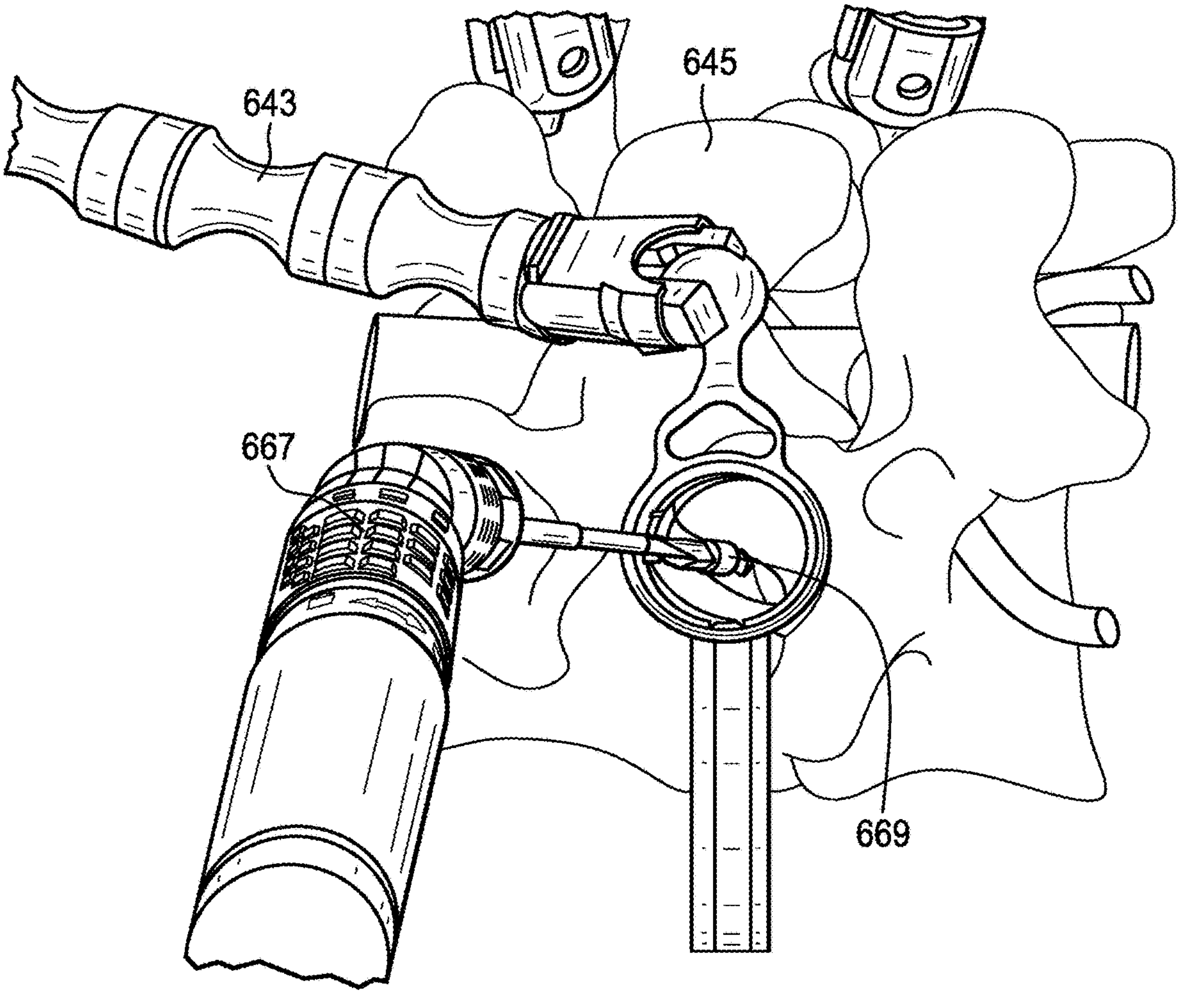

Now referring to FIG. 79, there is provided carrying out SAP removal via the use of MIS high-speed drills or manual tools. The SAP will be (partly) removed using a high speed Power Tool such as an Anspach System 667. The Burr 669 will be partly shielded to increase safety.

Figure 80:
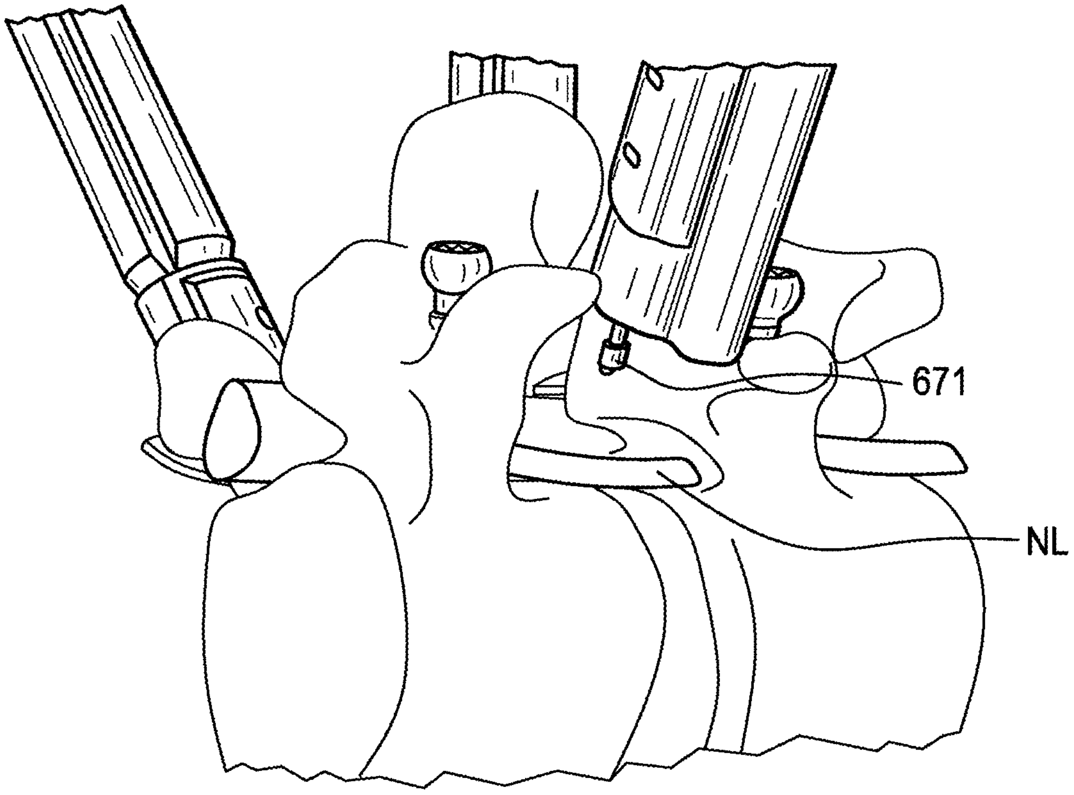

Now referring to FIG. 80, further SAP removal by MIS high-speed drills or manual tools is demonstrated with respect to the different anatomical planes. The removal of the SAP with a Burr 671 takes place about 10 mm-20 mm above the nerve (2) level NL.

Step 5 Soft Tissue Retraction

Figure 81:
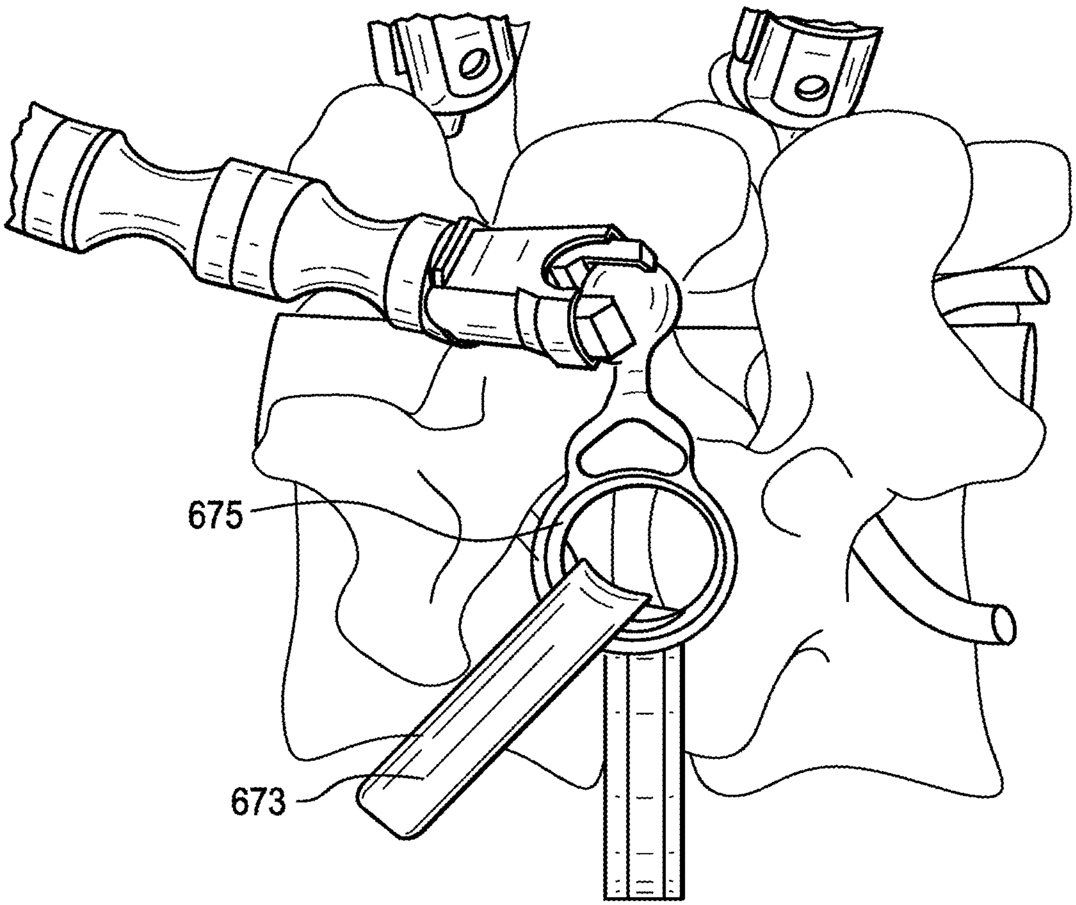
Figure 82:
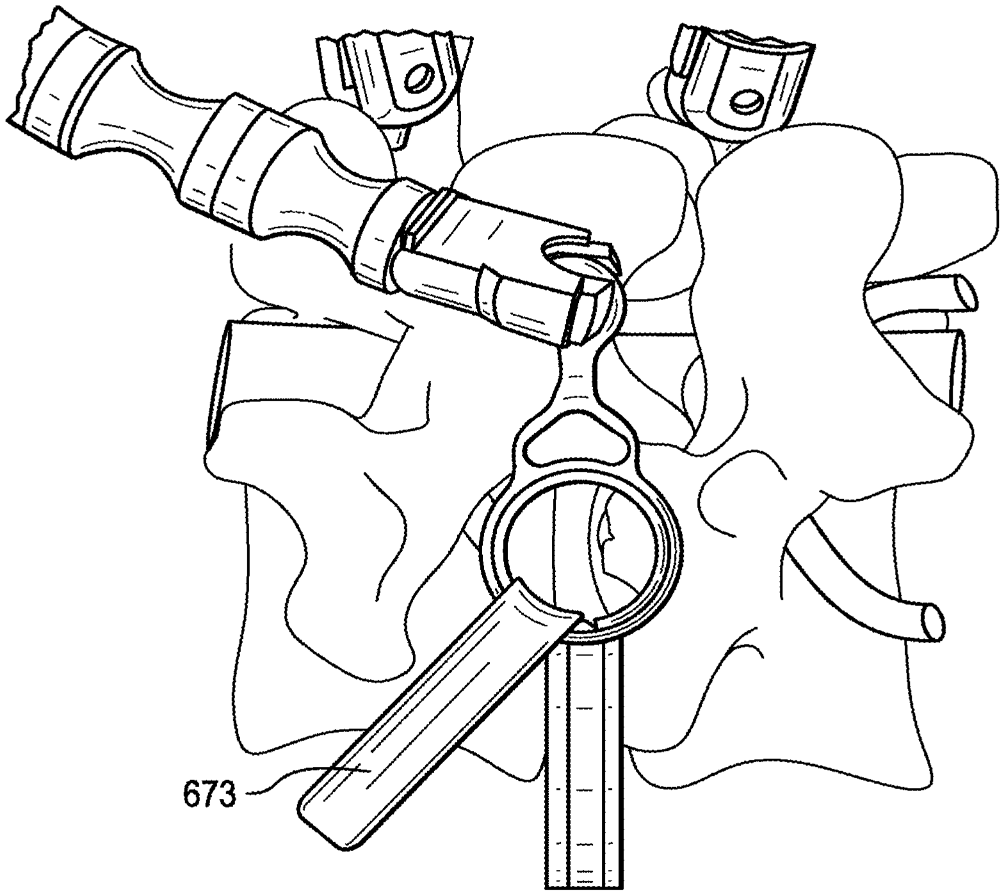

FIG. 81-82 disclose Soft tissue retraction, showing a clip directly on access tube, medial to lateral retraction. FIG. 81 shows the Soft Tissue Retractor 673 before radial retraction of the nerve. At this state, the Soft Tissue Retractor is already engaged with the Access Tube 675. FIG. 82 discloses the Soft Tissue Retractor 673 after radial retraction of the nerve.

Figure 83:
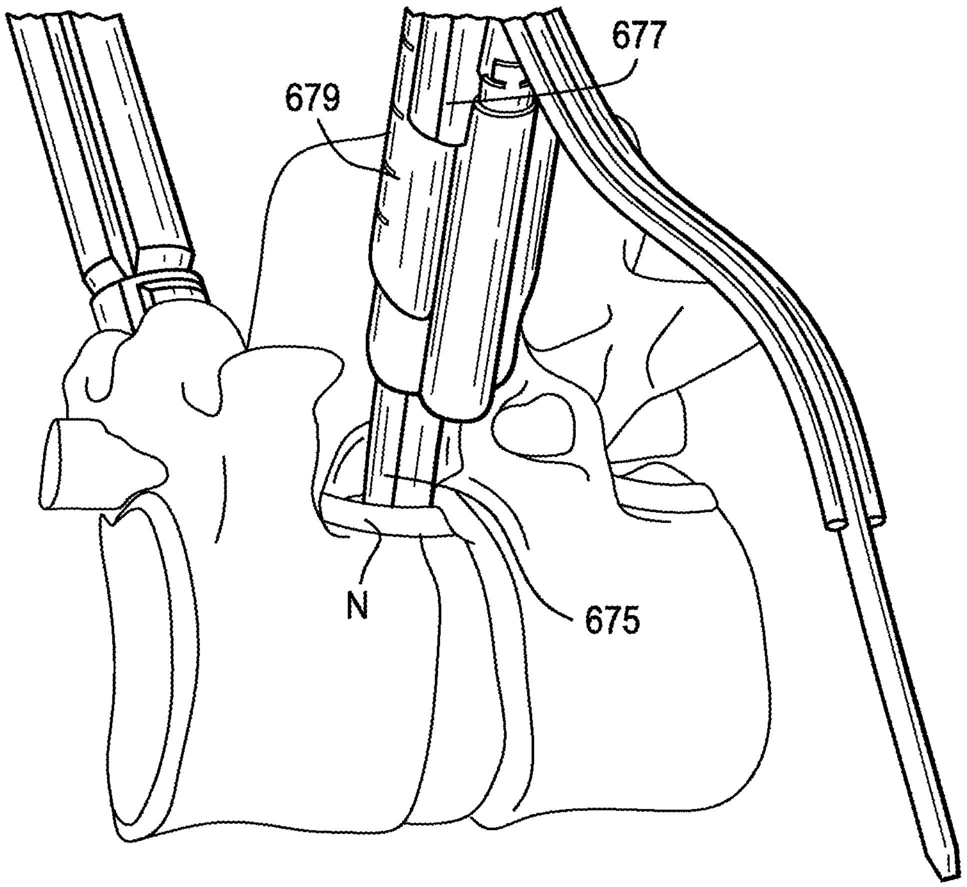

FIG. 83 discloses nerve Shielding and Positioning according patient anatomy. FIG. 83 shows the fully engaged Soft Tissue Retractor 675 with a Clip 677 holding it on the proximal outer Tube 679 of the Telescopic Access Tube. The nerve N is fully retracted and protected by the Soft Tissue Retractor.

Step 6 Disc Removal

Figure 84:
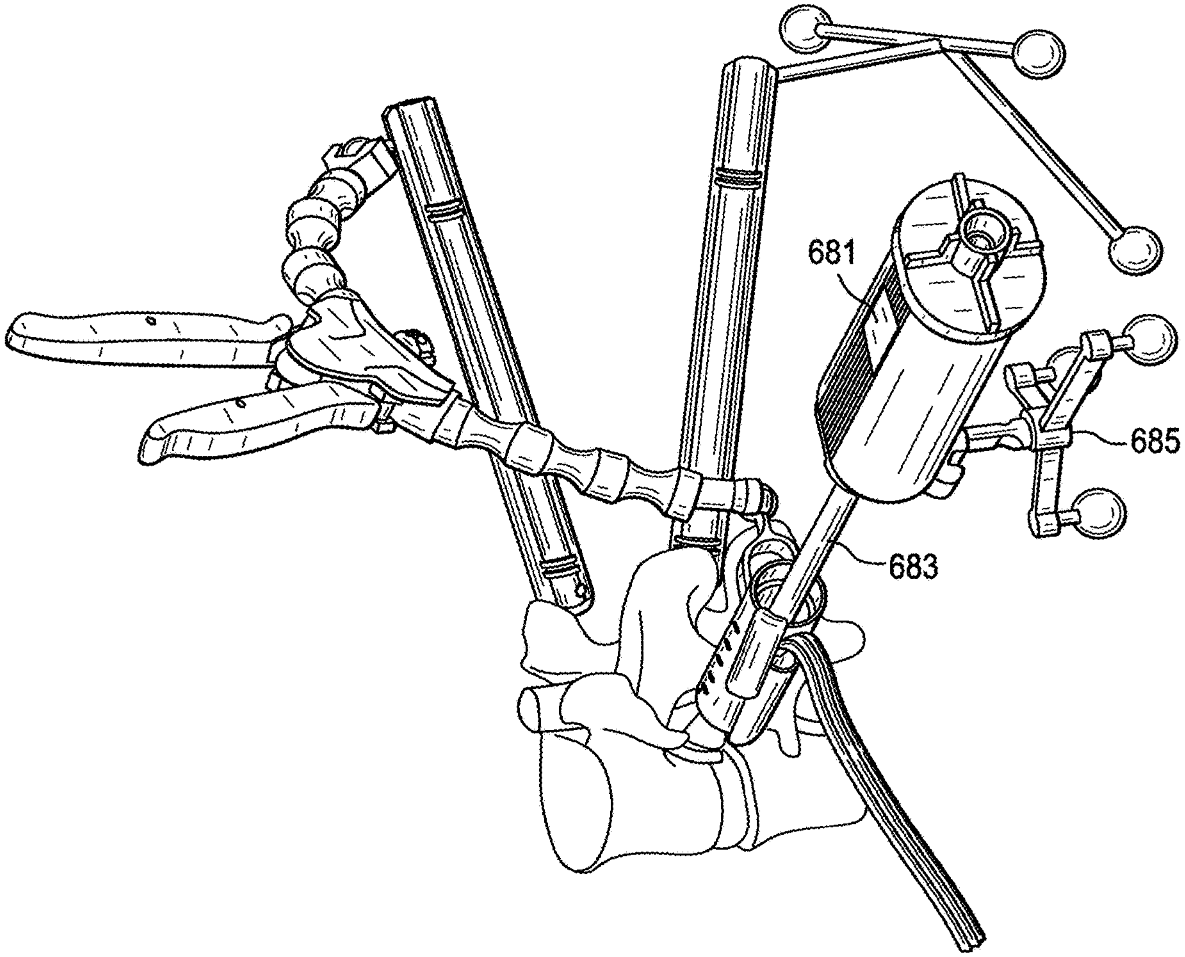
Figure 85:
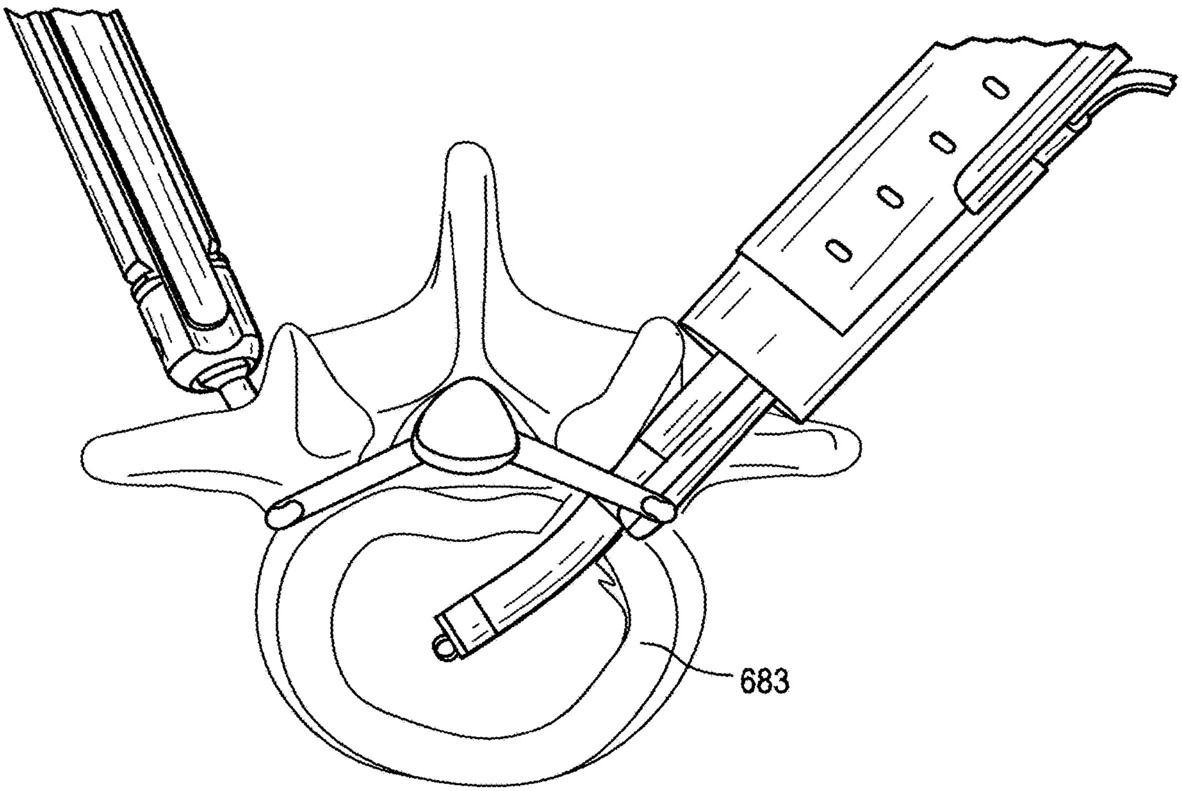

Now referring to FIGS. 84-85, disc clearing is performed with a suction-based discectomy tool 681 that holds the option to be navigated. Therefore there is a ring (not visible) mounted (welded/glued) on the shaft 683 of the discectomy tool that allows a play free mounting of a Navigation Array 685.

Step 7 Cage Insertion

Figure 86:
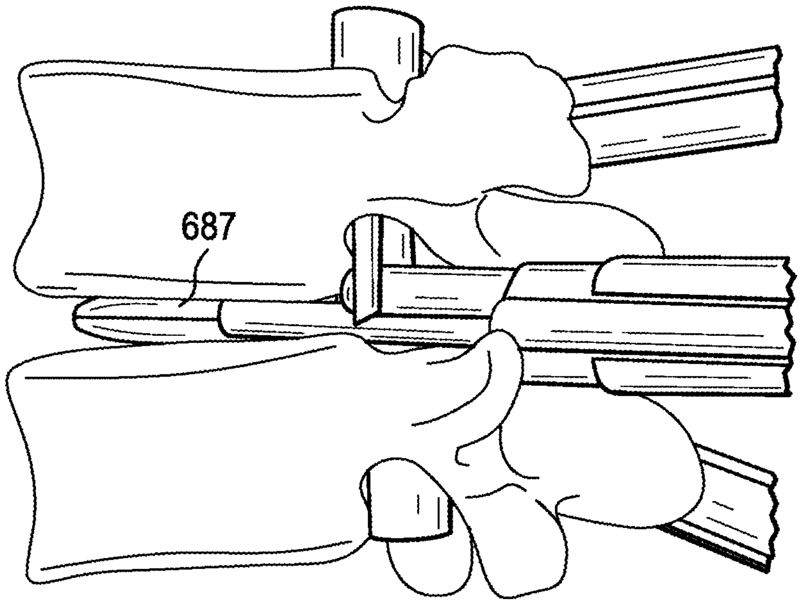
Figure 87:
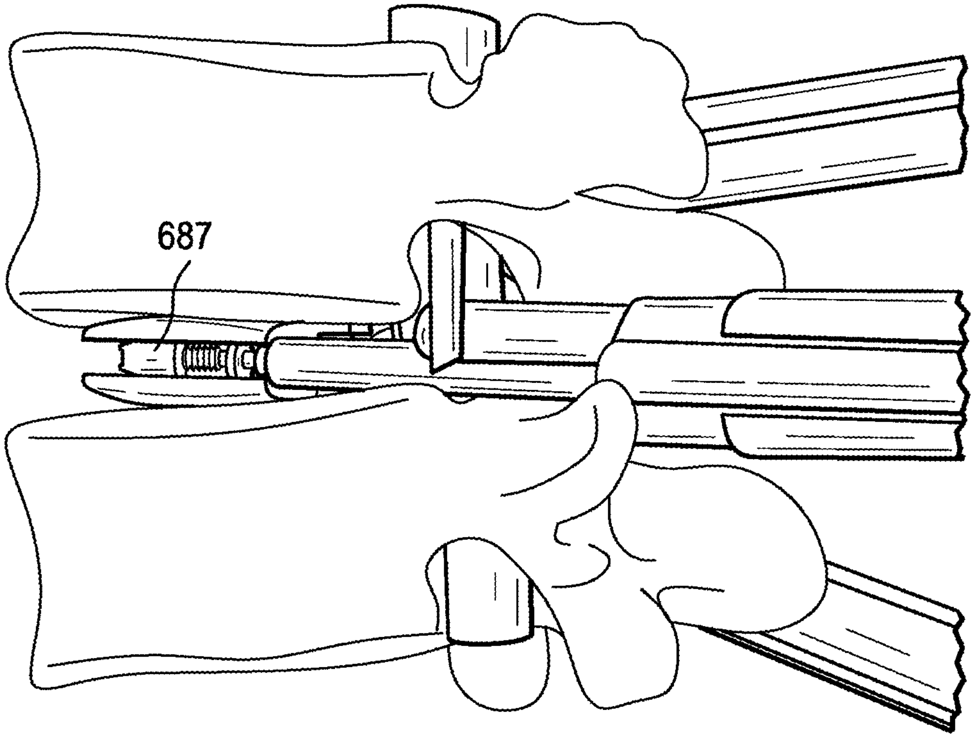

In FIG. 86 an expandable cage 687 is inserted into the disc space. In FIG. 87, the cage 687 is expanded to full expansion.

Figure 88:
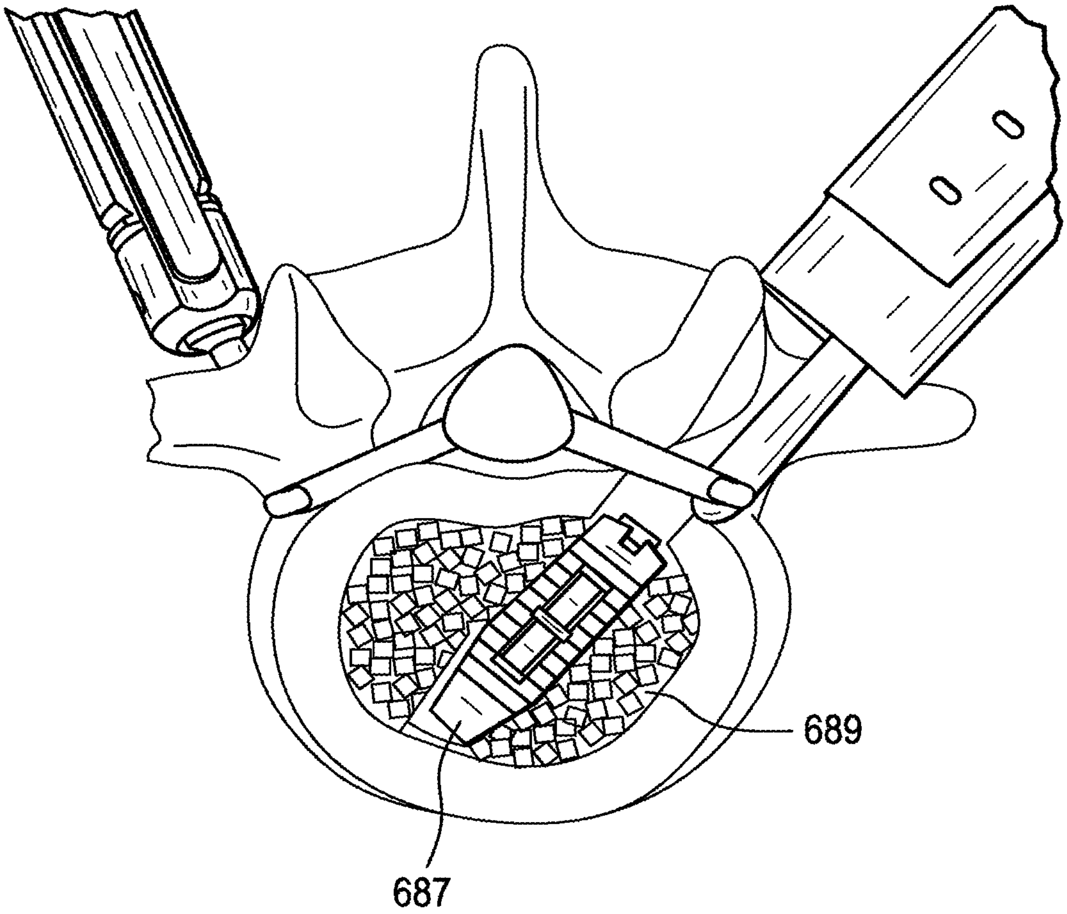

Now referring to FIG. 88, Bone graft 689 is inserted around the cage via a delivery system. The Expandable cage 687 is in its final position before detaching the Inserter. Bone Substitute 689 has been placed around the device (before and after inserting the cage) to ensure a proper fusion process.

Step 8 Posterior Fixation

Figure 89:
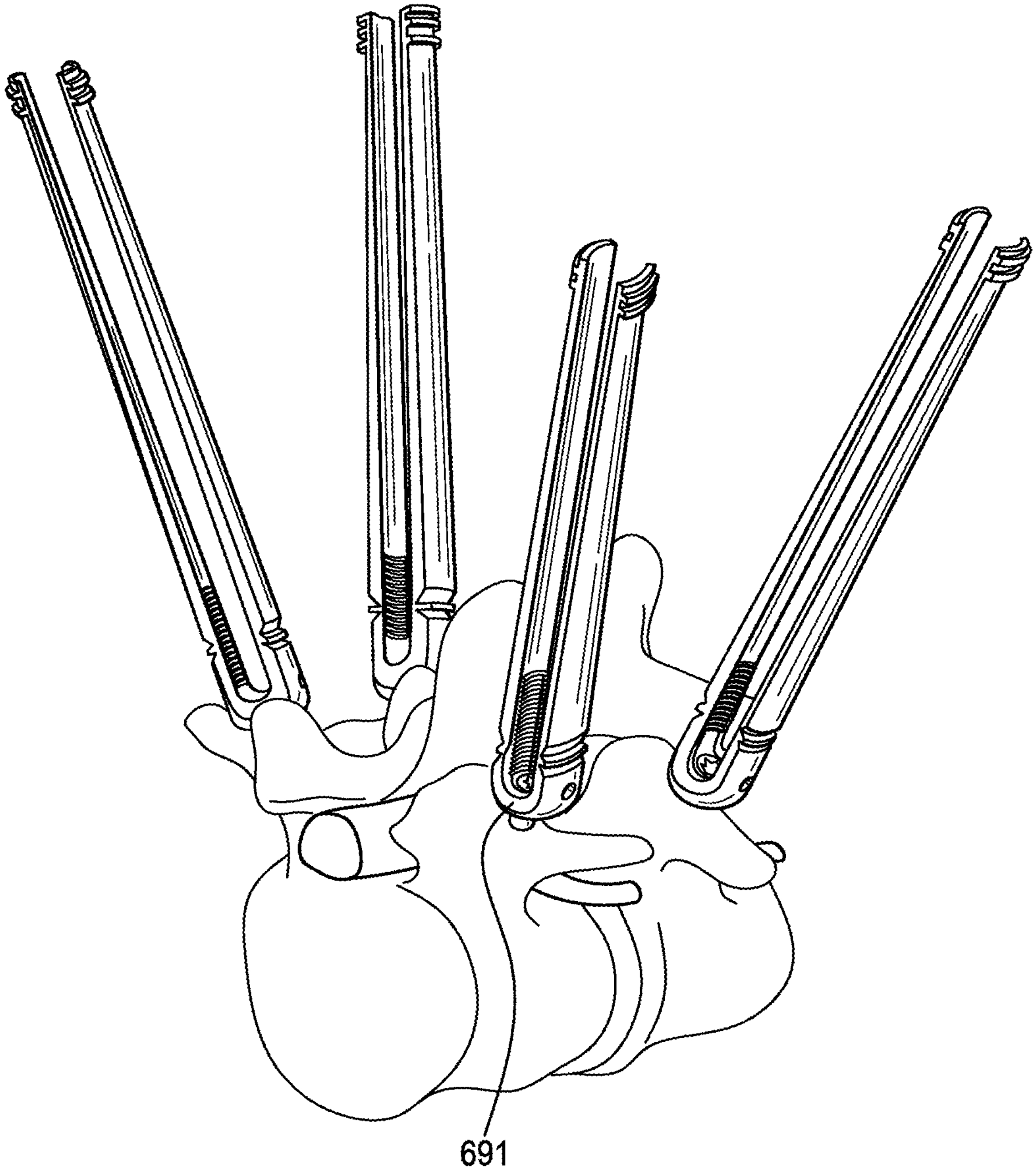
Figure 90:
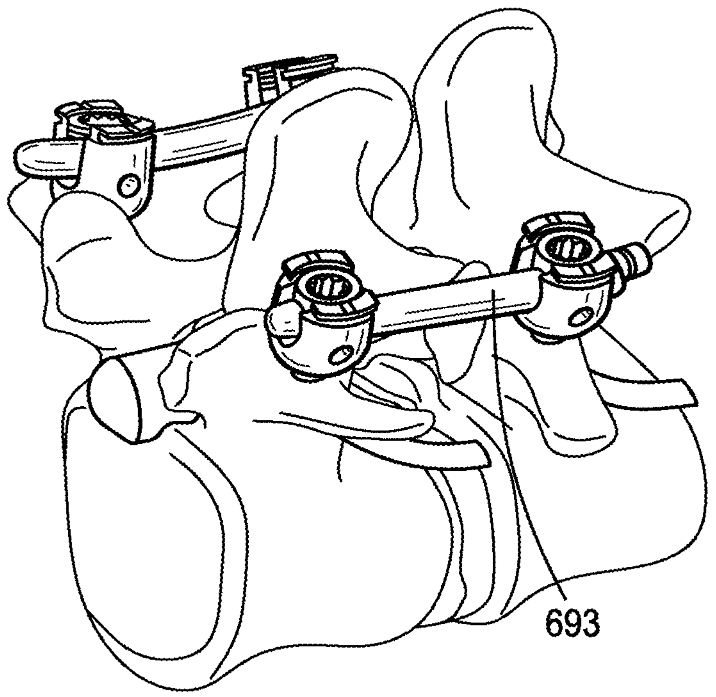

FIG. 89 discloses inserting the remaining screws 691, while FIG. 90 discloses placing rods 693 and fixing the construct.

Figure 91:
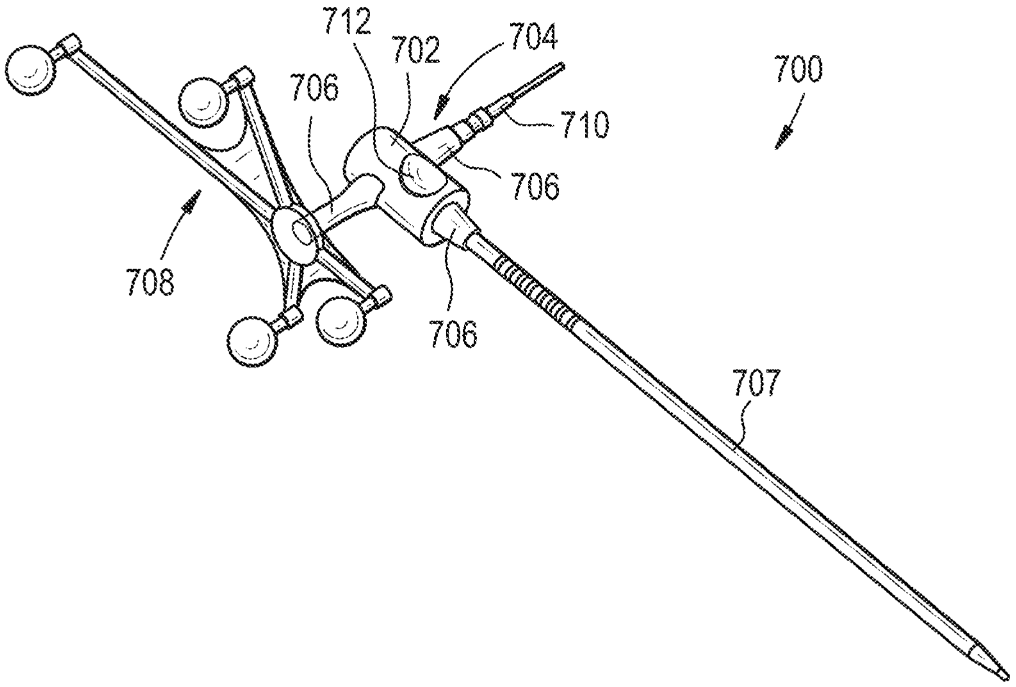
FIG. 91 is a perspective view of an embodiment of a multi-tool.

FIG. 91 illustrates another embodiment of a multi-tool 700 that can be used for surgery, e.g., posterior lumbar surgery. For example, the multi-tool 700 can include a cap 702 having one or more coupling features 704 thereon. The coupling features 704 can couple or integrate one or more surgical devices, instruments, implants, and/or other objects into a single tool, e.g., the multi-tool 700. The instruments coupled to the multi-tool 700 can then be tracked using surgical navigation, thereby eliminating the need to track the individual instruments separately.

The coupling features 704 can include one or more arms or connectors 706 that extend or protrude from the cap 702. Each arm 706 can integrate with one or more instruments to form the multi-tool 700. The arms 706 can be spaced apart along the surface of the cap 702 to prevent the instruments from cluttering a single location and providing access to the surgical area. The instruments that can couple to the cap 702 can assist with navigation and insertion of the shaft component into a surgical site to dilate the site. For example, as shown, a shaft component 707, a navigation marker or array 708, and a nerve mapping tool 710 can mate to the arms 706 to form the multi-tool 700, though, in some embodiments, one or more of these instruments can be omitted or replaced by other instruments. Some non-limiting examples of instruments that can be coupled to the multi-tool 700 can include dilation instruments, e.g., serial dilators or tube inserters, cutting instruments, e.g. scalpels, scissors, and so forth, and/or mapping instruments, e.g., ultrasound, can be added to the multi-tool.

The instruments can be shaped so as to be received in openings in the arms 706, though in some embodiments, the instruments can be integrally formed with, or fixedly attached to, the arms 706, or snap-fit, glued, stapled, or received in recesses, openings, and/or other surfaces of the cap 702. In some embodiments, the arms 706 of the cap 702 can include one or more securement features adapted to retain one or more of the instruments therein. For example, the arms 706 can include a throughhole 711 formed therein. The throughhole 711 can be formed in one or more surfaces of the cap 702 to form a channel that extends through the cap 702. The throughhole 711 can extend through a portion of the cap 702, as shown, in FIG. 94A, or extend entirely through the cap. The throughholes 722 can retain one or more of the instruments therein.

The cap 702 of the multi-tool 700 can couple to a shaft component 707. For example, the shaft component 707 can be received in one or more of the coupling features 704 in the cap to couple thereto. The shaft component 707 can be introduced into an incision in a target site of the patient to increase or dilate the target site. As shown, the shaft component 707 can be advanced proximally through the cap 702 until one or more grasping features (not shown) within the cap 702 secure the cap to the shaft component 707. In some embodiments, the grasping features can include a releasable member 712 or another feature that regulates the distance which the shaft component 707 can travel through the cap 702. The releasable member 712 can be actuated by the user to toggle the cap 702 between a plurality of shaft components, or between other instruments, as described further below.

The navigation marker 708 can be attached to the multi-tool 700 such that a position and orientation of the multi-tool 700 with respect to the marker 708 is known. The marker 708 can be embedded in a surface of the multi-tool or can extend outward from the multi-tool. In some embodiments, the marker 708 can be rigid or formed integrally with the cap 702, as described further below, to ensure navigational accuracy and/or precision.

For example, as shown, the navigation marker 708 can connect to one of the arms 706 that protrude from the cap 702. The navigation marker 708 can be a symbol or image having a known size, shape, or other characteristics to facilitate recognition of the position marker in captured images of the multi-tool 700. While a single navigation marker 708 is shown, the multi-tool 700 can include multiple markers, e.g., one at each end. Use of multiple markers 708 can improve tracking accuracy, field of view, or redundancy. The marker 708 can be detected by a navigation system 101, can communicate with the navigation system 101, or can be otherwise operably coupled to the navigation system 101 to allow the position and/or orientation of the multi-tool 700 and the underlying anatomy to be registered with and tracked by the navigation system 101. Having the multi-tool 700 connect the instruments as a single functional unit allows for tracking of the unit as a whole relative to one another and the target site when the shaft component is docked in the target site, which can prevent the need to place a separate marker on each instrument and conduct a cumbersome and time-consuming registration process for a large number of markers. The cost and complexity of the navigation system 101 can be reduced by reducing the number of markers that the system must track. Use of a single marker 708 can also provide greater access to the vertebral column and a less cluttered surgical site.

It will be appreciated that the structure and operation of the marker 708 can vary depending on the type of navigation system 101 used. In the illustrated embodiment, the marker 708 includes four sphere-shaped fiducials for use with an optical navigation system. The fiducials can be arranged in predetermined positions and orientations with respect to one another. The fiducials can be positioned within a field of view of the navigation system 101 and can be identified in images captured by the navigation system. Exemplary fiducials include infrared reflectors, LEDs, and so forth. The marker 708 can be or can include an inertial measurement unit (IMU), an accelerometer, a gyroscope, a magnetometer, other sensors, or combinations thereof. The sensors can transmit position and/or orientation information to the navigation system 101, e.g., to a processing unit of the navigation system.

The marker 708 can be configured to be visible or detectable in patient imaging performed preoperatively, intraoperatively, or postoperatively. For example, the marker 708 can include radiopaque portions to facilitate visualization of the marker in X-ray, CT, or fluoroscopy. By way of further example, the marker 708 can include metallic, magnetic, or other materials visible under MRI.

Any of a variety of surgical navigation systems 101 can be used, including commercially available systems such as those offered by BRAINLAB AG of Germany. The navigation system 101 can include an imaging system with a camera or image sensor that captures images of a surgical site and objects within the surgical site, such as the marker 708 and a similar marker attached to an instrument. The captured images can be registered to one or more patient images. The captured images and/or the patient images can be processed using a processor to determine a position and/or orientation of the instrument relative to an anatomy of the patient. This information can be communicated to a user, e.g., using an electronic display or a tactile, audible, or visual feedback mechanism.

The nerve mapping tool 710 can be attached to the multi-tool 700 to provide feedback and plans of nerve location. For example, the nerve mapping tool 710 can include a plug that is configured to be received in one or more of the arms 704 of the multi-tool 700 to track the distances of one or more of the instruments, e.g., the shaft component 707, from nerves. Any of a variety of nerve mapping tools can be used, including those using various technologies, such as electromyography (EMG) and mechanomyography (MMG), as in commercially available systems offered by Sentio. The nerve mapping tool 710 can detect nerve location so as to prevent damage during insertion of the shaft component or use of the other instruments of the multi-tool.

For example, the nerve mapping tool 710 can include an invasive stimulator capable of providing an electrical stimulus, mechanical sensors to monitor muscle movement, and a processor that can determine if a sensed movement was caused by the provided electrical stimulus. The nerve mapping tool 710 can identify the presence of nerves during a lateral approach to the spine, though it can be modified to detect nerves in a variety of target sites. Some non-limiting examples of the nerve mapping tool 710 can include the use of MMG in robotic surgical procedures, avoiding nerve damage in pelvic floor procedures such as prostate surgery, using MMG system in a diagnostic capacity to evaluate changes nerve health, and so forth.

Figure 92:
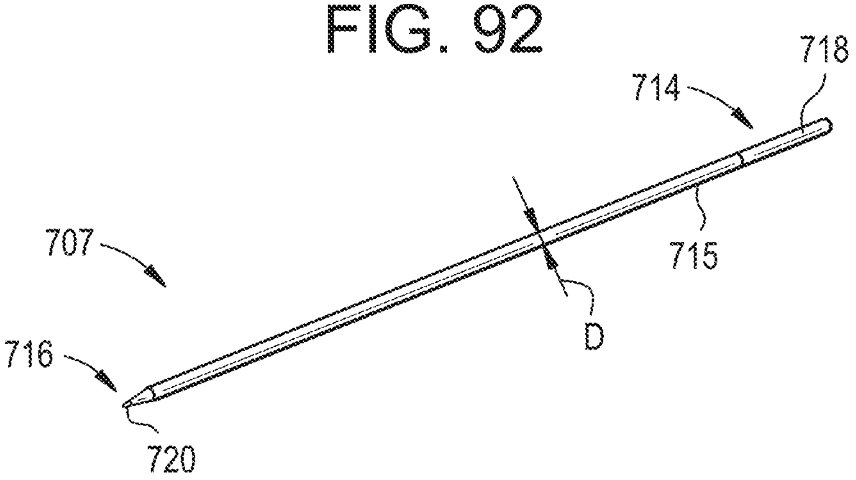
FIG. 92 is perspective view of a shaft component that is used with the multi-tool of FIG. 91.

FIG. 92 illustrates one embodiment of the shaft component 707 used with the multi-tool 700. The shaft component 707 can be inserted into an incision in the patient to dilate the surgical site. The shaft component 707 can include a solid shaft, though, in some embodiments, the shaft component can be hollow to allow one or more surgical devices to pass therethrough. The shaft component can be made from metal, plastic, polymer, or any other material that can be used during dilation as appreciated by one skilled in the art. The shaft component 707 can have a generally cylindrical shape as shown, though the shaft component can be circular, triangular, pyramidal, and so forth.

As shown, the shaft component 707 can include a proximal handle 714 that tapers to a distal tip 716. The handle 714 can be adapted to be received in the cap 702 as mentioned above, and described in further detail below. In some embodiments, the proximal handle 714 can include grooves or annular rings 715 that extend along a portion thereof to allow for enhanced gripping of the shaft component. The shaft component 707 can have a diameter D that ranges from about 1 mm to about 10 mm, about 2 mm to about 9 mm, about 3 mm to about 8 mm, about 4 mm to about 7 mm, or about 5 mm to about 6 mm.

Figure 93:
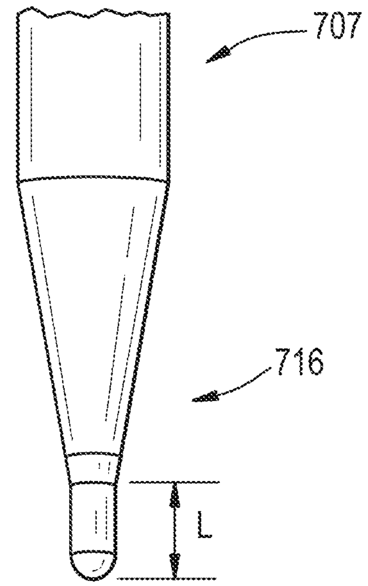
FIG. 93 is a schematic view of a distal end of the shaft component of FIG. 92.

An embodiment of the distal tip 716 is shown in greater detail in FIG. 93. The distal tip 716 can be adapted to be docked into target tissue to secure shaft component 707 within the surgical site. The distal tip can include a hemispherical shape, as shown, though, in some embodiments, the tip can be pointed, sharp, blunt, and so forth. In the embodiment shown, the hemispherical geometry of the distal tip can allow the tip to be swept over the target site and gently pushed into the target tissue, e.g., disc or bony surface. The distal tip 216 can have a length L that ranges from about 1 mm to about 10 mm, about 1.5 mm to about 9 mm, about 2 mm to about 8 mm, about 2.5 mm to about 6 mm, or about 3 mm to about 4 mm and a diameter that ranges from about 0.25 mm to about 3 mm, about 0.5 mm to about 2.5 mm, about 1 mm to about 2 mm, or about 1.5 mm.

In some embodiments, the shaft component 707 can include a dielectric coating along a length thereof to insulate the shaft component, though one or more portions thereof can be free of electrical insulation so as to conduct electrical current. For example, the shaft component 707 can include one or more conducting regions that are adapted to electrically communicate with, and/or conduct electric current to, instruments of the multi-tool and/or the target site. As shown, the proximal handle 714 can include a first conducting region 718 on a proximal-most end thereof and the distal tip 716 can include a second conducting region 720 on a distal-most end thereof. Each of the first and second conducting regions 718, 720 can form an electrode surface or serve as an interface which can form an electrical connection to one or more instruments of the multi-tool 700. For example, the first conducting region 718 can form an electrical connection with the nerve mapping tool 710, as described further below, while the second conducting region 720 can form an electrode surface by which the shaft component 707 can conduct electric current from a source, e.g., the nerve mapping tool 710, to tissue. While two conducting regions are shown, it will be appreciated that one or three or more conducting regions can be formed on the shaft component 707 to form electrical connections therewith.

Figure 94A:
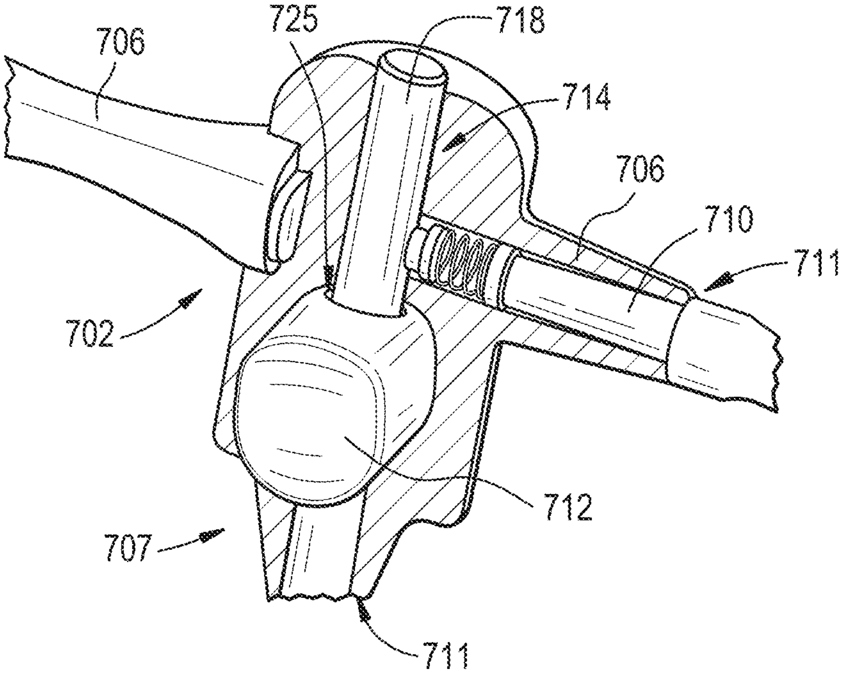
FIG. 94A is a cross-sectional view of the multi-tool of FIG. 91.
Figure 94B:
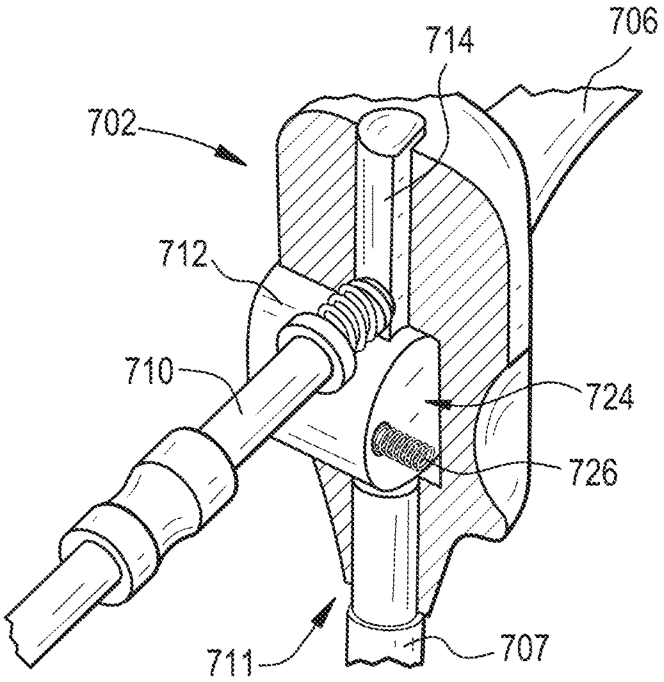
FIG. 94B is another cross-sectional view of the multi-tool of FIG. 91.
Figure 94C:
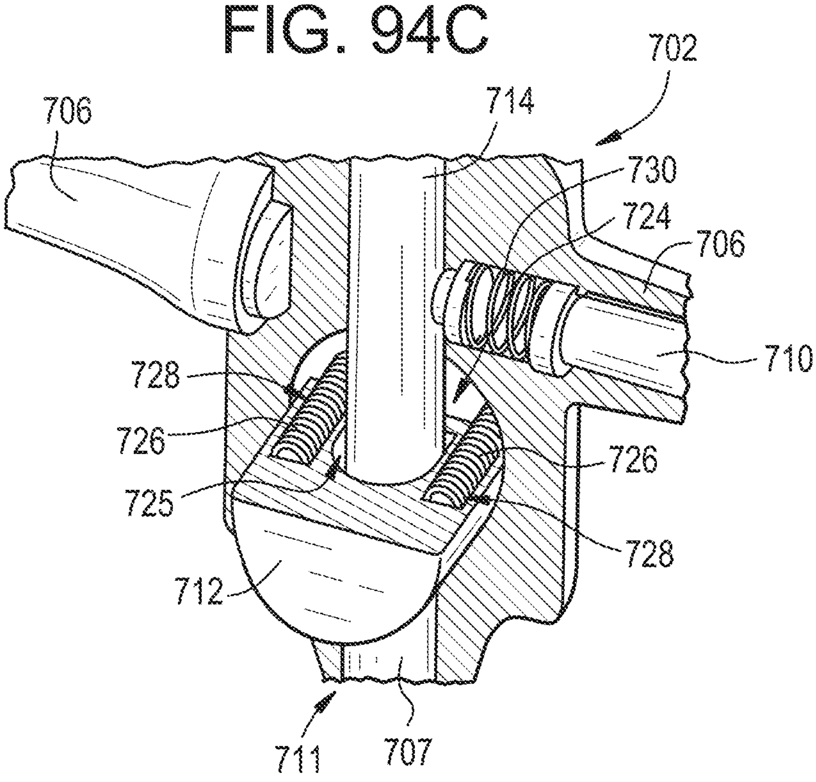
FIG. 94C is another cross-sectional view of the multi-tool of FIG. 91.

FIGS. 94A-94C illustrate the components of the cap 702 in greater detail. In some embodiments, the cap 702 can include a throughbore 724 formed therein. The throughbore 724 can be positioned in an intermediate portion of the cap 702, as shown in FIG. 94B, to couple one or more features of the multi-tool thereto. For example, as shown, the throughbore 724 can be adapted to receive the releasable member or button 712 therein. The button 712 can be positioned within the throughbore, as shown in FIG. 94A, or can be fixedly attached to the cap 702. In some embodiments, the button can be a single, monolithic component, or formed from two or more separate pieces that are configured to move relative to one another to toggle the button between one or more configurations.

The button 712 can be adapted to retain surgical devices within the cap. For example, the button 712 include one or more features for coupling to surgical devices. In some embodiments, the button 712 can include a hollow interior to allow surgical devices to pass therethrough. For example, as shown in FIG. 94A, the shaft component 707 can pass through an interior bore 725 of the button 712 to attach the shaft component 707 to the cap 702. The bore 725 can extend through a diameter of the button to pass the shaft component 707 therethrough. The bore 725 can be shaped in the manner of the shaft component, e.g., D-shaped as shown in FIG. 94C, to prevent rotation of the shaft component 707 relative to the cap 702.

The button 712 can include one or more biasing features configured to toggle the button 712 between the locked and unlocked configurations. For example, the button 712 can include one or more bias elements or springs 726 that extend through the button. The bias elements 726 can abut an inner surface of the button and a wall of the throughbore 724 to exert a biasing force on the button. The button 712 can include two bias elements 726, as shown, though it will be appreciated that one, or three or more bias elements can be used.

The button 712 can be adapted to be toggled between a locked configuration and an unlocked configuration. For example, the button 712 can be depressed or pushed into the throughbore 724 to move the button from the locked configuration to the unlocked configuration. In the locked configuration, the button 712 can prevent the shaft component 707 from moving relative to the cap 702, while in the unlocked configuration, the button 712 can allow the shaft component 707 to move relative to the cap 702 within the bore 725. In the locked configuration, the bias element 726 can be fully extended to apply an outward force on the button 712 relative to the throughbore 724. The outward force can bias the button 712 to protrude from the throughbore 724 which can prevent the shaft component 707 from traveling freely through the throughbore.

In some embodiments, one or more features of the button 712 can be configured to engage the shaft component 707 to lock the shaft component 707 within the cap 702. For example, the button 712 can include a grasper (not shown) to secure a longitudinal position of the shaft component 707 within the bore 725. The grasper can be located in an interior portion of the button 712 to mate with the handle 714 of the shaft component 707. For example, as the shaft component 707 advances proximally through the bore 725, the shaft component 707 can contact the grasper to prevent further proximal translation of the shaft component. In some embodiments, the shaft component 707 can include an indentation configured to form a male-female interlock with the grasper. In such embodiments, the grasper can be configured to travel along a surface of the shaft component 707 until contacting the indentation. At the indentation, the grasper can extend into the indentation to lock the longitudinal position of the shaft component 707 relative to the button 712. In some embodiments, the button 712 can provide tactile feedback to a user when the button 712 locks to the shaft component 707. Imparting a force in an opposite direction of the outward force can detach the grasper from the shaft component 707 to toggle the button 712 from the locked configuration to the unlocked configuration to allow the shaft component 707 to longitudinally translate relative to the cap 702 and to detach the cap from the shaft component, e.g., once the shaft component is implanted and/or docked in target tissue. The ability to detach the cap 702 from the shaft component 707 can allow the cap 702 to be attached to other instruments, such as other shaft components, as well as allow for serial dilation or other instruments to be inserted over the shaft component 707 to increase a size of the target site, as described further below.

The button 712 can include one or more channels 728 therein. For example, the bias elements 726 can be disposed in channels 728 that run through the button 712. As shown, the channels 728 can run perpendicular to the shaft component 707 through the interior of the button 712 to move the button in a direction perpendicular to the shaft component. The channels 728 can run through a width of the button 712, or terminate in an intermediate portion thereof, as shown.

The cap 702 can allow for communication between system components disposed therein. For example, the through-holes 711 in each of the arms 706 can lead into a hollow portion of the cap to allow communication between the components disposed therein. In some embodiments, the cap 702 can facilitate an electrical connection between multiple components of the multi-tool 700. For example, the nerve mapping tool 710 can interface with the shaft component 707 to establish an electrical connection therebetween. For example, the nerve mapping tool 710 can include a conductive member 730 thereon to conduct the electrical connection. As shown, the conductive member 730 can be a spring member that can vary a distance between the nerve mapping tool 710 and the shaft component 707. The conductive member 730 can contact an exposed core of the shaft component 707 to complete a circuit between the shaft component 707 and a distal electrode coupled to the nerve mapping tool 710. In some embodiments, the electrical connection with the nerve mapping tool 710 can be used as a stimulation electrode having muscle activity sensors thereon to detect movement of muscles in response to a stimulus applied to the spine by the shaft component. As shown, the conductive member 730 can be a spring member that can vary a distance between the nerve mapping tool 710 and the shaft component 707. In some embodiments, the conductive member 730 can be made of a metal, or another material that is adapted to conduct electricity.

Figure 95:
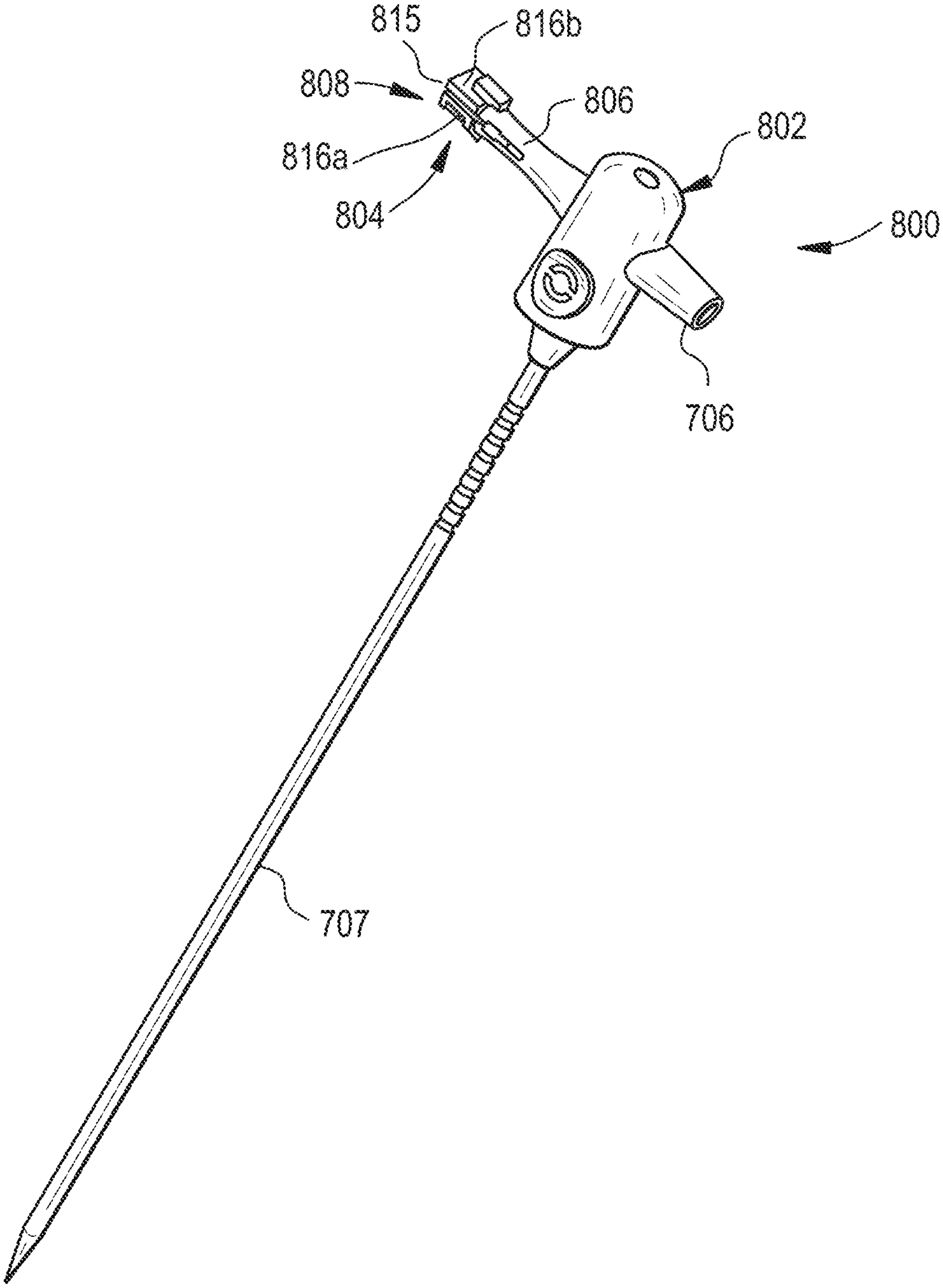
FIG. 95 is a perspective view of another embodiment of a multi-tool.
Figure 96:
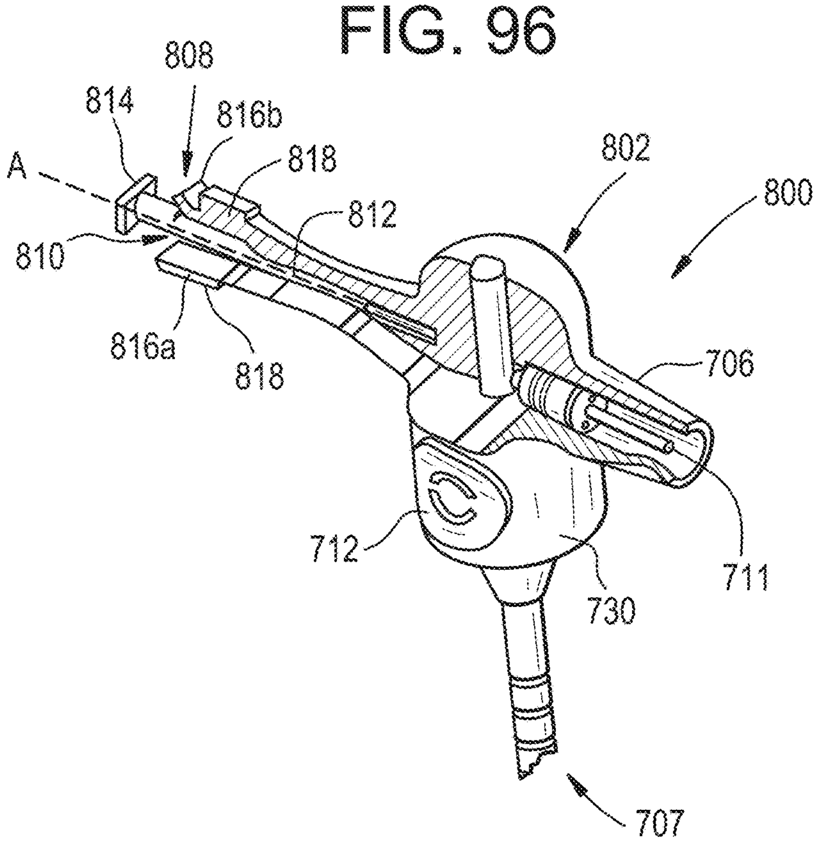
FIG. 96 is a cross-sectional view of the multi-tool of FIG. 95.
Figure 97:
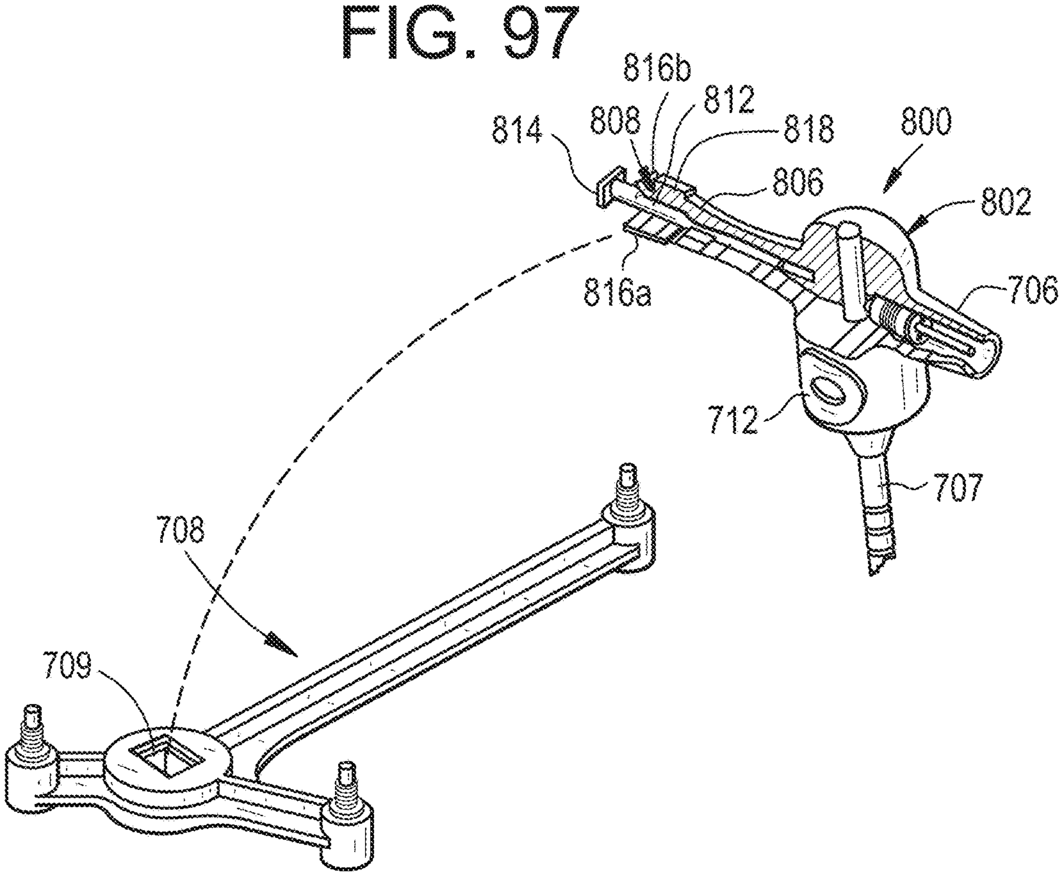
FIG. 97 is another cross-sectional view of the multi-tool of FIG. 91 being coupled to a navigation array.
Figure 98:
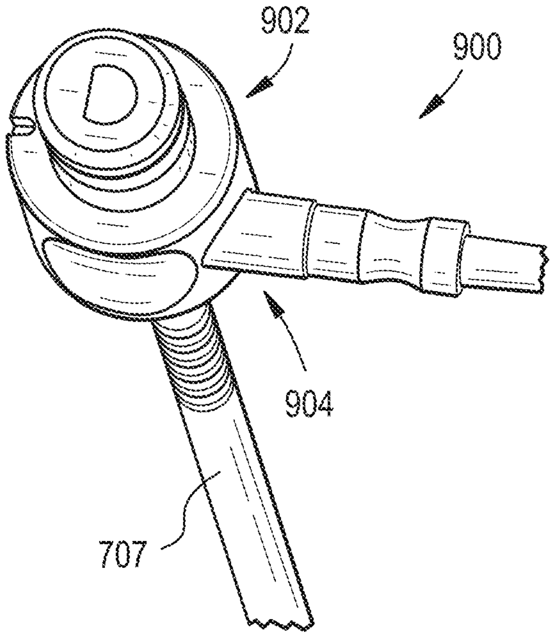
FIG. 98 is a perspective view of another embodiment of a multi-tool.

FIGS. 95-97 illustrate an alternate embodiment of a cap 802 of a multi-tool 800. Except as indicated below and as will be readily appreciated by one having ordinary skill in the art, the structure and function of the multi-tool 800 is substantially the same as that of the embodiment of the multi-tool 700 described above, and therefore a detailed description is omitted here for the sake of brevity.

The cap 802 can include one or more coupling features 804 thereon in lieu of, or in addition to, the coupling features 704, e.g., arms 706, discussed above with regards to FIGS. 94A-94C. For example, as shown, the coupling features 804 can include one or more modular attachment arms 806 that can be adapted to support a modular coupling of one or more components thereto. The modular attachment arms 806 can be formed in lieu of, or in addition to, the arms 706 discussed above with regards to FIGS. 94A-94C.

Use of a modular attachment arm 806 can allow the multi-tool 800 to be used in procedures that do not require navigation and/or to couple to other surgical devices, e.g., a second shaft component, a nerve mapping tool 710, and so forth. The cap 802 can include a single modular attachment arm 806 for modular coupling, though, in some embodiments, the cap 802 can include two or more such arms. Further, although the navigation array 708 is described herein as being modularly coupled to the cap, as shown and described in FIG. 97, in some embodiments, one or more of the nerve mapping tool 710 and/or the shaft component 707 can also be modularly coupled to the cap 802.

The modular attachment of the navigation array 708 to the cap 802 can be made in a variety of ways. For example, the modular attachment arm 806 can include a collet 808 configured to expand when the navigation array 708 is inserted therein. The collet 808 can be sized such that the collet can be received within, or otherwise interface with, a component of the multi-tool 800, e.g., the navigation array 708. The design of the collet 808 can allow the navigation array 708 to move relative to the modular attachment arm 806 to rigidly lock the array 708 to the multi-tool 800. A rigid connection between the array 708 and the multi-tool can increase and maintain navigational accuracy. In some embodiments, the navigation array 708 can couple to the cap 802 in a single orientation.

The modular attachment arm 806 can include a bore 810 extending therethrough. The bore 810 can extend through an entire length of the modular attachment arm 806, as shown, though, in some embodiments, the bore 810 can terminate along an intermediate portion of the arm 806. The bore 810 can define a central longitudinal axis A therethrough for receiving coupling features and/or surgical devices therethrough to facilitate the modular coupling.

For example, the bore 810 can include a pin 812 extending therethrough. As shown, the pin 812 can extend along the central longitudinal axis A of the bore into the cap 802 to secure the pin within the bore 810. The pin 812 can be configured to travel through the bore 810 to adjust the modular coupling to attach the surgical devices to the multi-tool 800.

The pin 812 can include a pin head 814 formed thereon. As shown, the pin head 814 can protrude from the bore 810 in the modular attachment arm 806. The pin head 814 can be formed of a square or rectangular element configured to be received in a coupling feature 709 of a surgical device, e.g., an opening in the navigation array 708, though the pin head 814 can be circular, triangular, or another shape that corresponds to the coupling feature 816, as shown in FIG. 97. In some embodiments, the pin head 814 can be keyed such that the opening 709 can be prevented from coupling to the pin head 814 in all but one orientation, thereby ensuring a rigid connection is formed for enhanced navigational accuracy.

In some embodiments, the modular attachment arm 806 can include one or more slots 815 therein. As shown, the slots 809 can extend through a portion of the arm 806, though, in some embodiments, the slots 809 can extend along an entire length of the arm 806. The slots 815 in the arm can separate the modular attachment arm into a pair of fingers 816*a*, 816*b*. The slots 815 allow the fingers 816*a*,

816*b* to move flex and/or bend with respect to one another, which limits the rigidity of the modular attachment arm 806.

In some embodiments, the pin 812 can be preloaded between the fingers 816*a*, 816*b* such that pin head 814 protrudes from the modular attachment arm 806 as shown in FIGS. 96-97. The pin 812 can travel along the axis A through the bore. For example, a force applied onto the pin head 814, e.g., by mounting a surgical device thereto, can cause the pin 812 to retract longitudinally into the modular attachment arm 806. Retraction of the pin head 814 into the bore 810 as the surgical device, e.g., the navigation array 708, is mounted onto the arm 806 can flex the fingers 816*a*, 816*b* outward as the pin head 814 advances through the bore 810. As shown, the pin head 814 can be larger than the pin 812 to abut one or more surfaces of an interior surface of the modular attachment arm 806 to resist and/or movement of the pin 812. During retraction of the pin head 814, the size of the bore expands, separating the distance between the fingers. Retraction of the pin head 814 can continue until the fingers 816*a*, 816*b* abut the walls of an opening 709 in the array to secure the array to the modular attachment arm 806. The fingers 816*a*, 816*b* can grip one or more interior surfaces of the opening 709 to maintain a rigid connection of the array 708 for accurate navigation. In some embodiments, the fingers 816*a*, 816*b* can include graspers 818 thereon to increase the surface area of the contact between the modular attachment arm 806 and the opening 709 of the navigation array 708 to increase rigidity of the coupling.

FIGS. 98-101 illustrate an alternate embodiment of a multi-tool 900. Except as indicated below and as will be readily appreciated by one having ordinary skill in the art, the structure and function of the multi-tool 900 is substantially the same as that of the embodiments of the multi-tool 700, 800 described above, and therefore a detailed description is omitted here for the sake of brevity.

The multi-tool 900 can include a cap 902 thereon. As shown, the cap 902 can include one or more coupling features 904 thereon in lieu of, or in addition to, the coupling features 704, e.g., arms 706, discussed above with regards to FIGS. 94A-94C. For example, as shown, the coupling features 904 can include one or more arms 906 that can be adapted to support coupling of one or more surgical devices thereto. The arms 906 can be formed in lieu of, or in addition to, the arms 706 discussed above with regards to FIGS. 95-97. It will be appreciated that a combination of arms and modular attachment arms can be formed on the cap 902 to vary the manner in which surgical devices are coupled to the multi-tool 900.

Figure 100:
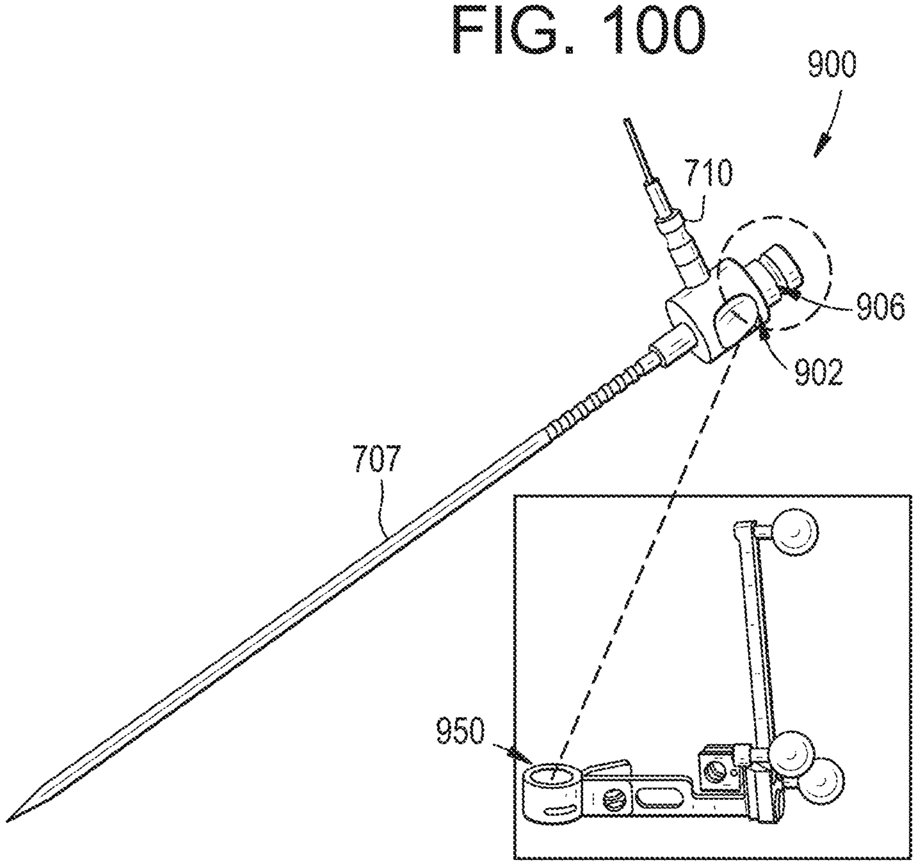
FIG. 100 is a perspective of the multi-tool of FIG. 98 being coupled to a navigation array.

For example, as shown, an arm 906 of the cap 902 can include a protrusion 907 that extends proximal to a body of the cap 902. The protrusion 907 can be used in lieu of, or in addition to, the arms 706 or the modular attachment arm 806 described above. The shape of the protrusion 907 can correspond to that of a surgical device coupled thereto, or protruding therefrom, or the protrusion 907 can have a different shape than the surgical devices, such as oval, oblong, square, rectangular, triangular, and so forth. As shown in FIG. 100, the protrusion 907 can be received in an opening of a coupling 950 that is attached to the navigation array 708, though, in some embodiments, the navigation array 708 can be inserted into an opening of the protrusion 907.

The protrusion 907 can include an exterior sidewall 908 that defines a lumen 911 that extends through the protrusion 907 into the cap 902. The lumen 911 can extend through the protrusion into a hollow portion of the cap 902, as described with respect to the embodiments above. The lumen can extend along an axis A1 that is parallel to the axis of the shaft component 707 inserted through the cap 902 from a proximal end 902*p* of the cap to a distal end 902*d* of the cap. The lumen 911 can receive instruments or tools therethrough for performing rod reduction, derotation, drilling, set screw insertion, and so forth. The instruments can be inserted proximally or distally through the lumen 911.

Figure 99:
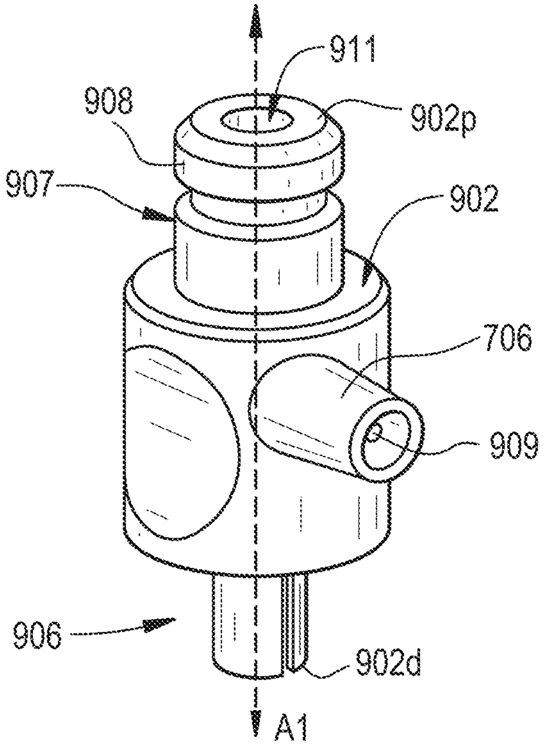
FIG. 99 is a perspective view of a cap of the multi-tool of FIG. 98.

In this embodiment, the cap 902 can facilitate electrical connections between several surgical devices. For example, any surgical device, e.g., the shaft component 707, that is advanced into the cap 902 can become disposed within the lumen 911. In some embodiments, the proximal handle 714 of the shaft component 707 can extend through the lumen 911 and the protrusion 907 to abut the proximal end 902 of the cap 902. In some embodiments, and as shown in FIGS. 99 and 100, the proximal handle 714 of the shaft component 707 can extend through the hollow portion of the cap 902 such that the proximal handle 714 protrudes from the proximal end 902*p* of the cap 902. When the proximal handle 714 protrudes from the proximal end 902*p*, the proximal handle 714 creates a contact point to which an electrical connection can be coupled, as described further below.

One or more of the arms 906 that extend from the cap 902 can include an electrical component 909 therein to establish an electrical connection of the cap 902 to other surgical devices. The electrical component 909 can be in the form of a pin, bolt, spring, or another feature known to one skilled in the art that is configured to interface between two components. The electrical component 909 can be made from a metal, or another conductive material, to enable two or more devices to send an electrical signal to one another. In some embodiments, and as shown in FIGS. 100-101, the nerve mapping tool 710 can be inserted into the arm 906 to interface the nerve mapping tool 710 with the electrical component 909 and to connect the nerve mapping tool 710 to the other devices coupled to the multi-tool.

Figure 101:
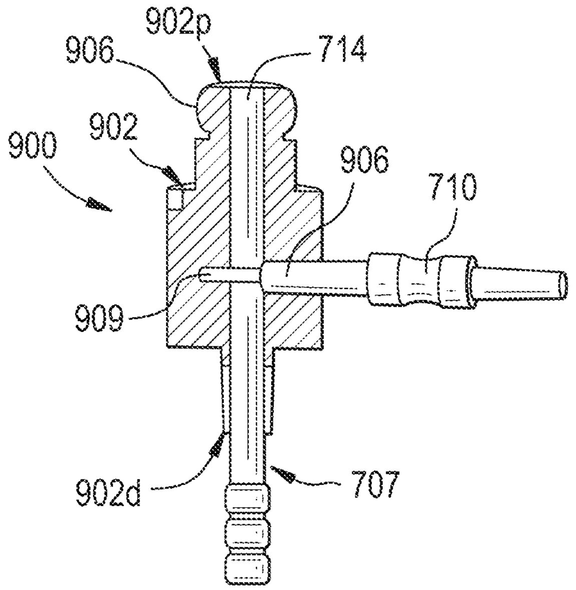
FIG. 101 is a cross-sectional view of the cap of the multi-tool of FIG. 98.

FIG. 101 illustrates the electrical connection that is established between the shaft component 707 and the nerve mapping tool 710 within the cap 902 in greater detail. The nerve mapping tool 710 can be inserted into the arm 906 over the electrical component 909 to receive the electrical component 909 therein. Insertion of the nerve mapping tool 710 over the electrical component 909 can advance the electrical component 909 further into the hollow portion of the cap 902 to abut the shaft component. The connection between the shaft component 707 and the nerve mapping tool 710 at the electrical connection can allow current to travel from the nerve mapping tool 710, through the pin, through the shaft component 707 to the distal tip 716 into tissue in which the shaft component 707 is disposed. In some embodiments, the shaft component 707 can include a throughhole therein configured to receive the electrical component 909. The throughhole can be configured to receive a portion of the electrical component 909 therethrough, as shown, to establish an electrical connection between both devices.

In some embodiments, the multi-tool 900 can allow for more than two devices to be electrically connected. For example, one or more devices can attach to the protrusion 907, and to the handle of the shaft component 707 protruding proximally therefrom, to establish an electrical connection therebetween. The first conducting region 718 of the shaft component 707 can provide another surface that couples to surgical devices that is configured to establish an electrical connection therebetween. Electrical signals can travel from the electrical component 909 through the shaft component 707 and into the first conducting region 718, and travel to surgical devices coupled thereto.

Figure 102:
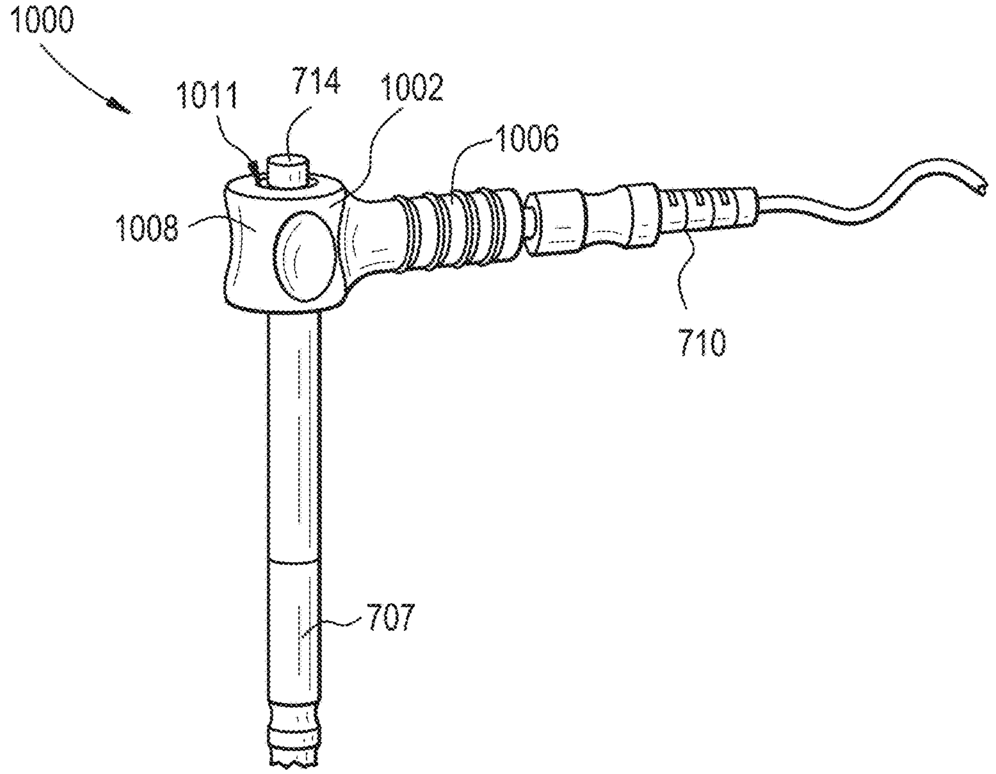
FIG. 102 is a perspective view of another embodiment of a multi-tool.

FIG. 102 illustrates an alternate embodiment of a multi-tool 1000. The multi-tool 1000 can include a cap 1002 having a single arm 1006 extending therefrom. The arm 1006 can be fixedly coupled to, or integrally formed with, the cap. As shown, the cap 1002 can include an exterior sidewall 1008 that defines a lumen 1011 that extends therethrough and is configured to receive the shaft component 707 therein. The nerve mapping tool 710 can be received in the arm 1006 to establish an electrical connection therebetween.

Figure 103:
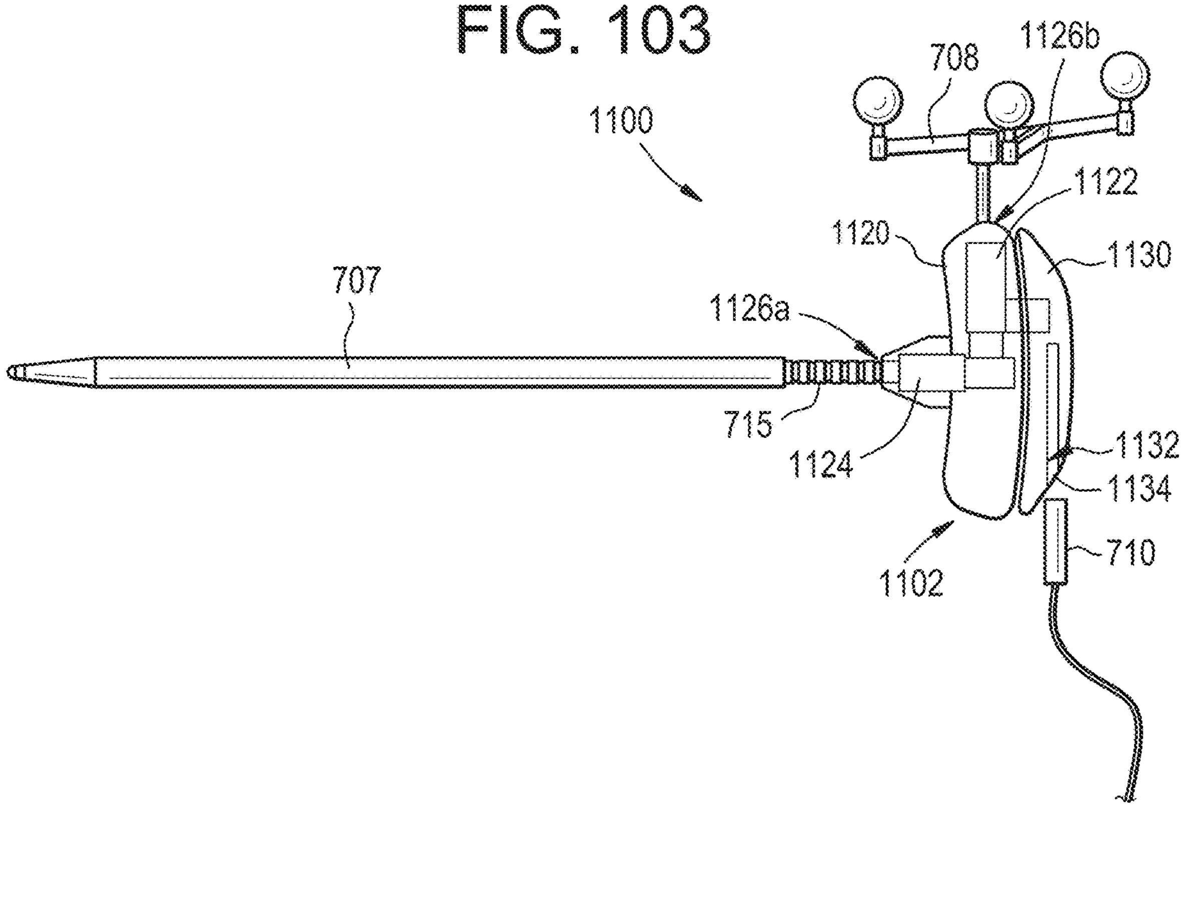
FIG. 103 is a perspective view of another embodiment of a multi-tool.

FIG. 103 illustrates an alternate embodiment of a multi-tool 1100. Except as indicated below and as will be readily appreciated by one having ordinary skill in the art, the structure and function of the multi-tool 1100 is substantially the same as that of the embodiments of the multi-tool 700, 800, 900, 1000 described above, and therefore a detailed description is omitted here for the sake of brevity.

The multi-tool 1100 can include a cap or locking handle 1102 having multiple components that are configured to move relative to one another to couple one or more surgical devices thereto. As shown, the locking handle 1102 can include a base clamp 1120 and a top clamp 1130, each having one or more surgical devices coupled thereto. One skilled in the art will appreciate that surgical devices can be coupled to either, or both, of the base clamp 1120 and the top clamp 1130, as described further below. In use, the base clamp 1120 and the top clamp 1130 can rotate relative to one another to move the locking handle 1102 from an open position to a closed position to lock the shaft component 707 to the locking handle 1102.

The locking handle 1102 can include one or more connection points or ports 1122, 1132 therein to which the surgical devices can be coupled. For example, as shown, the locking handle 1102 can include two ports 1122, 1132, each having one of the navigation array 708 and the nerve mapping tool 710 coupled thereto, though, in some embodiments, the locking handle 1102 can be coupled to one or three or more surgical devices. While the navigation array 708 is shown being coupled to the base clamp 1120 and the nerve mapping tool 710 being coupled to the top clamp 1130, in some embodiments, both the array 708 and the nerve mapping tool 710 can be coupled to the base clamp 1120 or to the top clamp 1130.

In some embodiments, the base clamp 1120 can include a core 1124 for coupling to the surgical devices, e.g., the shaft component. The core 1124 can be overmolded and/or made of a durable material, e.g., metal, plastic, polymer, and so forth, that is configured to promote a more rigid connection with surgical devices received therein.

The core 1124 can include one or more bores 1126 extending therethrough that are adapted to receive surgical devices therein, though, in some embodiments, the core 1124 can be received within the surgical devices. The core 1124 can prevent surgical devices from moving or otherwise flexing relative to the locking handle 1102 to ensure that dimensional accuracy is maintained with the locking handle 1102. In some embodiments, the core can overlap with one or more of the ports 1122, 1132 to further stabilize the surgical devices coupled to the multi-tool 1100. For example, as shown, the core 1124 can extend along the port 1122 to receive the navigation array 708 within the base clamp 1120. Reinforcing the coupling of the navigation array 708 with the core 1124 can decrease and/or eliminate movement of the array 708 relative to the base clamp 1120, thereby improving navigational accuracy.

The core 1124 can include two bores **1126*a*, 1126*b*, though, in some embodiments, the core can include one or three or more bores. The bores 1126*a*, 1126*b* can be positioned substantially perpendicular to one another, as shown, though other orientations of the bores is possible, e.g., parallel or at an oblique angle. The bores 1126*a*, 1126*b* can be in communication with one another such that surgical devices disposed therein can interact with one another, e.g., establish an electrical connection, as discussed further below. The core 1124 can be disposed substantially in the base clamp 1120, as shown, though, in some embodiments, the bore 1126*a* can extend through the base clamp 1120 and the top clamp 1130 to allow surgical devices to extend through both portions of the locking handle 1102 to ensure greater stability of the shaft component 707 within the multi-tool 1100. In some embodiments, the bores 1126*a*, 1126*b*** can be shaped so as to restrict the surgical devices, e.g., the shaft component and/or the navigation array, to a single orientation to promote navigational accuracy and establish a defined frame of reference between devices.

The top clamp 1130 can extend proximally from the base clamp 1120. In some embodiments, the top clamp 1130 can be juxtaposed with the base clamp 1120 such that the top clamp 130 moves freely relative to the base clamp 1120. The top clamp 1130 can include one or more ports 1132 therein for coupling to surgical devices. As shown, the port 1132 can include a connecting member 1134 for coupling the nerve mapping tool 710 thereto, though, in some embodiments, other surgical devices, e.g., a navigation array, an imaging machine, and so forth can be coupled thereto. The port 1132 can extend into an opposite direction of the bore **1126*b* of the base clamp 1120 so as not to clutter the surgical site with devices, as shown, though, in some embodiments, the port 1132 can extend in the same direction as the bore 1126*b***.

Figure 104:
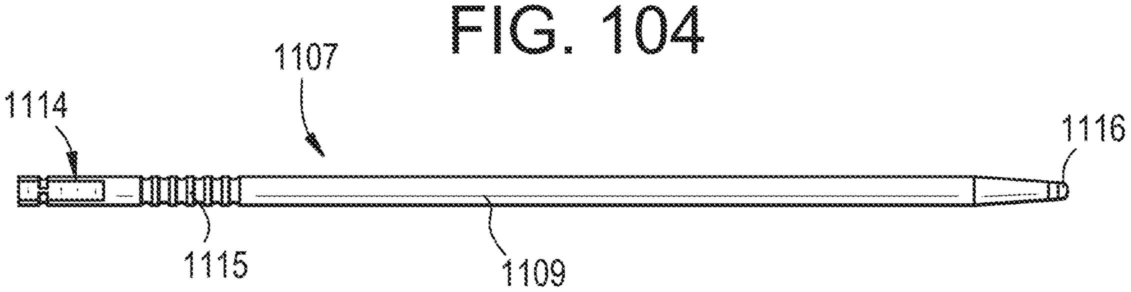
FIG. 104 is perspective view of a shaft component that is used with the multi-tool of FIG. 103.
Figure 105:
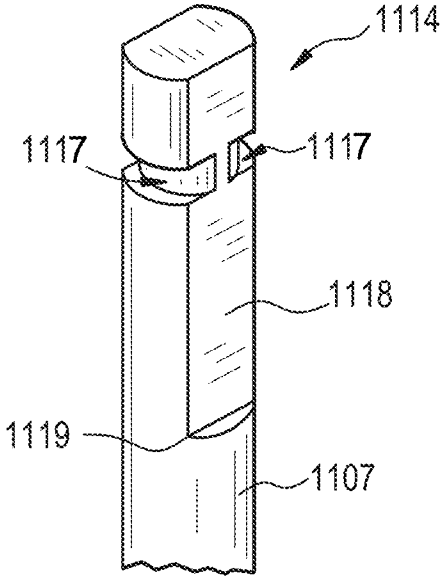
FIG. 105 is a perspective view of a proximal handle of the shaft component of FIG. 104.

FIGS. 104-105 illustrate an embodiment of a shaft component 1107 that can be used with the locking handle 1102. The shaft component 1107 can be received in one or more of the base clamp 1120 and the top clamp 1130 to secure the shaft 1107 to the locking handle 1102. As discussed above, the shaft component 1107 can include an elongate body 1109 having a solid inner core, though, in some embodiments, the elongate body can be hollow. The shaft component 1107 can have a generally cylindrical shape as shown, though the shaft component 1107 can be circular, triangular, pyramidal, and so forth. In some embodiments, a portion of the elongate body 1109 can include grooves or annular rings 1115 thereon to facilitate grasping of the body 1109 by a user. As shown, the grooves 1115 can be annular indentations formed in the elongate body 1109, though, in some embodiments, roughened surfaces or Velcro adhesives can be used to enhance grip of the shaft component 1107 and minimize the risk of slippage, which can cause significant structural damage in the surgical site.

The elongate body 1109 can extend from a proximal handle 1114 to a distal tip 1116. The elongate body 1109 can include a dielectric coating on an exterior surface thereof adapted to insulate the elongate body 1109 from electrical current. As discussed above, the distal tip 1116 can include an uncoated material thereon such that the distal tip 1116 can conduct electrical current to tissue when docked therein. In some embodiments, the elongate body 1109 can be made of an insulating material, e.g., plastic, polyurethane, glass, and so forth, to insulate and/or dampen electrical current passing therethrough.

FIG. 105 illustrates the proximal handle 1114 in greater detail. As shown, the proximal handle 1114 can include a locking groove 1117 thereon. The locking groove 1117 can include one or more indentations to retain a position of the shaft component 1107 within the locking handle 1102. For example, the locking groove 1117 can extend around a perimeter of the proximal handle 1114 to form a space for receiving retention features (not shown) of the locking handle 1102. The proximal handle 1114 can be advanced through the locking handle 1102 until the retention feature engages the locking groove 1117 to prevent further advancement of the shaft component 1107. The locking groove 1117 can be located distal to a proximal-most end of the locking handle 1102, as shown, though, in some embodiments, the locking groove 1117 can be disposed at the proximal-most end of the locking handle 1108. In some embodiments, the locking groove 1117 can be made of an uncoated material to facilitate electrical contact. The uncoated material can be the same material as that of the distal tip 1116 of the shaft component 1107, though the type of uncoated material can differ.

The proximal handle 1114 can include one or more flats 1118 on a surface thereof. The flats 1118 can provide indexing and torque transmission when the shaft component 1107 is disposed in the locking handle 1102. The flats 1118 can extend from the proximal-most end of the proximal handle to a shoulder 1119, as shown. In some embodiments, the shoulder 1119 can abut one or more components of the locking handle 1102 to prevent further proximal advancement of the shaft component 1107 therethrough. In some embodiments, the retention features can abut a surface of the shoulder 1119 to set a position of the shaft component 1107 within the locking handle 1102.

Figure 106A:
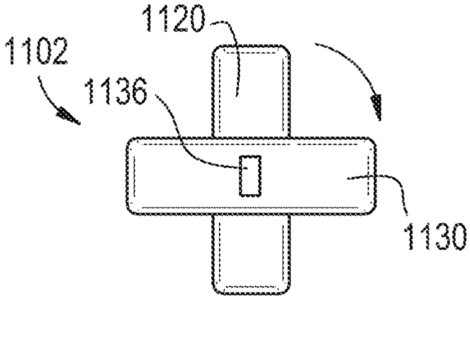
FIG. 106A is a top view of a cap of the multi-tool of FIG. 103 in an open position.
Figure 106B:
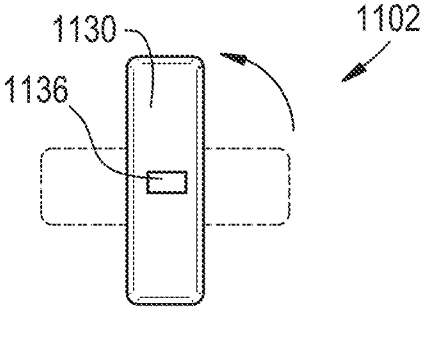
FIG. 106B is a top view of a cap of the multi-tool of FIG. 103 in a closed position.

FIGS. 106A-106B illustrate a locking mechanism of the locking handle 1102 that is configured to lock the shaft component 1107 to a surgical device that passes through the locking handle 1102. For example, the base clamp 1120 and the top clamp 1130 can rotate relative to one another to move the locking handle 1102 from the open position to the closed position to secure the shaft component 1107 therein. As shown in FIG. 106A, the base clamp 1120 and the top clamp 1130 can be disposed substantially perpendicular to one another in the open position, though, in some embodiments, the base clamp 1120 and the top clamp 1130 can be aligned or at an oblique angle with respect to one another in the open position.

In some embodiments, the top clamp 1130 can also include a channel 1136 therein. The channel 1136 can be in communication with the base clamp 1120 such that the surgical device, e.g., the shaft component 1107, disposed in the locking handle 1102 can be advanced into and/or through the top clamp 1130. As shown, the channel 1136 can be substantially rectangular such that the proximal handle 1114 of the shaft component 1007 disposed therein can be flush therewith, though, in some embodiments, the opening can be circular, cylindrical, triangular, pyramidal, and so forth.

In use, the shaft component 1107 can be advanced or slid proximally through the channel 1136 such that the shaft component 1107 protrudes proximally through the channel 1136 in the top clamp 1130, though, in some embodiments, the shaft component can be advanced or slid distally through the opening in the top clamp 1130. The shaft component 1107 can advance through one or more of the base clamp 1120 and the top clamp 1130 until the retention features of the locking handle 1102 engage the locking groove 1117 to fix a position of the shaft component 1107 with respect to the locking handle 1102. To move the locking handle 1102 to the closed position lock the position of the shaft component 1107 therein, the top clamp 1130 can rotate a quarter turn, e.g., approximately 90 degrees, with respect to the base clamp such that the base clamp 1120 and the top clamp 1130 are aligned, as shown in FIG. 106B. As shown, the top clamp 1130 can rotate in a first direction, e.g., counterclockwise, to lock the locking handle 1102, though in some embodiments, clockwise rotation of the top clamp 1130, or, alternatively, clockwise or counterclockwise rotation of the base clamp 1120 can lock the locking handle 1102. During rotation of the clamps, the retention features of the locking handle travel through the locking groove 1117 until the retention features disengage from the locking groove 1117 to abut an outer wall of the shaft component 1107. When the retention features abut the wall, the shaft component 1107 is prevented from translating or rotating relative to the clamps 1120, 1130, thereby locking the shaft component 1107 to the locking handle 1102. In some embodiments, once the multi-tool 1100 is in the locked position, an electrical connection can be established between surgical devices using a washer (not shown) disposed within the locking handle. The washer can include a throughhole having a pin disposed therein for establishing an electrical connection between devices.

To disengage the shaft component 1107 from the multi-tool 1100, the top clamp 1130 can be rotated in a second, opposite direction relative to the base clamp 1120 to return the locking handle 1102 to the open position. Once in the open position, the shaft component 1107 can move relative to the locking handle 1102 or be removed from the locking handle 1102 to allow introduction of other surgical devices through the locking handle 1102.

Figure 107:
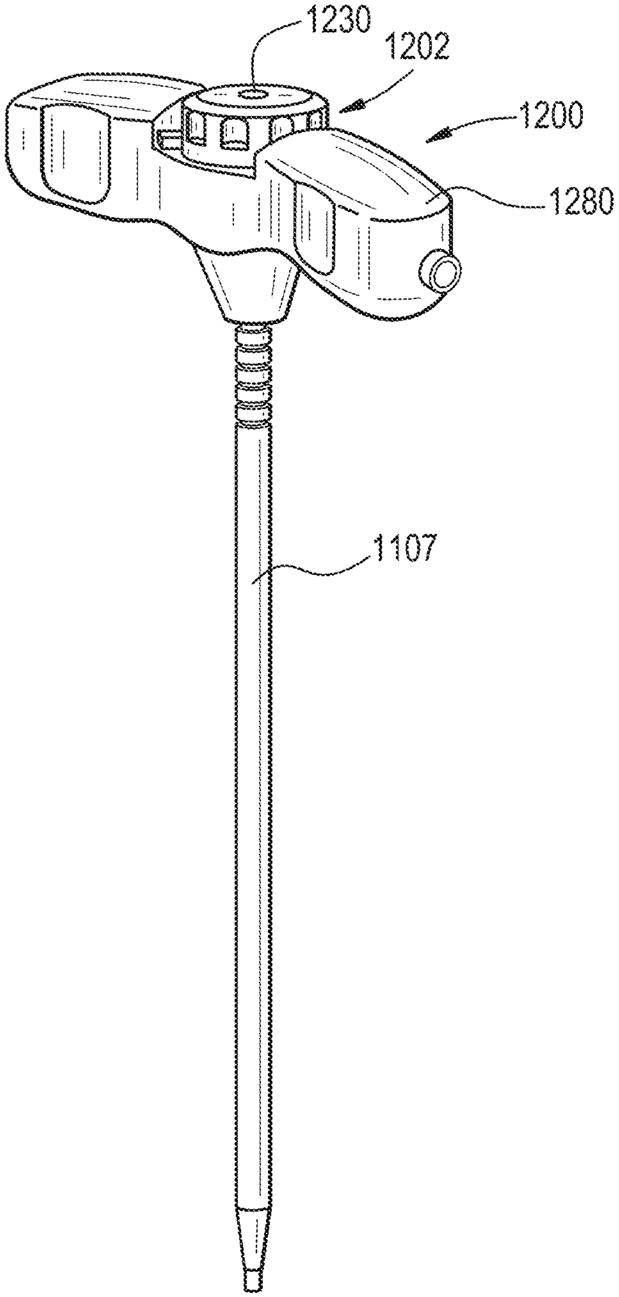
FIG. 107 is a perspective view of another embodiment of a multi-tool.

FIG. 107 illustrates an alternate embodiment of a multi-tool 1200. Except as indicated below and as will be readily appreciated by one having ordinary skill in the art, the structure and function of the multi-tool is substantially the same as that of the embodiments of the multi-tool 700, 800, 900, 1000, 1100 described above, and therefore a detailed description is omitted here for the sake of brevity.

The multi-tool 1200 can include a cap 1202 coupled thereto. As shown, the cap 1202 can include a knob 1230 instead of or in addition to the top clamp described above. The knob 1230 can be positioned proximal to a base 1220, as shown, to couple the shaft component 1107 to the cap 1202. While not shown, various configurations of these features can be used. For example, the knob 1230 can be disposed distal to the base 1220 to fix a position of, and/or lock, the shaft component 1107 within the multi-tool 1200. By way of further example, the shaft component 1107 can protrude proximally from the base 1220 to allow the knob 1230 to lie along a surface of the base 1220 to engage the shaft component 1107. The knob 1230 can be secured to the base 1220 using one or more retention pins 1240, as shown.

Figure 108:
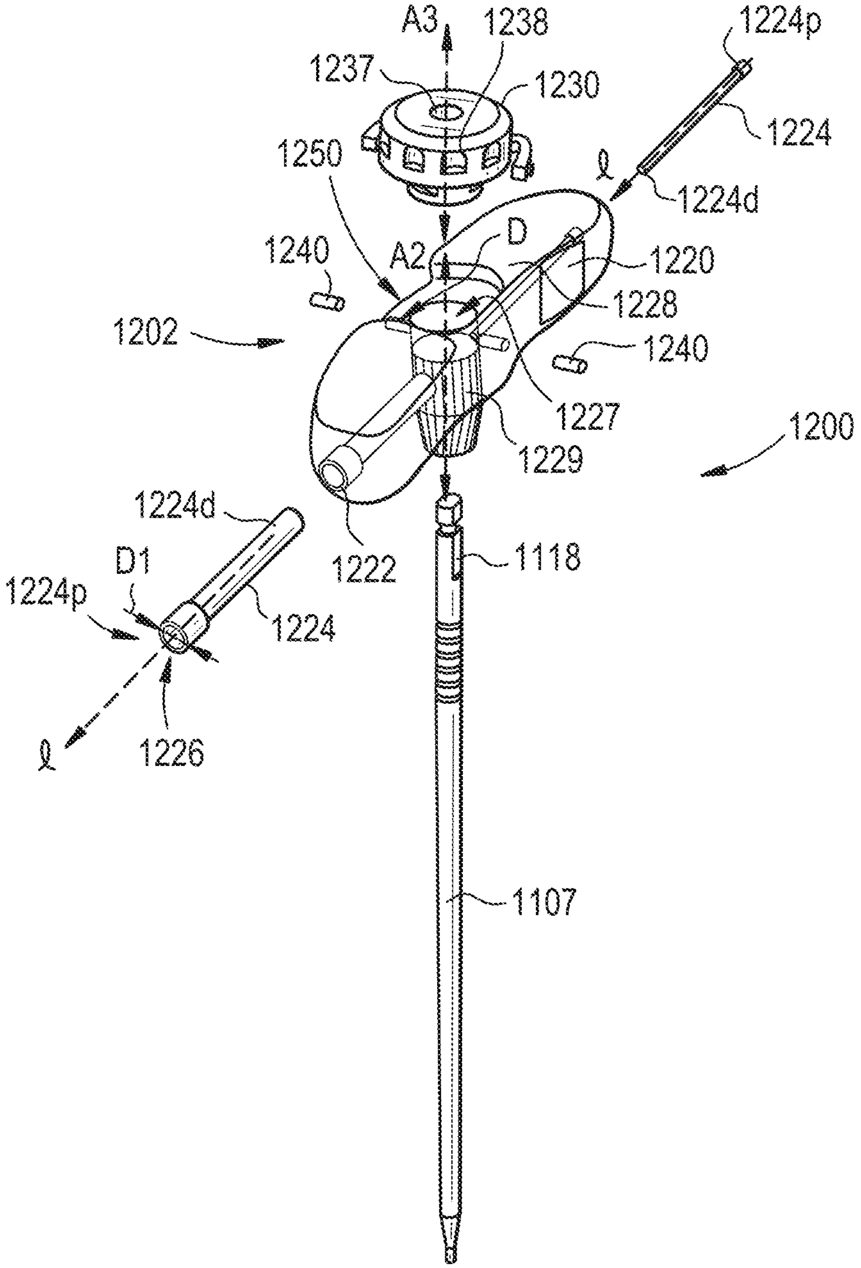
FIG. 108 is an exploded perspective view of the multi-tool of FIG. 107.
Figure 109:
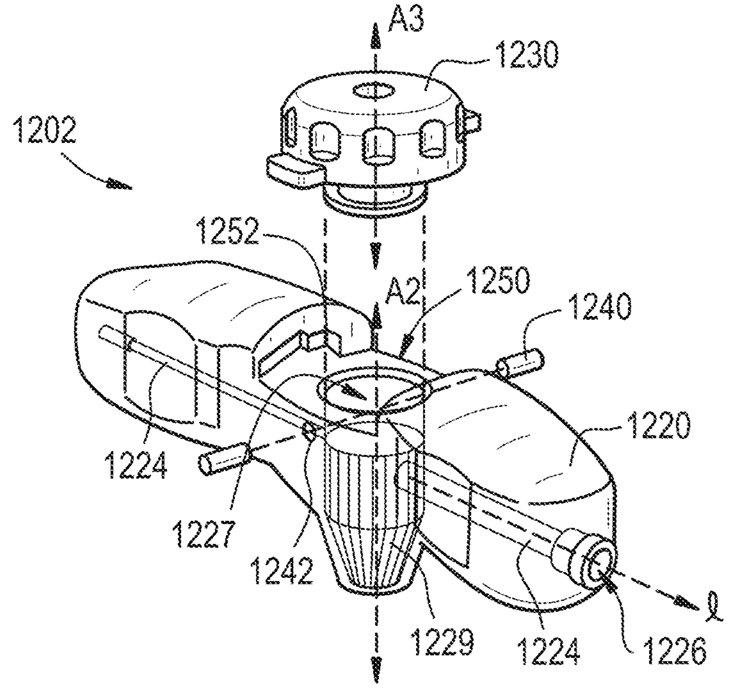
FIG. 109 is an exploded perspective view of a cap of the multi-tool of FIG. 107.

FIGS. 108-109 illustrate the cap 1202 of the multi-tool 1200 in greater detail. The base 1220 can include a receiving orifice 1250 therein. The receiving orifice 1250 can be formed as a recess in a surface of the base 1220 to couple one or more components of the multi-tool 1200 to the cap. For example, the receiving orifice 1250 can be formed in a proximal surface 1220*p* of the base 1220 so as to form an indentation in the proximal surface 1220*p* thereof. As shown, the knob 1230 can be disposed in the indentation formed by the receiving orifice 1250 during assembly of the multi-tool 1200. In some embodiments, the receiving orifice 1250 can be shaped such that the knob 1230 can be placed flush with the wall of the orifice 1250, though, in some embodiments, the shape of the indentation formed by the receiving orifice 1250 can be rectangular, square, triangular, and so forth to create one or more relief areas between the knob 1230 and the base 1220. In some embodiments, the receiving orifice 1250 can include one or more abutment surfaces 1252 for selectively engaging with the knob, as described further below.

The base 1220 can include one or more ports 1222 extending therethrough. The ports 1222 are configured to receive surgical devices, e.g., the navigation array 708, the nerve mapping tool 710, and so forth, therein for coupling to the multi-tool 1200.

As shown, and as discussed with respect to the embodiments above, each port 1222 can include a core or connector 1224 for reinforcing the coupling of surgical instruments to the base 1220 and the multi-tool 1200. The connectors 1224 can be integratedly coupled to the base 1220 such that the connectors 1224 cannot be separated from the base, though, in some embodiments, the connectors 1224 can be removably coupled to the handle. The connectors 1224 can include a generally tubular central portion defined by a sidewall circumscribing a bore 1226. The bore 1226 can define a diameter D1 through which instruments, implants, or other objects can be inserted. The bore 1226 can extend along a central longitudinal axis l of the connector 1224 from a proximal end 1224*p* to a distal end 1224*d*. As shown, the central longitudinal axis l can be generally perpendicular to the shaft component 707, though, in some embodiments, the axes can be aligned or obliquely angled with respect to one another.

The base 1220 can include a channel 1227 therein. The channel 1227 can be configured to allow surgical devices, e.g., the shaft component 1107 to be inserted therethrough. As shown, the ports 1222 and/or the core 1224 can be in communication with the channel to allow surgical devices inserted through the ports to interface with the shaft component 707. The channel 1227 can be defined by a sidewall 1228 circumscribing the channel 1227. The channel 1227 can extend along a central longitudinal axis A2 of the base 1220 from the proximal surface 1220 to the distal surface 1220*d*. In some embodiments, and as shown, the channel 1227 can terminate in the receiving orifice 1250. The channel 1227 can define a diameter D through which instruments, implants, or other objects can be inserted. The channel 1227 can be configured to allow either proximal or distal loading of the instruments therethrough. An interior surface of the channel 1227 can be threaded or can include other mating features for cooperating with an instrument inserted therethrough, e.g., the shaft component 1107, to advance the instrument longitudinally relative to the base 1220. In some embodiments, the base 1220 can include two or more channels to allow insertion of multiple instruments therethrough.

In some embodiments, the channel 1227 can include a stabilizing component 1229. The stabilizing component can be disposed in the base 1220 to provide a rigid interface between surgical instruments inserted therethrough. For example, the stabilizing component 1229 can be aligned with central longitudinal axis A2 of the channel 1227 to allow the shaft component 1107 to pass through the stabilizing component 1229. In some embodiments, the stabilizing component can be fixedly coupled to, or integrally formed with, the base 1220, though, in some embodiments, the stabilizing component 1220 can be an insert that can be removably coupled to an interior of the base 1220.

As shown, the connectors 1224 can protrude from the stabilizing component 1229 so as to allow the shaft component 1107 disposed within the stabilizing component 1229 to interface with surgical instruments received within the connectors 1224. For example, the channel 1227 and the bores 1226 can be in communication with one another such that instruments inserted through the bores 1226 can interface with, e.g., establish an electrical connection, surgical devices disposed in the channel 1227. For example, the two connectors 1224 shown in FIG. 109 can receive the navigation array 708 and the nerve mapping tool 710, as described above, to allow one or more of the navigation array 708, the nerve mapping tool 710, and/or the shaft component 1107 to electrically communicate. In some embodiments, the base 1220 can include one, or three or more connectors 1224 extending therethrough.

As shown in FIG. 109, the base 1220 can receive a retention pin or a cross pin 1240 for coupling the knob thereto. For example, the base 1220 can include one or more openings 1242 in a surface thereof that are configured to receive the retention pins 1240 therethrough. The retention pin 1240 can couple the knob 1130 to the base 1120 while allowing the knob 1130 to rotate relative therewith. The retention pin 1240 can travel within pin slots or paths formed in the knob, as described further below.

Figure 110A:
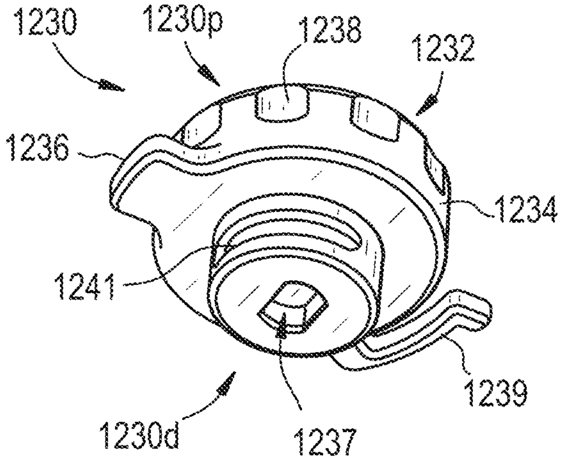
FIG. 110A is a perspective view of a knob of the multi-tool of FIG. 107.
Figure 110B:
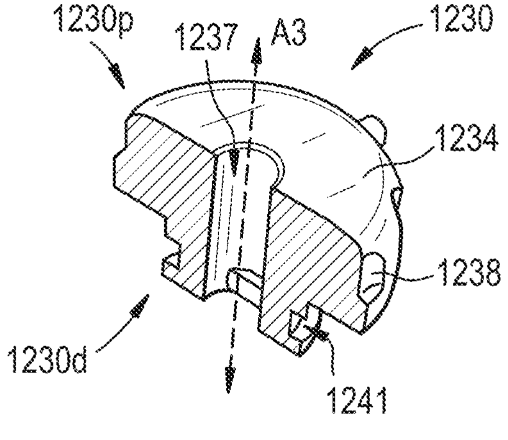
FIG. 110B is a cross-sectional view of the knob of FIG. 110A.

FIGS. 110A-110B illustrate the knob 1230 in greater detail. The knob 1230 can include a generally rounded or ring-shaped body 1232 defined by a sidewall 1234 having a channel 1237. The channel 1237 can extend along an axis A3 from a proximal end 1230*p* of the knob 1230 to a distal end 1230*d* of the knob 1230. In some embodiments, the channel 1237 can correspond with a shape of an instrument inserted therethrough. In some embodiments, the shape of the channel 1237 can vary across a length of the channel. For example, the channel 1237 at the distal end 1230*d*, as shown in FIG. 110A, can include a rectangular shape while the channel 1237 at the proximal end 1230*p*, as shown in FIG. 110B, can include a rounded shape. The shape of the channel 1237 at the distal end 1230*d* can allow distal loading and proximal advancement of the shaft component 1107, while the shape of the channel 1237 at the proximal end 1230*p* can allow proximal loading and distal advancement of the shaft component 1107. In some embodiments, the shape of the channel 1237 can be independent of the direction of loading and advancement of the shaft component 1107.

The knob 1230 can have a circular shape, as shown, or can have various other shapes, such as oval, oblong, square, rectangular, triangular, and so forth. In some embodiments, as discussed above, the knob 1230 can correspond with a shape of the receiving orifice 1250 in which it is disposed.

The knob 1230 can include one or more handles or gripping surfaces 1238 located along the sidewall 1234 thereof. The gripping surfaces 1238 can be in the form of indentations or grooves formed in the exterior of the knob 1230 such that a force that is exerted on the gripping surfaces 1238 can move the knob 1230 between the open position and the closed position, as discussed further below. While the gripping surfaces 1238 are shown as being evenly distributed along a circumference of the knob 1230, in some embodiments, the gripping surfaces 1238 can extend from the knob 1230 such that a force that is exerted on the gripping surfaces 1238 can move the gripping surfaces 1238 and the knob 1230 between the open and closed positions.

The knob 1230 can include a mating tab 1236 extending therefrom. The mating tab 1239 can be a separate component mounted to the knob 1230 or, as shown, can be formed integrally or monolithically with the knob to fixedly couple to the knob 1230 such that a force that is exerted on the knob 1230 can move the mating tab 1236 and the knob as a single unit. The mating tab 1236 can be configured to engage the abutment surfaces 1252 on the receiving orifice 1250 to maintain the rotational position of the knob 1230 relative to the base 1220, as described further below.

The knob 1230 can include a wing tab or projection 1239 extending therefrom. The wing tab 1239 can be a separate component mounted to the knob 1230 or, as shown, can be formed integrally or monolithically with the knob 1230 to fixedly couple to the knob such that a force that is exerted on the knob 1230 can move the wing tab 1239 and the knob as a single unit. In other arrangements, the knob 1230 can include fewer or additional springs and mating tabs. The wing tab 1239 can be configured to flex or bend relative to the knob 1230 to allow the knob to move into and out of engagement with the receiving orifice 1250 when switching between the open position and the closed position, as discussed further below. In some embodiments, the wing tab 1239 can be connected to the knob by a spring (not shown) such as a leaf spring, coil spring, wave spring, non-cantilevered projection, or other bias element that can move the wing tab 1239 between an open configuration and a closed configuration.

The knob 1230 can include one or more pin paths 1241 therein. The pin paths can be defined as ports formed in the knob 1230 that can receive the retention pin 1240 therethrough. In some embodiments, the pin paths 1241 can be circumferential cut-outs in the knob 1230 that can receive the retention pin 1240 therethrough. The retention pin 1240 can travel through the pin path 1241 as the knob 1230 is rotated relative to the base 1230 to move the multi-tool 1200 between the open and closed positions. In some embodiments, the knob 1230 can have two or more pin paths 1241 therein.

Figure 111A:
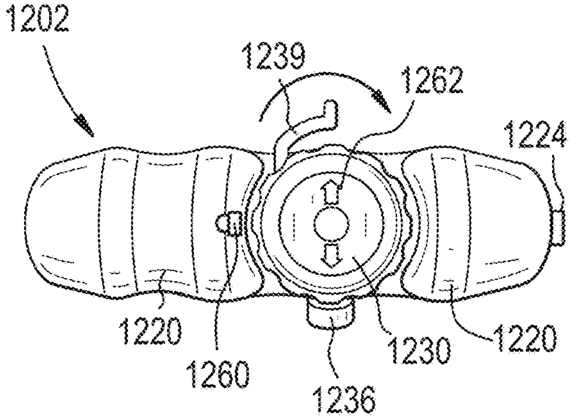
FIG. 111A is a top view of a cap of the multi-tool of FIG. 107 in an open position.
Figure 111B:
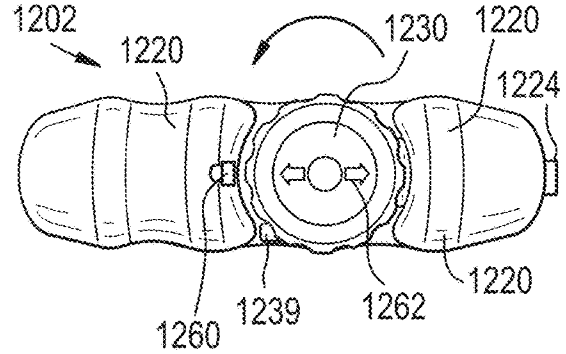
FIG. 111B is a top view of a cap of the multi-tool of FIG. 107 in a closed position.
Figure 112:
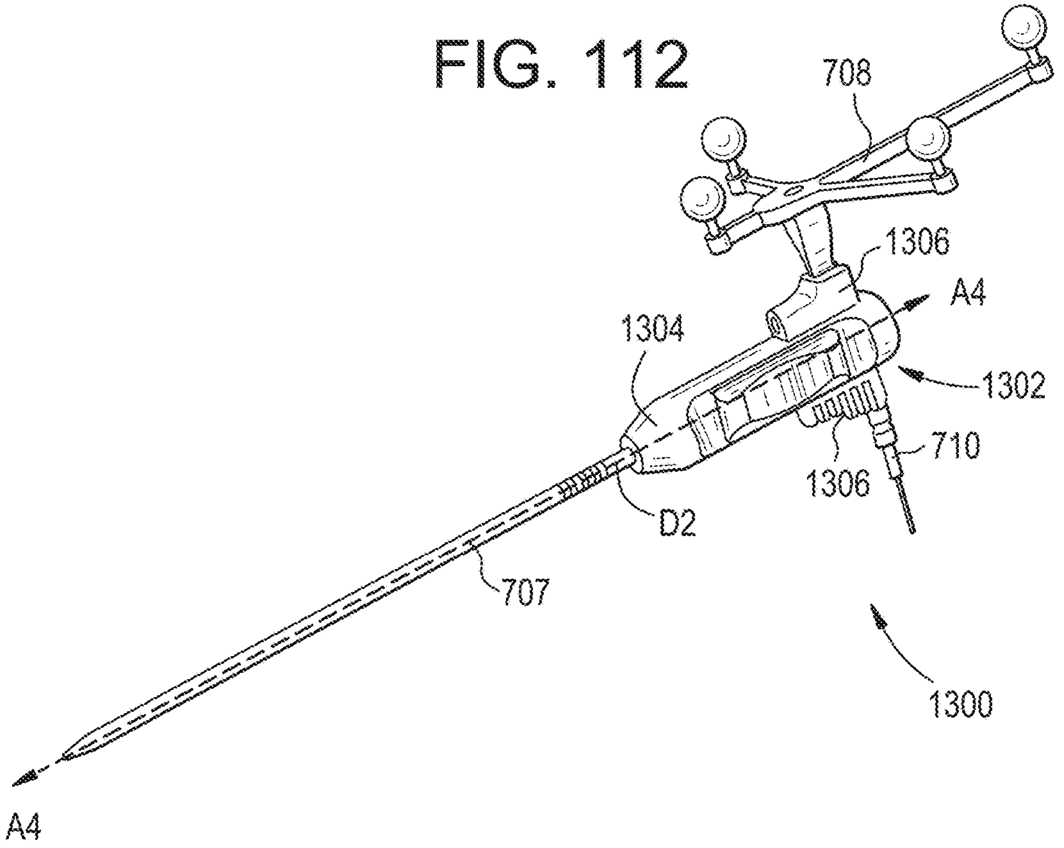
FIG. 112 is a perspective view of another embodiment of a multi-tool.

FIG. 111A illustrates the cap 1202 of the multi-tool 1200 in the open position and FIG. 111B illustrates the cap 1202 of the multi-tool 1200 in the closed position. The knob 1230 can be rotated to move the multi-tool 1200 between (i) an open position in which the shaft component 1107 is free to translate and rotate relative to the cap 1202, and (ii) a closed position in which the shaft component 1107 is restrained from translating and rotating relative to the cap 1202 to limit or prevent relative movement of the shaft component 1107.

The base 1220 and the knob 1230 can include one or more indicators that show whether the multi-tool 1200 is in the open position or in the closed position. For example, as shown in FIG. 111A, the base 1220 and/or the knob 1230 can include labels or images thereon to indicate the position of the multi-tool 1200. The base 1220 can include a first image 1260 of a padlock in a closed position that can be aligned with a second image of arrows 1262 on the knob 1230. While a set of arrows 1262 is shown, a circle, or another mark that can align with, or point to, the padlock image on the base 1220 can be used. When the arrow 1262 points away from the padlock image 1260, the multi-tool 1200 is not in the closed position, e.g., in the open position. The multi-tool 1200 can include additional indicators for communicating the position of the multi-tool 1200. In some embodiments, the base 1220 can include an image of a padlock in an unlocked or open position that can be aligned with the arrows on the cap 1230 to indicate that the multi-tool is in the open position. It will be appreciated other images can be used instead or in addition, such as text labels, e.g., that read "open" and "closed," or "unlocked" and "locked," respectively, other drawings, and the like.

Additional features of the relative arrangement of the base 1220 and the knob 1230 can suggest that the multi-tool 1200 is in open position. For example, as shown in FIG. 111A, the wing tab 1239 can protrude at an angle from the knob 1230, which can indicate that the knob 1230 is in the open position. The arrows 1262 on the knob 1230 do not point to the indicator 1260 on the base 1260, which can also indicate that the multi-tool is in the open position. In some embodiments, the mating tab 1236 can be disposed outside of any relief areas in the receiving orifice 1250, which can also indicate that the multi-tool 1200 is in the open position.

The knob 1230 can be rotatable about the axis A3 to move between an open position and a closed position. As shown in FIG. 111B, the knob 1230 can be rotated in a counterclockwise direction, when viewed from a proximal perspective, to move the knob 1230 into the closed position, though, in other embodiments, the direction of rotation can be reversed. As a rotational force is imparted onto the knob 1230, the one or more retention pins 1240 can travel from a first end of the pin path 1241 towards a second end of the pin path 1241. As the retention pins 1240 approach the second end of the pin path 1241, the retention pins 1240 can engage the flats 1118 of the shaft component 1107, thereby preventing further rotation of the knob 1230. During rotation of the knob 1230, the wing tab 1239 can enter the relief area in the receiving orifice 1250 and abut the abutment surface 1252 in the receiving orifice 1250. As the knob 1230 rotates further, the abutment surface 1252 can move or snap the wing tab 1239 towards the knob 1230 such that the wing tab 1239 is moved to a position that is flush with the knob 1230 to prevent further rotation of the knob. Further rotation of the knob 1230 can also be prevented by the pin path 1241, which can restrict further travel of the retention pin 1240 therein.

FIG. 111B illustrates the multi-tool 1200 with the knob 1230 in the closed position. As shown, the wing tab 1239 and the mating tab 1236 can be disposed in the relief areas of the receiving orifice 1250 to prevent the knob 1230 from rotating with respect to the base 1220. The indicator 1262 on the knob 1230 can be aligned with the indicator 1262 on the knob 1230. That is, the arrows 1262 on the knob 1230 can point to the first image 1260 to suggest that multi-tool 1200 is in the closed position. To switch the multi-tool 1200 to the open position, the knob 1230 can be rotated in a second, opposite direction, e.g., clockwise, to release the wing tab 1239 from the receiving orifice 1250. As a rotational force is imparted onto the knob 1230 into the second direction, the retention pins 1240 can disengage from the flats 1118 of the shaft component 1107 and travel from the second end of the pin path 1241 towards the first end of the pin path 1241. As the knob 1230 continues to rotate, the wing tab 1239 exists the relief area to pivot the wing tab 1239 away from the knob 1230 to return the multi-tool 1200 to the open position. Once in the open position, the shaft component 1107 is free to translate and/or rotate within the multi-tool 1200.

FIGS. 112-115 illustrates an alternate embodiment of a multi-tool 1300. Except as indicated below and as will be readily appreciated by one having ordinary skill in the art, the structure and function of the multi-tool is substantially the same as that of the embodiments of the multi-tool 700, 800, 900, 1000, 1100, 1200 described above, and therefore a detailed description is omitted here for the sake of brevity.

The multi-tool 1300 can include quick-connect features that enable easy toggling between components of the tool, e.g., the shaft component and the cap. As shown, the multi-tool 1300 can include a clamp 1302 in lieu of, or in addition to, the cap described with respect to the embodiments above. The clamp 1302 can be defined by a sidewall 1304 circumscribing a channel 1305 that extends therethrough. The channel 1305 can be configured to receive at least a portion of another tool or instrument therein. The channel 1305 can extend along a central longitudinal axis A4 that aligns with the central longitudinal axis A1 of the shaft component 707. The channel 1305 can define a diameter D2 through which instruments, e.g., the shaft component 707, can be inserted. The clamp 1302 can further include one or more arms 1306 that protrude from the sidewall 1304 for coupling the navigation array 708 and the nerve mapping tool 710 thereto.

Figure 113A:
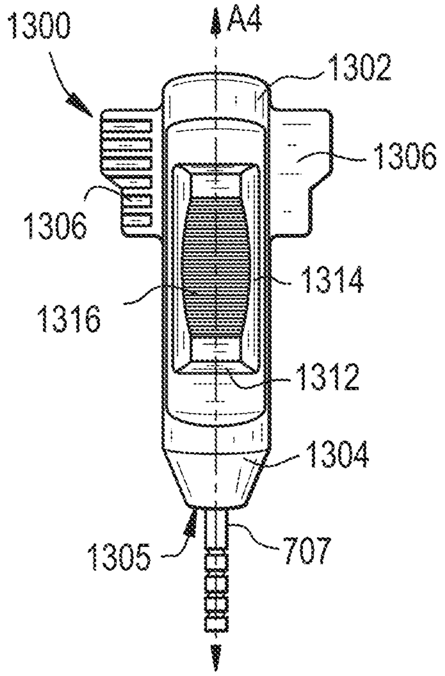
FIG. 113A is a perspective front view of a clamp of the multi-tool of FIG. 112.
Figure 113B:
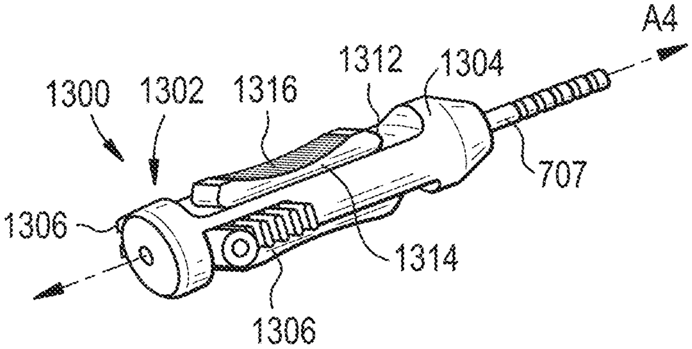
FIG. 113B is another perspective view of the clamp of FIG. 113A.

The clamp 1302 is shown in greater detail in FIGS. 113A-113B. The clamp 1302 can include a slider 1312 that translates along a surface thereof. The slider 1312 can be configured to operate as a one directional clamp to lock an axial position of the shaft component 707 to the clamp 1302. For example, the slider 1312 can translate between a first position in which the clamp 1302 is in an open position to allow the shaft component 1302 to rotate and/or translate freely relative to the multi-tool 1300, and a second position in which the clamp 1302 is in a closed position which prevents the shaft component 707 from rotating and/or translating relative to the multi-tool 1300.

The clamp 1302 can include one or more tracks or slots 1314 on a surface thereof. The tracks 1314 can be formed as indentations or throughholes in the sidewall 1304 of the clamp. For example, as shown, in FIG. 115, the clamp can include a first track 1314*a* and a second track 1314*b* formed therein. The first track 1314*a* can be positioned substantially parallel to a length of the clamp 1302 and the second track 1314*b* can be angled with respect to the axis of the clamp 1302 and/or a shaft component inserted therethrough, as shown and described further below. The tracks 1314*a*, 1314*b* can extend substantially through an entire width of the clamp, e.g., from arm to arm, as shown, though, in some embodiments, the tracks can encompass narrower sections of the sidewall.

The slider 1312 can be disposed in the track 1314*a*, 1314*b* and move relative thereto to lock and unlock the shaft component 707 relative to the clamp 1302. As shown, the slider 1312 can include a length that is smaller than a length of the tracks 1314*a*, 1314*b* such that the slider 1312 can move proximally and distally within the tracks 1314*a*, 1314*b*. The slider 1312 can extend through the tracks 1214*a*, 1314*b* to protrude from opposite sidewalls 1304 of the clamp 1302, though, in some embodiments, the slider 1312 can terminate within the tracks 1314*a*, 1314*b* such that the slider 1312 protrudes from only one side of the clamp 1302.

The slider 1312 can include one or more gripping surfaces 1316 on a surface thereof. The gripping surfaces 1316 can include grooves or ridges in a surface thereof to provide friction when held by a user. As shown, the gripping surfaces 1316 can be located on opposite sides of the slider 1312, though, in some embodiments, the gripping surfaces can be located on a single side of the slider 1312. When a force is exerted on the gripping surfaces 1316, the gripping surfaces 1316 and the slider can move as a single unit.

Figure 114:
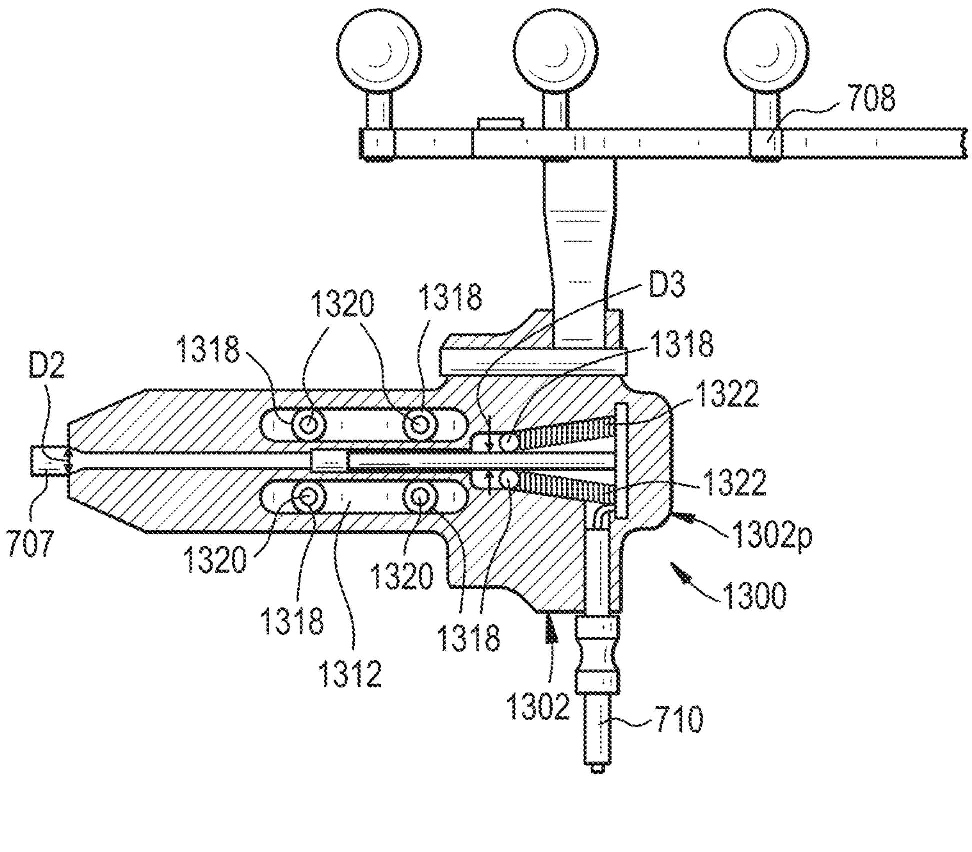
FIG. 114 is a cross-sectional view of the multi-tool of FIG. 112.

The slider 1312 can include one or more orifices or holders 1318 formed therein. The holders 1318 can be defined in an interior surface of the slider 1312 to receive one or more gripping pins 1320 therein, as described further below. The holders 1318 can have a cylindrical shape, as shown, or can have various other shapes, such as oval, oblong, square, rectangular, triangular, and so forth. As shown, the slider 1312 can include one or more sets of holders 1318 that lie along the length of the slider. As shown, two sets of holders 1318 can be distributed on opposite sides of the slider 1312 such that the shaft component 707 is disposed between the holders 1318. The holders 1318 can lie along a common axis, though, as shown in FIG. 114, one or more holders 1318 in each set can be biased relative to the remaining holders to promote engagement with surgical devices disposed within the clamp, as described further below.

Figure 115:
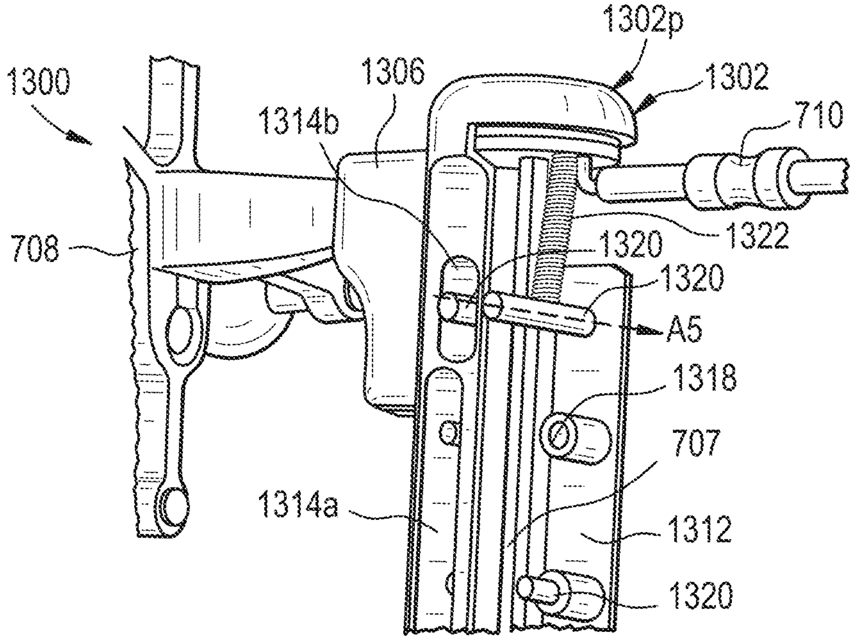
FIG. 115 is a perspective cross-sectional view of the multi-tool of FIG. 112.

The gripping pins 320 can extend interiorly from the holders 1318. The gripping pins 1320 can extend along an axis A5 that is substantially perpendicular to the axis A1 of the shaft component 707. While each holder 1318 can include gripping pins 1320 therein, in some embodiments, as shown in FIG. 115, one or more holders 1318 can be devoid of pins 1320. The gripping pins 1320 can be fixedly coupled to the holders 1318 such that a force that is exerted on the gripping pins 1320 can move the gripping pins 1320 and the slider 1312 as a single unit. In some embodiments, the gripping pins 1320 can be formed integrally or monolithically with the holders, though, in some embodiments, the gripping pins 1320 can be removably received within the holders 1318. As shown, the gripping pins 1320 can have a cylindrical shape, as shown, or can have various other shapes, such as oval, oblong, square, rectangular, triangular, and so forth that correspond to the shape of the holder 1318 in which the pin is disposed.

The clamp 1302 can include one or more bias elements or springs 1322 coupled thereto. The springs 1322 can extend distally from a proximal end 1302*p* of the clamp 1302 to the holder 1318 and/or gripping pins 1320 disposed in the slider 1312 to create separation between the slider 1312 and the proximal end 1302*p* of the clamp 1302. A force exerted by the springs 1322 can bias the slider 1312 distally such that the slider 1312 is spaced apart from the proximal end 1302*p* of the clamp 1302 by a length of the spring 1322. The springs 1322 can bias the gripping pins 1320 towards one another such that a distance between the biased gripping pins is smaller than a distance between unbiased gripping pins. While two biased gripping pins 1320 are shown, in some embodiments, one or three or more gripping pins 1320 can be biased by springs 1322. The gripping pins 1320 can be configured to engage with instruments, implants, or other objects, e.g., the shaft component 707, received therebetween to secure their position within the clamp 1302.

In use, the gripping pins 1320 can ride within the tracks 1314*a*, 1314*b* formed in the sidewall 1304 of the clamp 1302 to allow proximal-distal translation of the pins 1320 and the slider 1312 associated therewith. For example, as shown, the gripping pins 1320 can ride in the first track 1314*a* and the biased gripping pins can ride in the second track 1314*b*. When assembling the multi-tool, the shaft component 707 can be inserted distally and advanced proximally through the clamp 1302. Continued proximal advancement of the shaft component 707 can exert a force on the biased gripping pins 1320 to counter the biasing force exerted by the springs 1322 to move the gripping pins 1320 proximally. Proximal movement of the gripping pins 1320 can contract the length of the springs 1322 to move the gripping pins 1320 proximally in the second track 1314*b* at an angle to the axis of the shaft component 707, thereby separating the gripping pins 1320. Proximal movement of the gripping pins 1320 can also move the slider 1312 proximally.

The gripping pins 1320 and the slider 1312 can continue to travel proximally in the second track 1314*b* until the distance between the gripping pins 1320 is substantially equal to a diameter D3 of the shaft component, as shown in FIG. 114. In this configuration, the gripping pins 1320 stop moving proximally and the pins 1320 are biased distally by the springs 1322. The bias force allows the gripping pins 1320 to engage the shaft component 707 to exert a clamping force thereon prevent further translation and/or rotation of the shaft component 707 relative to the clamp 1302. Any attempt to pull the proximal handle 714 of the shaft component 707 out of the clamp reinforces the clamping force exerted by the gripping pins 1320 on the shaft component 707.

Once secured, an electrical connection can be established between the shaft component 707 and one or more of the navigation array 708 and the nerve mapping tool 710. For example, in the multi-tool 1300 shown in FIG. 115, current can pass through contact between the gripping pins 1320 and the shaft component 707, through the springs 1322, and into the proximal end 1302*p* of the clamp 1302 that is attached to the nerve mapping tool 710.

To change a position and/or disengage the shaft component 707 from the clamp 1302, a proximal force can be exerted on the slider 1312, such as with the hand of a user. Exerting a proximal force on the slider 1312 to counter the distally biasing force of the bias element 1322 can proximally advance the slider 1312 to release the gripping pins 1320 from the shaft component 707. Once the gripping pins 1320 are released, the position of the shaft component 707 can be changed and the shaft component 707 can be disengaged from the clamp 1302. The clamp 1302 can then be coupled to another instrument, e.g., a second shaft component.

Figure 116A:
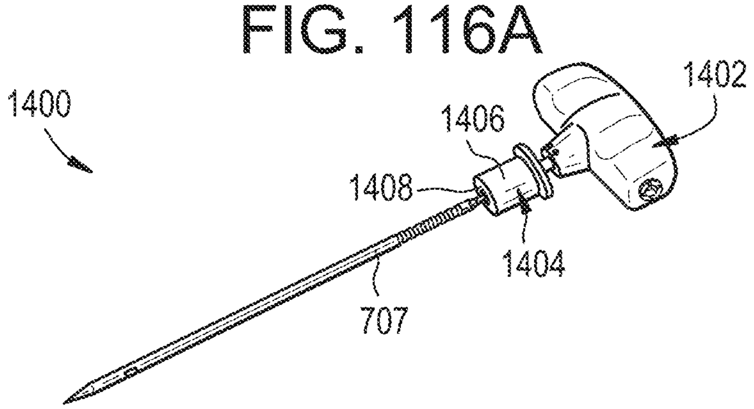
FIG. 116A is a perspective view of another embodiment of a multi-tool.
Figure 116B:
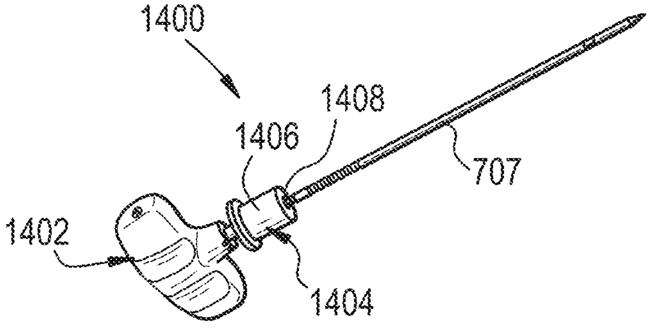
FIG. 116B is a perspective view of the multi-tool of FIG. 116A.

FIGS. 116A-116B illustrate an alternate embodiment of a multi-tool 1400 quick-connect feature. Except as indicated below and as will be readily appreciated by one having ordinary skill in the art, the structure and function of the multi-tool is substantially the same as that of the embodiments of the multi-tool 700, 800, 900, 1000, 1100, 1200, 1300 described above, and therefore a detailed description is omitted here for the sake of brevity.

As shown, the multi-tool 1400 can include a cap 1402 configured to receive the shaft component 707 therein. A stopper 1404 can extend distally from the cap 1402 that can be used in lieu of, or in addition to, the slider 1312 having gripping pins 1320 to secure the shaft component 707 to the cap 1402. For example, the stopper 1404 can include a sidewall 1406 that defines an opening 1408 therein configured to receive the shaft component 707 therethrough.

The proximal handle 714 of the shaft component 707 can be received through the opening 1408 in the stopper 1404 and advanced proximally therethrough. The stopper 1404 can include a retention mechanism (not shown) that can engage the grooves 715 in the shaft component 707 to prevent further translation and/or rotation of the shaft component 707 relative to the cap 1402. To deploy the retention mechanism, the stopper 1404 can be advanced distally such that the retention mechanism snaps into the groove 715. To change a position and/or disengage the shaft component 707 from the stopper 1404, the stopper 1404 can be advanced proximally, such as with the hand of a user, to disengage the stopper 1404 from the groove of the shaft component 707 to release the shaft component 707 therefrom.

Figure 117:
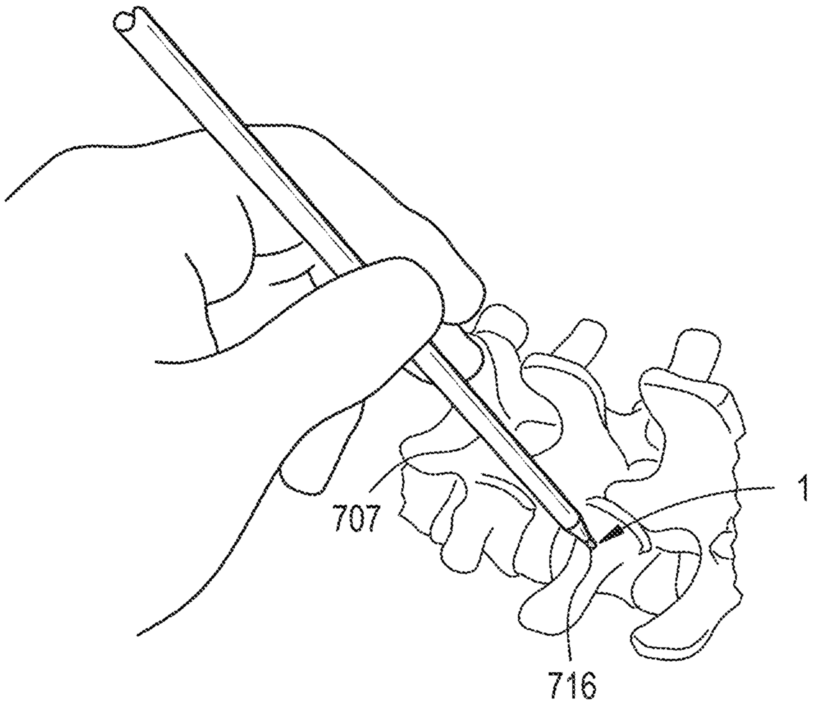
FIG. 117 is a schematic view of inserting a shaft component into a target site of a patient.
Figure 118:
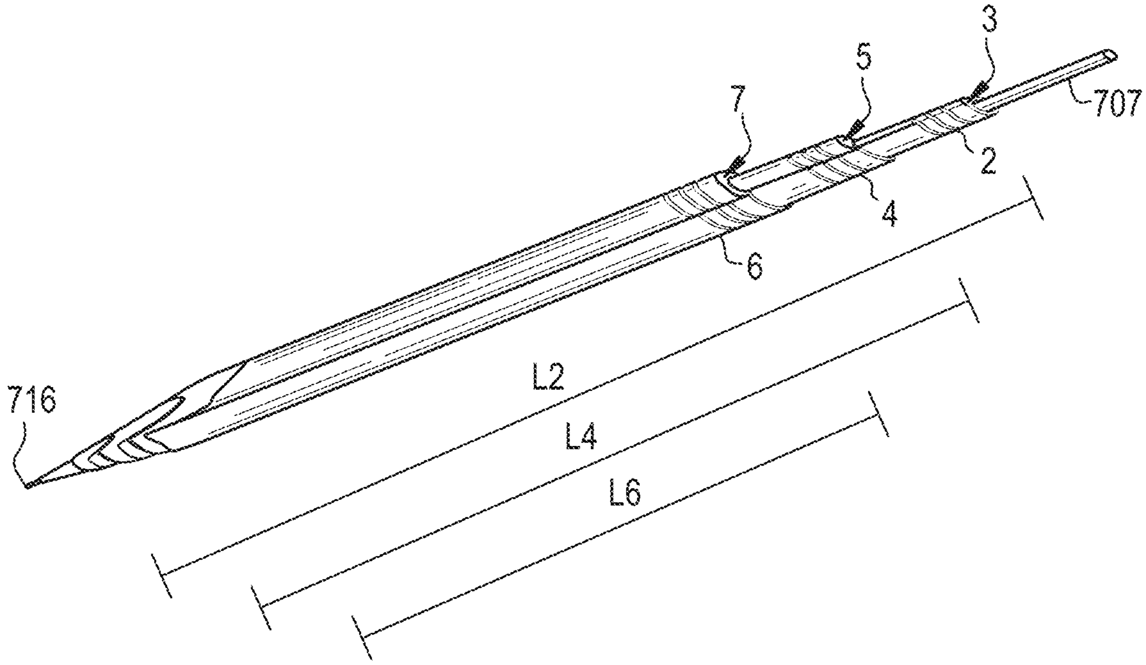
FIG. 118 is a perspective view of the shaft component of FIG. 117 having a series of dilators disposed thereon.

FIGS. 117-118 illustrate one method of using an embodiment of the multi-tools disclosed herein for docking a shaft component in target tissue to insert an access port for performing a procedure, e.g., a posterior lumbar surgery. Except as indicated below and will be readily appreciated by one having ordinary skill in the art, the steps of the described method can be performed in various sequences, and one or more steps can be omitted or added. A detailed description of every sequence of steps and of every embodiment is omitted here for the sake of brevity. While the method is discussed with respect a given set of embodiments, it will be appreciated that any of the embodiments discussed herein can be used to perform the steps below.

In use, a bone anchor or a contra-lateral screw can be implanted in a body of a patient, e.g., in a pedicle or in the lumber spine of the patient. In some embodiments, the bone anchor can be inserted with a navigation array to calibrate the array to the system and pre-operative and post-operative images of the patient. Calibration can include analysis of position and/or orientation of the bone anchor within the dimensions of the patient. Using the location of the array and its position within the patient, a target site for insertion of an access port can be determined.

To insert the access port, an incision can be made at the target site 1. Once the incision is sufficiently sized, the shaft component 707 of the multi-tool 700 can be inserted into the target site 1. The shaft component 707 can be inserted under guidance from one or more of the navigation array 708 and the nerve mapping tool 710 to ensure precision of placement of the shaft component 707 and that surrounding tissues, nerves, and/or bones are not damaged during insertion. The distal tip 716 of the shaft component 707 can be configured to slide along bone while also being sharp such that the distal tip 716 can dock to the bone when impacted with sufficient force. Force that is sufficient to dock the shaft component 707 to the target site 1 can include finger pressure or via manual force by a user, though, in some embodiments, the shaft component can be tapped 707 into the bone using a mallet, hammer, or the like. As shown in FIG. 117, in some embodiments, the distal tip 716 can sweep across a bone surface until the tip 716 reaches the target site 1, at which point the tip 716 can advance into the target site 1 while avoiding the exiting nerve root.

Once the shaft component 707 is docked, the cap 702 of the multi-tool 700 can be disassembled from the shaft component in the variety of ways described above, while leaving the shaft component 707 docked in the target site 1. The target site 1 can then be enlarged by serial dilation to allow an access port to be received therein. In serial dilation, one or more cannulated dilators can be inserted sequentially into the target site 1 over the shaft component 707 to increase the opening in the target site 1. For example, a series of cannulated dilators 2, 4, 6, each having a diameter that is larger than the shaft component 707, and each previous dilator, can slide over the shaft component 707 and the previously-inserted dilator into the target site 1.

The cannulated dilators 2, 4, 6 can include a generally tubular shape having a sidewall that circumscribes a channel 3, 5, 7 that extends therethrough. The channels 3, 5, 7 can extend parallel to the central longitudinal axis A1 of the shaft component 707 to receive the shaft component 707, as well as cannulated dilators of smaller diameters, therethrough. As shown, the first dilator 2 can be inserted over the shaft component 707 such that the shaft component passes through the channel 3, the second dilator 4 can be inserted over the shaft component 707 and the first dilator 2, the third dilator 6 can be inserted over the shaft component 707 and the first 2 and second dilators 4, and so forth.

In some embodiments, each of the cannulated dilators 2, 4, 6 of the series of dilators used in serial dilation can have a different length. For example, as shown, a length L2 of the first dilator 2 can be longer than a length L4 of the second dilator 4, which can be longer than a length L6 of the third dilator 6, and so forth. The larger length of the previously-inserted dilator allows the dilator to protrude distally from the subsequently-inserted dilator to allow removal of the previously-inserted dilator from the target site. That is, as shown in FIG. 118, the first and second dilators 2, 4 protrude distally from the third dilator 6, allowing for removal of the first and second dilators 2, 4 from the target site 1 prior to introduction of a fourth dilator, and/or an access port.

Serial dilation can proceed by continuing to add cannulated dilators of increasing diameter into the target site 1 until the opening at the target site is sized to receive the access port therein. As shown, three dilators 2, 4, 6 are inserted into the target site, though in some embodiments, two or fewer, or four or more dilators can be used until the target site is sufficiently dilated to receive the port therein. In some embodiments, the access port can have a length that is smaller than the previously-inserted dilator, e.g., the third dilator 6, in order to allow the previously-inserted dilator to be removed from the target site 1.

Figure 119:
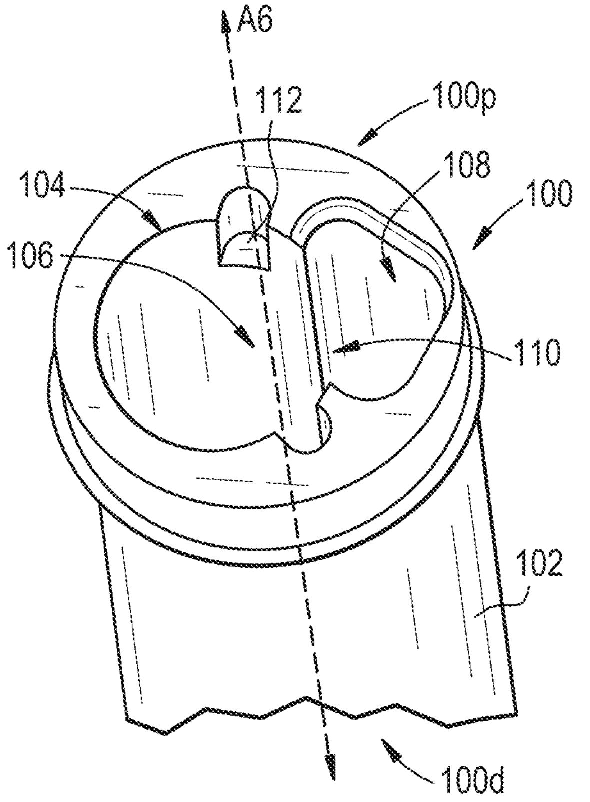
FIG. 119 is a perspective view of an access port inserted over the dilators in FIG. 118.

FIG. 119 illustrates an embodiment of an access port 100 that can be inserted into the target site 1. For example, the access port 100 can be used to create an access path for objects, e.g., devices such as bone anchors, instruments and/or surgical material, e.g., sutures, to be introduced into a surgical site. The access port 100 can include a generally tubular or cylindrical-shaped body defined by a sidewall 102 having a central opening 104. The opening 104 can extend along an axis A6 from a proximal end 100*p* of the access port 100 to a distal end of the access port 100*d*. In some embodiments, the opening 104 can be shaped to correspond with a shape of an object or an instrument being inserted therethrough. It will be appreciated that the access port 100 can be a cannula, tube, retractor, bladed retractor, dilator, and/or another example of an access device known to one having ordinary skill in the art for creating an access path into a surgical site of a patient. The opening 104 of the access port 100 can have a uniform diameter, though, in some embodiments, the access port 100 can have two or more diameters, as discussed further below.

Figure 122:
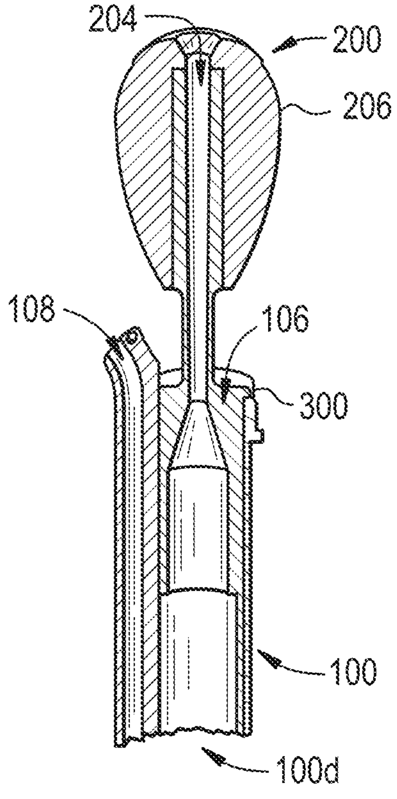
FIG. 122 is a schematic view of the assembly of FIG. 121.

In some embodiments, the central opening 104 of the access port 100 can include multiple channels therein. As shown, the central opening 104 can include a working channel 106 and a camera channel 108. The working channel 106 can be configured to receive objects and/or instruments therethrough while the camera channel 108 can support a camera being inserted therein to allow users to observe the distal end of the access port 100 and the target site 1. The working channel 106 and the camera channel 108 can be separated from one another with a wall 110 that passes through an interior portion of the access port 100, though, in some embodiments, the channels can be in communication with one another to allow objects to pass between the channels. In some embodiments, the working channel 106 and the camera channel 108 can be recesses formed in the proximal end 100*p* of the access port 100, as shown, though, as shown in FIG. 122, one or more of the camera channel 108 and the working channel 106 can protrude proximally from the access port 100 to receive devices, instruments, and/or objects therethrough.

The access port 100 disclosed herein can be made from a rigid or a flexible material. Some non-limiting examples of rigid materials can include stainless steel, titanium, nickel, cobalt-chromium, or alloys and combinations thereof, polymers such as PEEK, ceramics, carbon fiber, and so forth. Some non-limiting examples of flexible materials can include rubber, any of a variety of flexible polymers, and so forth. The material can be chosen based on the surgical site, type of surgery, and/or the objects used during the procedure. Rigid materials can provide added support for objects introduced into the surgical site, while flexible materials can be more easily manipulated by a surgeon to increase an amount of space at the surgical site. It will be appreciated that flexible materials that are sufficiently deformable can allow the access port to be removed when intended, without damaging surrounding tissue.

The sidewall 102 of the illustrated access port 100 can be smooth to facilitate insertion of the access port with minimal friction. While minimizing damage to surrounding tissue, having a smooth sidewall 102 can make the access port 100 prone to unintended backing out of the patient. In some embodiments, surface structures can be added to the access port 100 to retain the access port within the surgical site and prevent ejection. The surface structures can include screws, pins, serrations, or other features known in the art to increase friction to prevent backing out of a structure from a target site 1.

In some embodiments, the access port 100 can couple to instruments and/or devices to manipulate the orientation of the access port in situ, e.g., adjust a position of the access port. For example, the central opening 104 can include one or more mating features 112 thereon for receiving corresponding mating features of an instrument and/or device. As shown, the mating features 112 can include indentations formed in the proximal end 102*p* of the access port 100. In some embodiments, the mating features 112 can be protrusions that are received in corresponding mating features of the instruments and/or device coupled to the access port.

Figure 120:
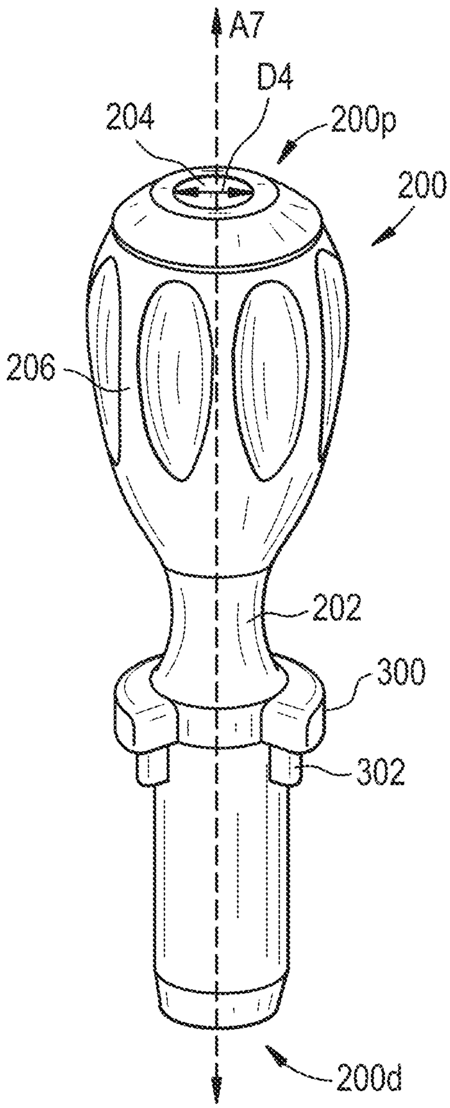
FIG. 120 is a perspective view of a port adjuster configured to be received in the access port of FIG. 119.
Figure 121:
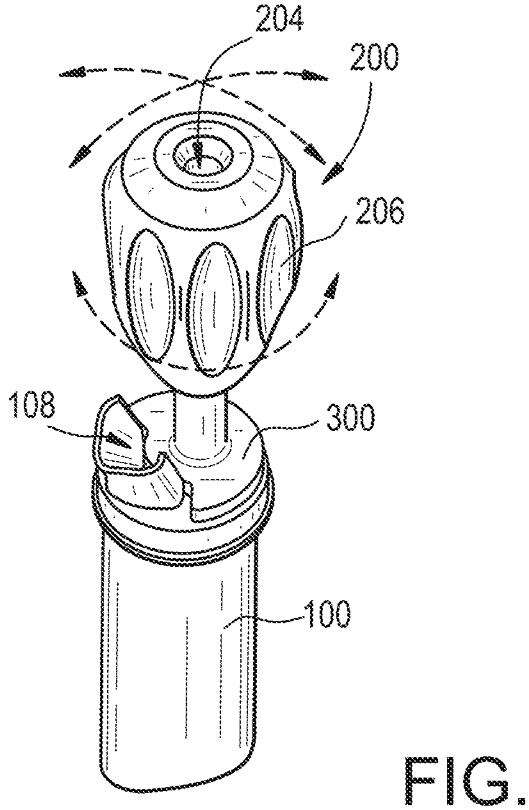
FIG. 121 is a perspective view of an assembly of the port adjuster of FIG. 120 coupled to the access port of FIG. 119.

FIGS. 120-122 illustrate an embodiment of a plug or port adjuster 120 that can be coupled to the access port 100 to adjust an orientation of the port. For example, the port adjuster 120 can couple to the proximal end 100*p* of the access port 100 to facilitate one-handed operation and adjustment of the orientation and/or angle of the port.

The port adjuster 200 can be defined by a sidewall 202 having a central lumen 204 that extends therethrough. The central lumen 204 can extend along a central longitudinal axis A7 of the port adjuster 200 from a proximal end 200*p* of the port adjuster 200 to a distal portion 200*d*. The central lumen 204 can define a space through which instruments, implants, or other objects can be inserted. For example, the central lumen 204 can define an inner diameter D4 that extends through the port adjuster 200. The inner diameter D4 can be smaller than the diameters of the working channel 106 and/or the camera channel 108 of the access port such that instruments received through the central lumen 204 of the port adjuster 200 can be advanced through the access port 100. The instruments can be inserted proximally or distally through the central lumen 204.

The distal portion 200*d* of the port adjuster 200 can be configured to be received in the proximal end 100*p* of the access port 100. For example, the distal portion 200*d* can include a generally cylindrical shaft in which the central lumen 204 passes. The distal portion 200*d* can be sized such that it can be inserted through the central opening 104 in the access port 100. As shown in FIG. 121, the distal portion 200*d* can be received in either of the working channel 106 or the camera channel 108 to couple the port adjuster 200 to the access port 100 without blocking one of the working channel 106 or the camera channel 108.

The proximal end 200*p* of the port adjuster 200 can include a handle 206 or another feature that facilitates gripping of the instrument by the user. The handle 206 can be configured to adjust an angle and/or orientation of the access port 100 prior to, or after, insertion into the target site 1. For example, the handle 206 can include a bulb or a joystick extending proximally from the distal portion 200*d*. The handle 206 can be used similar to a gear shift in a car to manipulate a position of the port. In some embodiments, the port adjuster 200 can position the port into a desired position under guidance from the navigation array 708 and the nerve mapping tool 710. The handle 206 can include a handle lumen (not shown) therein that is in communication with the central lumen 204 of the distal portion 200*d* such that tools inserted through the central lumen 204 can pass through the handle lumen, and tools inserted through the handle lumen can pass through the central lumen 204.

The handle 206 and the distal portion 200*d* can be separated by an abutment surface or shoulder 300 that is defined by a platform that can rest against the proximal end 100*p* of the access port 100, as shown in FIG. 121. The abutment surface 300 can prevent the adjustment port 200 from advancing too far distally into the central opening 104 of the access port 100. The abutment surface 300 can wrap around the circumference of the port adjuster 200, although, in some embodiments, the abutment surface 300 can include a cutout therein so as not to block access to the camera channel 108, as shown in FIGS. 121-122. The abutment surface 300 can also include one or more mating features 302 thereon configured to be received in the mating features of the access port 100 to couple the port adjuster 200 to the access port.

As shown in FIG. 122, the port adjuster 200 can be received in the working channel 106 such that the central axis A7 of the port adjuster 200 is aligned or coincident with the axis A6 of the access port 100 to allow instruments, devices, and/or other objects to be advanced therethrough. In some embodiments, the handle 206 can flex and/or bend to change the position of the access port 100 to increase the ease with which tools are inserted through the access port 100 and/or to change the position of a camera disposed through the working channel 106 in the target site 1. For example, in some embodiments, the handle 206 can be configured to move in all six degrees of freedom (surge, heave, sway, yaw, pitch, and roll) to adjust an angle of the access port 100 and/or to rotate the port to change camera position. Adjustment of the access port 100 can occur prior to passing tools through the central opening 104 of the access port and the port adjuster 200 or once the tools are disposed therein to reposition the port. In some embodiments, the port adjuster 200 can be coupled to the access port 100 prior to insertion of the access port 100 into the target site 1 to provide better control during insertion of the access port over the cannulated dilators into the target site.

Figure 123:
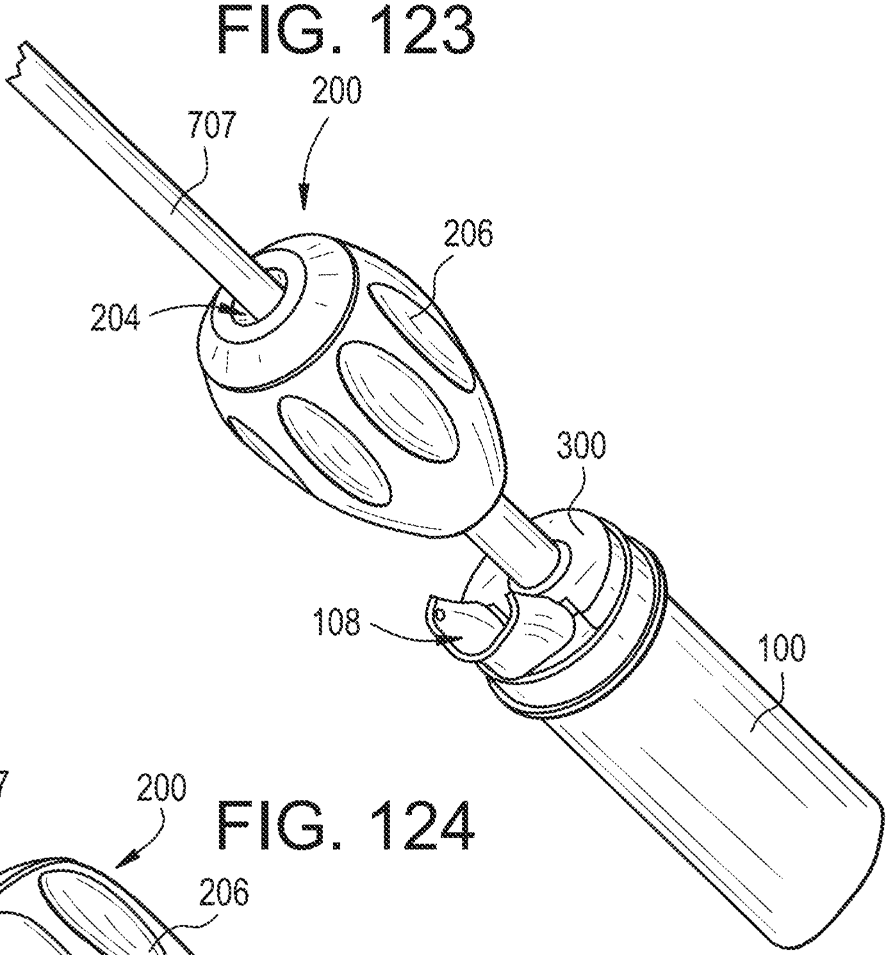
FIG. 123 is a perspective view of a shaft component disposed in the assembly of FIG. 121.
Figure 124:
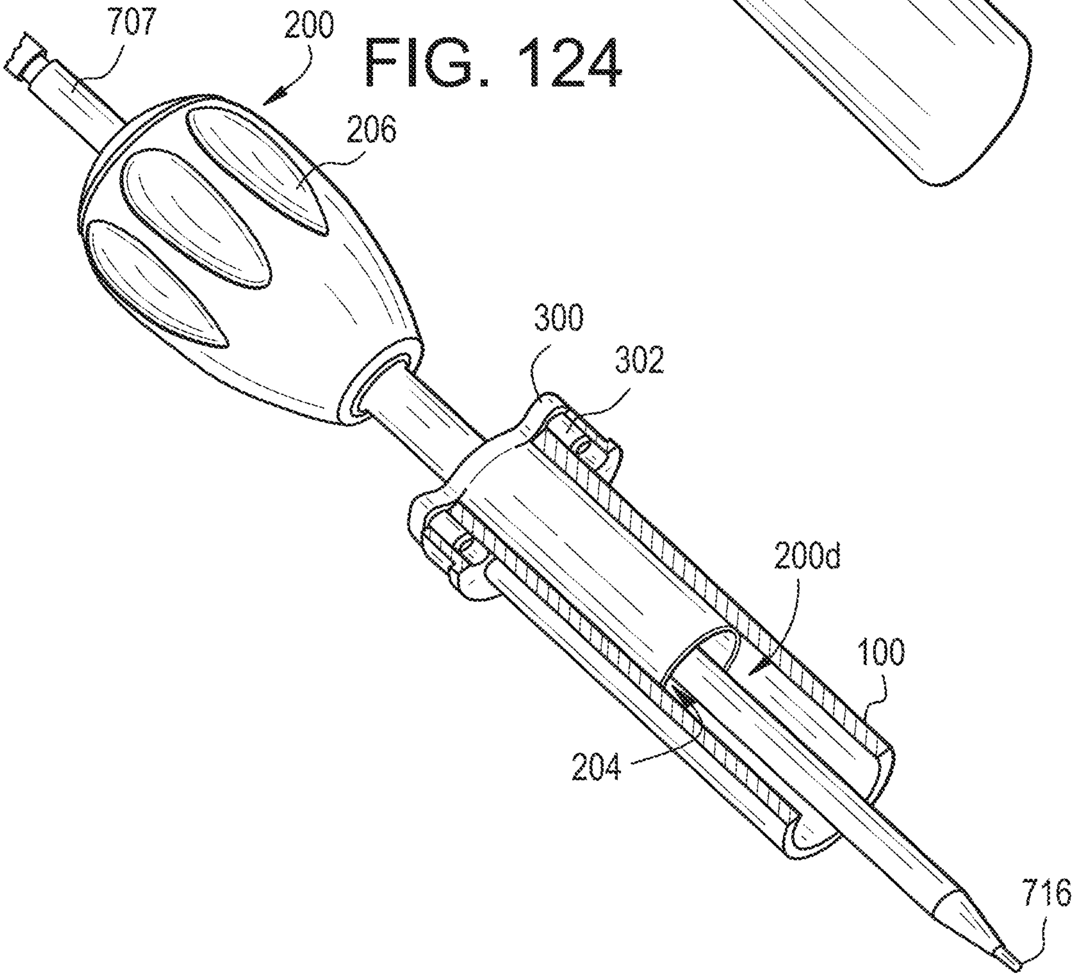
FIG. 124 is another perspective view of the shaft component disposed in the assembly of FIG. 121.
Figure 125:
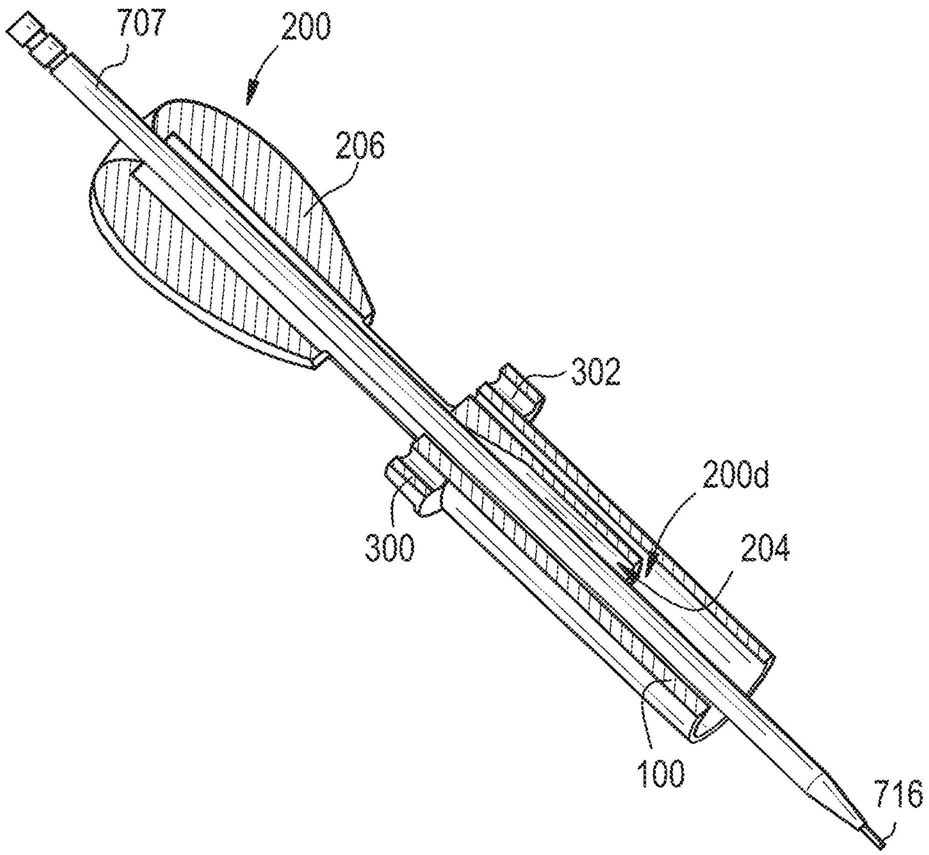
FIG. 125 is a cross-sectional view of the of the shaft component disposed in the assembly of FIG. 121.

FIGS. 123-125 illustrate an embodiment in which the multi-tool 700 can be used to navigate the access port 100. For example, the multi-tool 700 can be inserted through the port adjuster 200 and the access port 100 to position the access port 100 in the target site 1. As shown in FIG. 123, the shaft component 707 of the multi-tool 700 can be received through the coincident lumens of the port adjuster 200 and the working channel 106 of the access port 100 to enter the target site 1. In such a configuration, the shaft component 707 can advance distally through the access port 100 such that the distal tip 716 extends distally from the access port 100, as shown in FIGS. 124-125. The shaft component 707 can then contact tissue at the target site 1 distal of the access port 100. The shaft component 707 can be docked to the target site 1 in this configuration. Inserting the shaft component 707 through the working channel 106 can allow for indirect navigation of the access port 100 without requiring a permanently affixed navigation array to be coupled thereto, which can be bulky and interfere with the procedure. A camera or another visualization device can be inserted through the camera channel 108 and advanced into the target site 1 to visualize the distal tip 716 of the shaft component 707 and assess the trajectory and/or path of the shaft component 707 into the target site 1.

In some embodiments, the navigation array 708 and the nerve mapping tool 710 can be attached to the shaft component 707, as described in the embodiments above, in addition to the camera in the camera channel 108 to ensure precision of the placement of the shaft component 707 in the target site 1.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The instruments and methods disclosed herein can be used in minimally-invasive surgery and/or open surgery. While the instruments and methods disclosed herein are generally described in the context of spinal surgery on a human patient, it will be appreciated that the methods and instruments disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A multi-tool, comprising:

a body that extends from a proximal end to a distal end and includes a hollow interior portion defined therebetween;

a first arm extending from the body, the first arm being defined by an exterior sidewall having a reduced diameter relative to the body, and having a first lumen that leads into the hollow interior portion of the body, the first arm being configured to support coupling one or more surgical devices to the exterior sidewall;

a throughbore formed in the body that is in communication with the hollow interior portion;

a shaft having an elongate body that defines a central longitudinal axis extending from a proximal end to a distal tip, the shaft being configured to pass through each of the first lumen, the throughbore, and the hollow interior portion;

a second arm extending from the body having a second lumen that leads into the hollow interior portion of the body; and a button received in the throughbore, the button having a bore formed therein to allow the shaft to extend therethrough.

2. The multi-tool of claim 1, wherein the one or more surgical devices comprise one or more of a nerve-mapping tool or a navigation array.

3. The multi-tool of claim 2, wherein the navigation array is attached to the exterior sidewall of the first arm and the nerve-mapping tool is configured to be received in the lumen of the second arm.

4. The multi-tool of claim 3, wherein the second lumen is configured to establish an electrical connection between the shaft and the one or more surgical devices.

5. The multi-tool of claim 4, wherein the second lumen includes any of a pin, bolt, or spring disposed in the lumen of the second arm to facilitate establishing the electrical connection.

6. The multi-tool of claim 5, wherein the nerve-mapping tool advances the pin, bolt, or spring into the hollow interior portion to contact the shaft component-when the nerve-mapping tool is received within the second arm.

7. The multi-tool of claim 2, wherein the navigation array is attached to a coupling that includes an opening therein for receiving one or more portions of the body therethrough.

8. The multi-tool of claim 7, wherein at least a portion of the shaft is received through the coupling of the navigation array.

9. The multi-tool of claim 1, wherein the button is configured to translate within the throughbore in a direction that is transverse to the central longitudinal axis of the shaft to toggle the shaft between an unlocked configuration and a locked configuration relative to the body.

10. The multi-tool of claim 9, further comprising one or more springs disposed between the button and the throughbore to translate the button within the throughbore.

11. The multi-tool of claim 10, wherein the one or more springs are fully extended in the locked configuration to apply an outward force on the button relative to the throughbore to prevent the shaft from translating relative to the body.

12. The multi-tool of claim 9, wherein the button further comprises a grasper configured to secure a longitudinal position of the shaft within the bore in the locked configuration to prevent translation of the shaft.

13. The multi-tool of claim 1, wherein the throughbore is disposed distal to a location of an intersection of the hollow interior portion and the second lumen.

14. The multi-tool of claim 1, wherein the first arm and the second arm are oriented substantially perpendicular to one another.

15. The multi-tool of claim 1, wherein the button is a single, monolithic component received in the throughbore.

16. The multi-tool of claim 1, wherein the proximal end of the shaft extends proximal to the proximal end of the body.

17. A surgical method, comprising:

introducing a shaft having an elongate body that defines a central longitudinal axis extending from a proximal end to a distal tip into an incision formed in a patient;

advancing the shaft proximally into a hollow interior portion of a cap defined by a body that extends from a proximal end to a distal end to couple the shaft thereto, the cap having:

a first arm extending from the body and a first lumen that leads into the hollow interior portion of the body, the first arm being configured to support coupling one or more surgical devices to the body;

a throughbore formed in the body that is in communication with the hollow interior portion; and a second arm extending from the body having a second lumen that leads into the hollow interior portion of the body; and a button received in the throughbore, the button having a bore formed therein to allow the shaft to extend therethrough.

18. The method of claim 17, further comprising actuating the button of the cap to toggle the cap between coupling to the shaft and to other devices configured to be received within the hollow interior portion.

19. The method of claim 17, further comprising actuating the button to toggle the cap between a locked configuration in which the button prevents the shaft from moving relative to the cap, and an unlocked configuration in which the button allows the shaft to move relative to the cap.

20. The method of claim 17, further comprising coupling a navigation array to the body.

* * * * *